(12) United States Patent
Carlo et al.

(10) Patent No.: US 11,332,760 B2
(45) Date of Patent: May 17, 2022

(54) COMPOSITIONS AND METHODS FOR GENOMIC EDITING BY INSERTION OF DONOR POLYNUCLEOTIDES

(71) Applicant: CRISPR THERAPEUTICS AG, Zug (CH)

(72) Inventors: Troy Dean Carlo, Cambridge, MA (US); Roman Lvovitch Bogorad, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

(21) Appl. No.: 17/178,737

(22) Filed: Feb. 18, 2021

(65) Prior Publication Data
US 2021/0171985 A1 Jun. 10, 2021

Related U.S. Application Data

(63) Continuation of application No. 16/457,528, filed on Jun. 28, 2019.

(60) Provisional application No. 62/691,573, filed on Jun. 28, 2018.

(51) Int. Cl.
*C12N 15/11* (2006.01)
*C12N 15/90* (2006.01)
*C12N 9/22* (2006.01)

(52) U.S. Cl.
CPC .............. *C12N 15/907* (2013.01); *C12N 9/22* (2013.01); *C12N 15/11* (2013.01); *C12N 2310/18* (2013.01); *C12N 2310/20* (2017.05); *C12N 2800/80* (2013.01)

(58) Field of Classification Search
CPC ........ C12N 15/907; C12N 15/11; C12N 9/22; C12N 2310/20; C12N 2310/18; C12N 2800/80
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts et al. |
| 4,476,301 A | 10/1984 | Imbach et al. |
| 5,013,556 A | 5/1991 | Woodle et al. |
| 5,023,243 A | 6/1991 | Tullis |
| 5,031,272 A | 7/1991 | Carmien |
| 5,034,506 A | 7/1991 | Summerton et al. |
| 5,166,315 A | 11/1992 | Summerton et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,321,131 A | 6/1994 | Agrawal et al. |
| 5,399,676 A | 3/1995 | Froehler |
| 5,405,938 A | 4/1995 | Summerton et al. |
| 5,405,939 A | 4/1995 | Suhadolnik et al. |
| 5,434,257 A | 7/1995 | Matteucci et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,519,126 A | 5/1996 | Hecht |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | Mesmaeker et al. |
| 5,608,046 A | 3/1997 | Cook et al. |

(Continued)

FOREIGN PATENT DOCUMENTS

WO 2005/001248 A1 1/2005
WO 2010/029303 A1 3/2010

(Continued)

OTHER PUBLICATIONS

Matera, A. and Wang, Z. A day in the life of the spliceosome. Nat Rev Mol Cell Biol. 15, 108-121. (Year: 2014).*
Wang et al., Cyclohexene nucleic acids (CeNA): Serum stable oligonucleotides that activate RNase H and increase duplex stability with complementary RNA, J. Am. Chem. Soc., 122(36):8595-8602 (2000).
Wang et al., General and specific functions of exonic splicing silencers in splicing control, Mol. Cell., 23(1):61-70 (2006).

(Continued)

*Primary Examiner* — Antonio Galisteo Gonzalez
*Assistant Examiner* — Khaleda B Hasan
(74) *Attorney, Agent, or Firm* — Marshall, Gerstein & Borun LLP

(57) ABSTRACT

The present disclosure provides donor polynucleotides, genome editing systems, methods, pharmaceutical compositions, and kits which correct or induce a mutation that causes Glycogen Storage Disease 1a in a genomic DNA (gDNA) molecule in a cell. In some embodiments the present disclosure provides donor polynucleotides comprising two strands capable of correcting a mutation that causes Glycogen Storage Disease 1a.

9 Claims, 10 Drawing Sheets

Specification includes a Sequence Listing.

(56) References Cited

U.S. PATENT DOCUMENTS

| | | |
|---|---|---|
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,663,312 A | 9/1997 | Chaturvedula |
| 5,677,437 A | 10/1997 | Teng et al. |
| 5,677,439 A | 10/1997 | Weis et al. |
| 5,817,491 A | 10/1998 | Yee et al. |
| 6,027,726 A | 2/2000 | Ansell |
| 7,404,969 B2 | 7/2008 | Chen et al. |
| 8,691,750 B2 | 4/2014 | Constien et al. |
| 2005/0222064 A1 | 10/2005 | Vargeese et al. |
| 2016/0314245 A1 | 10/2016 | Silver et al. |
| 2019/0382798 A1 | 12/2019 | Cowan et al. |

FOREIGN PATENT DOCUMENTS

| | | | |
|---|---|---|---|
| WO | 2011/125054 A2 | 10/2011 | |
| WO | 2011/130749 A2 | 10/2011 | |
| WO | 2012/099755 A1 | 7/2012 | |
| WO | 2013/052523 A1 | 4/2013 | |
| WO | 2013/086354 A1 | 6/2013 | |
| WO | 2013/103659 A1 | 7/2013 | |
| WO | 2013/116126 A1 | 8/2013 | |
| WO | 2013/151666 A2 | 10/2013 | |
| WO | 2014/089212 A1 | 6/2014 | |
| WO | 2014/135998 A1 | 9/2014 | |
| WO | 2015/009952 A1 | 1/2015 | |
| WO | 2015/081101 A1 | 6/2015 | |
| WO | 2017/072590 A1 | 5/2017 | |
| WO | WO-2017077386 A1 * | 5/2017 | ............... C12N 9/16 |
| WO | 2018/096356 A1 | 5/2018 | |
| WO | 2019/239361 A1 | 12/2019 | |
| WO | 2020/003006 A2 | 1/2020 | |

OTHER PUBLICATIONS

Wang et al., In vitro evaluation of novel antisense oligonucleotides is predictive of in vivo exon skipping activity for Duchenne muscular dystrophy, J. Gene. Med., 12(4):354-364 (2010).

Wang et al., Intronic splicing enhancers, cognate splicing factors and context-dependent regulation rules, Nat. Struct. Mol. Biol., 19(10):1044-1052 (2012).

Wang et al., Systematic identification and analysis of exonic splicing silencers, Cell., 119(6):831-845 (2004).

Yin et al., Therapeutic genome editing by combined viral and non-viral delivery of CRISPR system components in vivo, Nat. Biotechnol., 34(3):328-333 (2016).

Zalipsky et al., Long circulating, cationic liposomes containing amino-PEG-phosphatidylethanolamine, FEBS Letters, 353(1):71-74 (1994).

Zalipsky, Synthesis of an end-group functionalized polyethylene glycol-lipid conjugate for preparation of polymer-grafted liposomes, Bioconjugate Chemistry, 4(4):296-299 (1993).

Zetsche et al., Cpf1 is a single RNA-guided endonuclease of a class 2 CRISPR-cas system, Cell., 163(3):759-71 (2015).

Landau et al., In vivo zinc finger nuclease-mediated targeted integration of a glucose-6-phosphatase transgene promotes survival in mice with glycogen storage disease type IA, Molecular Therapy, 24(4):697-706 (2016).

Landau et al., Zinc finger nuclease-mediated cleavage of the rosa locus to allow targeted integration of a glucose-6-phosphatase gene promotes survival in mice with glycogen storage disease type-IA, Molecular Therapy, 22(Suppl. 1):S7 (2014).

Leonetti et al., Antibody-targeted liposomes containing oligodeoxyribonucleotides complementary to viral RNA selectively inhibit viral replication, Proc. Natl. Acad. Sci. USA., 87(7):2448-2451 (1990).

Leslie et al., Pompe disease, synonyms: acid alpha-glucosidase deficiency, acid maltase deficiency, GM deficiency, glycogen storage disease type II (GSD II), glycogenosis type II, GeneReviews, 26 (2007).

Li et al., DNA double-strand break repair: a tale of pathway choices, Acta. Biochim. Biophys. Sin., 48(7):641-646 (2016).

Lin et al., The CRISPR/Cas9 system facilitates clearance of the intrahepatic HBV templates in vivo, Mol. Ther. Nucleic Acids, 3(8):e186 (2014).

Liu et al., Designer lipids advance systemic siRNA delivery, Molecular Therapy, 18(4):669-670 (2010).

Long et al., Correction of diverse muscular dystrophy mutations in human engineered heart muscle by single-site genome editing, Science Advances, 4(1):eaap9004 (2018).

Long et al., Postnatal genome editing partially restores dystrophin expression in a mouse model of muscular dystrophy, Science, 351(6271):400-403 (2016).

Long et al., Prevention of muscular dystrophy in mice by CRISPR/Cas9-mediated editing of germline DNA, Science, 345:1184-1188 (2014).

Love et al., Lipid-like materials for low-dose, in vivo gene silencing, Proc. Natl. Acad. Sci. USA., 107(5):1864-1869 (2010).

Lyama et al., DNA repair mechanisms in dividing and non-dividing cells, DNA Repair, 12(8):620-636 (2013).

Magadan et al., Cleavage of phage DNA by the Streptococcus thermophilus CRISPR3-Cas system, PLoS ONE, 7:e40913 (2012).

Mahon et al., Combinatorial approach to determine functional group effects on lipidoid-mediated siRNA delivery, Bioconjug. Chem., 21(8):1448-1454 (2010).

Makarova et al., An updated evolutionary classification of CRISPR-Cas systems, Nat. Rev. Microbiol., 13(11):722-36 (2015).

Masella et al., PANDAseq: paired-end assembler for illumina sequences, BMC Bioinformatics, 13:31 (2012).

Mateos-Gomez et al., Mammalian polymerase θ promotes alternative NHEJ and suppresses recombination, Nature, 518:254-57 (2015).

Mersch et al., Automatic detection of exonic splicing enhancers (ESEs) using SVMs, BMC Bioinformatics, 9:369 (2008).

Mesmaeker et al., Antisense oligonucleotides, Acc. Chem. Res., 28(9):366-374 (1995).

Murugaiah et al., Reversed-phase high-performance liquid chromatography method for simultaneous analysis of two liposome-formulated short interfering RNA duplexes, Analytical Biochemistry, 401(1):61-7 (2010).

Myers et al., Optimal alignments in linear space, CABIOS, 4:11-17 (1988).

Nasevicius et al., Effective targeted gene 'knockdown' in zebrafish, Nat. Genet., 26(2):216-220 (2000).

Needleman et al., A general method applicable to the search for similarities in the amino acid sequence of two proteins, J. Mol. Biol., 48:443-53 (1970).

Nielsen et al., Sequence-selective recognition of DNA by strand displacement with a thymine-substituted polyamide, Science, 254:1497-1500 (1991).

Oda et al., NMR studies for identification of dI:dG mismatch base-pairing structure in DNA, Nucleic Acids Res, 19(19):5263-5267 (1991).

Orlando et al., Zinc-finger nuclease-driven targeted integration into mammalian genomes using donors with limited chromosomal homology, Nucleic Acids Research Advance Access, 38(15):e152-1 (2010).

Orthwein et al., A mechanism for the suppression of homologous recombination in G1 cells, Nature, 528(7582):422-6 (2015).

Panyam et al., Biodegradable nanoparticles for drug and gene delivery to cells and tissue, Adv. Drug Deliv. Rev., 55(3):329-347 (2003).

Pearson et al., Improved tools for biological sequence comparison, Proc. Natl. Acad. Sci. U.S.A., 85(8):2444-2448 (1988).

Peer et al., Nanocarriers as an emerging platform for cancer therapy, Nature Nanotech., 2(12):751-760 (2007).

Piccolo et al., Liver-directed gene-based therapies for inborn errors of metabolism, Expert Opinion on Biological Therapy, 1-2:13 (2020).

Ran et al., In vivo genome editing using Staphylococcus aureus Cas9, Nature, 520:186-191 (2015).

Reed, The organization of 3' splice-site sequences in mammalian introns, Genes. Dev., 3(12B):2113-2123 (1989).

Reese, Oligo-and poly-nucleotides: 50 years of chemical synthesis, Organic & Biomolecular Chemistry, 3(21):3851-68 (2005).

(56) References Cited

OTHER PUBLICATIONS

Renaud et al., Improved genome editing efficiency and flexibility using modified oligonucleotides with TALEN and CRISPR-cas9 nucleases, Cell Reports, 14(9):2263-2272 (2016).
Renneisen et al., Inhibition of expression of human immunodeficiency virus-1 in vitro by antibody-targeted liposomes containing antisense RNA to the env region, J. Bio. Chem., 265:16337-16342 (1990).
Rye et al., Phosphate isosteres in medicinal chemistry, Curr. Med. Chem., 12(26):3127-3141 (2005).
Sapra et al., Ligand-targeted liposomal anticancer drugs, Prog. Lipid Res., 42(5):439-62 (2003).
Schneller et al., Genome editing for inborn errors of metabolism: advancing towards the clinic, BMC Medicine, 15(43):1-12 (2017).
Schroeder et al., Lipid-based nanotherapeutics for siRNA delivery, J. Intern. Med., 267(1):9-21 (2010).
Shmakov et al., Discovery and functional characterization of diverse class 2 CRISPR-cas systems, Mol. Cell., 60:385-397 (2015).
Siegwart et al., Combinatorial synthesis of chemically diverse core-shell nanoparticles for intracellular delivery, Proc. Natl. Acad. Sci. USA., 108(32):12996-3001 (2011).
Slaymaker et al., Rationally engineered Cas9 nucleases with improved specificity, Science, 351:84-88 (2016).
Smith et al., Comparison of biosequences, Adv. Appl. Math., 2:482-89 (1981).
Sterner et al., Architectural limits on split genes, Proc. Natl. Acad. Sci. USA., 93(26):15081-15085 (1996).
Tabebordbar et al., In vivo gene editing in dystrophic mouse muscle and muscle stem cells#, Science, 351(6271):407-411 (2016).
Tsai et al., Dimeric CRISPR RNA-guided FokI nucleases for highly specific genome editing, Nat. Biotechnol., 32(6):569-576 (2014).
Tsai et al., GUIDE-seq enables genome-wide profiling of off-target cleavage by CRISPR-cas nucleases, Nature Biotechnology, 33(2):187-197 (2015).
Van Der Wal et al., Large-scale expansion of human iPSC-derived skeletal muscle cells for disease modeling and cell-based therapeutic strategies, Stem Cell Reports, 10(6):1975-1990 (2018).
Verma et al., Modified oligonucleotides: synthesis and strategy for users, Annual Review of Biochemistry, 67:99-134 (1998).
Abra et al., The next generation of liposome delivery systems: recent experience with tumor-targeted, sterically-stabilized immunoliposomes and active-loading gradients, J. Liposome Res., 12:1-3 (2002).
Akinc et al., A combinatorial library of lipid-like materials for delivery of RNAi therapeutics, Nat. Biotechnol., 26(5):561-569 (2008).
Akinc et al., Development of lipidoid-siRNA formulations for systemic delivery to the liver, Mol. Ther., 17(5):872-879 (2009).
Allen et al., A new strategy for attachment of antibodies to sterically stabilized liposomes resulting in efficient targeting to cancer cells, Biochim. Biophys. Acta., 1237(2):99-108 (1995).
Altschul et al., Basic local alignment search tool, J. Mol. Biol., 215(3):403-410 (1990).
Altschul et al., Gapped BLAST and PSI-BLAST: a new generation of protein database search programs, Nucleic Acids Res., 25(17):3389-3402 (1997).
Anders et al., Structural Plasticity of PAM Recognition by Engineered Variants of the RNA-Guided Endonuclease Cas9, Mol. Cell., 61:895-902 (2016).
Bali et al., Glycogen storage disease type I, GeneReviews, 22 (2016).
Berge et al., Pharmaceutical Salts, J. Pharm. Sci., 66(1):1-19 (1977).
Berget, Exon recognition in vertebrate splicing, J. Biol. Chem., 270(6):2411-2414 (1995).
Blencowe, Exonic splicing enhancers: mechanism of action, diversity and role in human genetic diseases, Trends Biochem. Sci., 25(3):106-110 (2000).
Blume et al., Specific targeting with poly(ethylene glycol)-modified liposomes: coupling of homing devices to the ends of the polymeric chains combines effective target binding with long circulation times, Biochim. Biophys. Acta., 1149(1):180-184 (1993).
Braasch et al., Novel antisense and peptide nucleic acid strategies for controlling gene expression, Biochemistry, 41(14):4503-4510 (2002).
Cannan et al., Mechanisms and Consequences of Double-Strand DNA Break Formation in Chromatin, J. Cell. Physiol., 231(1):3-14 (2015).
Carroll, Genome engineering with targetable nucleases, Ann. Rev. Biochem., 83:409-39 (2014).
Carstens et al., An intronic splicing silencer causes skipping of the IIIb exon of fibroblast growth factor receptor 2 through involvement of polypyrimidine tract binding protein, Mol. Cell. Biol., 20(19):7388-7400 (2000).
Ceccaldi et al., Homologous-recombination-deficient tumours are dependent on PolQ-mediated repair, Nature, 518:258-62 (2015).
Chiruvella et al., Repair of double-strand breaks by end joining, Cold Spring Harb Perspect Biol., 5(5):a012757 (2013).
Cho et al., DNA repair: Familiar ends with alternative endings, Nature, 518:174-76 (2015).
Cong et al., Multiplex genome engineering using CRISPR/Cas systems, Science, 339:819-823 (2013).
Coolidge et al., Functional analysis of the polypyrimidine tract in pre-mRNA splicing, Nucleic Acids Res., 25(4):888-896 (1997).
Cox et al., Therapeutic genome editing: prospects and challenges, Nature Medicine, 21(2):121-31 (2015).
Cristea et al., In vivo cleavage of transgene donors promotes nuclease-mediated targeted integration, Biotechnology and Bioengineering, 110(3):871-880 (2013).
Defrees et al., Sialyl lewis X liposomes as a multivalent ligand and inhibitor of E-selectin mediated cellular adhesion, J. Am. Chem. Soc., 118:6101-6104 (1996).
Elliot et al., The use of phosphate bioisosteres in medicinal chemistry and chemical biology, Med. Chem. Com., 3(7):735-751 (2012).
Esvelt et al., Orthogonal Cas9 proteins for RNA-guided gene regulation and editing, Nat. Methods, 10(11):1116-1121 (2013).
Fonfara et al., Phylogeny of Cas9 determines functional exchangeability of dual-RNA and Cas9 among orthologous type II CRISPR-Cas systems, Nucleic Acids Research, 42(4):2577-2590 (2014).
Gao et al., Human branch point consensus sequence is yUnAy, Nucleic Acids Res., 36(7):2257-2267 (2008).
Garneau et al., The CRISPR/Cas bacterial immune system cleaves bacteriophage and plasmid DNA, Nature, 468:67-71 (2010).
Goodchild, Conjugates of oligonucleotides and modified oligonucleotides: a review of their synthesis and properties, Bioconjugate Chemistry, 1(3):165-187 (1990).
Gupta et al., Expanding the genetic editing tool kit: ZFNs, TALENs, and CRISPR-Cas9, J. Clin. Invest., 124(10):4154-61 (2014).
Hafez et al., Homing endonucleases: DNA scissors on a mission, Genome., 55:553-69 (2012).
Havens et al., Targeting RNA splicing for disease therapy, RNA, 4(3):247-266 (2013).
Heasman, Morpholino oligos: making sense of antisense?, Dev. Biol., 243(2):209-214 (2002).
Heath et al., Covalent Attachment of proteins to liposomes, Methods in Enzymology, Academic Press, Inc., 149:111-119 (1987).
Heyer et al., Regulation of homologous recombination in eukaryotes, Annu. Rev. Genet., 44:113-139 (2010).
International Preliminary Report on Patentability, PCT/IB2016/001709, dated May 8, 2018, 6 pages.
International Preliminary Report on Patentability, PCT/IB2019/000833, dated Dec. 28, 2020, 9 pages.
International Search Report and Written Opinion, PCT/IB2016/001709, dated Mar. 31, 2017, 10 pages.
International Search Report and Written Opinion, PCT/IB2019/000833, dated Jan. 28, 2020, 19 pages.
Jinek et al., RNA-programmed genome editing in human cells, eLife, 2:e00471:1-9 (2013).
Karanam et al., Quantitative live cell imaging reveals a gradual shift between DNA repair mechanisms and a maximal use of HR in mid S phase, Mol. Cell., 47(2):320-329 (2012).
Kim et al., In vivo genome editing with a small Cas9 orthologue derived from Campylobacter jejuni, Nat. Comm., 8:14500 (2017).

(56) References Cited

OTHER PUBLICATIONS

Kirpotin et al., Liposomes with detachable polymer coating: destabilization and fusion of dioleoylphosphatidylethanolamine vesicles triggered by cleavage of surface-grafted poly(ethylene glycol), FEBS Letters, 388:115-118 (1996).

Kleinstiver et al., Broadening the targeting range of *Staphylococcus aureus* CRISPR-Cas9 by modifying PAM recognition, Nat. Biotechnol., 33:1293-1298 (2015).

Kleinstiver et al., High-fidelity CRISPR-Cas9 nucleases with no detectable genome-wide off-target effects, Nature, 529:490-495 (2016).

Klibanov et al., Long-Circulating Liposomes: Development and Perspectives, Journal of Liposome Research, 2(3):321-334 (1992).

Koonin et al., Diversity, classification and evolution of CRISPR-Cas systems, Curr. Opin. Microbiol., 37:67-78 (2017).

Kreutz et al., Hepatocyte Ploidy Is a Diversity Factor for Liver Homeostasis, Front Physiol., 8:862 (2017).

Lacerra et al., Restoration of hemoglobin A synthesis in erythroid cells from peripheral blood of thalassemic patients, Proc. Natl. Acad. Sci., 97(17):9591-9596 (2000).

\* cited by examiner

FIG. 6A

50nt donor dsODN:

Sense strand: 5' - tggaagaagagagaagaagctgggTATTAACgcattttttctttttaattc - 3'

Antisense strand: 3' - accttcttctcttcttcgaccATAATTGcgtaaaaagaaaaattaag - 5'

Branch point: TATTAAC / ATAATT (bold)

Py tract: gcatttttctttttaattc

FIG. 6B

Py Tract Mutation — Inserted in forward orientation

5' —— tggaagaagagagaagaagctgggTATTAACgcatttttctttttaattc —— [GAA exon] 3'

Py Tract Mutation — Inserted in reverse orientation

5' —— gaattaaaaagaaaaatgcGTTAATAcccagcttcttctttcttcca —— [GAA exon] 3'

COMPOSITIONS AND METHODS FOR GENOMIC EDITING BY INSERTION OF DONOR POLYNUCLEOTIDES

RELATED INFORMATION

This application is a continuation of U.S. application Ser. No. 16/457,528, filed on Jun. 28, 2019, which claims the benefit of U.S. Provisional Application Ser. No. 62/691,573, filed on Jun. 28, 2018. The entire contents of the above-referenced patent applications are incorporated herein by reference.

SEQUENCE LISTING

The instant application contains a Sequence Listing which has been submitted electronically in ASCII format and is hereby incorporated by reference in its entirety. Said ASCII copy, created on Feb. 18, 2021, is named CRTN-002CN_Sequence_Listing.txt and is 35416 bytes in size.

BACKGROUND

Genome editing therapies using programmable and/or engineered nucleases, combined with designed exogenous DNA repair template molecules, have been developed to treat intractable disease such as, for example, viral infection (Lin et al., (2014) Mol Ther Nucleic Acids 3:e186), enzymatic deficiency (Yin et al., (2016) Nat Biotechnol 34(3): 328-333), and hereditary myopathies (Long et al., (2014) Science 345:1184-1188; Long et al., (2016) Science 351: 400-403; Tabebordbar et al., (2016) Science 351:407-411). Approaches to therapeutically target the genome often rely on the homology-directed repair (HDR) pathway, which enables accurate genome repair of introduced double-stranded breaks (DSBs) using exogenous single- or double-stranded DNA repair templates (e.g., donor polynucleotides), but is often highly suppressed in non-dividing cells (e.g., $G_1$ phase cells) (Orthwein et al., (2015) Nature 528 (7582):422-6). Despite rapid advances in this area of biomedical research and the potential for clinical applications, targeted integration of transgenes or other polynucleotides for therapeutic purposes in vivo remains challenging because current methods are inefficient, particularly for non-dividing cells, which compose most adult tissues.

DSBs induced into the genome by exogenous sources (e.g., an engineered nuclease) may be repaired in cells by double-strand break repair (DSBR) mechanisms, such as the HDR pathway and the non-homologous end joining (NHEJ) DNA repair pathway. The canonical HDR pathway is known to operate in dividing cells (e.g., cells in S phase), as it requires a homologous sister chromatid for execution, whereas the NHEJ pathway can function in both dividing and non-dividing cells and independent of the cell cycle (Iyama & Wilson (2013) DNA Repair 12(8), 620-636). In contrast to the HDR pathway, the NHEJ repair pathway is often used in genome editing approaches that do not employ an exogenous DNA repair template (e.g., a donor polynucleotide) and that are directed toward the formation of an stochastic insertion or deletion ('indel') of one or more nucleotides at the DSB site, resulting in, for example, disruption of the translational reading frame of a coding sequence or the binding sites of trans-acting factors in promoters or enhancers.

As genetic abnormalities are widely recognized as a major etiological basis of numerous diseases, the inability or inefficiency of therapeutic targeted genome editing poses a technical barrier for developing treatments for a broad range of genetic disorders. Thus, new approaches to therapeutically target the genome, particularly in non-dividing cells, are needed.

SUMMARY OF THE DISCLOSURE

Accurate pre-messenger RNA (pre-mRNA) splicing is critical for correct protein expression. Vertebrate gene architecture often consists of relatively long introns and short internal exons. Without being bound by theory, the model of exon definition posits splice sites paired across an exon as opposed to across an intron and that in pre-mRNAs with large introns, the splicing machinery searches for a pair of closely spaced splice sites in an exonic polarity (i.e., 3' splice site upstream and 5' splice site downstream) (Berget (1995) J Biol Chem 270:2411-2414). Recognition of a pair of splice sites in a relatively short (50 to 300 nucleotides) region surrounding an exon by the splicing machinery reduces the frequency of recognizing cryptic intronic splice sites that are randomly distributed within introns, thus increasing the accuracy of splicing. Numerous disease-causing mutations are known to be located within exons (e.g. protein-coding mutations) or within introns (e.g., splicing signal mutations) that can lead to an aberrancy in protein production or function, ultimately resulting or contributing to a disease.

The present disclosure is based, at least in part, on the discovery that a mutation (e.g., a deleterious or disease-causing mutation) can be corrected or induced in a genomic DNA molecule (gDNA) by genome editing compositions and methods, in particular by use of a donor polynucleotide as described herein, that results in a desired alteration in the nucleotide sequence of the gDNA and modulates exon definition, thereby resulting in the inclusion of a desired alteration in an RNA transcript (e.g., a pre-mRNA) transcribed from the edited gDNA. Accordingly, the disclosure provides donor polynucleotides that, when used to repair a double-strand break (DSB) introduced into a gDNA by a site-directed nuclease (e.g., a Cas nuclease), correct or induce a mutation and modulate exon definition by the incorporation of one or more splicing signals proximal to the corrected or induced mutation. In some embodiments, the donor polynucleotides provided by the disclosure are designed to comprise a nucleotide sequence comprising a desired alteration correct a mutation in a target nucleic acid (e.g., a genomic DNA) and one or more splicing signals that function to modulate splice site recognition. In some embodiments, the donor polynucleotides provided by the disclosure are designed to comprise a nucleotide sequence comprising a desired alteration and one or more splicing signals that function to modulate exon definition, directing the splicing machinery of the cell to incorporate the desired alteration into a transcription product (e.g., a pre-mRNA).

The disclosure also provides methods for correcting or inducing a mutation (e.g., a disease-causing mutation) in gDNA, including cellular, ex vivo and in vivo methods, by the insertion of a linear, double-stranded DNA donor polynucleotide into a CRISPR/Cas9-mediated DSB generated proximal to the mutation. While actively dividing cells can repair DNA damage using both HDR and NHEJ pathways, non-dividing cells predominately use the NHEJ pathway. The use of CRISPR/Cas9 allows for the introduction of site-specific DNA breaks that can be repaired by the NHEJ pathway such that exogenous DNA polynucleotides are ligated, or inserted, into the genomic DNA of dividing or non-dividing cells. In some embodiments, the donor polynucleotides of the disclosure comprise nucleotide sequences that both correct or induce a mutation and comprise one or more splicing signals, thereby promoting a desired RNA processing event to occur by establishing exon definition for a desired exon (e.g., an exon comprising a corrected mutation) and/or destroying exon definition for an undesired exon (e.g., an exon comprising a disease-causing mutation). Also provided herein are compositions, systems, and kits for performing such methods. Also provided are cells produced by such methods.

In some embodiments, the disclosure provides a donor polynucleotide comprising a non-replicative double-stranded DNA molecule (dsDNA) comprising:

(i) a first strand comprising from 5' to 3' a nucleotide sequence which corrects or induces a mutation in a genomic DNA (gDNA) molecule in a cell and a nucleotide sequence comprising one or more splicing signals to control processing of a precursor mRNA (pre-mRNA) transcribed from the gDNA; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising:

(i) a first strand comprising from 5' to 3' a nucleotide sequence which corrects or induces a mutation in a genomic DNA (gDNA) molecule in a cell and a nucleotide sequence comprising one or more splicing signals to control processing of a precursor mRNA (pre-mRNA) transcribed from the gDNA; and (ii) a second strand comprising a nucleotide sequence complementary to the first strand, wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the mutation is a substitution, missense, nonsense, insertion, deletion or frameshift mutation. In some embodiments, the mutation is a substitution mutation. In some embodiments, the mutation is a missense mutation. In some embodiments, the mutation is a nonsense mutation. In some embodiments, the mutation is an insertion mutation. In some embodiments, the mutation is a deletion mutation. In some embodiments, the mutation is a frameshift mutation.

In some embodiments, the mutation is in an exon. In some embodiments, the mutation is a substitution, insertion or deletion, and the mutation is in an intron. In some embodiments, the mutation is a substitution mutation located in an intron. In some embodiments, the mutation is an insertion mutation located in an intron. In some embodiments, the mutation is a deletion mutation located in an intron.

In some embodiments, the mutation is proximal to a splicing signal in a gDNA. In some embodiments, the mutation is proximal to a 3' splice site in a gDNA. In some embodiments, the mutation is proximal to a 5' splice site in a gDNA. In some embodiments, the mutation is in a splicing signal in a gDNA. In some embodiments, the mutation is in a 3' splice site in a gDNA. In some embodiments, the mutation is in a 5' splice site in a gDNA. In some embodiments, the mutation is in a polypyrimidine tract. In some embodiments, the mutation is in a branch point sequence. In some embodiments, the mutation is a protein-coding mutation. In some embodiments, the mutation is associated with or causes a disease.

In some embodiments, the donor polynucleotides provided by the disclosure comprise an intronic sequence. In some embodiments, the intronic sequence corrects the mutation.

In some embodiments, the donor polynucleotides provided by the disclosure comprise an exonic sequence. In some embodiments, the exonic sequence corrects the mutation.

In some embodiments, the donor polynucleotides provided by the disclosure comprise one or more splicing signals is selected from the group consisting of:
   (a) a natural or enhanced 3' splice site;
   (b) a natural or enhanced 5' splice site;
   (c) a polypyrimidine tract;
   (d) a branch point;
   (e) an exon splicing enhancer (ESE);
   (f) an intron splicing enhancer (ISE);
   (g) an exon splicing silencer (ESS);
   (h) an intron splicing silencer (ISS); and
   (i) a combination of any of (a)-(h).

In some embodiments, the one or more splicing signals is a natural or enhanced 3' splice site. In some embodiments, the one or more splicing signals is a natural 3' splice site. In some embodiments, the one or more splicing signals is an enhanced 3' splice site. In some embodiments, the one or more splicing signals is a natural or enhanced 5' splice site. In some embodiments, the one or more splicing signals is a natural 5' splice site. In some embodiments, the one or more splicing signals is an enhanced 3' splice site. In some embodiments, the one or more splicing signals is a polypyrimidine tract. In some embodiments, the one or more splicing signals is a branch point. In some embodiments, the one or more splicing signals is a nucleotide sequence comprising a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the one or more splicing signals is a combination comprising a natural or enhanced 3' splice site and a polypyrimidine tract. In some embodiments, the one or more splicing signals is a combination comprising a natural or enhanced 3' splice site, a polypyrimidine tract, and a branch point.

In some embodiments, the disclosure provides a donor polynucleotide comprising a non-replicative double-stranded DNA molecule (dsDNA) which corrects or induces a mutation in a genomic DNA (gDNA) molecule in a cell and one or more splicing signals to control processing of a precursor mRNA (pre-mRNA) transcribed from the gDNA, wherein the donor polynucleotide comprises a first splicing signal comprising a branch point sequence, wherein the donor polynucleotide comprises:

(i) a first strand comprising from 5' to 3' a nucleotide sequence comprising a first branch point sequence and a first nucleotide sequence which corrects the mutation in the gDNA; and (ii) a second strand comprising from 5' to 3' a nucleotide sequence comprising a second branch point sequence and a second nucleotide sequence which corrects the mutation in the gDNA, wherein the second strand is complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the nucleotide sequence comprising the first splicing signal conforms to a branch point consensus sequence on either strand, wherein the nucleotide sequences of the first branch point sequence and second branch point sequence are complementary.

In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) which corrects or induces a mutation in a genomic DNA (gDNA) molecule in a cell and one or more splicing signals to control processing of a precursor mRNA (pre-mRNA) transcribed from the gDNA, wherein the donor polynucleotide comprises a first splicing signal comprising a branch point sequence, wherein the donor polynucleotide comprises:

(i) a first strand comprising from 5' to 3' a nucleotide sequence comprising a first branch point sequence and a first nucleotide sequence which corrects the mutation in the gDNA; and (ii) a second strand comprising from 5' to 3' a nucleotide sequence comprising a second branch point sequence and a second nucleotide sequence which corrects the mutation in the gDNA, wherein the second strand is complementary to the first strand, wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the nucleotide sequence comprising the first splicing signal conforms to a branch point consensus sequence on either strand, wherein the nucleotide sequences of the first branch point sequence and second branch point sequence are complementary.

In some embodiments, the branch point consensus sequence is YTNAY (SEQ ID NO: 49), wherein Y is a nucleotide comprising either a cytosine (C) or thymine (T) nucleobase, and wherein N is a nucleotide comprising a nucleobase selected from the group consisting of: adenine (A), guanine (G), thymine (T) and cytosine (C). In some embodiments, Y comprises a cytosine (C). In some embodiments, Y comprises a thymine (T). In some embodiments, N comprises an adenine (A). In some embodiments, N comprises a guanine (G). In some embodiments, N comprises a thymine (T). In some embodiments, N comprises a cytosine (C).

In some embodiments, the first branch point sequence is TATTAAC (SEQ ID NO: 50).

In some embodiments, the second branch point sequence is GTTAATA (SEQ ID NO: 51).

In some embodiments, the second branch point sequence is TACTGAC (SEQ ID NO: 52).

In some embodiments, the donor polynucleotide comprises a second splicing signal comprising a polypyrimidine tract, wherein the first strand comprises a first polypyrimidine tract located downstream of the first branch point sequence; and the second strand comprises a second polypyrimidine tract located downstream of the second branch point sequence. In some embodiments, the nucleotide sequence comprising the first and second polypyrimidine tracts each comprise nucleobases selected from the group consisting of: adenine (A), guanine (G), thymine (T) and cytosine (C), and wherein the nucleotide sequence is about 100%, about 90%-100%, or about 80%-90% pyrimidine nucleobases. In some embodiments, the nucleotide sequence is about 100% pyrimidine nucleobases. In some embodiments, the nucleotide sequence is about 90%-100% pyrimidine nucleobases. In some embodiments, the nucleotide sequence is about 80%-90% pyrimidine nucleobases.

In some embodiments, the nucleotide sequence comprising the polypyrimidine tract is TTTTTTTCT (SEQ ID NO: 53). In some embodiments, the nucleotide sequence comprising the polypyrimidine tract is TTTTTTTCTTTTT (SEQ ID NO: 54). In some embodiments, the nucleotide sequence comprising the polypyrimidine tract is CTTCTTCTCTTCTTCC (SEQ ID NO: 55).

In some embodiments, the first branch point sequence and the first polypyrimidine tract are adjacent to each other. In some embodiments, the second branch point sequence and the second polypyrimidine tract are adjacent to each other.

In some embodiments, the donor polynucleotide comprises a third splicing signal, wherein the third splicing signal comprises a 3' splice site, wherein the first strand comprises a nucleotide sequence comprising a first 3' splice site located downstream of the first polypyrimidine tract; and wherein second strand comprises a nucleotide sequence comprising a second 3' splice site located downstream of the second polypyrimidine tract. In some embodiments, the first and second 3' splice sites comprise the nucleotide sequence YAG, and wherein Y is a nucleotide comprising a nucleobase selected from the group consisting of: thymine (T) and cytosine (C). In some embodiments, Y comprises a thymine (T). In some embodiments, Y comprises a cytosine (C).

In some embodiments, the donor polynucleotide comprises a coding sequence, wherein the first strand comprises a first coding sequence, wherein the second strand comprises a second coding sequence, wherein the first nucleotide sequence that corrects the mutation in the gDNA comprises the first coding sequence, wherein the second nucleotide sequence that corrects the mutation in the gDNA comprises the second coding sequence, wherein the first coding sequence is located downstream of the first 3' splice site, and wherein the second coding sequence is located downstream of the second 3' splice site. In some embodiments, the nucleotide sequence comprising the first and second coding sequences comprise nucleobases selected from the group consisting of: adenine (A), guanine (G), thymine (T) and cytosine (C). In some embodiments, the coding sequence comprising (i) and (ii) are not identical or complementary to reduce self-annealing.

In some embodiments, the donor polynucleotide comprises one or more delimiter sequences comprising a nucleotide sequence comprising nucleobases selected from the group consisting of: adenine (A), guanine (G), thymine (T) and cytosine (C), wherein the nucleotide sequence is about 1-40, about 1-30, about 1-20, about 1-15, about 1-10, about 30, about 20, about 10, about 9, about 8, about 7, about 6, about 5, about 4, about 3, about 2 or 1 nucleotide(s) in length. In some embodiments, the nucleotide sequence comprising one or more delimiter sequences is about 1-40 nucleotides in length. In some embodiments, the nucleotide sequence comprising one or more delimiter sequences is about 1-30 nucleotides in length. In some embodiments, the nucleotide sequence comprising one or more delimiter sequences is about 1-20 nucleotides in length. In some embodiments, the nucleotide sequence comprising one or more delimiter sequences is about 1-15 nucleotides in length. In some embodiments, the nucleotide sequence comprising one or more delimiter sequences is about 1-10 nucleotides in length. In some embodiments, the nucleotide sequence comprising one or more delimiter sequences is about 30 nucleotides in length. In some embodiments, the nucleotide sequence comprising one or more delimiter sequences is about 20 nucleotides in length. In some embodiments, the nucleotide sequence comprising one or more delimiter sequences is about 10 nucleotides in length. In some embodiments, the nucleotide sequence comprising one or more delimiter sequences is about 9 nucleotides in length. In some embodiments, the nucleotide sequence comprising one or more delimiter sequences is about 8 nucleotides in length. In some embodiments, the nucleotide sequence comprising one or more delimiter sequences is about 7 nucleotides in length. In some embodiments, the nucleotide sequence comprising one or more delimiter sequences is about 6 nucleotides in length. In some embodiments, the nucleotide sequence comprising one or more delimiter sequences is about 5 nucleotides in length. In some embodiments, the nucleotide sequence comprising one or more delimiter sequences is about 4 nucleotides in length. In some embodiments, the nucleotide sequence comprising one or more delimiter sequences is about 3 nucleotides in length. In some embodiments, the nucleotide sequence comprising one or more delimiter sequences is about 2 nucleotides in length. In some embodiments, the nucleotide sequence comprising one or more delimiter sequences is about 1 nucleotide in length.

In some embodiments, the one or more delimiter sequences is located between the first branch point sequence and the second branch point sequence. In some embodiments, the one or more delimiter sequences is located between the first branch point sequence and the first polypyrimidine tract. In some embodiments, the one or more delimiter sequences is located between the second branch point and the second polypyrimidine tract.

In some embodiments, the disclosure provides donor polynucleotides configured for bi-directional insertion into the DSB, wherein, when a donor polynucleotide is inserted into the DSB in either orientation, the first splicing signal and second splicing signal, optionally, the third splicing signal and coding sequence comprise a sense strand, thereby correcting the mutation and providing one or more splicing signals to control processing of a pre-mRNA transcribed from the gDNA.

In some embodiments, the disclosure provides a donor polynucleotide comprising a non-replicative double-stranded DNA molecule (dsDNA) which corrects or induces a mutation in a genomic DNA (gDNA) molecule in a cell and one or more splicing signals to control processing of a precursor mRNA (pre-mRNA) transcribed from the gDNA, wherein the donor polynucleotide comprises:

(i) a first strand comprising from 5' to 3' a nucleotide sequence comprising a first 5' splice site and a first nucleotide sequence which corrects the mutation in the gDNA; and (ii) a second strand comprising from 5' to 3' a nucleotide sequence comprising a second 5' splice site and a second nucleotide sequence which corrects the mutation in the gDNA, wherein the second strand is complementary to the first strand, wherein the donor polynucleotide is about 10-500, about 10-400, about 10-300, about 10-200, about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the first strand comprises a first coding sequence, wherein the second strand comprises a second coding sequence, wherein the first coding sequence is located upstream of the first 5' splice site, and wherein the second coding sequence is located upstream of the second 5' splice site, and wherein the coding sequences in the first and second strand are not complementary (or comprise one, two, three, four or more mismatches) to reduce self-annealing. In some embodiments, the donor polynucleotide comprises a delimiter sequence comprising a nucleotide sequence comprising nucleobases selected from the group consisting of: adenine (A), guanine (G), thymine (T) and cytosine (C), wherein the nucleotide sequence is about 1-40, about 1-30, about 1-20, about 1-15, about 1-10, about 30, about 20, about 10, about 9, about 8, about 7, about 6, about 5, about 4, about 3, about 2 or 1 nucleotide(s) in length located between the first and second 5' splice sites. In some embodiments, the donor polynucleotide is configured for bi-directional insertion into the DSB, wherein when the donor polynucleotide is inserted into the DSB in a first orientation, the first 5' splice site and first coding sequence comprise a sense strand, thereby correcting the mutation and providing splicing signals to control processing of a pre-mRNA transcribed from the gDNA, and wherein when the donor polynucleotide is inserted into the DSB in a second orientation, the second 5' splice site and second coding sequence comprise a sense strand, thereby correcting the mutation and providing one or more splicing signals to control processing of a pre-mRNA transcribed from the gDNA. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) which corrects or induces a mutation in a genomic DNA (gDNA) molecule in a cell and one or more splicing signals to control processing of a precursor mRNA (pre-mRNA) transcribed from the gDNA, wherein the donor polynucleotide comprises:

(i) a first strand comprising from 5' to 3' a nucleotide sequence comprising a first 5' splice site and a first nucleotide sequence which corrects the mutation in the gDNA; and (ii) a second strand comprising from 5' to 3' a nucleotide sequence comprising a second 5' splice site and a second nucleotide sequence which corrects the mutation in the gDNA, wherein the second strand is complementary to the first strand, wherein the donor polynucleotide is about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the first strand comprises a first coding sequence, wherein the second strand comprises a second coding sequence, wherein the first coding sequence is located upstream of the first 5' splice site, and wherein the second coding sequence is located upstream of the second 5' splice site, and wherein the coding sequences in the first and second strand are not complementary (or comprise one, two, three, four or more mismatches) to reduce self-annealing. In some embodiments, the donor polynucleotide comprises a delimiter sequence comprising a nucleotide sequence comprising nucleobases selected from the group consisting of: adenine (A), guanine (G), thymine (T) and cytosine (C), wherein the nucleotide sequence is about 1-40, about 1-30, about 1-20, about 1-15, about 1-10, about 30, about 20, about 10, about 9, about 8, about 7, about 6, about 5, about 4, about 3, about 2 or 1 nucleotide(s) in length located between the first and second 5' splice sites. In some embodiments, the donor polynucleotide is configured for bi-directional insertion into the DSB, wherein when the donor polynucleotide is inserted into the DSB in a first orientation, the first 5' splice site and first coding sequence comprise a sense strand, thereby correcting the mutation and providing splicing signals to control processing of a pre-mRNA transcribed from the gDNA, and wherein when the donor polynucleotide is inserted into the DSB in a second orientation, the second 5' splice site and second coding sequence comprise a sense strand, thereby correcting the mutation and providing one or more splicing signals to control processing of a pre-mRNA transcribed from the gDNA.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:

(a) a natural or enhanced 3' splice site;
(b) a polypyrimidine tract;
(c) a branch point;
(d) an exon splicing enhancer (ESE);
(e) an intron splicing enhancer (ISE);
(f) an exon splicing silencer (ESS);
(g) an intron splicing silencer (ISS); and
(h) a combination of any of (a)-(g), wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is a natural or enhanced 3' splice site. In some embodiments, the one or more splicing signals is a polypyrimidine tract. In some embodiments, the one or more splicing signals is a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:
 (a) a natural or enhanced 3' splice site;
 (b) a polypyrimidine tract;
 (c) a branch point;
 (d) an exon splicing enhancer (ESE);
 (e) an intron splicing enhancer (ISE);
 (f) an exon splicing silencer (ESS);
 (g) an intron splicing silencer (ISS); and
 (h) a combination of any of (a)-(g),
wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is a natural or enhanced 3' splice site. In some embodiments, the one or more splicing signals is a polypyrimidine tract. In some embodiments, the one or more splicing signals is a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA (gDNA) molecule in a cell, wherein the disease-causing mutation is a protein-coding mutation proximal to a 5' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, and (ii) a second strand comprising a nucleotide sequence complementary to the first strand, wherein the one or more splicing signals is selected from the group consisting of:
 (a) a natural or enhanced 5' splice site;
 (b) an exon splicing enhancer (ESE);
 (c) an intron splicing enhancer (ISE);
 (d) an exon splicing silencer (ESS);
 (e) an intron splicing silencer (ISS); and
 (f) a combination of any of (a)-(e),
wherein the donor polynucleotide is about 10-500, about 10-400, about 10-300, about 10-200, about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is a natural or enhanced 5' splice site. In some embodiments, the one or more splicing signals is a polypyrimidine tract. In some embodiments, the one or more splicing signals is a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA (gDNA) molecule in a cell, wherein the disease-causing mutation is a protein-coding mutation proximal to a 5' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, and (ii) a second strand comprising a nucleotide sequence complementary to the first strand, wherein the one or more splicing signals is selected from the group consisting of:

(a) a natural or enhanced 5' splice site;
(b) an exon splicing enhancer (ESE);
(c) an intron splicing enhancer (ISE);
(d) an exon splicing silencer (ESS);
(e) an intron splicing silencer (ISS); and
(f) a combination of any of (a)-(e), wherein the donor polynucleotide is about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is a natural or enhanced 5' splice site. In some embodiments, the one or more splicing signals is a polypyrimidine tract. In some embodiments, the one or more splicing signals is a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein at least one splicing signal is a natural or enhanced 3' splice site; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein at least one splicing signal is a natural or enhanced 3' splice site; and (ii) a second strand comprising a nucleotide sequence complementary to the first strand, wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the one or more splicing signals is a combination of a natural or enhanced 3' splice site and a polypyrimidine tract; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the one or more splicing signals is a combination of a natural or enhanced 3' splice site and a polypyrimidine tract; and (ii) a second strand comprising a nucleotide sequence complementary to the first strand, wherein the donor polynucleotide is about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the one or more splicing signals is a combination of a natural or enhanced 3' splice site, a polypyrimidine tract, and a branch point; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the one or more splicing signals is a combination of a natural or enhanced 3' splice site, a polypyrimidine tract, and a branch point; and (ii) a second strand comprising a nucleotide sequence complementary to the first strand, wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising 5' to 3' a nucleotide sequence which corrects a disease-causing mutation in a genomic DNA molecule (gDNA) in a cell, wherein the disease-causing mutation is in a 3' splice site, wherein the first strand comprises an intronic sequence, optionally, an exonic sequence, wherein the intronic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:
  (a) a polypyrimidine tract;
  (b) a branch point;
  (c) an exon splicing enhancer (ESE);
  (d) an intron splicing enhancer (ISE);
  (e) an exon splicing silencer (ESS);
  (f) an intron splicing silencer (ISS); and
  (g) a combination of any of (a)-(f), wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is a polypyrimidine tract. In some embodiments, the one or more splicing signals is a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising 5' to 3' a nucleotide sequence which corrects a disease-causing mutation in a genomic DNA molecule (gDNA) in a cell, wherein the disease-causing mutation is in a 3' splice site, wherein the first strand comprises an intronic sequence, optionally, an exonic sequence, wherein the intronic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:
  (a) a polypyrimidine tract;
  (b) a branch point;
  (c) an exon splicing enhancer (ESE);
  (d) an intron splicing enhancer (ISE);
  (e) an exon splicing silencer (ESS);
  (f) an intron splicing silencer (ISS); and
  (g) a combination of any of (a)-(f), wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is a polypyrimidine tract. In some embodiments, the one or more splicing signals is a branch point. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 5' splice site, wherein the donor polynucleotide comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein at least one splicing signal is a natural or enhanced 5' splice site; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 5' splice site, wherein the donor polynucleotide comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein at least one splicing signal is a natural or enhanced 5' splice site; and (ii) a second strand comprising a nucleotide sequence complementary to the first strand, wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is in a 5' splice site, wherein the first strand comprises an intronic sequence, optionally, an exonic sequence, wherein the intronic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:

(a) an exon splicing enhancer (ESE);
(b) an intron splicing enhancer (ISE);
(c) an exon splicing silencer (ESS);
(d) an intron splicing silencer (ISS); and
(e) a combination of any of (a)-(d), wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is in a 5' splice site, wherein the first strand comprises an intronic sequence, optionally, an exonic sequence, wherein the intronic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:

(a) an exon splicing enhancer (ESE);
(b) an intron splicing enhancer (ISE);
(c) an exon splicing silencer (ESS);

(d) an intron splicing silencer (ISS); and
(e) a combination of any of (a)-(d),
wherein the donor polynucleotide is about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the one or more splicing signals is an exon splicing enhancer (ESE). In some embodiments, the one or more splicing signals is an intron splicing enhancer (ISE). In some embodiments, the one or more splicing signals is an exon splicing silencer (ESS). In some embodiments, the one or more splicing signals is an intron splicing silencer (ISS). In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, insertion of the donor polynucleotide into the DSB results in the formation of an exon in the gDNA comprising the exonic sequence. In some embodiments, the one or more splicing signals directs the inclusion of the exon comprising the exonic sequence which corrects the mutation into an mRNA.

In some embodiments, the insertion of the donor polynucleotide results in the formation of an intron comprising the intronic sequence, wherein the intronic sequence corrects the mutation.

In some embodiments, the disclosure provides a donor polynucleotide comprising a non-replicative double-stranded DNA molecule (dsDNA) comprising a first strand and a second strand, wherein the second strand is complementary to the first strand, wherein the first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the first strand comprises the formula:

5'-[B]$_a$-[S1]$_b$-[P]$_c$-[S2]$_d$-X-E-3', wherein (i) B, if present, is a branch point sequence comprising a nucleotide sequence that conforms to a branch point consensus sequence on each strand of the donor polynucleotide, wherein B comprises a nucleotide sequence comprising nucleobases selected from the group consisting of: adenine (A), guanine (G), thymine (T) and cytosine (C), wherein a is an integer whose value indicates the number of nucleotides comprising B, wherein a=0 or 5-7;

(ii) P is a polypyrimidine tract comprising a nucleotide sequence comprising nucleobases selected from the group consisting of: adenine (A), guanine (G), thymine (T) and cytosine (C), wherein c is an integer whose value indicates the number of nucleotides comprising P, wherein c=9-20, wherein the nucleotide sequence comprising P is about 100%, about 90%-100%, about 80%-90% pyrimidine nucleobases;

(iii) E is an exonic sequence comprising a nucleotide sequence which corrects the mutation, wherein the nucleotide sequence comprises nucleobases selected from the group consisting of: adenine (A), guanine (G), thymine (T) and cytosine (C);

(iv) X is a nucleotide sequence comprising a 3' splice site; and (v) S1 and S2, if either is present, are each delimiter sequences comprising one or more nucleotides comprising nucleobases selected from the group consisting of: adenine (A), guanine (G), thymine (T) and cytosine (C), wherein b and d are each integers whose value indicates the number of nucleotides comprising the delimiter sequence, respectively, wherein b and d=0-20, wherein the donor polynucleotide is about 10-500, about 10-400, about 10-300, about 10-200, about 10-100, about 20-80, about 30-70, or about 40-60 nucleotides in length, wherein the donor polynucleotide is configured for directional insertion into a double-stranded DNA break (DSB), wherein when the donor polynucleotide is inserted into the DSB, B, if present, P, X, if present, and E, if present, comprise a sense strand, wherein B, if present, P, and X, if present, comprise the one or more splicing signals, thereby correcting the mutation and providing splicing signals to control processing of a pre-mRNA transcribed from the gDNA, and wherein when the donor polynucleotide is introduced into the cell in combination with an site-directed nuclease, a non-homologous end-joining (NHEJ) DNA repair pathway inserts the donor polynucleotide into the DSB introduced into the gDNA by the site-directed nuclease at a location proximal to the mutation, thereby correcting the mutation. In some embodiments, B is present. In some embodiments, B is absent. In some embodiments, a=0. In some embodiments, a=5-7. In some embodiments, a=5. In some embodiments, a=6. In some embodiments, a=7. In some embodiments, the nucleotide sequence comprising P is about 100% pyrimidine nucleobases. In some embodiments, the nucleotide sequence comprising P is about 90%-100% pyrimidine nucleobases. In some embodiments, the nucleotide sequence comprising P is about 80%-90% pyrimidine nucleobases. In some embodiments, c=9. In some embodiments, c=10. In some embodiments, c=11. In some embodiments, c=12. In some embodiments, c=13. In some embodiments, c=14. In some embodiments, c=15. In some embodiments, c=16. In some embodiments, c=17. In some embodiments, c=18. In some embodiments, c=19. In some embodiments, c=20. In some embodiments, S1 is present. In some embodiments, S1 is absent. In some embodiments, S2 is present. In some embodiments, S2 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments b=20. In some embodiments, d=0. In some embodiments, d=1. In some embodiments, d=2. In some embodiments, d=3. In some embodiments, d=4. In some embodiments, d=5. In some embodiments, d=6. In some embodiments, d=7. In some embodiments, d=8. In some embodiments, d=9. In some embodiments, d=10. In some embodiments, d=11. In some embodiments, d=12. In some embodiments, d=13. In some embodiments, d=14. In some embodiments, d=15. In some embodiments, d=16. In some embodiments, d=17. In some embodiments, d=18. In some embodiments, d=19. In some embodiments d=20. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising a first strand and a second strand, wherein the second strand is complementary to the first strand, wherein the first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the first strand comprises the formula:

$$5'\text{-}[B]_a\text{-}[S1]_b\text{-}[P]_c\text{-}[S2]_d\text{-}X\text{-}E\text{-}3', \text{ wherein}$$

(i) B, if present, is a branch point sequence comprising a nucleotide sequence that conforms to a branch point consensus sequence on each strand of the donor polynucleotide, wherein B comprises a nucleotide sequence comprising nucleobases selected from the group consisting of: adenine (A), guanine (G), thymine (T) and cytosine (C), wherein a is an integer whose value indicates the number of nucleotides comprising B, wherein a=0 or 5-7;

(ii) P is a polypyrimidine tract comprising a nucleotide sequence comprising nucleobases selected from the group consisting of: adenine (A), guanine (G), thymine (T) and cytosine (C), wherein c is an integer whose value indicates the number of nucleotides comprising P, wherein c=9-20, wherein the nucleotide sequence comprising P is about 100%, about 90%-100%, about 80%-90% pyrimidine nucleobases;

(iii) E is an exonic sequence comprising a nucleotide sequence which corrects the mutation, wherein the nucleotide sequence comprises nucleobases selected from the group consisting of: adenine (A), guanine (G), thymine (T) and cytosine (C);

(iv) X is a nucleotide sequence comprising a 3' splice site; and (v) S1 and S2, if either is present, are each delimiter sequences comprising one or more nucleotides comprising nucleobases selected from the group consisting of: adenine (A), guanine (G), thymine (T) and cytosine (C), wherein b and d are each integers whose value indicates the number of nucleotides comprising the delimiter sequence, respectively, wherein b and d=0-20, wherein the donor polynucleotide is about 10-100, about 20-80, about 30-70, or about 40-60 nucleotides in length, wherein the donor polynucleotide is configured for directional insertion into a double-stranded DNA break (DSB), wherein when the donor polynucleotide is inserted into the DSB, B, if present, P, X, if present, and E, if present, comprise a sense strand, wherein B, if present, P, and X, if present, comprise the one or more splicing signals, thereby correcting the mutation and providing splicing signals to control processing of a pre-mRNA transcribed from the gDNA, and wherein when the donor polynucleotide is introduced into the cell in combination with an site-directed nuclease, a non-homologous end-joining (NHEJ) DNA repair pathway inserts the donor polynucleotide into the DSB introduced into the gDNA by the site-directed nuclease at a location proximal to the mutation, thereby correcting the mutation. In some embodiments, B is present. In some embodiments, B is absent. In some embodiments, a=0. In some embodiments, a=5-7. In some embodiments, a=5. In some embodiments, a=6. In some embodiments, a=7. In some embodiments, the nucleotide sequence comprising P is about 100% pyrimidine nucleobases. In some embodiments, the nucleotide sequence comprising P is about 90%-100% pyrimidine nucleobases. In some embodiments, the nucleotide sequence comprising P is about 80%-90% pyrimidine nucleobases. In some embodiments, c=9. In some embodiments, c=10. In some embodiments, c=11. In some embodiments, c=12. In some embodiments, c=13. In some embodiments, c=14. In some embodiments, c=15. In some embodiments, c=16. In some embodiments, c=17. In some embodiments, c=18. In some embodiments, c=19. In some embodiments, c=20. In some embodiments, S1 is present. In some embodiments, S1 is absent. In some embodiments, S2 is present. In some embodiments, S2 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments b=20. In some embodiments, d=0. In some embodiments, d=1. In some embodiments, d=2. In some embodiments, d=3. In some embodiments, d=4. In some embodiments, d=5. In some embodiments, d=6. In some embodiments, d=7. In some embodiments, d=8. In some embodiments, d=9. In some embodiments, d=10. In some embodiments, d=11. In some embodiments, d=12. In some embodiments, d=13. In some embodiments, d=14. In some embodiments, d=15. In some embodiments, d=16. In some embodiments, d=17. In some embodiments, d=18. In some embodiments, d=19. In some embodiments d=20. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising a first strand and a second strand, wherein the second strand is complementary to the first strand, wherein the first strand from 5' to 3' comprises a nucleotide sequence which corrects a disease-causing mutation in a genomic DNA molecule (gDNA) in a cell, wherein the disease-causing mutation is a protein-coding mutation proximal to a 5' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the first strand comprises the formula:

5'-E-Y-I-3', wherein (i) E is an exonic sequence comprising a nucleotide sequence which corrects the mutation, wherein the nucleotide sequence comprises nucleobases selected from the group consisting of: adenine (A), guanine (G), thymine (T) and cytosine (C);

(ii) Y is a nucleotide sequence comprising a 5' splice site; and (iii) I, if present, comprises an intronic sequence comprising nucleotides comprising nucleobases selected from the group consisting of: adenine (A), guanine (G), thymine (T) and cytosine (C), wherein the donor polynucleotide is about 10-500, about 10-400, about 10-300, about 10-200, about 10-100, about 20-80, about 30-70, or about 40-60 nucleotides in length, wherein the donor polynucleotide is configured for directional insertion into a double-stranded DNA break (DSB), wherein when the donor polynucleotide is inserted into the DSB, E, if present, Y, and I, if present, comprise a sense strand, wherein Y comprises the one or more splicing signals, thereby correcting the mutation and providing splicing signals to control processing of a pre-mRNA transcribed from the gDNA, and wherein when the donor polynucleotide is introduced into the cell in combination with an site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, E is present. In some embodiments E is absent. In some embodiments, I is present. In some embodiments, I is absent. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising a first strand and a second strand, wherein the second strand is complementary to the first strand, wherein the first strand from 5' to 3' comprises a nucleotide sequence which corrects a disease-causing mutation in a genomic DNA molecule (gDNA) in a cell, wherein the disease-causing mutation is a protein-coding mutation proximal to a 5' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the first strand comprises the formula:

5'-E-Y-I-3', wherein (i) E is an exonic sequence comprising a nucleotide sequence which corrects the mutation, wherein the nucleotide sequence comprises nucleobases selected from the group consisting of: adenine (A), guanine (G), thymine (T) and cytosine (C);

(ii) Y is a nucleotide sequence comprising a 5' splice site; and (iii) I, if present, comprises an intronic sequence comprising nucleotides comprising nucleobases selected from the group consisting of: adenine (A), guanine (G), thymine (T) and cytosine (C), wherein the donor polynucleotide is about 10-100, about 20-80, about 30-70, or about 40-60 nucleotides in length, wherein the donor polynucleotide is configured for directional insertion into a double-stranded DNA break (DSB), wherein when the donor polynucleotide is inserted into the DSB, E, if present, Y, and I, if present, comprise a sense strand, wherein Y comprises the one or more splicing signals, thereby correcting the mutation and providing splicing signals to control processing of a pre-mRNA transcribed from the gDNA, and wherein when the donor polynucleotide is introduced into the cell in combination with an site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, E is present. In some embodiments E is absent. In some embodiments, I is present. In some embodiments, I is absent. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is proximal to a 3' splice site, wherein the first strand comprises a first intronic sequence, wherein the first intronic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is proximal to a 3' splice site, wherein the second strand comprises a second intronic sequence, wherein the second intronic sequence corrects the mutation, wherein the second strand comprises one or more splicing signals to control processing of a precursor mRNA (pre-mRNA) transcribed from the gDNA, wherein the second strand is complementary to the first strand, and wherein the first strand and the second strand each comprise the formula:

$$5'\text{-}[P1]_a\text{-}[S1]_b\text{-}[B]_c\text{-}[S2]_d\text{-}[P2]_e\text{-}3', \text{ wherein}$$

(a) B comprises a branch point sequence comprising a nucleotide sequence that conforms to a branch point consensus sequence on each strand of the donor polynucleotide, wherein B comprises a nucleotide sequence comprising nucleobases selected from the group consisting of: adenine (A), guanine (G), thymine (T) and cytosine (C), wherein c is an integer whose value indicates the number of nucleotides comprising B, wherein $c=5\text{-}7$;

(b) P1 and P2 are polypyrimidine tracts each comprising a nucleotide sequence comprising nucleobases selected from the group consisting of: adenine (A), guanine (G), thymine (T) and cytosine (C), wherein a and e are integers whose value indicates the number of nucleotides comprising P1 and P2, respectively, wherein $a=9\text{-}20$ and $e=9\text{-}20$, wherein the nucleotide sequence comprising P1 and P2 are each about 100%, about 90%-100%, about 80%-90% pyrimidine nucleobases, and wherein P1 is in the reverse orientation and on the opposite strand of the donor polynucleotide relative to P2; and (c) S1 and S2, if either is present, are each delimiter sequences comprising one or more nucleotides comprising nucleobases selected from the group consisting of: adenine (A), guanine (G), thymine (T) and cytosine (C), wherein b and d are each integers whose value indicates the number of nucleotides comprising the delimiter sequence, respectively, wherein b and $d=0\text{-}20$, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B and P2 comprise a sense strand and B and P2 comprise the first and second splicing signals, respectively, thereby correcting the mutation and providing splicing signals to control processing of a pre-mRNA transcribed from the gDNA, wherein, when the donor polynucleotide is inserted into the DSB in the second orientation, B and P1 comprise a sense strand and B and P2 comprise the first and second splicing signals, respectively, thereby correcting the mutation and providing splicing signals to control processing of a pre-mRNA transcribed from the gDNA, and wherein when the donor polynucleotide is introduced into the cell in combination with a site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, $c=5$. In some embodiments, $c=6$. In some embodiments, $c=7$. In some embodiments, $a=9$. In some embodiments, $a=10$. In some embodiments, $a=11$. In some embodiments, $a=12$. In some embodiments, $a=13$. In some embodiments, $a=14$. In some embodiments, $a=15$. In some embodiments, $a=16$. In some embodiments, $a=17$. In some embodiments, $a=18$. In some embodiments, $a=19$. In some embodiments, $a=20$. In some embodiments, $e=9$. In some embodiments, $e=10$. In some embodiments, $e=11$. In some embodiments, $e=12$. In some embodiments, $e=13$. In some embodiments, $e=14$. In some embodiments, $e=15$. In some embodiments, $e=16$. In some embodiments, $e=17$. In some embodiments, $e=18$. In some embodiments, $e=19$. In some embodiments, $e=20$. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, $b=0$. In some embodiments, $b=1$. In some embodiments, $b=2$. In some embodiments, $b=3$. In some embodiments, $b=4$. In some embodiments, $b=5$. In some embodiments, $b=6$. In some embodiments, $b=7$. In some embodiments, $b=8$. In some embodiments, $b=9$. In some embodiments, $b=10$. In some embodiments, $b=11$. In some embodiments, $b=12$. In some embodiments, $b=13$. In some embodiments, $b=14$. In some embodiments, $b=15$. In some embodiments, $b=16$. In some embodiments, $b=17$. In some embodiments, $b=18$. In some embodiments, $b=19$. In some embodiments $b=20$. In some embodiments, $d=0$. In some embodiments, $d=1$. In some embodiments, $d=2$. In some embodiments, $d=3$. In some embodiments, $d=4$. In some embodiments, $d=5$. In some embodiments, $d=6$. In some embodiments, $d=7$. In some embodiments, $d=8$. In some embodiments, $d=9$. In some embodiments, $d=10$. In some embodiments, $d=11$. In some embodiments, $d=12$. In some embodiments, $d=13$. In some embodiments, $d=14$. In some embodiments, $d=15$. In some embodiments, $d=16$. In some embodiments, $d=17$. In some embodiments, $d=18$. In some embodiments, $d=19$. In some embodiments $d=20$. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is proximal to a 3' splice site, wherein the first strand comprises a first intronic sequence, wherein the first intronic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is proximal to a 3' splice site, wherein the second strand comprises a second intronic sequence, wherein the second intronic sequence corrects the mutation, wherein the second strand comprises one or more splicing signals to control processing of a precursor mRNA (pre-mRNA) transcribed from the gDNA, wherein the second strand is complementary to the first strand, and wherein the first strand and the second strand each comprise the formula:

5'-[P1]$_a$-[S1]$_b$-[B]$_c$-[S2]$_d$-[P2]$_e$-3', wherein (a) B comprises a branch point sequence comprising a nucleotide sequence that conforms to a branch point consensus sequence on each strand of the donor polynucleotide, wherein B comprises a nucleotide sequence comprising nucleobases selected from the group consisting of: adenine (A), guanine (G), thymine (T) and cytosine (C), wherein c is an integer whose value indicates the number of nucleotides comprising B, wherein c=5-7;

(b) P1 and P2 are polypyrimidine tracts each comprising a nucleotide sequence comprising nucleobases selected from the group consisting of: adenine (A), guanine (G), thymine (T) and cytosine (C), wherein a and e are integers whose value indicates the number of nucleotides comprising P1 and P2, respectively, wherein a=9-20 and e=9-20, wherein the nucleotide sequence comprising P1 and P2 are each about 100%, about 90%-100%, about 80%-90% pyrimidine nucleobases, and wherein P1 is in the reverse orientation and on the opposite strand of the donor polynucleotide relative to P2; and (c) S1 and S2, if either is present, are each delimiter sequences comprising one or more nucleotides comprising nucleobases selected from the group consisting of: adenine (A), guanine (G), thymine (T) and cytosine (C), wherein b and d are each integers whose value indicates the number of nucleotides comprising the delimiter sequence, respectively, wherein b and d=0-20, wherein the donor polynucleotide is about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B and P2 comprise a sense strand and B and P2 comprise the first and second splicing signals, respectively, thereby correcting the mutation and providing splicing signals to control processing of a pre-mRNA transcribed from the gDNA, wherein, when the donor polynucleotide is inserted into the DSB in the second orientation, B and P1 comprise a sense strand and B and P2 comprise the first and second splicing signals, respectively, thereby correcting the mutation and providing splicing signals to control processing of a pre-mRNA transcribed from the gDNA, and wherein when the donor polynucleotide is introduced into the cell in combination with a site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, c=5. In some embodiments, c=6. In some embodiments, c=7. In some embodiments, a=9. In some embodiments, a=10. In some embodiments, a=11. In some embodiments, a=12. In some embodiments, a=13. In some embodiments, a=14. In some embodiments, a=15. In some embodiments, a=16. In some embodiments, a=17. In some embodiments, a=18. In some embodiments, a=19. In some embodiments, a=20. In some embodiments, e=9. In some embodiments, e=10. In some embodiments, e=11. In some embodiments, e=12. In some embodiments, e=13. In some embodiments, e=14. In some embodiments, e=15. In some embodiments, e=16. In some embodiments, e=17. In some embodiments, e=18. In some embodiments, e=19. In some embodiments, e=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments b=20. In some embodiments, d=0. In some embodiments, d=1. In some embodiments, d=2. In some embodiments, d=3. In some embodiments, d=4. In some embodiments, d=5. In some embodiments, d=6. In some embodiments, d=7. In some embodiments, d=8. In some embodiments, d=9. In some embodiments, d=10. In some embodiments, d=11. In some embodiments, d=12. In some embodiments, d=13. In some embodiments, d=14. In some embodiments, d=15. In some embodiments, d=16. In some embodiments, d=17. In some embodiments, d=18. In some embodiments, d=19. In some embodiments d=20. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is proximal to a 3' splice site, wherein the first strand comprises a first intronic sequence, wherein the first intronic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is proximal to a 3' splice site, wherein the second strand comprises a second intronic sequence, wherein the second intronic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'\text{-}[P1]_a\text{-}[S1]_b\text{-}[B1]_c\text{-}[S2]_d\text{-}[B2]_e\text{-}[S3]_f\text{-}[P2]_g\text{-}3',$$
wherein (a) B1, if present, and B2 are each branch point sequences, wherein B2 comprises a nucleotide sequence that conforms to a branch point consensus sequence on each strand of the donor polynucleotide, wherein the branch point sequence comprising B1, if present, is in a reverse orientation and on the opposite strand of the donor polynucleotide relative to the branch point sequence comprising B2, wherein B1 and B2 each comprise a nucleotide sequence comprising nucleobases selected from the group consisting of: adenine (A), guanine (G), thymine (T) and cytosine (C), wherein c and e are integers whose value indicates the number of nucleotides comprising B1 and B2, respectively, wherein c=0 or 5-7, wherein e=5-7;

(b) P1 and P2 are polypyrimidine tracts each comprising a nucleotide sequence comprising nucleobases selected from the group consisting of: adenine, guanine, thymine and cytosine, wherein a and g are integers whose value indicates the number of nucleotides comprising P1 and P2, respectively, wherein a=9-20 and g=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2; and (c) S1, S2 and S3, if any are present, are each delimiter sequences comprising one or more nucleotides comprising nucleobases selected from the group consisting of: adenine (A), guanine (G), thymine (T) and cytosine (C), wherein b, d and f are each integers whose value indicates the number of nucleotides comprising the delimiter sequence, respectively, wherein b and f=0 or 1-20, wherein d=0 or 1-40, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B2 and P2 comprise a sense strand and B2 and P2 comprise the first and second splicing signals, respectively, thereby correcting the mutation and providing splicing signals to control processing of a pre-mRNA transcribed from the gDNA, wherein when the donor polynucleotide is inserted into the DSB in the second orientation, B1 and P1 comprise a sense strand and B1 and P1 provide the first and second splicing signals, respectively, thereby correcting the mutation and providing splicing signals to control processing of a pre-mRNA transcribed from the gDNA, and wherein when the donor polynucleotide is introduced into the cell in combination with an site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, B1 is present. In some embodiments, B1 is absent. In some embodiments, c=0. In some embodiments, c=5-7. In some embodiments, c=5. In some embodiments, c=6. In some embodiments, c=7. In some embodiments, e=5. In some embodiments, e=6. In some embodiments, e=7. In some embodiments, a=9. In some embodiments, a=10. In some embodiments, a=11. In some embodiments, a=12. In some embodiments, a=13. In some embodiments, a=14. In some embodiments, a=15. In some embodiments, a=16. In some embodiments, a=17. In some embodiments, a=18. In some embodiments, a=19. In some embodiments, a=20. In some embodiments, g=9. In some embodiments, g=10. In some embodiments, g=11. In some embodiments, g=12. In some embodiments, g=13. In some embodiments, g=14. In some embodiments, g=15. In some embodiments, g=16. In some embodiments, g=17. In some embodiments, g=18. In some embodiments, g=19. In some embodiments, g=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, S3 is present. In some embodiments, S3 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, f=0. In some embodiments, f=1. In some embodiments, f=2. In some embodiments, f=3. In some embodiments, f=4. In some embodiments, f=5. In some embodiments, f=6. In some embodiments, f=7. In some embodiments, f=8. In some embodiments, f=9. In some embodiments, f=10. In some embodiments, f=11. In some embodiments, f=12. In some embodiments, f=13. In some embodiments, f=14. In some embodiments, f=15. In some embodiments, f=16. In some embodiments, f=17. In some embodiments, f=18. In some embodiments, f=19. In some embodiments, f=20. In some embodiments, d=0. In some embodiments, d=1. In some embodiments, d=2. In some embodiments, d=3. In some embodiments, d=4. In some embodiments, d=5. In some embodiments, d=6. In some embodiments, d=7. In some embodiments, d=8. In some embodiments, d=9. In some embodiments, d=10. In some embodiments, d=11. In some embodiments, d=12. In some embodiments, d=13. In some embodiments, d=14. In some embodiments, d=15. In some embodiments, d=16. In some embodiments, d=17. In some embodiments, d=18. In some embodiments, d=19. In some embodiments, d=20. In some embodiments, d=21. In some embodiments, d=22. In some embodiments, d=23. In some embodiments, d=24. In some embodiments, d=25. In some embodiments, d=26. In some embodiments, d=27. In some embodiments, d=28. In some embodiments, d=29. In some embodiments, d=30. In some embodiments, d=31. In some embodiments, d=32. In some embodiments, d=33. In some embodiments, d=34. In some embodiments, d=35. In some embodiments, d=36. In some embodiments, d=37. In some embodiments, d=38. In some embodiments, d=39. In some embodiments, d=40. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is proximal to a 3' splice site, wherein the first strand comprises a first intronic sequence, wherein the first intronic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is proximal to a 3' splice site, wherein the second strand comprises a second intronic sequence, wherein the second intronic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'\text{-}[P1]_a\text{-}[S1]_b\text{-}[B1]_c\text{-}[S2]_d\text{-}[B2]_e\text{-}[S3]_f\text{-}[P2]_g\text{-}3',$$
wherein (a) B1, if present, and B2 are each branch point sequences, wherein B2 comprises a nucleotide sequence that conforms to a branch point consensus sequence on each strand of the donor polynucleotide, wherein the branch point sequence comprising B1, if present, is in a reverse orientation and on the opposite strand of the donor polynucleotide relative to the branch point sequence comprising B2, wherein B1 and B2 each comprise a nucleotide sequence comprising nucleobases selected from the group consisting of: adenine (A), guanine (G), thymine (T) and cytosine (C), wherein c and e are integers whose value indicates the number of nucleotides comprising B1 and B2, respectively, wherein c=0 or 5-7, wherein e=5-7;

(b) P1 and P2 are polypyrimidine tracts each comprising a nucleotide sequence comprising nucleobases selected from the group consisting of: adenine, guanine, thymine and cytosine, wherein a and g are integers whose value indicates the number of nucleotides comprising P1 and P2, respectively, wherein a=9-20 and g=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2; and (c) S1, S2 and S3, if any are present, are each delimiter sequences comprising one or more nucleotides comprising nucleobases selected from the group consisting of: adenine (A), guanine (G), thymine (T) and cytosine (C), wherein b, d and f are each integers whose value indicates the number of nucleotides comprising the delimiter sequence, respectively, wherein b and f=0 or 1-20, wherein d=0 or 1-40, wherein the donor polynucleotide is about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B2 and P2 comprise a sense strand and B2 and P2 comprise the first and second splicing signals, respectively, thereby correcting the mutation and providing splicing signals to control processing of a pre-mRNA transcribed from the gDNA, wherein when the donor polynucleotide is inserted into the DSB in the second orientation, B1 and P1 comprise a sense strand and B1 and P1 provide the first and second splicing signals, respectively, thereby correcting the mutation and providing splicing signals to control processing of a pre-mRNA transcribed from the gDNA, and wherein when the donor polynucleotide is introduced into the cell in combination with an site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, B1 is present. In some embodiments, B1 is absent. In some embodiments, c=0. In some embodiments, c=5-7. In some embodiments, c=5. In some embodiments, c=6. In some embodiments, c=7. In some embodiments, e=5. In some embodiments, e=6. In some embodiments, e=7. In some embodiments, a=9. In some embodiments, a=10. In some embodiments, a=11. In some embodiments, a=12. In some embodiments, a=13. In some embodiments, a=14. In some embodiments, a=15. In some embodiments, a=16. In some embodiments, a=17. In some embodiments, a=18. In some embodiments, a=19. In some embodiments, a=20. In some embodiments, g=9. In some embodiments, g=10. In some embodiments, g=11. In some embodiments, g=12. In some embodiments, g=13. In some embodiments, g=14. In some embodiments, g=15. In some embodiments, g=16. In some embodiments, g=17. In some embodiments, g=18. In some embodiments, g=19. In some embodiments, g=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, S3 is present. In some embodiments, S3 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, f=0. In some embodiments, f=1. In some embodiments, f=2. In some embodiments, f=3. In some embodiments, f=4. In some embodiments, f=5. In some embodiments, f=6. In some embodiments, f=7. In some embodiments, f=8. In some embodiments, f=9. In some embodiments, f=10. In some embodiments, f=11. In some embodiments, f=12. In some embodiments, f=13. In some embodiments, f=14. In some embodiments, f=15. In some embodiments, f=16. In some embodiments, f=17. In some embodiments, f=18. In some embodiments, f=19. In some embodiments, f=20. In some embodiments, d=0. In some embodiments, d=1. In some embodiments, d=2. In some embodiments, d=3. In some embodiments, d=4. In some embodiments, d=5. In some embodiments, d=6. In some embodiments, d=7. In some embodiments, d=8. In some embodiments, d=9. In some embodiments, d=10. In some embodiments, d=11. In some embodiments, d=12. In some embodiments, d=13. In some embodiments, d=14. In some embodiments, d=15. In some embodiments, d=16. In some embodiments, d=17. In some embodiments, d=18. In some embodiments, d=19. In some embodiments, d=20. In some embodiments, d=21. In some embodiments, d=22. In some embodiments, d=23. In some embodiments, d=24. In some embodiments, d=25. In some embodiments, d=26. In some embodiments, d=27. In some embodiments, d=28. In some embodiments, d=29. In some embodiments, d=30. In some embodiments, d=31. In some embodiments, d=32. In some embodiments, d=33. In some embodiments, d=34. In some embodiments, d=35. In some embodiments, d=36. In some embodiments, d=37. In some embodiments, d=38. In some embodiments, d=39. In some embodiments, d=40. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'-[E1]_a-X1-[P1]_b-[S1]_c-[B]_d-[S2]_e-[P2]_f-X2-[E2]_g-3',$$
wherein (a) B is a branch point sequence comprising a nucleotide sequence that conforms to a branch point consensus sequence on each strand of the donor polynucleotide, wherein B comprises a nucleotide sequence comprising nucleobases selected from the group consisting of: adenine, guanine, thymine and cytosine, wherein d is an integer whose value indicates the number of nucleotides comprising B, wherein d=5-7;

(b) P1 and P2 are polypyrimidine tracts each comprising a nucleotide sequence comprising nucleobases selected from the group consisting of: adenine (A), guanine (G), thymine (T) and cytosine (C), wherein b and f are integers whose value indicates the number of nucleotides comprising P1 and P2, respectively, wherein b=9-20 and f=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2;

(c) E1 and E2 are each exonic sequences each comprising a nucleotide sequence which corrects the mutation, wherein the nucleotide sequence comprises nucleobases selected from the group consisting of: adenine (A), guanine (G), thymine (T) and cytosine (C), wherein a and g are integers whose value indicates the number of nucleotides comprising E1 and E2, respectively, wherein the exonic sequence comprising E1 is in a reverse orientation and on the opposite strand of the donor polynucleotide relative to the exonic sequence comprising E2, wherein the nucleotide sequences comprising E1 and E2 are not complementary;

(d) X1 and X2 are each nucleotide sequences comprising a 3' splice site, wherein the nucleotide sequence comprising X1 is in the reverse orientation and on the opposite strand relative to the nucleotide sequence comprising X2; and (e) S1 and S2, if either is present, are each delimiter sequences comprising one or more nucleotides comprising nucleobases selected from the group consisting of: adenine, guanine, thymine and cytosine, wherein c and e are each integers whose value indicates the number of nucleotides comprising the delimiter sequence, respectively, wherein c=0 or 1-20 and e=0 or 1-20, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B, P2, E2 and X2 and comprise a sense strand, wherein B, P2 and X2 comprise the first, second and third splicing signal, respectively, thereby correcting the mutation and providing splicing signals to control processing of a pre-mRNA transcribed from the gDNA, wherein when the donor polynucleotide is inserted into the DSB in a second orientation, B, P1, E1 and X1 comprise a sense strand, wherein B, P1 and X1 comprise the first, second and third splicing signal, respectively, thereby correcting the mutation and providing splicing signals to control processing of a pre-mRNA transcribed from the gDNA, and wherein, when the donor polynucleotide is introduced into the cell in combination with an site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, d=5. In some embodiments, d=6. In some embodiments, d=7. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, f=9. In some embodiments, f=10. In some embodiments, f=11. In some embodiments, f=12. In some embodiments, f=13. In some embodiments, f=14. In some embodiments, f=15. In some embodiments, f=16. In some embodiments, f=17. In some embodiments, f=18. In some embodiments, f=19. In some embodiments, f=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, c=0. In some embodiments, c=1. In some embodiments, c=2. In some embodiments, c=3. In some embodiments, c=4. In some embodiments, c=5. In some embodiments, c=6. In some embodiments, c=7. In some embodiments, c=8. In some embodiments, c=9. In some embodiments, c=10. In some embodiments, c=11. In some embodiments, c=12. In some embodiments, c=13. In some embodiments, c=14. In some embodiments, c=15. In some embodiments, c=16. In some embodiments, c=17. In some embodiments, c=18. In some embodiments, c=19. In some embodiments, c=20. In some embodiments, e=0. In some embodiments, e=1. In some embodiments, e=2. In some embodiments, e=3. In some embodiments, e=4. In some embodiments, e=5. In some embodiments, e=6. In some embodiments, e=7. In some embodiments, e=8. In some embodiments, e=9. In some embodiments, e=10. In some embodiments, e=11. In some embodiments, e=12. In some embodiments, e=13. In some embodiments, e=14. In some embodiments, e=15. In some embodiments, e=16. In some embodiments, e=17. In some embodiments, e=18. In some embodiments, e=19. In some embodiments, e=20. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'\text{-}[E1]_a\text{-}X1\text{-}[P1]_b\text{-}[S1]_c\text{-}[B]_d\text{-}[S2]_e\text{-}[P2]_f\text{-}X2\text{-}[E2]_g\text{-}3',$$
wherein (a) B is a branch point sequence comprising a nucleotide sequence that conforms to a branch point consensus sequence on each strand of the donor polynucleotide, wherein B comprises a nucleotide sequence comprising nucleobases selected from the group consisting of: adenine, guanine, thymine and cytosine, wherein d is an integer whose value indicates the number of nucleotides comprising B, wherein d=5-7;

(b) P1 and P2 are polypyrimidine tracts each comprising a nucleotide sequence comprising nucleobases selected from the group consisting of: adenine (A), guanine (G), thymine (T) and cytosine (C), wherein b and f are integers whose value indicates the number of nucleotides comprising P1 and P2, respectively, wherein b=9-20 and f=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2;

(c) E1 and E2 are each exonic sequences each comprising a nucleotide sequence which corrects the mutation, wherein the nucleotide sequence comprises nucleobases selected from the group consisting of: adenine (A), guanine (G), thymine (T) and cytosine (C), wherein a and g are integers whose value indicates the number of nucleotides comprising E1 and E2, respectively, wherein the exonic sequence comprising E1 is in a reverse orientation and on the opposite strand of the donor polynucleotide relative to the exonic sequence comprising E2, wherein the nucleotide sequences comprising E1 and E2 are not complementary;

(d) X1 and X2 are each nucleotide sequences comprising a 3' splice site, wherein the nucleotide sequence comprising X1 is in the reverse orientation and on the opposite strand relative to the nucleotide sequence comprising X2; and (e) S1 and S2, if either is present, are each delimiter sequences comprising one or more nucleotides comprising nucleobases selected from the group consisting of: adenine, guanine, thymine and cytosine, wherein c and e are each integers whose value indicates the number of nucleotides comprising the delimiter sequence, respectively, wherein c=0 or 1-20 and e=0 or 1-20, wherein the donor polynucleotide is about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B, P2, E2 and X2 and comprise a sense strand, wherein B, P2 and X2 comprise the first, second and third splicing signal, respectively, thereby correcting the mutation and providing splicing signals to control processing of a pre-mRNA transcribed from the gDNA, wherein when the donor polynucleotide is inserted into the DSB in a second orientation, B, P1, E1 and X1 comprise a sense strand, wherein B, P1 and X1 comprise the first, second and third splicing signal, respectively, thereby correcting the mutation and providing splicing signals to control processing of a pre-mRNA transcribed from the gDNA, and wherein, when the donor polynucleotide is introduced into the cell in combination with an site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, d=5. In some embodiments, d=6. In some embodiments, d=7. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, f=9. In some embodiments, f=10. In some embodiments, f=11. In some embodiments, f=12. In some embodiments, f=13. In some embodiments, f=14. In some embodiments, f=15. In some embodiments, f=16. In some embodiments, f=17. In some embodiments, f=18. In some embodiments, f=19. In some embodiments, f=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, c=0. In some embodiments, c=1. In some embodiments, c=2. In some embodiments, c=3. In some embodiments, c=4. In some embodiments, c=5. In some embodiments, c=6. In some embodiments, c=7. In some embodiments, c=8. In some embodiments, c=9. In some embodiments, c=10. In some embodiments, c=11. In some embodiments, c=12. In some embodiments, c=13. In some embodiments, c=14. In some embodiments, c=15. In some embodiments, c=16. In some embodiments, c=17. In some embodiments, c=18. In some embodiments, c=19. In some embodiments, c=20. In some embodiments, e=0. In some embodiments, e=1. In some embodiments, e=2. In some embodiments, e=3. In some embodiments, e=4. In some embodiments, e=5. In some embodiments, e=6. In some embodiments, e=7. In some embodiments, e=8. In some embodiments, e=9. In some embodiments, e=10. In some embodiments, e=11. In some embodiments, e=12. In some embodiments, e=13. In some embodiments, e=14. In some embodiments, e=15. In some embodiments, e=16. In some embodiments, e=17. In some embodiments, e=18. In some embodiments, e=19. In some embodiments, e=20. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

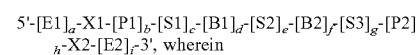

5'-[E1]$_a$-X1-[P1]$_b$-[S1]$_c$-[B1]$_d$-[S2]$_e$-[B2]$_f$-[S3]$_g$-[P2]$_h$-X2-[E2]$_i$-3', wherein (a) B1, if present, and B2 are each branch point sequences, wherein B2 comprises a nucleotide sequence that conforms to a branch point consensus sequence on each strand of the donor polynucleotide, wherein the branch point sequence comprising B1, if present, is in a reverse orientation and on the opposite strand of the donor polynucleotide relative to the branch point sequence comprising B2, wherein B1 and B2 each comprise a nucleotide sequence comprising nucleobases selected from the group consisting of: adenine (A), guanine (G), thymine (T) and cytosine (C), wherein d and f are integers whose value indicates the number of nucleotides comprising B1 and B2, respectively, wherein d and f=5-7;

(b) P1 and P2 are polypyrimidine tracts each comprising a nucleotide sequence comprising nucleobases selected from the group consisting of: adenine, guanine, thymine and cytosine, wherein b and h are integers whose value indicates the number of nucleotides comprising P1 and P2, respectively, wherein b=9-20 and h=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2;

(c) E1 and E2 are each exonic sequences each comprising a nucleotide sequence which corrects the mutation, wherein the nucleotide sequence comprises nucleobases selected from the group consisting of: adenine (A), guanine (G), thymine (T) and cytosine (C), wherein a and i are integers whose value indicates the number of nucleotides comprising E1 and E2, respectively, wherein the exonic sequence comprising E1 is in the reverse orientation and on the opposite strand relative to the exonic sequence comprising E2, wherein the nucleotide sequences comprising E1 and E2 are not complementary;

(d) X1 and X2 each comprise a nucleotide sequence comprising a 3' splice site, wherein the nucleotide sequence of X1 is in a reverse orientation and on the opposite strand of the donor polynucleotide relative to the nucleotide sequence of X2; and (e) S1, S2 and S3, if any present, are each delimiter sequences comprising one or more nucleotides comprising nucleobases selected from the group consisting of: adenine (A), guanine (G), thymine (T) and cytosine (C), wherein c, e and g are each integers whose value indicates the number of nucleotides comprising the delimiter sequence, respectively, wherein c=0 or 1-20 and g=0 or 1-20, wherein e=0 or 1-40, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in a first orientation, B2, P2, E2 and X2 comprise a sense strand, wherein B2, P2 and X2 comprise the first, second and third splicing signal, respectively, thereby correcting the mutation and providing splicing signals to control processing of a pre-mRNA transcribed from the gDNA, wherein when the donor polynucleotide is inserted into the DSB in a second orientation, B1, P1, E1 and X1 comprise a sense strand, wherein B1, P1 and X1 comprise the first, second and third splicing signal, respectively, thereby correcting the mutation and providing splicing signals to control processing of a pre-mRNA transcribed from the gDNA, and wherein, when the donor polynucleotide is introduced into the cell in combination with a site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, B1 is present. In some embodiments, B1 is absent. In some embodiments, d=5. In some embodiments, d=6. In some embodiments, d=7. In some embodiments, f=5. In some embodiments, f=6. In some embodiments, f=7. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, h=9. In some embodiments, h=10. In some embodiments, h=11. In some embodiments, h=12. In some embodiments, h=13. In some embodiments, h=14. In some embodiments, h=15. In some embodiments, h=16. In some embodiments, h=17. In some embodiments, h=18. In some embodiments, h=19. In some embodiments, h=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, S1 is absent. In some embodiments, S2 is present. In some embodiments, S2 is absent. In some embodiments, S3 is present. In some embodiments, S3 is absent. In some embodiments, c=0. In some embodiments, c=1. In some embodiments, c=2. In some embodiments, c=3. In some embodiments, c=4. In some embodiments, c=5. In some embodiments, c=6. In some embodiments, c=7. In some embodiments, c=8. In some embodiments, c=9. In some embodiments, c=10. In some embodiments, c=11. In some embodiments, c=12. In some embodiments, c=13. In some embodiments, c=14. In some embodiments, c=15. In some embodiments, c=16. In some embodiments, c=17. In some embodiments, c=18. In some embodiments, c=19. In some embodiments, c=20. In some embodiments, g=0. In some embodiments, g=1. In some embodiments, g=2. In some embodiments, g=3. In some embodiments, g=4. In some embodiments, g=5. In some embodiments, g=6. In some embodiments, g=7. In some embodiments, g=8. In some embodiments, g=9. In some embodiments, g=10. In some embodiments, g=11. In some embodiments, g=12. In some embodiments, g=13. In some embodiments, g=14. In some embodiments, g=15. In some embodiments, g=16. In some embodiments, g=17. In some embodiments, g=18. In some embodiments, g=19. In some embodiments, g=20. In some embodiments, e=0. In some embodiments, e=1. In some embodiments, e=2. In some embodiments, e=3. In some embodiments, e=4. In some embodiments, e=5. In some embodiments, e=6. In some embodiments, e=7. In some embodiments, e=8. In some embodiments, e=9. In some embodiments, e=10. In some embodiments, e=11. In some embodiments, e=12. In some embodiments, e=13. In some embodiments, e=14. In some embodiments, e=15. In some embodiments, e=16. In some embodiments, e=17. In some embodiments, e=18. In some embodiments, e=19. In some embodiments, e=20. In some embodiments, e=21. In some embodiments, e=22. In some embodiments, e=23. In some embodiments, e=24. In some embodiments, e=25. In some embodiments, e=26. In some embodiments, e=27. In some embodiments, e=28. In some embodiments, e=29. In some embodiments, e=30. In some embodiments, e=31. In some embodiments, e=32. In some embodiments, e=33. In some embodiments, e=34. In some embodiments, e=35. In some embodiments, e=36. In some embodiments, e=37. In some embodiments, e=38. In some embodiments, e=39. In some embodiments, e=40. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

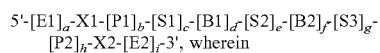

(a) B1, if present, and B2 are each branch point sequences, wherein B2 comprises a nucleotide sequence that conforms to a branch point consensus sequence on each strand of the donor polynucleotide, wherein the branch point sequence comprising B1, if present, is in a reverse orientation and on the opposite strand of the donor polynucleotide relative to the branch point sequence comprising B2, wherein B1 and B2 each comprise a nucleotide sequence comprising nucleobases selected from the group consisting of: adenine (A), guanine (G), thymine (T) and cytosine (C), wherein d and f are integers whose value indicates the number of nucleotides comprising B1 and B2, respectively, wherein d and f=5-7;

(b) P1 and P2 are polypyrimidine tracts each comprising a nucleotide sequence comprising nucleobases selected from the group consisting of: adenine, guanine, thymine and cytosine, wherein b and h are integers whose value indicates the number of nucleotides comprising P1 and P2, respectively, wherein b=9-20 and h=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2;

(c) E1 and E2 are each exonic sequences each comprising a nucleotide sequence which corrects the mutation, wherein the nucleotide sequence comprises nucleobases selected from the group consisting of: adenine (A), guanine (G), thymine (T) and cytosine (C), wherein a and i are integers whose value indicates the number of nucleotides comprising E1 and E2, respectively, wherein the exonic sequence comprising E1 is in the reverse orientation and on the opposite strand relative to the exonic sequence comprising E2, wherein the nucleotide sequences comprising E1 and E2 are not complementary;

(d) X1 and X2 each comprise a nucleotide sequence comprising a 3' splice site, wherein the nucleotide sequence of X1 is in a reverse orientation and on the opposite strand of the donor polynucleotide relative to the nucleotide sequence of X2; and (e) S1, S2 and S3, if any present, are each delimiter sequences comprising one or more nucleotides comprising nucleobases selected from the group consisting of: adenine (A), guanine (G), thymine (T) and cytosine (C), wherein c, e and g are each integers whose value indicates the number of nucleotides comprising the delimiter sequence, respectively, wherein c=0 or 1-20 and g=0 or 1-20, wherein e=0 or 1-40, wherein the donor polynucleotide is about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in a first orientation, B2, P2, E2 and X2 comprise a sense strand, wherein B2, P2 and X2 comprise the first, second and third splicing signal, respectively, thereby correcting the mutation and providing splicing signals to control processing of a pre-mRNA transcribed from the gDNA, wherein when the donor polynucleotide is inserted into the DSB in a second orientation, B1, P1, E1 and X1 comprise a sense strand, wherein B1, P1 and X1 comprise the first, second and third splicing signal, respectively, thereby correcting the mutation and providing splicing signals to control processing of a pre-mRNA transcribed from the gDNA, and wherein, when the donor polynucleotide is introduced into the cell in combination with a site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, B1 is present. In some embodiments, B1 is absent. In some embodiments, d=5. In some embodiments, d=6. In some embodiments, d=7. In some embodiments, f=5. In some embodiments, f=6. In some embodiments, f=7. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, h=9. In some embodiments, h=10. In some embodiments, h=11. In some embodiments, h=12. In some embodiments, h=13. In some embodiments, h=14. In some embodiments, h=15. In some embodiments, h=16. In some embodiments, h=17. In some embodiments, h=18. In some embodiments, h=19. In some embodiments, h=20. In some embodiments, the nucleotide sequence comprising P1 is about 100% pyrimidine nucleobases. In some embodiments, the nucleotide sequence comprising P1 is about 90%-100% pyrimidine nucleobases. In some embodiments, the nucleotide sequence comprising P1 is about 80%-90% pyrimidine nucleobases. In some embodiments, the nucleotide sequence comprising P2 is about 100% pyrimidine nucleobases. In some embodiments, the nucleotide sequence comprising P2 is about 90%-100% pyrimidine nucleobases. In some embodiments, the nucleotide sequence comprising P2 is about 80%-90% pyrimidine nucleobases. In some embodiments, S1 is present. In some embodiments, 51 is absent. In some embodiments, S2 is present. In some embodiments, S2 is absent. In some embodiments, S3 is present. In some embodiments, S3 is absent. In some embodiments, c=0. In some embodiments, c=1. In some embodiments, c=2. In some embodiments, c=3. In some embodiments, c=4. In some embodiments, c=5. In some embodiments, c=6. In some embodiments, c=7. In some embodiments, c=8. In some embodiments, c=9. In some embodiments, c=10. In some embodiments, c=11. In some embodiments, c=12. In some embodiments, c=13. In some embodiments, c=14. In some embodiments, c=15. In some embodiments, c=16. In some embodiments, c=17. In some embodiments, c=18. In some embodiments, c=19. In some embodiments, c=20. In some embodiments, g=0. In some embodiments, g=1. In some embodiments, g=2. In some embodiments, g=3. In some embodiments, g=4. In some embodiments, g=5. In some embodiments, g=6. In some embodiments, g=7. In some embodiments, g=8. In some embodiments, g=9. In some embodiments, g=10. In some embodiments, g=11. In some embodiments, g=12. In some embodiments, g=13. In some embodiments, g=14. In some embodiments, g=15. In some embodiments, g=16. In some embodiments, g=17. In some embodiments, g=18. In some embodiments, g=19. In some embodiments, g=20. In some embodiments, e=0. In some embodiments, e=1. In some embodiments, e=2. In some embodiments, e=3. In some embodiments, e=4. In some embodiments, e=5. In some embodiments, e=6. In some embodiments, e=7. In some embodiments, e=8. In some embodiments, e=9. In some embodiments, e=10. In some embodiments, e=11. In some embodiments, e=12. In some embodiments, e=13. In some embodiments, e=14. In some embodiments, e=15. In some embodiments, e=16. In some embodiments, e=17. In some embodiments, e=18. In some embodiments, e=19. In some embodiments, e=20. In some embodiments, e=21. In some embodiments, e=22. In some embodiments, e=23. In some embodiments, e=24. In some embodiments, e=25. In some embodiments, e=26. In some embodiments, e=27. In some embodiments, e=28. In some embodiments, e=29. In some embodiments, e=30. In some embodiments, e=31. In some embodiments, e=32. In some embodiments, e=33. In some embodiments, e=34. In some embodiments, e=35. In some embodiments, e=36. In some embodiments, e=37. In some embodiments, e=38. In some embodiments, e=39. In some embodiments, e=40. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'\text{-}[E1]_a\text{-}Y1\text{-}[S1]_b\text{-}Y2\text{-}[E2]_c\text{-}3', \text{ wherein}$$

(a) E1 and E2 each are exonic sequences each comprising a nucleotide sequence which corrects the mutation, wherein the nucleotide sequence comprises nucleobases selected from the group consisting of: adenine (A), guanine (G), thymine (T) and cytosine (T), wherein a and c are integers whose value indicates the number of nucleotides comprising E1 and E2, respectively, wherein the exonic sequence comprising E1 is in the reverse orientation and on the opposite strand relative to the exonic sequence comprising E2, wherein the nucleotide sequences comprising E1 and E2 are not complementary;

(b) Y1 and Y2 each comprise a nucleotide sequence comprising a 5' splice site, wherein the nucleotide sequence of Y1 is in a reverse orientation and on the opposite strand of the donor polynucleotide relative to the nucleotide sequence of Y2; and (c) S1, if present, is a delimiter sequence comprising one or more nucleotides comprising nucleobases selected from the group consisting of: adenine (A), guanine (G), thymine (T) and cytosine (C), wherein b is an integers whose value indicates the number of nucleotides comprising the delimiter sequence, wherein b=0 or 1-50, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in a first orientation, E2 and Y2 comprise a sense strand and E2 comprises the splicing signal, thereby correcting the mutation and providing splicing signals to control processing of a pre-mRNA transcribed from the gDNA, wherein when the donor polynucleotide is inserted into the DSB in a second orientation, E1 and Y1 comprise a sense strand and E1 comprises the splicing signal, thereby correcting the mutation and providing splicing signals to control processing of a pre-mRNA transcribed from the gDNA and wherein when the donor polynucleotide is introduced into the cell in combination with an site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, S1 is present. In some embodiments, S1 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, b=21. In some embodiments, b=22. In some embodiments, b=23. In some embodiments, b=24. In some embodiments, b=25. In some embodiments, b=26. In some embodiments, b=27. In some embodiments, b=28. In some embodiments, b=29. In some embodiments, b=30. In some embodiments, b=31. In some embodiments, b=32. In some embodiments, b=33. In some embodiments, b=34. In some embodiments, b=35. In some embodiments, b=36. In some embodiments, b=37. In some embodiments, b=38. In some embodiments, b=39. In some embodiments, b=40. In some embodiments, b=41. In some embodiments, b=42. In some embodiments, b=43. In some embodiments, b=44. In some embodiments, b=45. In some embodiments, b=46. In some embodiments, b=47. In some embodiments, b=48. In some embodiments, b=49. In some embodiments, b=50. In some embodiments, the donor polynucleotide is about 10-400, about 10-300, or about 10-200 nucleotides in length. In some embodiments, the donor polynucleotide is about 10-100, about 20-80, about 30-70, or about 40-60 nucleotides in length. In some embodiments, the donor polynucleotide is about 40-70 nucleotides or about 50-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'\text{-}[E1]_a\text{-}Y1\text{-}[S1]_b\text{-}Y2\text{-}[E2]_c\text{-}3', \text{ wherein}$$

(a) E1 and E2 each are exonic sequences each comprising a nucleotide sequence which corrects the mutation, wherein the nucleotide sequence comprises nucleobases selected from the group consisting of: adenine (A), guanine (G), thymine (T) and cytosine (T), wherein a and c are integers whose value indicates the number of nucleotides comprising E1 and E2, respectively, wherein the exonic sequence comprising E1 is in the reverse orientation and on the opposite strand relative to the exonic sequence comprising E2, wherein the nucleotide sequences comprising E1 and E2 are not complementary;

(b) Y1 and Y2 each comprise a nucleotide sequence comprising a 5' splice site, wherein the nucleotide sequence of Y1 is in a reverse orientation and on the opposite strand of the donor polynucleotide relative to the nucleotide sequence of Y2; and (c) S1, if present, is a delimiter sequence comprising one or more nucleotides comprising nucleobases selected from the group consisting of: adenine (A), guanine (G), thymine (T) and cytosine (C), wherein b is an integers whose value indicates the number of nucleotides comprising the delimiter sequence, wherein b=0 or 1-50, wherein the donor polynucleotide is about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in a first orientation, E2 and Y2 comprise a sense strand and E2 comprises the splicing signal, thereby correcting the mutation and providing splicing signals to control processing of a pre-mRNA transcribed from the gDNA, wherein when the donor polynucleotide is inserted into the DSB in a second orientation, E1 and Y1 comprise a sense strand and E1 comprises the splicing signal, thereby correcting the mutation and providing splicing signals to control processing of a pre-mRNA transcribed from the gDNA and wherein when the donor polynucleotide is introduced into the cell in combination with an site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation. In some embodiments, S1 is present. In some embodiments, S1 is absent. In some embodiments, b=0. In some embodiments, b=1. In some embodiments, b=2. In some embodiments, b=3. In some embodiments, b=4. In some embodiments, b=5. In some embodiments, b=6. In some embodiments, b=7. In some embodiments, b=8. In some embodiments, b=9. In some embodiments, b=10. In some embodiments, b=11. In some embodiments, b=12. In some embodiments, b=13. In some embodiments, b=14. In some embodiments, b=15. In some embodiments, b=16. In some embodiments, b=17. In some embodiments, b=18. In some embodiments, b=19. In some embodiments, b=20. In some embodiments, b=21. In some embodiments, b=22. In some embodiments, b=23. In some embodiments, b=24. In some embodiments, b=25. In some embodiments, b=26. In some embodiments, b=27. In some embodiments, b=28. In some embodiments, b=29. In some embodiments, b=30. In some embodiments, b=31. In some embodiments, b=32. In some embodiments, b=33. In some embodiments, b=34. In some embodiments, b=35. In some embodiments, b=36. In some embodiments, b=37. In some embodiments, b=38. In some embodiments, b=39. In some embodiments, b=40. In some embodiments, b=41. In some embodiments, b=42. In some embodiments, b=43. In some embodiments, b=44. In some embodiments, b=45. In some embodiments, b=46. In some embodiments, b=47. In some embodiments, b=48. In some embodiments, b=49. In some embodiments, b=50.

In some embodiments, the exonic sequence comprising the sense strand corrects the mutation. In some embodiments, the nucleotide sequence comprising a 3' splice site comprising the sense strand corrects the mutation. In some embodiments, the nucleotide sequence comprising a 5' splice site comprising the sense strand corrects the mutation. In some embodiments, the nucleotide sequence comprising a polypyrimidine tract comprising the sense strand corrects the mutation. In some embodiments, the nucleotide sequence comprising a branch point sequence comprising the sense strand corrects the mutation.

In some embodiments, the 5' most nucleotide of the donor polynucleotide comprises a 5' phosphate group. In some embodiments, the donor polynucleotide is about 40-70 nucleotides or about 50-60 nucleotides in length. In some embodiments, the donor polynucleotide is about 50-60 nucleotides in length. In some embodiments, the donor polynucleotide is 40, 41, 42, 43, 44, 45, 46, 47, 48, 49, 50, 51, 52, 53, 54, 55, 56, 57, 58, 59 or 60 nucleotides in length. In some embodiments, the donor polynucleotide is 40 nucleotides in length. In some embodiments, the donor polynucleotide is 41 nucleotides in length. In some embodiments, the donor polynucleotide is 42 nucleotides in length. In some embodiments, the donor polynucleotide is 43 nucleotides in length. In some embodiments, the donor polynucleotide is 44 nucleotides in length. In some embodiments, the donor polynucleotide is 45 nucleotides in length. In some embodiments, the donor polynucleotide is 46 nucleotides in length. In some embodiments, the donor polynucleotide is 47 nucleotides in length. In some embodiments, the donor polynucleotide is 49 nucleotides in length. In some embodiments, the donor polynucleotide is 42 nucleotides in length. In some embodiments, the donor polynucleotide is 50 nucleotides in length. In some embodiments, the donor polynucleotide is 51 nucleotides in length. In some embodiments, the donor polynucleotide is 52 nucleotides in length. In some embodiments, the donor polynucleotide is 53 nucleotides in length. In some embodiments, the donor polynucleotide is 54 nucleotides in length. In some embodiments, the donor polynucleotide is 55 nucleotides in length. In some embodiments, the donor polynucleotide is 56 nucleotides in length. In some embodiments, the donor polynucleotide is 57 nucleotides in length. In some embodiments, the donor polynucleotide is 58 nucleotides in length. In some embodiments, the donor polynucleotide is 59 nucleotides in length. In some embodiments, the donor polynucleotide is 60 nucleotides in length.

In some embodiments, the donor polynucleotide comprises natural nucleotides. In some embodiments, the donor polynucleotide comprises naturally occurring nucleotides. In some embodiments, the donor polynucleotide comprises one or more non-natural and/or modified nucleotides. In some embodiments, the one or more non-natural and/or modified nucleotides is a 2'-O-methyl nucleotide. In some embodiments, the donor polynucleotide comprises one or more backbone modifications. In some embodiments, the one or more backbone modification is a phosphorothioate. In some embodiments, the donor polynucleotide comprises two blunt ends. IN some embodiments, the donor polynucleotide comprises one blunt end and comprises one end comprising an overhang (e.g. a 5' or 3' overhang). In some embodiments, the nucleotide sequence of the donor polynucleotide comprises one or more nucleotides that prevent the site-directed nuclease from recognizing and cleaving the donor polynucleotide.

In some embodiments, the disease is Glycogen Storage Disease 1a (GSD1a). In some embodiments, the mutation is located in the human G6PC gene on human chromosome 17q21. In some embodiments, the mutation in the G6PC gene results in an R83C, an R83H, or an E110K amino acid substitution in the human G6PC protein. In some embodiments, the mutation in the G6PC gene results in an R83C amino acid substitution in the human G6PC protein. In some embodiments, the mutation in the G6PC gene results in an R83H amino acid substitution in the human G6PC protein. In some embodiments, the mutation in the G6PC gene results in an E110K amino acid substitution in the human G6PC protein.

In some embodiments, the disclosure provides a donor polynucleotide comprising a non-replicative double-stranded DNA molecule (dsDNA) comprising a nucleotide sequence which corrects a mutation that causes Glycogen Storage Disease 1a in a genomic DNA molecule (gDNA) in a cell, wherein the mutation is located in the human G6PC gene on human chromosome 17q21 and results in the amino acid substitution R83C or R83H, the donor polynucleotide comprising:

(i) a first strand comprising from 5' to 3' a nucleotide sequence comprising an exonic sequence which corrects the mutation, wherein the exonic sequence comprises a codon encoding arginine (R) corresponding to the codon at position 83 in the G6PC gene, and a nucleotide sequence comprising one or more splicing signals to control processing of a precursor mRNA (pre-mRNA) transcribed from the genomic DNA molecule, wherein the one or more splicing signals is a combination of a 3' splice site, a polypyrimidine tract, and a branch point sequence; and (ii) a second strand comprising a nucleotide sequence complementary to the first strand, wherein the donor polynucleotide is about 40-70 nucleotides in length and comprises two blunt ends, wherein the 5' most nucleotide of each strand of the donor polynucleotide comprises a 5' phosphate moiety, wherein when the donor polynucleotide is introduced into the cell in combination with an site-directed nuclease a non-homologous end-joining (NHEJ) DNA repair pathway inserts the donor polynucleotide into a double-stranded DNA break (DSB) introduced into the gDNA by the site-directed nuclease at a location proximal to the mutation, wherein the insertion of the donor polynucleotide forms an exon in the gDNA comprising the exonic sequence that corrects the mutation, wherein the splicing signals direct the inclusion of the exon into an mRNA, thereby correcting the mutation. In some embodiments, the branch point sequence comprises the nucleotide sequence TTCAT, wherein the polypyrimidine tract comprises the nucleotide sequence CTTGTTCTGTTTTTTT (SEQ ID NO: 109), wherein the 3' splice site comprises the nucleotide sequence TAG, and wherein the exonic sequence comprises the nucleotide sequence GATTCTCTTTGGACAGCGCCCTTACT (SEQ ID NO: 110).

In some embodiments, the nucleotide sequence of the donor polynucleotide is set forth in SEQ ID NO: 30 (CH34 54-0). In some embodiments, the nucleotide sequence of the donor polynucleotide is set forth in SEQ ID NO: 20 (CH32 50-0).

In some embodiments, the disease is Pompe's Disease. In some embodiments, the mutation is located in the human glucosidase alpha (GAA) gene on human chromosome 17q25.3. In some embodiments, the mutation is in a splicing signal of GAA that results in mRNA transcripts of the GAA gene lacking exon2 and/or activation of one or more cryptic splice sites.

In some embodiments, the disclosure provides a donor polynucleotide comprising a non-replicative dsDNA molecule comprising a nucleotide sequence which corrects a mutation that causes Pompe's Disease in a gDNA molecule in a cell, wherein the mutation is in a splicing signal of GAA that results in mRNA transcripts of the GAA gene lacking exon2 and/or activation of one or more cryptic splice sites, the donor polynucleotide comprising:

(i) a first strand comprising from 5' to 3' a first nucleotide sequence which corrects the mutation, wherein the first strand comprises a first intronic sequence, wherein the first intronic sequence corrects the mutation, wherein the first strand comprises one or more splicing signals to control processing of a precursor mRNA (pre-mRNA) transcribed from the gDNA, wherein the one or more splicing signals comprises a combination of a 3' splice site, a polypyrimidine tract, and a branch point sequence; and (ii) a second strand comprising from 5' to 3' a second intronic sequence, wherein the second intronic sequence corrects the mutation, wherein the second strand comprises one or more splicing signals to control processing of a pre-mRNA transcribed from the gDNA, wherein the one or more splicing signals comprises a combination of a 3' splice site, a polypyrimidine tract, and a branch point sequence, wherein the second strand is complementary to the first strand wherein the donor polynucleotide is about 10-500, about 10-400, about 10-300, about 10-200, about 10-100, about 20-80, about 30-70, or about 40-60 nucleotides in length and comprises two blunt ends, wherein the 5' most nucleotide of each strand of the donor polynucleotide comprises a 5' phosphate moiety, wherein when the donor polynucleotide is introduced into the cell in combination with a site-directed nuclease a NHEJ DNA repair pathway inserts the donor polynucleotide into a DSB introduced into the gDNA by the site-directed nuclease at a location proximal to the mutation, wherein the donor polynucleotide is configured for bi-directional insertion into a DSB break, wherein insertion in either direction forms a 3' splice site, a polypyrimidine tract, and a branch point sequence that corrects the mutation, wherein the splicing signals direct the inclusion of exon2 into an mRNA, thereby correcting the mutation.

In some embodiments, the nucleotide sequence of the donor polynucleotide is set forth in SEQ ID NO: 63 (GAA_50-0).

In some embodiments, the disclosure provides a system to correct a mutation in a genomic DNA molecule (gDNA) in a cell, the system comprising the components:

(a) any one of the aforementioned donor polynucleotides;
(b) one or more gRNA molecules; and
(c) a site-directed nuclease, wherein when the system is introduced into a cell, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the site-directed nuclease is encoded by an mRNA. In some embodiments, the site-directed nuclease is a polypeptide. In some embodiments, the one or more gRNA molecules and the site-directed nuclease comprise a ribonucleoprotein. In some embodiments, the site-directed nuclease is a Cas nuclease. In some embodiments, the Cas nuclease is *S. pyogenes* Cas9 (SpCas9) or a homolog, derivative or modified version thereof. In some embodiments, the Cas nuclease is *S. aureus* Cas9 (SaCas9) or a homolog, derivative or modified version thereof.

In some embodiments, the one or more gRNA molecules comprises a modification selected from the group consisting of: a backbone modification, a sugar modification, a modified internucleoside linkage, or a modified or non-natural nucleobase. In some embodiments, the one or more gRNA molecules comprise a backbone modification. In some embodiments, the backbone modification is a phosphorothioate modification.

In some embodiments of the system provided by the disclosure, the donor polynucleotide, the gRNA molecule and the site-directed nuclease are individually formulated or co-formulated in a liposome or lipid nanoparticle. In some embodiments, the donor polynucleotide, the gRNA molecule and the site-directed nuclease are individually formulated in a liposome or lipid nanoparticle. In some embodiments, the donor polynucleotide, the gRNA molecule and the site-directed nuclease are co-formulated in a liposome or lipid nanoparticle. In some embodiments, the nucleotide sequence of the gRNA comprises the sequence set forth in SEQ ID NO: 107 (CH32 Mutant-CTX1 sgRNA spacer). In some embodiments, the nucleotide sequence of the gRNA comprises the sequence set forth in SEQ ID NO: 108 (CH34 Mutant-CTX1 sgRNA spacer). In some embodiments, the nucleotide sequence of the gRNA comprises the sequence set forth in SEQ ID NO: 127 (mutant GAA sgRNA spacer).

In some embodiments, the disclosure provides a cell comprising any one of the aforementioned donor polynucleotides or systems. In some embodiments, the cell is a dividing or non-dividing cell. In some embodiments, the cell is a dividing cell. In some embodiments, the cell is a non-dividing cell. In some embodiments, the cell is a patient-specific induced pluripotent stem cell (iPSC). In some embodiments, the cell is a primary hepatocyte.

In some aspects, the disclosure provides a pharmaceutical composition comprising any one of the aforementioned donor polynucleotides and a pharmaceutically acceptable carrier. In some embodiments, the disclosure provides a pharmaceutical composition comprising any one of the aforementioned systems and a pharmaceutically acceptable carrier. In some embodiments, the disclosure provides a pharmaceutical composition comprising any one of the aforementioned cells and a pharmaceutically acceptable carrier.

In some embodiments, the disclosure provides any one of the aforementioned donor polynucleotides, systems, or pharmaceutical compositions, for use in treating a patient with a disease by correcting a mutation in a genomic DNA molecule (gDNA) in a cell, the treatment comprising: isolating a cell from the patient, contacting the cell with the donor polynucleotide, the system, or the pharmaceutical composition, wherein when the donor polynucleotide, the system, or the pharmaceutical composition contacts the cell, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the disclosure provides any one of the aforementioned donor polynucleotides, systems, or pharmaceutical compositions, for use in treating a patient with a disease by correcting a mutation in a genomic DNA molecule (gDNA) in a cell, the treatment comprising: administering to the patient an effective amount of the donor polynucleotide, the system, or the pharmaceutical composition, wherein, when the donor polynucleotide, system or composition is administered, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the disclosure provides a method to correct a mutation in a genomic DNA molecule (gDNA) in a cell, the method comprising: contacting the cell with any one of the aforementioned donor polynucleotides, systems, or pharmaceutical compositions, wherein when the donor polynucleotide, system or composition contacts the cell, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising: isolating a cell from the patient, contacting the cell with any one of the aforementioned donor polynucleotides, systems, or pharmaceutical compositions, wherein, when the donor polynucleotide, system or composition contacts the cell, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising: administering to the patient an effective amount of any one of the aforementioned donor polynucleotides, systems, or pharmaceutical compositions, wherein, when the donor polynucleotide, system or composition is administered, a non-homologous end-joining (NHEJ) DNA repair pathway inserts the donor polynucleotide into a double-stranded DNA break introduced into the gDNA at a location proximal to the mutation, thereby correcting the mutation. (in vivo).

In some embodiments of the methods provided by the disclosure, the cell is a patient-specific induced pluripotent stem cell (iPSC). In some embodiments, the cell is a hepatocyte. In some embodiments, of the methods provided by the disclosure, the method further comprises differentiating the iPSC comprising the corrected mutation into a differentiated cell; and implanting the differentiated cell into a patient.

In some embodiments of the methods provided by the disclosure, treatment results in the translation of an mRNA transcribed from the genomic DNA molecule (gDNA) comprising the inserted donor polynucleotide, wherein the translation results in the formation of a translation product (protein) that alleviates the disease or that does not cause or contribute to the disease.

In some embodiments, the disclosure provides a kit comprising a container comprising any one of the aforementioned donor polynucleotides, systems, or pharmaceutical composition, for correcting a mutation in a genomic DNA molecule (gDNA) in a cell, and a package insert comprising instructions for use.

BRIEF DESCRIPTION OF THE DRAWINGS

FIGS. 2A-2C depict the percentage of corrective edits of a DSB in the G6PC exon 2 genomic DNA (gDNA) locus induced by three different gRNAs.

FIGS. 6A-6B (SEQ ID NOS: 63 and 67) provide a schematic describing the design of a bidirectional donor polynucleotide for insertion into the GAA gene. FIG. 6A depicts splicing signals in the sense and antisense strand of the dsODN donor polynucleotide. FIG. 6B depicts insertion of desired splicing signals regardless of whether the dsODN donor inserts into the GAA cut site in either the forward or reverse direction.

DETAILED DESCRIPTION

Figure 1:
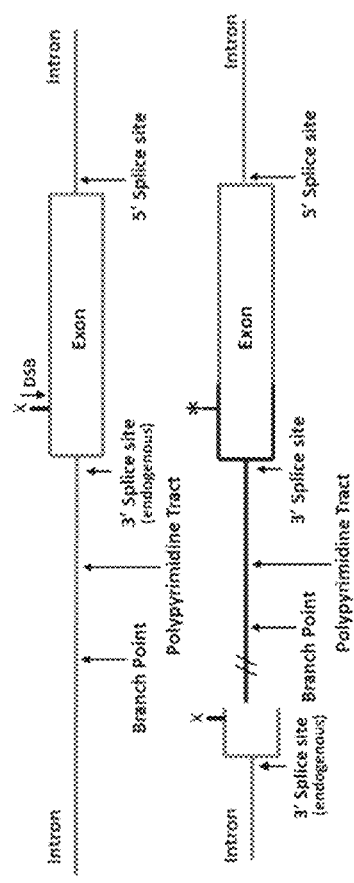
FIG. 1 provides a schematic showing an endogenous locus in a target nucleic acid and the locus after insertion of a donor polynucleotide. The relative locations of splice signals, splice sites, introns and exons are indicated.

The dominant pathways for repair of a DNA double-strand break (DSB) are the non-homologous end joining (NHEJ) pathway and the homology-directed repair (HDR) pathway (e.g., also known as homologous recombination or HR). By using a site-directed nuclease (e.g., a CRISPR/Cas9 endonuclease) to induce a site-specific DSB in a target gene, a gene edit can be introduced by HDR repair using a homology donor polynucleotide as a template. However, HDR repair is inefficient, particularly in non-dividing cells. Thus, methods for inducing a desired gene edit provided by a donor polynucleotide using NHEJ repair are advantageous for editing both non-dividing and dividing cells. The present disclosure is based, at least in part, on the design of donor polynucleotides that insert at a DSB induced in a target gene by a site-directed nuclease (e.g., a CRISPR/Cas9 endonuclease) using the NHEJ repair pathway. The donor polynucleotides are designed for NHEJ-mediated insertion in a target gene DSB to both correct disease-causing mutations located within exons (e.g. protein-coding mutations) and within introns (e.g., splicing signal mutations) that result in aberrant protein production or function. Thus, provided herein are methods and compositions comprising donor polynucleotides that provide a desired alteration in the nucleotide sequence of the genomic DNA (gDNA) and/or modulate exon definition, thereby resulting in the inclusion of a desired alteration in an RNA transcript (e.g., a pre-mRNA) transcribed from the edited gDNA.

Genome Editing

Genome editing generally refers to the process of editing or changing the nucleotide sequence of a genome, preferably in a precise, desirable and/or pre-determined manner. Examples of compositions, systems, and methods of genome editing described herein use of site-directed nucleases to cut or cleave DNA at precise target locations in the genome, thereby creating a double-strand break (DSB) in the DNA. Such breaks can be repaired by endogenous DNA repair pathways, such as homology directed repair (HDR) and/or non-homologous end-joining (NHEJ) repair (see e.g., Cox et al., (2015) Nature Medicine 21(2):121-31). One of the major obstacles to efficient genome editing in non-dividing cells is lack of homology directed repair (HDR). Without HDR, non-dividing cells rely on non-homologous end joining (NHEJ) to repair double-strand breaks (DSB) that occur in the genome. The results of NHEJ-mediated DNA repair of DSBs can include correct repair of the DSB, or deletion or insertion of one or more nucleotides or polynucleotides.

Donor Polynucleotides

In humans, exon definition is determined by splice sites paired across an exon as opposed to across an intron. Other splicing signals, including, but not limited to, branch point sequences, polypyrimidine tracts, as well as exonic and intronic splicing enhancers and silencers, also contribute to proper splicing together of exons to form an mature mRNA. During pre-mRNA splicing, the splicing machinery searches for a pair of closely spaced splice sites in an exonic polarity (i.e. 3' splice site upstream and 5' splice site downstream) (Berget (1995) J Biol Chem 270:2411-2414).

Accordingly, the disclosure provides donor polynucleotides that, upon insertion into a DSB, corrects or induces a mutation in a target nucleic acid (e.g., a genomic DNA) and comprise splicing signals (e.g., one or more splicing signals) that allow the splicing machinery to incorporate the corrected mutation (or induce a mutation) into a transcription product (e.g., a pre-mRNA), in part, by the modulation of exon definition. In some embodiments, the donor polynucleotides provided by the disclosure are recognized and used by the NHEJ machinery of a cell to repair a double strand break (DSB) introduced into a target nucleic acid by a site-directed nuclease, wherein repair of the DSB results in the insertion of the donor polynucleotide into the target nucleic acid. In some embodiments, the donor polynucleotides are configured for unidirectional insertion into the DSB. In some embodiments, the donor polynucleotides are configured for bi-directional insertion into the DSB.

Unidirectional Donor Polynucleotides

In some embodiments, the donor polynucleotides provided by the disclosure are linear, non-replicative, double-stranded DNA molecules (dsDNA) comprising a nucleotide sequence which corrects or induces a mutation in a genomic DNA (gDNA) molecule in a cell and a nucleotide sequence comprising one or more splicing signals to control processing of a precursor mRNA (pre-mRNA) transcribed from the gDNA, wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotide is comprised of a first and a second DNA strand, wherein the second DNA strand comprises a nucleotide sequence that is complementary to a first DNA strand.

In some embodiments, the donor polynucleotide comprises a nucleotide sequence which corrects or induces a mutation, wherein the nucleotide sequence that corrects or induces a mutation comprises a single nucleotide. In some embodiments, the nucleotide sequence which corrects or induces a mutation comprises two or more nucleotides. In some embodiments, the nucleotide sequence which corrects or induces a mutation comprises a codon. In some embodiments, the nucleotide sequence which corrects or induces a mutation is comprises one or more codons. In some embodiments, the nucleotide sequence which corrects or induces a mutation comprises an exonic sequence.

In some embodiments, the donor polynucleotide comprises a nucleotide sequence which corrects or induces a mutation, wherein the nucleotide sequence which corrects or induces a mutation comprises an intronic sequence. In some embodiments, the nucleotide sequence which corrects or induces a mutation comprises a splicing signal.

In some embodiments, the donor polynucleotide sequence is identical to or substantially identical to (having at least one nucleotide difference) an endogenous sequence of a target nucleic acid. In some embodiments, the endogenous sequence comprises a genomic sequence of the cell. In some embodiments, the endogenous sequence comprises a chromosomal or extrachromosomal sequence. In some embodiments, the donor polynucleotide sequence comprises a sequence that is substantially identical (comprises at least one nucleotide difference/change) to a portion of the endogenous sequence in a cell at or near the DSB. In some embodiments, repair of the target nucleic acid molecule with the donor polynucleotide results in an insertion, deletion, or substitution of one or more nucleotides of the target nucleic acid molecule. In some embodiments, the insertion, deletion, or substitution of one or more nucleotides results in one or more amino acid changes in a protein expressed from a gene comprising the target sequence. In some embodiments, the insertion, deletion, or substitution of one or more nucleotides results in one or more nucleotide changes in an RNA expressed from the target gene. In some embodiments, the insertion, deletion, or substitution of one or more nucleotides alters the expression level of the target gene. In some embodiments, the insertion, deletion, or substitution of one or more nucleotides results in increased or decreased expression of the target gene. In some embodiments, the insertion, deletion, or substitution of one or more nucleotides results in gene knockdown. In some embodiments, the insertion, deletion, or substitution of one or more nucleotides results in gene knockout. In some embodiments, the repair of the target nucleic acid molecule with the donor polynucleotide results in replacement of an exon sequence, an intron sequence, a transcriptional control sequence, a translational control sequence, a sequence comprising a splicing signal, or a non-coding sequence of the target gene.

The donor polynucleotide is of a suitable length to correct or induce a mutation in a gDNA. In some embodiments, the donor polynucleotide comprises 10, 15, 20, 25, 50, 75, 100 or more nucleotides in length. In some embodiments (for example those described herein where a donor polynucleotide is incorporated into the cleaved nucleic acid as an insertion mediated by non-homologous end joining) the donor polynucleotide has no homology arms. In some embodiments, the donor polynucleotide is about 10-500, about 10-400, about 10-300, about 10-200, about 10-100, about 20-80, about 30-70, or about 40-60 nucleotides in length. In some embodiments, the donor polynucleotide is about 10-500 nucleotides in length. In some embodiments, the donor polynucleotide is about 10-400 nucleotides in length. In some embodiments, the donor polynucleotide is about 10-300 nucleotides in length. In some embodiments, the donor polynucleotide is about 10-200 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length. In some embodiments, the donor polynucleotide is 40, 41, 42, 43, 44, 45, 46, 46, 48, 49, 50, 51, 52, 53, 54, 55, 56, 57, 58, 59 or 60 nucleotides in length. In some embodiments, the donor polynucleotide is 40 nucleotides in length. In some embodiments, the donor polynucleotide is 41 nucleotides in length. In some embodiments, the donor polynucleotide is 42 nucleotides in length. In some embodiments, the donor polynucleotide is 43 nucleotides in length. In some embodiments, the donor polynucleotide is 44 nucleotides in length. In some embodiments, the donor polynucleotide is 45 nucleotides in length. In some embodiments, the donor polynucleotide is 46 nucleotides in length. In some embodiments, the donor polynucleotide is 47 nucleotides in length. In some embodiments, the donor polynucleotide is 48 nucleotides in length. In some embodiments, the donor polynucleotide is 49 nucleotides in length. In some embodiments, the donor polynucleotide is 50 nucleotides in length. In some embodiments, the donor polynucleotide is 51 nucleotides in length. In some embodiments, the donor polynucleotide is 52 nucleotides in length. In some embodiments, the donor polynucleotide is 53 nucleotides in length. In some embodiments, the donor polynucleotide is 54 nucleotides in length. In some embodiments, the donor polynucleotide is 55 nucleotides in length. In some embodiments, the donor polynucleotide is 56 nucleotides in length. In some embodiments, the donor polynucleotide is 57 nucleotides in length. In some embodiments, the donor polynucleotide is 58 nucleotides in length. In some embodiments, the donor polynucleotide is 59 nucleotides in length. In some embodiments, the donor polynucleotide is 60 nucleotides in length.

In some embodiments, a donor polynucleotide provided by the disclosure comprises an intronic sequence. In some embodiments, the donor polynucleotide comprises an intronic sequence which corrects or induces a mutation in a gDNA. In some embodiments, the donor polynucleotide comprises an exonic sequence. In some embodiments, the donor polynucleotide comprises an exonic sequence which corrects or induces a mutation in a gDNA.

In some embodiments, a donor polynucleotide provided by the disclosure comprises one or more splicing signals to control processing (e.g., splicing) of a precursor mRNA (pre-mRNA) transcribed from a gDNA into which the donor polynucleotide is inserted.

In some embodiments, the donor polynucleotides provided by the disclosure comprise one or more splicing signals to control processing (e.g., splicing) of a precursor mRNA (pre-mRNA) transcribed from a gDNA some embodiments, wherein the one or more splicing signals is selected from the group consisting of:
(a) a natural or enhanced 3' splice site;
(b) a natural or enhanced 5' splice site;
(c) a polypyrimidine tract;
(d) a branch point;
(e) an exonic splicing enhancer (ESE);
(f) an intronic splicing enhancer (ISE);
(g) an exonic splicing silencer (ESS);
(h) an intronic splicing silencer (ISS); and
(i) a combination of any of (a)-(h).

In some embodiments, the donor polynucleotide comprises a natural or enhanced 3' splice site. In some embodiments, the donor polynucleotide comprises a naturally-occurring 3' splice site. In some embodiments, the donor polynucleotide comprises an enhanced 3' splice site. A natural 3' splice site is a naturally-occurring 3' splice site. In some embodiments, the nucleotide sequence of a natural 3' splice site is identical to or substantially identical to (having at least one nucleotide difference) the nucleotide sequence of the 3' splice site at or near the donor polynucleotide insertion site. An enhanced 3' splice site is a splice site comprising a nucleotide sequence that is identical to or substantially identical to (having at least one nucleotide difference) to the consensus sequence of a 3' splice site. A consensus sequence for a 3' splice site is the nucleotide sequence YAG, and wherein Y is a nucleotide comprising a nucleobase selected from the group consisting of: thymine (T) and cytosine (C). See e.g., Reed (1989) Genes Dev 3(12B):2113-2123 further describes the organization of 3' splice site sequences in mammals.

In some embodiments, the donor polynucleotide comprises a natural or enhanced 5' splice site. In some embodiments, the donor polynucleotide comprises a natural 5' splice site. In some embodiments, the donor polynucleotide comprises an enhanced 5' splice site. In some embodiments, a natural 5' splice site is a naturally-occurring 5' splice site. In some embodiments, the nucleotide sequence of a natural 5' splice site is identical to or substantially identical to (having at least one nucleotide difference) to the nucleotide sequence of the 5' splice site at or near the donor polynucleotide insertion site. In some embodiments, an enhanced 5' splice site is a splice site comprising a nucleotide sequence is identical to or substantially identical to (having at least one nucleotide difference) o the consensus sequence of a 5' splice site. A consensus sequence for a 5' splice site is the nucleotide sequence GTRAG, and wherein R is a nucleotide comprising a nucleobase selected from the group consisting of: adenine (A) and guanine (G).

In some embodiments, the donor polynucleotide comprises a polypyrimidine tract. The polypyrimidine tract is a cis-acting sequence element directing intron removal in pre-mRNA splicing. Progressive deletions of the polypyrimidine tract have been found to abolish correct lariat formation, spliceosome assembly and splicing. Studies have shown that pyrimidine tracts containing continuous uridines are strong pyrimidine tracts (Coolidge et al., (1997) Nucleic Acids Res 25(4):888-896). In some embodiments, the polypyrimidine tract is 5, 6, 7, 8, 9, 10, 11, 12, 13, 14, 15, 16, 17 or 18 nucleotides in length. In some embodiments, the polypyrimidine tract is 16 nucleotides in length. In some embodiments, the polypyrimidine tract is 13 nucleotides in length. In some embodiments, the polypyrimidine tract comprises the nucleotide sequence TTTTTTTCTTTTT (SEQ ID NO: 54). In some embodiments, the polypyrimidine tract is 9 nucleotides in length. In some embodiments, the polypyrimidine tract comprises the nucleotide sequence TTTTTTTCT (SEQ ID NO: 53)

In some embodiments, the donor polynucleotide comprises a branch point. In some embodiments, the donor polynucleotide comprises a nucleotide sequence comprising a branch point. In higher eukaryotes, pre-mRNA splicing is mediated by degenerative splicing cis-elements comprised of the branch point sequence (BPS), the polypyrimidine tract (PPT), the 5' and 3' splice sites and exonic/intronic splicing enhancers/silencers and pre-mRNAs are spliced in two sequential transesterification reactions mediated by the spliceosome. In some embodiments, the donor polynucleotide comprises a branch point comprising a nucleotide sequence is identical to or substantially identical to (having at least one nucleotide difference) a branch point consensus sequence. In some embodiments, the branch point consensus sequence is YTNAY, wherein Y=C or T, and wherein N=A, G, C or T (SEQ ID NO: 49). In some embodiments, the branch point sequence is TATTAAC (SEQ ID NO: 50). In some embodiments, the branch point sequence is GTTAATA (SEQ ID NO: 51). In some embodiments, the branch point sequence is TACTGAC (SEQ ID NO: 52).

In some embodiments, the donor polynucleotide comprises an exonic splicing enhancer (ESE) (see e.g., Blencowe (2000) Trends Biochem Sci 25(3):106-110). In some embodiments, the donor polynucleotide comprises an exonic splicing silencer (ESS) (see e.g., Wang et al., (2006) Mol Cell 23(1):61-70). In some embodiments, the donor polynucleotide comprises an intronic splicing enhancer (ISE) (see e.g., Wang et al., (2012) Nat Struct Mol Biol 19(10): 1044-1052). In some embodiments, the donor polynucleotide comprises an intronic splicing silencer (ISS) (see e.g., Carstens et al., (2000) Mol Cell Biol 20(19): 7388-7400).

In some embodiments, the donor polynucleotide comprises a natural or enhanced 3' splice site and a polypyrimidine tract. In some embodiments, the donor polynucleotide comprises a natural or enhanced 3' splice site, a polypyrimidine tract, and a branch point.

In some embodiments, the disclosure provides a donor polynucleotide comprising a non-replicative double-stranded DNA molecule (dsDNA) comprising:
(i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA; and
(ii) a second strand comprising a nucleotide sequence complementary to the first strand, wherein the one or more splicing signals is selected from the group consisting of:
(a) a natural or enhanced 3' splice site;
(b) a polypyrimidine tract;
(c) a branch point;
(d) an exon splicing enhancer (ESE);
(e) an intron splicing enhancer (ISE);
(f) an exon splicing silencer (ESS);
(g) an intron splicing silencer (ISS); and
(h) a combination of any of (a)-(g),
wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA (gDNA) molecule in a cell, wherein the disease-causing mutation is a protein-coding mutation proximal to a 5' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, and (ii) a second strand comprising a nucleotide sequence complementary to the first strand, wherein the one or more splicing signals is selected from the group consisting of:
 (a) a natural or enhanced 5' splice site;
 (b) an exon splicing enhancer (ESE);
 (c) an intron splicing enhancer (ISE);
 (d) an exon splicing silencer (ESS);
 (e) an intron splicing silencer (ISS); and
 (f) a combination of any of (a)-(e), wherein the donor polynucleotide is about 10-500, about 10-400, about 10-300, about 10-200, about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA (gDNA) molecule in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein at least one splicing signal is a natural or enhanced 3' splice site; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the one or more splicing signals is a combination of a natural or enhanced 3' splice site and a polypyrimidine tract; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein, when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the one or more splicing signals is a combination of a natural or enhanced 3' splice site, a polypyrimidine tract, and a branch point; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising 5' to 3' a nucleotide sequence which corrects a disease-causing mutation in a genomic DNA molecule (gDNA) in a cell, wherein the disease-causing mutation is in a 3' splice site, wherein the first strand comprises an intronic sequence, optionally, an exonic sequence, wherein the intronic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:
(a) a polypyrimidine tract;
(b) a branch point;
(c) an exon splicing enhancer (ESE);
(d) an intron splicing enhancer (ISE);
(e) an exon splicing silencer (ESS);
(f) an intron splicing silencer (ISS); and
(g) a combination of any of (a)-(f), wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is a protein-coding mutation proximal to a 5' splice site, wherein the donor polynucleotide comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein at least one splicing signal is a natural or enhanced 5' splice site; and (ii) a second strand comprising a nucleotide sequence complementary to the first strand, wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, insertion of the donor polynucleotide into the DSB results in the formation of an exon in the gDNA comprising the exonic sequence. In some embodiments, the one or more splicing signals directs the inclusion of the exon comprising the exonic sequence into an mRNA.

In some embodiments, the disclosure provides a donor polynucleotide comprising a non-replicative double-stranded DNA molecule (dsDNA) comprising (i) a first strand comprising from 5' to 3' a nucleotide sequence which corrects a disease-causing mutation in a genomic DNA molecule (gDNA) in a cell, wherein the disease-causing mutation is in a 5' splice site, wherein the first strand comprises an intronic sequence, optionally, an exonic sequence, wherein the intronic sequence corrects the mutation, wherein the first strand comprises one or more splicing signals to control processing of a precursor mRNA (pre-mRNA) transcribed from the gDNA; and (ii) a second strand comprising a nucleotide sequence complementary to the first strand, wherein the one or more splicing signals is selected from the group consisting of:
(a) an exon splicing enhancer (ESE);
(b) an intron splicing enhancer (ISE);
(c) an exon splicing silencer (ESS);
(d) an intron splicing silencer (ISS); and
(e) a combination of any of (a)-(d), wherein the donor polynucleotide is about 10-500, about 10-400, about 10-300, about 10-200, about 10-100, about 20-80, about 30-70, or about 40-60 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation.

In some embodiments, the insertion of the donor polynucleotide results in the formation of an intron comprising the intronic sequence, wherein the intronic sequence corrects the mutation.

In some embodiments, the disclosure provides a donor polynucleotide comprising a non-replicative double-stranded DNA molecule (dsDNA) comprising a first strand and a second strand, wherein the second strand is complementary to the first strand, wherein the first strand comprising from 5' to 3' a nucleotide sequence which corrects a disease-causing mutation in a genomic DNA molecule (gDNA) in a cell, wherein the disease-causing mutation is a protein-coding mutation proximal to a 3' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the first strand comprises the formula:

$$5'\text{-}[B]a\text{-}[S1]b\text{-}[P]c\text{-}[S2]d\text{-}X\text{-}E\text{-}3', \text{ wherein}$$

(i) B, if present, is a branch point sequence comprising a nucleotide sequence that conforms to a branch point consensus sequence on each strand of the donor polynucleotide, wherein B comprises a nucleotide sequence comprising nucleobases selected from the group consisting of: adenine (A), guanine (G), thymine (T) and cytosine (C), wherein a is an integer whose value indicates the number of nucleotides comprising B, wherein a=0 or 5-7;

(ii) P is a polypyrimidine tract comprising a nucleotide sequence comprising nucleobases selected from the group consisting of: adenine (A), guanine (G), thymine (T) and cytosine (C), wherein c is an integer whose value indicates the number of nucleotides comprising P, wherein c=9-20, wherein the nucleotide sequence comprising P is about 100%, about 90%-100%, about 80%-90% pyrimidine nucleobases;

(iii) E is an exonic sequence comprising a nucleotide sequence which corrects the mutation, wherein the nucleotide sequence comprises nucleobases selected from the group consisting of: adenine (A), guanine (G), thymine (T) and cytosine (C);

(iv) X is a nucleotide sequence comprising a 3' splice site; and (v) S1 and S2, if either is present, are each delimiter sequences comprising one or more nucleotides comprising nucleobases selected from the group consisting of: adenine (A), guanine (G), thymine (T) and cytosine (C), wherein b and d are each integers whose value indicates the number of nucleotides comprising the delimiter sequence, respectively, wherein b and d=0-20, wherein the donor polynucleotide is about 10-500, about 10-400, about 10-300, about 10-200, about 10-100, about 20-80, about 30-70, or about 40-60 nucleotides in length, wherein the donor polynucleotide is configured for directional insertion into a double-stranded DNA break (DSB), wherein when the donor polynucleotide is inserted into the DSB, B, if present, P, X, if present, and E, if present, comprise a sense strand, wherein B, if present, P, and X, if present, comprise the one or more splicing signals, thereby correcting the mutation and providing splicing signals to control processing of a pre-mRNA transcribed from the gDNA, and wherein when the donor polynucleotide is introduced into the cell in combination with a site-directed nuclease, a non-homologous end-joining (NHEJ) DNA repair pathway inserts the donor polynucleotide into the DSB introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising a first strand and a second strand, wherein the second strand is complementary to the first strand, wherein the first strand from 5' to 3' comprises a nucleotide sequence which corrects a disease-causing mutation in a genomic DNA molecule (gDNA) in a cell, wherein the disease-causing mutation is a protein-coding mutation proximal to a 5' splice site, wherein the first strand comprises an intronic sequence and an exonic sequence, wherein the exonic sequence corrects the mutation, wherein the first strand comprises one or more splicing signals to control processing of a precursor mRNA (pre-mRNA) transcribed from the gDNA, wherein the first strand comprises the formula:

5'-E-Y-I-3', wherein (i) E is an exonic sequence comprising a nucleotide sequence which corrects the mutation, wherein the nucleotide sequence comprises nucleobases selected from the group consisting of: adenine (A), guanine (G), thymine (T) and cytosine (C);

(ii) Y is a nucleotide sequence comprising a 5' splice site; and (iii) I, if present, comprises an intronic sequence comprising nucleotides comprising nucleobases selected from the group consisting of: adenine (A), guanine (G), thymine (T) and cytosine (C), wherein the donor polynucleotide is about 10-500, about 10-400, about 10-300, about 10-200, about 10-100, about 20-80, about 30-70, or about 40-60 nucleotides in length, wherein the donor polynucleotide is configured for directional insertion into a double-stranded DNA break (DSB), wherein when the donor polynucleotide is inserted into the DSB, E, if present, Y, and I, if present, comprise a sense strand, wherein Y comprises the one or more splicing signals, thereby correcting the mutation and providing splicing signals to control processing of a pre-mRNA transcribed from the gDNA, and wherein when the donor polynucleotide is introduced into the cell in combination with a site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation.

Bi-Directional Donor Polynucleotides

In some embodiments, the donor polynucleotides provided by the disclosure are linear dsDNA molecules comprising two free DNA termini. As such, insertion of the donor polynucleotides into a DSB by the NHEJ machinery of a cell may occur in one of two orientations; forward and reverse. Accordingly, in some aspects, the disclosure provides donor polynucleotides that are configured for bi-directional insertion into a DSB introduced into gDNA by a site-directed nuclease, wherein the donor polynucleotide corrects or induces a mutation in a genomic DNA (gDNA) molecule in a cell and provides one or more splicing signals to control processing of a precursor mRNA (pre-mRNA) transcribed from the gDNA when inserted into a DSB in either orientation.

In some embodiments, the donor polynucleotide comprises a first splicing signal comprising a branch point sequence, wherein the donor polynucleotide comprises:

(i) a first strand comprising from 5' to 3' a nucleotide sequence comprising a first branch point sequence and a first nucleotide sequence which corrects the mutation in the gDNA; and (ii) a second strand comprising from 5' to 3' a nucleotide sequence comprising a second branch point sequence and a second nucleotide sequence which corrects the mutation in the gDNA, wherein the second strand is complementary to the first strand, wherein the donor polynucleotide is about 10-500, about 10-400, about 10-300, about 10-200, is about 10-100, about 20-80, about 30-70, or about 40-60 nucleotides in length. In some embodiments, the nucleotide sequences of the first branch point sequence and the second branch point sequence conform to a branch point consensus sequence and the nucleotide sequences of the first branch point sequence and second branch point sequence are complementary. In some embodiments, the branch point consensus sequence is YTNAY (SEQ ID NO: 49), wherein Y is a nucleotide comprising either a cytosine (C) or thymine (T) nucleobase, and wherein N is a nucleotide comprising a nucleobase selected from the group consisting of: adenine (A), guanine (G), thymine (T) and cytosine (C). In some embodiments, the first branch point sequence is TATTAAC (SEQ ID NO: 50). In some embodiments, the second branch point sequence is GTTAATA (SEQ ID NO: 51). In some embodiments, the second branch point sequence is TACTGAC (SEQ ID NO: 52).

In some embodiments, the donor polynucleotide comprises a second splicing signal comprising a polypyrimidine tract, wherein the first strand comprises a first polypyrimidine tract located downstream of the first branch point sequence; and the second strand comprises a second polypyrimidine tract located downstream of the second branch point sequence.

In some embodiments, the nucleotide sequence comprising the first and second polypyrimidine tracts each comprise nucleobases selected from the group consisting of: adenine (A), guanine (G), thymine (T) and cytosine (C), and wherein the nucleotide sequence is about 100%, about 90%-100%, or about 80%-90% pyrimidine nucleobases. In some embodiments, the nucleotide sequence comprising the polypyrimidine tract is TTTTTTTCT (SEQ ID NO: 53). In some embodiments, the nucleotide sequence comprising the polypyrimidine tract is TTTTTTTCTTTTT (SEQ ID NO: 54). In some embodiments, the nucleotide sequence comprising the polypyrimidine tract is CTTCTTCTCTTCTTCC (SEQ ID NO: 55).

In some embodiments, the first branch point sequence and the first polypyrimidine tract are adjacent to each other. In some embodiments, the second branch point sequence and the second polypyrimidine tract are adjacent to each other.

In some embodiments, the donor polynucleotide comprises a third splicing signal comprising a 3' splice site, wherein the first strand comprises a nucleotide sequence comprising a first 3' splice site located downstream of the first polypyrimidine tract and the second strand comprises a nucleotide sequence comprising a second 3' splice site located downstream of the second polypyrimidine tract. In some embodiments, the first and second 3' splice sites comprise the nucleotide sequence YAG, and wherein Y is a nucleotide comprising a nucleobase selected from the group consisting of: thymine (T) and cytosine (C).

In some embodiments, the donor polynucleotide comprises a coding sequence, wherein the first strand comprises a first coding sequence, wherein the second strand comprises a second coding sequence, wherein the first nucleotide sequence that corrects the mutation in the gDNA comprises the first coding sequence, wherein the second nucleotide sequence that corrects the mutation in the gDNA comprises the second coding sequence, wherein the first coding sequence is located downstream of the first 3' splice site, and wherein the second coding sequence is located downstream of the second 3' splice site. In some embodiments, the nucleotide sequence comprising the first and second coding sequences comprise nucleobases selected from the group consisting of: adenine (A), guanine (G), thymine (T) and cytosine (C). In some embodiments, the coding sequence and/or splicing signals comprising (i) and (ii) are not identical or complementary to reduce self-annealing.

In some embodiments, a donor polynucleotide provided by the disclosure comprises one or more delimiter sequences comprising a nucleotide sequence comprising nucleobases selected from the group consisting of: adenine (A), guanine (G), thymine (T) and cytosine (C), wherein the nucleotide sequence is about 1-40, about 1-30, about 1-20, about 1-15, about 1-10, about 30, about 20, about 10, about 9, about 8, about 7, about 6, about 5, about 4, about 3, about 2 or 1 nucleotide(s) in length. In some embodiments, the one or more delimiter sequences are located between the first branch point sequence and the second branch point sequence. In some embodiments, the one or more delimiter sequences are located between the first branch point sequence and the first polypyrimidine tract. In some embodiments, the one or more delimiter sequences are located between the second branch point and the second polypyrimidine tract.

In some embodiments, the donor polynucleotide is configured for bi-directional insertion into a DSB introduced into a gDNA by a site-directed nuclease, wherein, when the donor polynucleotide is inserted into the DSB in either orientation, the first splicing signal and second splicing signal, optionally, the third splicing signal and the coding sequence comprise a sense strand, thereby correcting the mutation and providing the one or more splicing signals to control processing of a pre-mRNA transcribed from the gDNA.

In some embodiments, the disclosure provides a donor polynucleotide comprising one or more splicing signals comprising a 5' splice site, wherein the donor polynucleotide comprises:

(i) a first strand comprising from 5' to 3' a nucleotide sequence comprising a first 5' splice site and a first nucleotide sequence which corrects the mutation in the gDNA; and (ii) a second strand comprising from 5' to 3' a nucleotide sequence comprising a second 5' splice site and a second nucleotide sequence which corrects the mutation in the gDNA, wherein the second strand is complementary to the first strand, wherein the donor polynucleotide is about 10-500, about 10-400, about 10-300, about 10-200, is about 10-100, about 20-80, about 30-70, or about 40-60 nucleotides in length. In some embodiments, the first strand comprising a first coding sequence and second strand comprises a second coding sequence, wherein the first coding sequence is located upstream of the first 5' splice site, and wherein the second coding sequence is located upstream of the second 5' splice site, and wherein the coding sequences in the first and second strand are not complementary (or comprise one, two, three, four or more mismatches) to reduce self-annealing. In some embodiments, the donor polynucleotide comprises a delimiter sequence between the first and second 5' splice site, wherein the delimiter sequence comprises a nucleotide sequence comprising nucleobases selected from the group consisting of: adenine (A), guanine (G), thymine (T) and cytosine (C), wherein the nucleotide sequence is about 1-40, about 1-30, about 1-20, about 1-15, about 1-10, about 30, about 20, about 10, about 9, about 8, about 7, about 6, about 5, about 4, about 3, about 2 or 1 nucleotide(s) in length.

In some embodiments, the donor polynucleotide is configured for bi-directional insertion into the DSB, wherein when the donor polynucleotide is inserted into the DSB in a first orientation, the first 5' splice site and first coding sequence comprise a sense strand, thereby correcting the mutation and providing splicing signals to control processing of a pre-mRNA transcribed from the gDNA, and wherein when the donor polynucleotide is inserted into the DSB in a second orientation, the second 5' splice site and second coding sequence comprise a sense strand, thereby correcting the mutation and providing one or more splicing signals to control processing of a pre-mRNA transcribed from the gDNA.

In some embodiments, the donor polynucleotide comprises a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is proximal to a 3' splice site, wherein the first strand comprises a first intronic sequence, wherein the first intronic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is proximal to a 3' splice site, wherein the second strand comprises a second intronic sequence, wherein the second intronic sequence corrects the mutation, wherein the second strand comprises one or more splicing signals to control processing of a precursor mRNA (pre-mRNA) transcribed from the gDNA, wherein the second strand is complementary to the first strand, and wherein the first strand and the second strand each comprise the formula:

5'-[P1]a-[S1]b-[B]c-[S2]d-[P2]e-3', wherein (a) B comprises a branch point sequence comprising a nucleotide sequence that conforms to a branch point consensus sequence on each strand of the donor polynucleotide, wherein B comprises a nucleotide sequence comprising nucleobases selected from the group consisting of: adenine (A), guanine (G), thymine (T) and cytosine (C), wherein c is an integer whose value indicates the number of nucleotides comprising B, wherein c=5-7;

(b) P1 and P2 are polypyrimidine tracts each comprising a nucleotide sequence comprising nucleobases selected from the group consisting of: adenine (A), guanine (G), thymine (T) and cytosine (C), wherein a and e are integers whose value indicates the number of nucleotides comprising P1 and P2, respectively, wherein a=9-20 and c=9-20, wherein the nucleotide sequence comprising P1 and P2 are each about 100%, about 90%-100%, about 80%-90% pyrimidine nucleobases, and wherein P1 is in the reverse orientation and on the opposite strand of the donor polynucleotide relative to P2; and (c) S1 and S2, if either is present, are each delimiter sequence comprising one or more nucleotides comprising nucleobases selected from the group consisting of: adenine (A), guanine (G), thymine (T) and cytosine (C), wherein b and d are each integers whose value indicates the number of nucleotides comprising the delimiter sequence, respectively, wherein b and d=0-20, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B and P2 comprise a sense strand and B and P2 comprise the first and second splicing signals, respectively, thereby correcting the mutation and providing splicing signals to control processing of a pre-mRNA transcribed from the gDNA, wherein, when the donor polynucleotide is inserted into the DSB in the second orientation, B and P1 comprise a sense strand and B and P2 comprise the first and second splicing signals, respectively, thereby correcting the mutation and providing splicing signals to control processing of a pre-mRNA transcribed from the gDNA, and wherein when the donor polynucleotide is introduced into the cell in combination with a site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation.

In some embodiments, the donor polynucleotide comprises a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is proximal to a 3' splice site, wherein the first strand comprises a first intronic sequence, wherein the first intronic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is proximal to a 3' splice site, wherein the second strand comprises a second intronic sequence, wherein the second intronic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

$$5'-[P1]a-[S1]b-[B1]c-[S2]d-[B2]e-[S3]f-[P2]g-3',$$
wherein (a) B1, if present, and B2 are each branch point sequences, wherein B2 comprises a nucleotide sequence that conforms to a branch point consensus sequence on each strand of the donor polynucleotide, wherein the branch point sequence comprising B1, if present, is in a reverse orientation and on the opposite strand of the donor polynucleotide relative to the branch point sequence comprising B2, wherein B1 and B2 each comprise a nucleotide sequence comprising nucleobases selected from the group consisting of: adenine, guanine, thymine and cytosine, wherein c and e are integers whose value indicates the number of nucleotides comprising B1 and B2, respectively, wherein c=0 or 5-7, wherein e=5-7;

(b) P1 and P2 are polypyrimidine tracts each comprising a nucleotide sequence comprising nucleobases selected from the group consisting of: adenine, guanine, thymine and cytosine, wherein a and g are integers whose value indicates the number of nucleotides comprising P1 and P2, respectively, wherein a=9-20 and g=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2; and (c) S1, S2 and S3, if any are present, are each delimiter sequences comprising one or more nucleotides comprising nucleobases selected from the group consisting of: adenine, guanine, thymine and cytosine, wherein b, d and f are each integers whose value indicates the number of nucleotides comprising the delimiter sequence, respectively, wherein b and f=1-20, wherein d=1-40, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B2 and P2 comprise a sense strand and B2 and P2 comprise the first and second splicing signals, respectively, thereby correcting the mutation and providing splicing signals to control processing of a pre-mRNA transcribed from the gDNA, wherein when the donor polynucleotide is inserted into the DSB in the second orientation, B1 and P1 comprise a sense strand and B1 and P1 provide the first and second splicing signals, respectively, thereby correcting the mutation and providing splicing signals to control processing of a pre-mRNA transcribed from the gDNA, and wherein when the donor polynucleotide is introduced into the cell in combination with a site-directed nuclease, a non-homologous end-joining (NHEJ) DNA repair pathway inserts the donor polynucleotide into a DSB introduced into the gDNA by the site-directed nuclease at a location proximal to the mutation, thereby correcting the mutation.

In some embodiments, the donor polynucleotide comprises a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

5'-[E1]a-X1-[P1]b-[S1]c-[B]d-[S2]e-[P2]f-X2-[E2]g-3', wherein (a) B is a branch point sequence comprising a nucleotide sequence that conforms to a branch point consensus sequence on each strand of the donor polynucleotide, wherein B comprises a nucleotide sequence comprising nucleobases selected from the group consisting of: adenine, guanine, thymine and cytosine, wherein d is an integer whose value indicates the number of nucleotides comprising B, wherein d=5-7;

(b) P1 and P2 are polypyrimidine tracts each comprising a nucleotide sequence comprising nucleobases selected from the group consisting of: adenine, guanine, thymine and cytosine, wherein b and f are integers whose value indicates the number of nucleotides comprising P1 and P2, respectively, wherein b=9-20 and f=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2;

(c) E1 and E2 are each exonic sequences each comprising a nucleotide sequence which corrects the mutation, wherein the nucleotide sequence comprises nucleobases selected from the group consisting of: adenine, guanine, thymine and cytosine, wherein a and g are integers whose value indicates the number of nucleotides comprising E1 and E2, respectively, wherein the exonic sequence comprising E1 is in a reverse orientation and on the opposite strand of the donor polynucleotide relative to the exonic sequence comprising E2, wherein the nucleotide sequences comprising E1 and E2 are not complementary;

(d) X1 and X2 are each nucleotide sequences comprising a 3' splice site, wherein the nucleotide sequence comprising X1 is in the reverse orientation and on the opposite strand relative to the nucleotide sequence comprising X2; and (e) S1 and S2, if either is present, are each delimiter sequences comprising one or more nucleotides comprising nucleobases selected from the group consisting of: adenine, guanine, thymine and cytosine, wherein c and e are each integers whose value indicates the number of nucleotides comprising the delimiter sequence, respectively, wherein c and e=1-20 wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in the first orientation, B, P2, E2 and X2 and comprise a sense strand, wherein B, P2 and X2 comprise the first, second and third splicing signal, respectively, thereby correcting the mutation and providing splicing signals to control processing of a pre-mRNA transcribed from the gDNA, wherein when the donor polynucleotide is inserted into the DSB in a second orientation, B, P1, E1 and X1 comprise a sense strand, wherein B, P1 and X1 comprise the first, second and third splicing signal, respectively, thereby correcting the mutation and providing splicing signals to control processing of a pre-mRNA transcribed from the gDNA, and wherein, when the donor polynucleotide is introduced into the cell in combination with a site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

5'-[E1]a-X1-[P1]b-[S1]c-[B1]d-[S2]e-[B2]f-[S2]g-[P2]h-X2-[E2]i-3', wherein (a) B1, if present, and B2 are each branch point sequences, wherein B2 comprises a nucleotide sequence that conforms to a branch point consensus sequence on each strand of the donor polynucleotide, wherein the branch point sequence comprising B1, if present, is in a reverse orientation and on the opposite strand of the donor polynucleotide relative to the branch point sequence comprising B2, wherein B1 and B2 each comprise a nucleotide sequence comprising nucleobases selected from the group consisting of: adenine, guanine, thymine and cytosine, wherein d and f are integers whose value indicates the number of nucleotides comprising B1 and B2, respectively, wherein d and f=5-7;

(b) P1 and P2 are polypyrimidine tracts each comprising a nucleotide sequence comprising nucleobases selected from the group consisting of: adenine, guanine, thymine and cytosine, wherein b and h are integers whose value indicates the number of nucleotides comprising P1 and P2, respectively, wherein b=9-20 and h=9-20, wherein the nucleotide sequence comprising P1 and P2 are each about 100%, about 90%-100%, about 80%-90% pyrimidine nucleobases, wherein P1 is in the reverse orientation and on the opposite strand of the donor polynucleotide relative to P2;

(c) E1 and E2 are each exonic sequences each comprising a nucleotide sequence which corrects the mutation, wherein the nucleotide sequence comprises nucleobases selected from the group consisting of: adenine, guanine, thymine and cytosine, wherein a and i are integers whose value indicates the number of nucleotides comprising E1 and E2, respectively, wherein the exonic sequence comprising E1 is in the reverse orientation and on the opposite strand relative to the exonic sequence comprising E2, wherein the nucleotide sequences comprising E1 and E2 are not complementary;

(d) X1 and X2 each comprise a nucleotide sequence comprising a 3' splice site, wherein the nucleotide sequence of X1 is in a reverse orientation and on the opposite strand of the donor polynucleotide relative to the nucleotide sequence of X2; and (e) S1, S2 and S3, if any present, are each delimiter sequences comprising one or more nucleotides comprising nucleobases selected from the group consisting of: adenine, guanine, thymine and cytosine, wherein c, e and g are each integers whose value indicates the number of nucleotides comprising the delimiter sequence, respectively, wherein c and g=1-20, wherein e=1-40, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in a first orientation, B2, P2, E2 and X2 comprise a sense strand, wherein B2, P2 and X2 comprise the first, second and third splicing signal, respectively, thereby correcting the mutation and providing splicing signals to control processing of a pre-mRNA transcribed from the gDNA, wherein when the donor polynucleotide is inserted into the DSB in a second orientation, B1, P1, E1 and X1 comprise a sense strand, wherein B1, P1 and X1 comprise the first, second and third splicing signal, respectively, thereby correcting the mutation and providing splicing signals to control processing of a pre-mRNA transcribed from the gDNA, and wherein, when the donor polynucleotide is introduced into the cell in combination with a site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation.

In some embodiments, the disclosure provides a donor polynucleotide comprising a non-replicative double-stranded DNA molecule (dsDNA) comprising (i) a first strand comprising from 5' to 3' a first nucleotide sequence which corrects a disease-causing mutation in a genomic DNA molecule (gDNA) in a cell, wherein the disease-causing mutation is a protein-coding mutation proximal to a 3' splice site, wherein the first strand comprises a first intronic sequence and a first exonic sequence, wherein the first exonic sequence corrects the mutation, wherein the first strand comprises one or more splicing signals to control processing of a precursor mRNA (pre-mRNA) transcribed from the gDNA; and (ii) a second strand comprising from 5' to 3' a second nucleotide sequence which corrects a disease-causing mutation in a gDNA in a cell, wherein the disease-causing mutation is a protein-coding mutation proximal to a 3' splice site, wherein the second strand comprises a second intronic sequence and a second exonic sequence, wherein the second exonic sequence corrects the mutation, wherein the second strand comprises one or more splicing signals to control processing of a pre-mRNA transcribed from the gDNA, wherein the second strand is complementary to the first strand, and wherein the first strand and the second strand each comprise the formula:

5'-[E1]a-X1-[P1]b-[S1]c-[B1]d-[S2]e-[B2]f-[S2]g-[P2]h-X2-[E2]i-3', wherein (a) E1 and E2 each are exonic sequences each comprising a nucleotide sequence which corrects the mutation, wherein the nucleotide sequence comprises nucleobases selected from the group consisting of: adenine, guanine, thymine and cytosine, wherein a and c are integers whose value indicates the number of nucleotides comprising E1 and E2, respectively, wherein the exonic sequence comprising E1 is in the reverse orientation and on the opposite strand relative to the exonic sequence comprising E2, wherein the nucleotide sequences comprising E1 and E2 are not complementary;

(b) Y1 and Y2 each comprise a nucleotide sequence comprising a 5' splice site, wherein the nucleotide sequence of Y1 is in a reverse orientation and on the opposite strand of the donor polynucleotide relative to the nucleotide sequence of Y2; and (c) S1, if present, is a delimiter sequence comprising one or more nucleotides comprising nucleobases selected from the group consisting of: adenine, guanine, thymine and cytosine, wherein b is an integers whose value indicates the number of nucleotides comprising the delimiter sequence, wherein b=1=50, wherein the donor polynucleotide is about 10-500, about 10-400, about 10-300, about 10-200, about 10-100, about 20-80, about 30-70, or about 40-60 nucleotides in length, wherein the donor polynucleotide is configured for bi-directional insertion into a double-stranded DNA break (DSB), wherein when the donor polynucleotide is inserted into the DSB in a first orientation, E2 and Y2 comprise a sense strand and E2 comprises the splicing signal, thereby correcting the mutation and providing splicing signals to control processing of a pre-mRNA transcribed from the gDNA, wherein when the donor polynucleotide is inserted into the DSB in a second orientation, E1 and Y1 comprise a sense strand and E1 comprises the splicing signal, thereby correcting the mutation and providing splicing signals to control processing of a pre-mRNA transcribed from the gDNA and wherein when the donor polynucleotide is introduced into the cell in combination with a site-directed nuclease a non-homologous end-joining (NHEJ) DNA repair pathway inserts the donor polynucleotide into a DSB introduced into the gDNA by the site-directed nuclease at a location proximal to the mutation, thereby correcting the mutation.

In some embodiments, the exonic sequence comprising the sense strand corrects the mutation. In some embodiments, the nucleotide sequence comprising a 3' splice site comprising the sense strand corrects the mutation. In some embodiments, the nucleotide sequence comprising a 5' splice site comprising the sense strand corrects the mutation. In some embodiments, the nucleotide sequence comprising a polypyrimidine tract comprising the sense strand corrects the mutation. In some embodiments, the nucleotide sequence comprising a branch point sequence comprising the sense strand corrects the mutation.

In some embodiments, the 5' most nucleotide of each strand of any of the donor polynucleotides provided by the disclosure comprises a 5' phosphate group. In some embodiments, the donor polynucleotide comprises two blunt ends.

In some embodiments, the donor polynucleotide comprises one blunt end and comprises one end comprising an overhang (e.g. a 5' or 3' overhang).

In some embodiments, the donor polynucleotide comprises a nucleotide sequence comprising one or more nucleotides that prevent the site-directed nuclease from recognizing and cleaving the donor polynucleotide.

In some embodiments, the disclosure provides a donor polynucleotide comprising a non-replicative double-stranded DNA molecule (dsDNA) comprising a nucleotide sequence which corrects a mutation that causes Glycogen Storage Disease 1a in a genomic DNA molecule (gDNA) in a cell, wherein the mutation is located in the human G6PC gene on human chromosome 17q21 and results in the amino acid substitution R83C or R83H, the donor polynucleotide comprising:

(i) a first strand comprising from 5' to 3' a nucleotide sequence comprising an exonic sequence which corrects the mutation, wherein the exonic sequence comprises a codon encoding arginine (R) corresponding to the codon at position 83 in the G6PC gene, and a nucleotide sequence comprising one or more splicing signals to control processing of a precursor mRNA (pre-mRNA) transcribed from the genomic DNA molecule, wherein the one or more splicing signals is a combination of a 3' splice site, a polypyrimidine tract, and a branch point sequence; and (ii) a second strand comprising a nucleotide sequence complementary to the first strand, wherein the donor polynucleotide is about 40-70 nucleotides in length and comprises two blunt ends, wherein the 5' most nucleotide of each strand of the donor polynucleotide comprises a 5' phosphate moiety, wherein when the donor polynucleotide is introduced into the cell in combination with an site-directed nuclease a non-homologous end-joining (NHEJ) DNA repair pathway inserts the donor polynucleotide into a double-stranded DNA break (DSB) introduced into the gDNA by the site-directed nuclease at a location proximal to the mutation, wherein the insertion of the donor polynucleotide forms an exon in the gDNA comprising the exonic sequence that corrects the mutation, wherein the splicing signals direct the inclusion of the exon into an mRNA, thereby correcting the mutation. In some embodiments, the branch point sequence comprises the nucleotide sequence TTCAT, wherein the polypyrimidine tract comprises the nucleotide sequence CTTGTTCTGTTTTTTT (SEQ ID NO: 109), wherein the 3' splice site comprises the nucleotide sequence TAG, and wherein the exonic sequence comprises the nucleotide sequence GATCTCTTTGGACAGCGCCCTTACT (SEQ ID NO: 110).

In some embodiments, the nucleotide sequence of the donor polynucleotide is set forth in SEQ ID NO: 30 (CH34 54-0)

In some embodiments, the nucleotide sequence of the donor polynucleotide is set forth in SEQ ID NO: 20 (CH32 50-0)

Methods of Making and Testing Donor Polynucleotides

The donor polynucleotides provided by the disclosure are produced by suitable DNA synthesis method or means known in the art. DNA synthesis is the natural or artificial creation of deoxyribonucleic acid (DNA) molecules. The term DNA synthesis refers to DNA replication, DNA biosynthesis (e.g., in vivo DNA amplification), enzymatic DNA synthesis (e.g., polymerase chain reaction (PCR); in vitro DNA amplification) or chemical DNA synthesis.

In some embodiments, each strand of the donor polynucleotide is produced by oligonucleotide synthesis. Oligonucleotide synthesis is the chemical synthesis of relatively short fragments or strands of single-stranded nucleic acids with a defined chemical structure (sequence). Methods of oligonucleotide synthesis are known in the art (see e.g., Reese (2005) Organic & Biomolecular Chemistry 3(21): 3851). The two strands can then be annealed together or duplexed to form a donor polynucleotide.

In some aspects, the insertion of a donor polynucleotide into a DSB is determined by a suitable method known in the art. For example, after the insertional event, the nucleotide sequence of PCR amplicons generated using PCR primer that flank the DSB site is analyzed for the presence of the nucleotide sequence comprising the donor polynucleotide. Next-generation sequencing (NGS) techniques are used to determine the extent of donor polynucleotide insertion into a DSB analyzing PCR amplicons for the presence or absence of the donor polynucleotide sequence. Further, since each donor polynucleotide is a linear, dsDNA molecule, which can insert in either of two orientations, NGS analysis can be used to determine the extent of insertion of the donor polynucleotide in either direction.

In some aspects, the insertion of the donor polynucleotide and its ability to correct a mutation is determined by nucleotide sequence analysis of mRNA transcribed from the gDNA into which the donor polynucleotide is inserted. An mRNA transcribed from gDNA containing an inserted donor polynucleotide is analyzed by a suitable method known in the art. For example, conversion of mRNA extracted from cells treated or contacted with a donor polynucleotide or system provided by the disclosure is enzymatically converted into cDNA, which is further by analyzed by NGS analysis to determine the extent of mRNA molecule comprising the corrected mutation.

In other aspects, the insertion of a donor polynucleotide and its ability to correct a mutation is determined by protein sequence analysis of a polypeptide translated from an mRNA transcribed from the gDNA into which the donor polynucleotide is inserted. In some embodiments, a donor polynucleotide corrects or induces a mutation by the incorporation of a codon into an exon that makes an amino acid change in a gene comprising a gDNA molecule, wherein translation of an mRNA from the gene containing the inserted donor polynucleotide generates a polypeptide comprising the amino acid change. The amino acid change in the polypeptide is determined by protein sequence analysis using techniques including, but not limited to, Sanger sequencing, mass spectrometry, functional assays that measure an enzymatic activity of the polypeptide, or immunoblotting using an antibody reactive to the amino acid change.

Use of Donor Polynucleotides
DNA Repair Pathways

The repair of DNA breaks (e.g. DSBs) in cells is accomplished primarily through two DNA repair pathways, namely the non-homologous end joining (NHEJ) repair pathway and homology-directed repair (HDR) pathway.

During NHEJ, the Ku70/80 heterodimers bind to DNA ends and recruit the DNA protein kinase (DNA-PK) (Cannan & Pederson (2015) J Cell Physiol 231:3-14). Once bound, DNA-PK activates its own catalytic subunit (DNA-PKcs) and further enlists the endonuclease Artemis (also known as SNM1c). At a subset of DSBs, Artemis removes excess single-strand DNA (ssDNA), and generates a substrate that will be ligated by DNA ligase IV. DNA repair by NHEJ involves blunt-end ligation mechanism independent of sequence homology via the canonical DNA-PKcs/Ku70/80 complex. During the cell cycle, NHEJ occurs predominantly in G0/G1 and G2 (Chiruvella et al., (2013) Cold Spring Harb Perspect Biol 5:a012757). Current studies have shown that NHEJ is the only DSB repair pathway active in G0 and G1, while HDR functions primarily in the S and G2 phases, playing a major role in the repair of replication-associated DSBs (Karanam et al., (2012) Mol Cell 47:320-329; Li and Xu (2016) Acta Biochim Biophys Sin 48(7): 641-646). NHEJ, unlike HDR, is active in both dividing and non-dividing cells, not just dividing cells, which enables the development of therapies based on genome editing for non-dividing adult cells, such as, for example, cells of the eye, brain, pancreas, or heart.

During DNA repair by HDR, DSB ends are resected to expose 3' ssDNA tails, primarily by the MRE11-RAD50-NBS1 (MRN) complex (Heyer et al., (2010) Annu Rev Genet 44: 113-139). Under physiological conditions, the adjacent sister chromatid will be used as a repair template, providing a homologous sequence, and the ssDNA will invade the template mediated by the recombinase Rad51, displacing an intact strand to form a D-loop. D-loop extension is followed by branch migration to produce double-Holliday junctions, the resolution of which completes the repair cycle. HDR often requires error-prone polymerases, yet is typically viewed as error-free (Li and Xu (2016) Acta Biochim Biophys Sin 48(7): 641-646)

A third repair mechanism is microhomology-mediated end joining (MMEJ), also referred to as "Alternative NHEJ", in which the genetic outcome is similar to NHEJ in that small deletions and insertions can occur at the cleavage site. MMEJ makes use of homologous sequences of a few nucleotides flanking the DNA break site to drive a more favored DNA end joining repair outcome, and recent reports have further elucidated the molecular mechanism of this process (Cho and Greenberg, (2015) Nature 518:174-176; Mateos-Gomez et al., (2015) Nature 518, 254-257; Ceccaldi et al., (2015) Nature 528, 258-262.

Use of Donor Polynucleotides to Correct or Induce a Mutation

In some embodiments, a donor polynucleotide provided by the disclosure is used to correct or induce a mutation in a gDNA in a cell by insertion of the donor polynucleotide into a target nucleic acid (e.g., gDNA) at a cleavage site (e.g, a DSB) induced by a site-directed nuclease, such as those described herein. In some embodiments, NHEJ DNA repair mechanisms of the cell repair the DSB using the donor polynucleotide, thereby inserting the donor polynucleotide into the DSB and adding the nucleotide sequence of the donor polynucleotide to the gDNA. In some embodiments, the donor polynucleotide comprises a nucleotide sequence which corrects a disease-causing mutation in a gDNA in a cell and comprises a nucleotide sequence comprising one or more splicing signals to control processing of a precursor mRNA (pre-mRNA) transcribed from the gDNA. In some embodiments, the donor polynucleotide is inserted at a location proximal to the mutation, thereby correcting the mutation. In some embodiments, the mutation is a substitution, missense, nonsense, insertion, deletion or frameshift mutation. In some embodiments the mutation is in an exon. In some embodiments, the mutation is a substitution, insertion or deletion and is located in an intron. In some embodiments, the mutation is proximal to a splicing signal in a gDNA. In some embodiments, the mutation is proximal to a 3' splice site in a gDNA. In some embodiments, the mutation is proximal to a 5' splice site in a gDNA. In some embodiments, the mutation is in a splicing signal, or a sequence comprising a splicing signal in a gDNA. In some embodiments, the mutation is in a 3' splice site in a gDNA. In some embodiments, the mutation is in a 5' splice site in a gDNA. In some embodiments, the mutation is in a polypyrimidine tract. In some embodiments the mutation is in a branch point sequence. In some embodiments, the mutation is a protein-coding mutation. In some embodiments, the mutation is associated with or causes a disease.

In some embodiments, the nucleotide sequence which corrects a disease-causing mutation in a gDNA in a cell comprises a branch point sequence. In some embodiments, the nucleotide sequence which corrects a disease comprises a polypyrimidine tract. In some embodiments, the donor polynucleotide is inserted into the DSB by NHEJ DNA repair. In some embodiments, the donor polynucleotide, a portion of the donor polynucleotide is inserted into the target nucleic acid cleavage site by NHEJ DNA repair. In certain aspects, insertion of a donor polynucleotide into the target nucleic acid via NHEJ repair can result in, for example, mutations, deletions, alterations, integrations, gene correction, gene replacement, gene tagging, transgene insertion, nucleotide deletion, gene disruption, translocations and/or gene mutation of the endogenous gene sequence.

In some embodiments, the disease-causing mutation causes the disease Glycogen Storage Disease 1a (GSD1a). In some embodiments, the disease-causing mutation is located in the human G6PC gene on human chromosome 17q21. In some embodiments, the disease causing mutation is located in the G6PC gene and results in an R83C, an R83H, or an E110K amino acid substitution in the human G6PC protein. In some embodiments, the disease-causing mutation in the G6PC gene results in an R83C amino acid substitution in the human G6PC protein. In some embodiments, the disease-causing mutation in the G6PC gene results in an R83H amino acid substitution in the human G6PC protein.

In some embodiments, the disease-causing mutation in the G6PC gene results in an E110K amino acid substitution in the human G6PC protein. In some embodiments, the disclosure provides donor polynucleotides used to repair a DSB introduced into a target nucleic acid molecule (e.g., gDNA) by a site-directed nuclease (e.g., Cas9) in a cell. In some embodiments, the donor polynucleotide is used by the non-homologous end joining (NHEJ) repair pathway of the cell to repair the DSB in the target nucleic acid molecule. In some embodiments, the site-directed nuclease is a Cas nuclease. In some embodiments, the Cas nuclease is Cas9. The site-directed nucleases described herein can introduce DSB in target nucleic acids (e.g., genomic DNA) in a cell. The introduction of a DSB in the genomic DNA of a cell, induced by a site-directed nuclease, will stimulate the endogenous DNA repair pathways, such as those described herein. In contrast, repair of an DSB by NHEJ occurs in non-dividing cells, but does not require the use of a homologous polynucleotide sequence for repair. However, the NHEJ pathway can be used to insert a polynucleotide (e.g., a donor polynucleotide) into the DSB during repair.

Accordingly, in some embodiments, the disclosure provides a donor polynucleotide comprising a non-replicative double-stranded DNA molecule (dsDNA) comprising a nucleotide sequence which corrects a mutation that causes Glycogen Storage Disease 1a in a genomic DNA molecule (gDNA) in a cell, wherein the mutation is located in the human G6PC gene on human chromosome 17q21 and results in the amino acid substitution R83C or R83H, the donor polynucleotide comprising:

(i) a first strand comprising from 5' to 3' a nucleotide sequence comprising an exonic sequence which corrects the mutation, wherein the exonic sequence comprises a codon encoding arginine (R) corresponding to the codon at position 83 in the G6PC gene, and a nucleotide sequence comprising one or more splicing signals to control processing of a precursor mRNA (pre-mRNA) transcribed from the genomic DNA molecule, wherein the one or more splicing signals is a combination of a 3' splice site, a polypyrimidine tract, and a branch point sequence; and (ii) a second strand comprising a nucleotide sequence complementary to the first strand, wherein the donor polynucleotide is about 40-70 nucleotides in length and comprises two blunt ends, wherein the 5' most nucleotide of each strand of the donor polynucleotide comprises a 5' phosphate moiety, wherein when the donor polynucleotide is introduced into the cell in combination with an site-directed nuclease a non-homologous end-joining (NHEJ) DNA repair pathway inserts the donor polynucleotide into a double-stranded DNA break (DSB) introduced into the gDNA by the site-directed nuclease at a location proximal to the mutation, wherein the insertion of the donor polynucleotide forms an exon in the gDNA comprising the exonic sequence that corrects the mutation, wherein the splicing signals direct the inclusion of the exon into an mRNA, thereby correcting the mutation. In some embodiments, the branch point sequence comprises the nucleotide sequence TTCAT, wherein the polypyrimidine tract comprises the nucleotide sequence CTTGTTCTGTTTTTTT (SEQ ID NO: 109), wherein the 3' splice site comprises the nucleotide sequence TAG, and wherein the exonic sequence comprises the nucleotide sequence GATTCTCTTTGGACAGCGCCCTTACT (SEQ ID NO: 110).

In some embodiments, the nucleotide sequence of the donor polynucleotide is set forth in SEQ ID NO: 30 (CH34 54-0). In some embodiments, the nucleotide sequence of the donor polynucleotide is set forth in SEQ ID NO: 20 (CH32 50-0).

In some embodiments, the disease-causing mutation causes the disease Pompe's Disease. In some embodiments, the disease-causing mutation is located in the human glucosidase alpha (GAA) gene on human chromosome 17q25.3. In some embodiments, the mutation is in a splicing signal of GAA that results in mRNA transcripts of the GAA gene lacking exon2. In some embodiments, the mutation is in a splicing signal of GAA that results in the activation of one or more cryptic splice sites. A cryptic splice site is an mRNA sequence that encodes splicing signals and has the potential for interacting with the spliceosome, but is not normally used for mRNA splicing to generate a functional protein product. Mutations in a gene can activate cryptic splicing signals that result in the production of aberrant protein products.

Accordingly, in some embodiments, the disclosure provides a donor polynucleotide comprising a non-replicative dsDNA molecule comprising a nucleotide sequence which corrects a mutation that causes Pompe's Disease in a gDNA molecule in a cell, wherein the mutation is in a splicing signal of GAA that results in mRNA transcripts of the GAA gene lacking exon2 and/or activation of one or more cryptic splice sites, the donor polynucleotide comprising:

(i) a first strand comprising from 5' to 3' a first nucleotide sequence which corrects the mutation, wherein the first strand comprises a first intronic sequence, wherein the first intronic sequence corrects the mutation, wherein the first strand comprises one or more splicing signals to control processing of a precursor mRNA (pre-mRNA) transcribed from the gDNA, wherein the one or more splicing signals comprises a combination of a 3' splice site, a polypyrimidine tract, and a branch point sequence; and (ii) a second strand comprising from 5' to 3' a second intronic sequence, wherein the second intronic sequence corrects the mutation, wherein the second strand comprises one or more splicing signals to control processing of a pre-mRNA transcribed from the gDNA, wherein the one or more splicing signals comprises a combination of a 3' splice site, a polypyrimidine tract, and a branch point sequence, wherein the second strand is complementary to the first strand wherein the donor polynucleotide is about 10-500, about 10-400, about 10-300, about 10-200, about 10-100, about 20-80, about 30-70, or about 40-60 nucleotides in length and comprises two blunt ends, wherein the 5' most nucleotide of each strand of the donor polynucleotide comprises a 5' phosphate moiety, wherein when the donor polynucleotide is introduced into the cell in combination with a site-directed nuclease a NHEJ DNA repair pathway inserts the donor polynucleotide into a DSB introduced into the gDNA by the site-directed nuclease at a location proximal to the mutation, wherein the donor polynucleotide is configured for bi-directional insertion into a DSB break, wherein insertion in either direction forms a 3' splice site, a polypyrimidine tract, and a branch point sequence that corrects the mutation, wherein the splicing signals direct the inclusion of exon2 into an mRNA, thereby correcting the mutation.

In some embodiments, the nucleotide sequence of the donor polynucleotide is set forth in SEQ ID NO: 63 (GAA_50-0).

Accordingly, in some embodiments, a single donor polynucleotide or multiple copies of the same donor polynucleotide are provided. In other embodiments, two or more donor polynucleotides are provided such that repair may occur at two or more target sites. For example, different donor polynucleotides are provided to repair a single gene in a cell, or two different genes in a cell. In some embodiments, the different donor polynucleotides are provided in independent copy numbers.

In some embodiments, the donor polynucleotide are incorporated into the target nucleic acid as an insertion mediated by non-homologous end joining (NHEJ). In some embodiments, the donor polynucleotide sequence has no similarity to the nucleic acid sequence near the cleavage site. In some embodiments, a single donor polynucleotide or multiple copies of the same donor polynucleotide are provided. In other embodiments, two or more donor polynucleotides having different sequences are inserted at two or more sites by non-homologous end joining. In some embodiments, the different donor polynucleotides are provided in independent copy numbers.

CRISPR/Cas Nuclease Systems

Naturally-occuring CRISPR/Cas systems are genetic defense systems that provides a form of acquired immunity in prokaryotes. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see e.g., Koonin et al., (2017) Curr Opin Microbiol 37:67-78).

Engineered versions of CRISPR/Cas systems has been developed in numerous formats to mutate or edit genomic DNA of cells from other species. The general approach of using the CRISPR/Cas system involves the heterologous expression or introduction of a site-directed nuclease (e.g.: Cas nuclease) in combination with a guide RNA (gRNA) into a cell, resulting in a DNA cleavage event (e.g., the formation a single-strand or double-strand break (SSB or DSB)) in the backbone of the cell's genomic DNA at a precise, targetable location. The manner in which the DNA cleavage event is repaired by the cell provides the opportunity to edit the genome by the addition, removal, or modification (substitution) of DNA nucleotide(s) or sequences (e.g. genes).

Cas Nuclease

In some embodiments, the disclosure provides compositions and systems (e.g. an engineered CRISPR/Cas system) comprising a site-directed nuclease, wherein the site-directed nuclease is a Cas nuclease. The Cas nuclease may comprise at least one domain that interacts with a guide RNA (gRNA). Additionally, the Cas nuclease are directed to a target sequence by a guide RNA. The guide RNA interacts with the Cas nuclease as well as the target sequence such that, once directed to the target sequence, the Cas nuclease is capable of cleaving the target sequence. In some embodiments, the guide RNA provides the specificity for the cleavage of the target sequence, and the Cas nuclease are universal and paired with different guide RNAs to cleave different target sequences.

In some embodiments, the CRISPR/Cas system comprise components derived from a Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease are from a Type-II CRISPR/Cas system (e.g., a Cas9 protein from a CRISPR/Cas9 system). In some embodiments, the Cas nuclease are from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

A Type-II CRISPR/Cas system component are from a Type-IIA, Type-IIB, or Type-IIC system. Cas9 and its orthologs are encompassed. Non-limiting exemplary species that the Cas9 nuclease or other components are from include *Streptococcus pyogenes, Streptococcus thermophilus, Streptococcus* sp., *Staphylococcus aureus, Listeria innocua, Lactobacillus gasseri, Francisella novicida, Wolinella succinogenes, Sutterella wadsworthensis, Gamma proteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria,* or *Acaryochloris marina*. In some embodiments, the Cas9 protein are from *Streptococcus pyogenes* (SpCas9). In some embodiments, the Cas9 protein are from *Streptococcus thermophilus* (StCas9). In some embodiments, the Cas9 protein are from *Neisseria meningitides* (NmCas9). In some embodiments, the Cas9 protein are from *Staphylococcus aureus* (SaCas9). In some embodiments, the Cas9 protein are from *Campylobacter jejuni* (Cj Cas9).

In some embodiments, a Cas nuclease may comprise more than one nuclease domain. For example, a Cas9 nuclease may comprise at least one RuvC-like nuclease domain (e.g. Cpf1) and at least one HNH-like nuclease domain (e.g. Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease uis modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the *S. pyogenes* Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the *S. pyogenes* Cas9 nuclease). In some embodiments, the nuclease system described herein comprises a nickase and a pair of guide RNAs that are complementary to the sense and antisense strands of the target sequence, respectively. The guide RNAs directs the nickase to target and introduce a DSB by generating a nick on opposite strands of the target sequence (i.e., double nicking). Chimeric Cas9 nucleases are used, where one domain or region of the protein is replaced by a portion of a different protein. For example, a Cas9 nuclease domain is replaced with a domain from a different nuclease such as Fok1. A Cas9 nuclease is a modified nuclease.

In alternative embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

Guide RNAs (gRNAs)

Engineered CRISPR/Cas systems comprise at least two components: 1) a guide RNA (gRNA) molecule and 2) a Cas nuclease, which interact to form a gRNA/Cas nuclease complex. A gRNA comprises at least a user-defined targeting domain termed a "spacer" comprising a nucleotide sequence and a CRISPR repeat sequence. In engineered CRISPR/Cas systems, a gRNA/Cas nuclease complex is targeted to a specific target sequence of interest within a target nucleic acid (e.g. a genomic DNA molecule) by generating a gRNA comprising a spacer with a nucleotide sequence that is able to bind to the specific target sequence in a complementary fashion. Thus, the spacer provides the targeting function of the gRNA/Cas nuclease complex.

In naturally-occurring type II-CRISPR/Cas systems, the "gRNA" is comprised of two RNA strands: 1) a CRISPR RNA (crRNA) comprising the spacer and CRISPR repeat sequence, and 2) a trans-activating CRISPR RNA (tracrRNA). In Type II-CRISPR/Cas systems, the portion of the crRNA comprising the CRISPR repeat sequence and a portion of the tracrRNA hybridize to form a crRNA: tracrRNA duplex, which interacts with a Cas nuclease (e.g., Cas9). As used herein, the terms "split gRNA" or "modular gRNA" refer to a gRNA molecule comprising two RNA strands, wherein the first RNA strand incorporates the crRNA function(s) and/or structure and the second RNA strand incorporates the tracrRNA function(s) and/or structure, and wherein the first and second RNA strands partially hybridize.

Accordingly, in some embodiments, a gRNA provided by the disclosure comprises two RNA molecules. In some embodiments, the gRNA comprises a CRISPR RNA (crRNA) and a trans-activating CRISPR RNA (tracrRNA). In some embodiments, the gRNA is a split gRNA. In some embodiments, the gRNA is a modular gRNA. In some embodiments, the split gRNA comprises a first strand comprising, from 5' to 3', a spacer, and a first region of complementarity; and a second strand comprising, from 5' to 3', a second region of complementarity; and optionally a tail domain.

In some embodiments, the crRNA comprises a spacer comprising a nucleotide sequence that is complementary to and hybridizes with a sequence that is complementary to the target sequence on a target nucleic acid (e.g., a genomic DNA molecule). In some embodiments, the crRNA comprises a region that is complementary to and hybridizes with a portion of the tracrRNA.

In some embodiments, the tracrRNA may comprise all or a portion of a wild-type tracrRNA sequence from a naturally-occurring CRISPR/Cas system. In some embodiments, the tracrRNA may comprise a truncated or modified variant of the wild-type tracr RNA. The length of the tracr RNA may depend on the CRISPR/Cas system used. In some embodiments, the tracrRNA may comprise 5, 6, 7, 8, 9, 10, 11, 12, 13, 14, 15, 16, 17, 18, 19, 20, 25, 30, 40, 50, 60, 70, 80, 90, 100, or more than 100 nucleotides in length. In certain embodiments, the tracrRNA is at least 26 nucleotides in length. In additional embodiments, the tracrRNA is at least 40 nucleotides in length. In some embodiments, the tracrRNA may comprise certain secondary structures, such as, e.g., one or more hairpins or stem-loop structures, or one or more bulge structures.

Single Guide RNA (sgRNA)

Engineered CRISPR/Cas nuclease systems often combine a crRNA and a tracrRNA into a single RNA molecule, referred to herein as a "single guide RNA" (sgRNA), by adding a linker between these components. Without being bound by theory, similar to a duplexed crRNA and tracrRNA, an sgRNA will form a complex with a Cas nuclease (e.g., Cas9), guide the Cas nuclease to a target sequence and activate the Cas nuclease for cleavage the target nucleic acid (e.g., genomic DNA). Accordingly, in some embodiments, the gRNA may comprise a crRNA and a tracrRNA that are operably linked. In some embodiments, the sgRNA may comprise a crRNA covalently linked to a tracrRNA. In some embodiments, the crRNA and the tracrRNA is covalently linked via a linker. In some embodiments, the sgRNA may comprise a stem-loop structure via base pairing between the crRNA and the tracrRNA. In some embodiments, a sgRNA comprises, from 5' to 3', a spacer, a first region of complementarity, a linking domain, a second region of complementarity, and, optionally, a tail domain.

Spacers

In some embodiments, the gRNAs provided by the disclosure comprise a spacer sequence. A spacer sequence is a sequence that defines the target site of a target nucleic acid (e.g.: DNA). The target nucleic acid is a double-stranded molecule: one strand comprises the target sequence adjacent to a PAM sequence and is referred to as the "PAM strand," and the second strand is referred to as the "non-PAM strand" and is complementary to the PAM strand and target sequence. Both gRNA spacer and the target sequence are complementary to the non-PAM strand of the target nucleic acid. The gRNA spacer sequence hybridizes to the complementary strand (e.g.: the non-PAM strand of the target nucleic acid/target site). In some embodiments, the spacer is sufficiently complementary to the complementary strand of the target sequence (e.g.: non-PAM strand), as to target a Cas nuclease to the target nucleic acid. In some embodiments, the spacer is at least 80%, 85%, 90% or 95% complementary to the non-PAM strand of the target nucleic acid. In some embodiments, the spacer is 100% complementary to the non-PAM strand of the target nucleic acid. In some embodiments, the spacer comprises 1, 2, 3, 4, 5, 6 or more nucleotides that are not complementary with the non-PAM strand of the target nucleic acid. In some embodiments, the spacer comprises 1 nucleotide that is not complementary with the non-PAM strand of the target nucleic acid. In some embodiments, the spacer comprises 2 nucleotides that are not complementary with the non-PAM strand of the target nucleic acid.

In some embodiments, the 5' most nucleotide of gRNA comprises the 5' most nucleotide of the spacer. In some embodiments, the spacer is located at the 5' end of the crRNA. In some embodiments, the spacer is located at the 5' end of the sgRNA. In some embodiments, the spacer is about 15-50, about 20-45, about 25-40 or about 30-35 nucleotides in length. In some embodiments, the spacer is about 19-22 nucleotides in length. In some embodiments the spacer is about 15, 16, 17, 18, 19, 20, 21, 22, 23, 24, 25, 26, 27, 28, 29 or 30 nucleotides in length. In some embodiments the spacer is 19 nucleotides in length. In some embodiments, the spacer is 20 nucleotides in length, in some embodiments, the spacer is 21 nucleotides in length.

In some embodiments, the nucleotide sequence of the target sequence and the PAM comprises the formula 5' $N_{19-21}$-N-R-G-3' (SEQ ID NO: 59), wherein N is any nucleotide, and wherein R is a nucleotide comprising the nucleobase adenine (A) or guanine (G), and wherein the three 3' terminal nucleic acids, N-R-G represent the *S. pyogenes* PAM. In some embodiments, the nucleotide sequence of the spacer is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, and/or presence of SNPs.

In some embodiments, the spacer comprise at least one or more modified nucleotide(s) such as those described herein. The disclosure provides gRNA molecules comprising a spacer which may comprise the nucleobase uracil (U), while any DNA encoding a gRNA comprising a spacer comprising the nucleobase uracil (U) will comprise the nucleobase thymine (T) in the corresponding position(s).

Methods of Making gRNAs

The gRNAs of the present disclosure is produced by a suitable means available in the art, including but not limited to in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in International Application PCT/US2013/30062. Accordingly, the present disclosure also includes polynucleotides, e.g., DNA, constructs and vectors are used to in vitro transcribe a gRNA described herein.

In some aspects, non-natural modified nucleobases are introduced into polynucleotides, e.g., gRNA, during synthesis or post-synthesis. In certain embodiments, modifications are on internucleoside linkages, purine or pyrimidine bases, or sugar. In particular embodiments, the modification is introduced at the terminal of a polynucleotide; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

In some aspects, enzymatic or chemical ligation methods are used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

Certain embodiments of the invention also provide nucleic acids, e.g., vectors, encoding gRNAs described herein. In some embodiments, the nucleic acid is a DNA molecule. In other embodiments, the nucleic acid is an RNA molecule. In some embodiments, the nucleic acid comprises a nucleotide sequence encoding a crRNA. In some embodiments, the nucleotide sequence encoding the crRNA comprises a spacer flanked by all or a portion of a repeat sequence from a naturally-occurring CRISPR/Cas system.

In some embodiments, the nucleic acid comprises a nucleotide sequence encoding a tracrRNA. In some embodiments, the crRNA and the tracrRNA is encoded by two separate nucleic acids. In other embodiments, the crRNA and the tracrRNA is encoded by a single nucleic acid. In some embodiments, the crRNA and the tracrRNA is encoded by opposite strands of a single nucleic acid. In other embodiments, the crRNA and the tracrRNA is encoded by the same strand of a single nucleic acid.

In some embodiments, the gRNAs provided by the disclosure are chemically synthesized by any means described in the art (see e.g., WO/2005/01248). While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together.

In some embodiments, the gRNAs provided by the disclosure are synthesized by enzymatic methods (e.g., in vitro transcription, IVT).

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In certain embodiments, more than one guide RNA can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

The guide RNA may target any sequence of interest via the targeting sequence (e.g.:spacer sequence) of the crRNA. In some embodiments, the degree of complementarity between the targeting sequence of the guide RNA and the target sequence on the target nucleic acid molecule is about 60%, 65%, 70%, 75%, 80%, 85%, 90%, 95%, 97%, 98%, 99%, or 100%. In some embodiments, the targeting sequence of the guide RNA and the target sequence on the target nucleic acid molecule is 100% complementary. In other embodiments, the targeting sequence of the guide RNA and the target sequence on the target nucleic acid molecule may contain at least one mismatch. For example, the targeting sequence of the guide RNA and the target sequence on the target nucleic acid molecule may contain 1, 2, 3, 4, 5, 6, 7, 8, 9, or 10 mismatches. In some embodiments, the targeting sequence of the guide RNA and the target sequence on the target nucleic acid molecule may contain 1-6 mismatches. In some embodiments, the targeting sequence of the guide RNA and the target sequence on the target nucleic acid molecule may contain 5 or 6 mismatches.

The length of the targeting sequence may depend on the CRISPR/Cas9 system and components used. For example, different Cas9 proteins from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence may comprise 18-24 nucleotides in length. In some embodiments, the targeting sequence may comprise 19-21 nucleotides in length. In some embodiments, the targeting sequence may comprise 20 nucleotides in length.

In some embodiments of the present disclosure, a CRISPR/Cas nuclease system includes at least one guide RNA. In some embodiments, the guide RNA and the Cas protein may form a ribonucleoprotein (RNP), e.g., a CRISPR/Cas complex. The guide RNA may guide the Cas protein to a target sequence on a target nucleic acid molecule (e.g., a genomic DNA molecule), where the the Cas protein cleaves the target nucleic acid. In some embodiments, the CRISPR/Cas complex is a Cpf1/guide RNA complex. In some embodiments, the CRISPR complex is a Type-II CRISPR/Cas9 complex. In some embodiments, the Cas protein is a Cas9 protein. In some embodiments, the CRISPR/Cas9 complex is a Cas9/guide RNA complex.

Engineered Nucleases

In additional embodiments, the donor polynucleotides provided by the disclosure are used in combination with a site-directed nuclease, wherein the site-directed nuclease is an engineered nuclease. Exemplary engineered nucleases are meganuclease (e.g., homing endonucleases), ZFN, TALEN, and megaTAL.

Naturally-occurring meganucleases may recognize and cleave double-stranded DNA sequences of about 12 to 40 base pairs, and are commonly grouped into five families. In some embodiments, the meganuclease are chosen from the LAGLIDADG family, the GIY-YIG family, the HNH family, the His-Cys box family, and the PD-(D/E)XK family. In some embodiments, the DNA binding domain of the meganuclease are engineered to recognize and bind to a sequence other than its cognate target sequence. In some embodiments, the DNA binding domain of the meganuclease are fused to a heterologous nuclease domain. In some embodiments, the meganuclease, such as a homing endonuclease, are fused to TAL modules to create a hybrid protein, such as a "megaTAL" protein. The megaTAL protein have improved DNA targeting specificity by recognizing the target sequences of both the DNA binding domain of the meganuclease and the TAL modules.

ZFNs are fusion proteins comprising a zinc-finger DNA binding domain ("zinc fingers" or "ZFs") and a nuclease domain. Each naturally-occurring ZF may bind to three consecutive base pairs (a DNA triplet), and ZF repeats are combined to recognize a DNA target sequence and provide sufficient affinity. Thus, engineered ZF repeats are combined to recognize longer DNA sequences, such as, e.g., 9-, 12-, 15-, or 18-bp, etc. In some embodiments, the ZFN comprise ZFs fused to a nuclease domain from a restriction endonuclease. For example, the restriction endonuclease is FokI. In some embodiments, the nuclease domain comprises a dimerization domain, such as when the nuclease dimerizes to be active, and a pair of ZFNs comprising the ZF repeats and the nuclease domain is designed for targeting a target sequence, which comprises two half target sequences recognized by each ZF repeats on opposite strands of the DNA molecule, with an interconnecting sequence in between (which is sometimes called a spacer in the literature). For example, the interconnecting sequence is 5 to 7 bp in length. When both ZFNs of the pair bind, the nuclease domain may dimerize and introduce a DSB within the interconnecting sequence. In some embodiments, the dimerization domain of the nuclease domain comprises a knob-into-hole motif to promote dimerization. For example, the ZFN comprises a knob-into-hole motif in the dimerization domain of FokI.

The DNA binding domain of TALENs usually comprises a variable number of 34 or 35 amino acid repeats ("modules" or "TAL modules"), with each module binding to a single DNA base pair, A, T, G, or C. Adjacent residues at positions 12 and 13 (the "repeat-variable di-residue" or RVD) of each module specify the single DNA base pair that the module binds to. Though modules used to recognize G may also have affinity for A, TALENs benefit from a simple code of recognition—one module for each of the 4 bases—which greatly simplifies the customization of a DNA-binding domain recognizing a specific target sequence. In some embodiments, the TALEN may comprise a nuclease domain from a restriction endonuclease. For example, the restriction endonuclease is FokI. In some embodiments, the nuclease domain may dimerize to be active, and a pair of TALENS is designed for targeting a target sequence, which comprises two half target sequences recognized by each DNA binding domain on opposite strands of the DNA molecule, with an interconnecting sequence in between. For example, each half target sequence is in the range of 10 to 20 bp, and the interconnecting sequence is 12 to 19 bp in length. When both TALENs of the pair bind, the nuclease domain may dimerize and introduce a DSB within the interconnecting sequence. In some embodiments, the dimerization domain of the nuclease domain may comprise a knob-into-hole motif to promote dimerization. For example, the TALEN may comprise a knob-into-hole motif in the dimerization domain of FokI.

Modified Nucleases

In certain embodiments, the nuclease is optionally modified from its wild-type counterpart. In some embodiments, the nuclease is fused with at least one heterologous protein domain. At least one protein domain is located at the N-terminus, the C-terminus, or in an internal location of the nuclease. In some embodiments, two or more heterologous protein domains are at one or more locations on the nuclease.

In some embodiments, the protein domain may facilitate transport of the nuclease into the nucleus of a cell. For example, the protein domain is a nuclear localization signal (NLS). In some embodiments, the nuclease is fused with 1-10 NLS(s). In some embodiments, the nuclease is fused with 1-5 NLS(s). In some embodiments, the nuclease is fused with one NLS. In other embodiments, the nuclease is fused with more than one NLS. In some embodiments, the nuclease is fused with 2, 3, 4, or 5 NLSs. In some embodiments, the nuclease is fused with 2 NLSs. In some embodiments, the nuclease is fused with 3 NLSs. In some embodiments, the nuclease is fused with no NLS. In some embodiments, the NLS may be a monopartite sequence, such as, e.g., the SV40 NLS, PKKKRKV (SEQ ID NO: 56) or PKKKRRV (SEQ ID NO: 57). In some embodiments, the NLS is a bipartite sequence, such as, e.g., the NLS of nucleoplasmin, KRPAATKKAGQAKKKK (SEQ ID NO: 58). In some embodiments, the NLS is genetically modified from its wild-type counterpart.

In some embodiments, the protein domain is capable of modifying the intracellular half-life of the nuclease. In some embodiments, the half-life of the nuclease may be increased. In some embodiments, the half-life of the nuclease is reduced. In some embodiments, the entity is capable of increasing the stability of the nuclease. In some embodiments, the entity is capable of reducing the stability of the nuclease. In some embodiments, the protein domain act as a signal peptide for protein degradation. In some embodiments, the protein degradation is mediated by proteolytic enzymes, such as, e.g., proteasomes, lysosomal proteases, or calpain proteases. In some embodiments, the protein domain comprises a PEST sequence. In some embodiments, the nuclease is modified by addition of ubiquitin or a polyubiquitin chain. In some embodiments, the ubiquitin is a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally downregulated protein-8 (NEDD8, also called Rub 1 in S. cerevisiae), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBL5).

In some embodiments, the protein domain is a marker domain. Non-limiting examples of marker domains include fluorescent proteins, purification tags, epitope tags, and reporter gene sequences. In some embodiments, the marker domain is a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain is a purification tag and/or an epitope tag. Non-limiting exemplary tags include glutathione-S-transferase (GST), chitin binding protein (CBP), maltose binding protein (MBP), thioredoxin (TRX), poly (NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His (HHHHHH; SEQ ID NO: 60), biotin carboxyl carrier protein (BCCP), and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the protein domain may target the nuclease to a specific organelle, cell type, tissue, or organ.

In further embodiments, the protein domain is an effector domain. When the nuclease is directed to its target nucleic acid, e.g., when a Cas9 protein is directed to a target nucleic acid by a guide RNA, the effector domain may modify or affect the target nucleic acid. In some embodiments, the effector domain is chosen from a nucleic acid binding domain, a nuclease domain, an epigenetic modification domain, a transcriptional activation domain, or a transcriptional repressor domain.

Certain embodiments of the invention also provide nucleic acids encoding the nucleases (e.g., a Cas9 protein) described herein provided on a vector. In some embodiments, the nucleic acid is a DNA molecule. In other embodiments, the nucleic acid is an RNA molecule. In some embodiments, the nucleic acid encoding the nuclease is an mRNA molecule. In certain embodiments, the nucleic acid is an mRNA encoding a Cas9 protein.

In some embodiments, the nucleic acid encoding the nuclease is codon optimized for efficient expression in one or more eukaryotic cell types. In some embodiments, the nucleic acid encoding the nuclease is codon optimized for efficient expression in one or more mammalian cells. In some embodiments, the nucleic acid encoding the nuclease is codon optimized for efficient expression in human cells. Methods of codon optimization including codon usage tables and codon optimization algorithms are available in the art.

Target Sites

In some embodiments, the site-directed nucleases described herein are directed to and cleave (e.g., introduce a DSB) a target nucleic acid molecule. In some embodiments, a Cas nuclease is directed by a guide RNA to a target site of a target nucleic acid molecule (gDNA), where the guide RNA hybridizes with the complementary strand of the target sequence and the Cas nuclease cleaves the target nucleic acid at the target site. In some embodiments, the complementary strand of the target sequence is complementary to the targeting sequence (e.g.: spacer sequence) of the guide RNA. In some embodiments, the degree of complementarity between a targeting sequence of a guide RNA and its corresponding complementary strand of the target sequence is about 50%, 55%, 60%, 65%, 70%, 75%, 80%, 85%, 90%, 95%, 97%, 98%, 99%, or 100%. In some embodiments, the complementary strand of the target sequence and the targeting sequence of the guide RNA is 100% complementary. In other embodiments, the complementary strand of the target sequence and the targeting sequence of the guide RNA contains at least one mismatch. For example, the complementary strand of the target sequence and the targeting sequence of the guide RNA contain 1, 2, 3, 4, 5, 6, 7, 8, 9, or 10 mismatches. In some embodiments, the complementary strand of the target sequence and the targeting sequence of the guide RNA contain 1-6 mismatches. In some embodiments, the complementary strand of the target sequence and the targeting sequence of the guide RNA contain 5 or 6 mismatches.

The length of the target sequence may depend on the nuclease system used. For example, the target sequence for a CRISPR/Cas system comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the target sequence comprise 18-24 nucleotides in length. In some embodiments, the target sequence comprise 19-21 nucleotides in length. In some embodiments, the target sequence comprise 20 nucleotides in length. When nickases are used, the target sequence comprises a pair of target sequences recognized by a pair of nickases on opposite strands of the DNA molecule.

In some embodiments, the target sequence for a meganuclease comprises 12-40 or more nucleotides in length. When ZFNs are used, the target sequence comprises two half target sequences recognized by a pair of ZFNs on opposite strands of the DNA molecule, with an interconnecting sequence in between. In some embodiments, each half target sequence for ZFNs independently comprise 9, 12, 15, 18, or more nucleotides in length. In some embodiments, the interconnecting sequence for ZFNs comprise 4-20 nucleotides in length. In some embodiments, the interconnecting sequence for ZFNs comprise 5-7 nucleotides in length.

When TALENs are used, the target sequence may similarly comprise two half target sequences recognized by a pair of TALENs on opposite strands of the DNA molecule, with an interconnecting sequence in between. In some embodiments, each half target sequence for TALENs may independently comprise 10-20 or more nucleotides in length. In some embodiments, the interconnecting sequence for TALENs may comprise 4-20 nucleotides in length. In some embodiments, the interconnecting sequence for TALENs may comprise 12-19 nucleotides in length.

The target nucleic acid molecule is any DNA molecule that is endogenous or exogenous to a cell. As used herein, the term "endogenous sequence" refers to a sequence that is native to the cell. In some embodiments, the target nucleic acid molecule is a genomic DNA (gDNA) molecule or a chromosome from a cell or in the cell. In some embodiments, the target sequence of the target nucleic acid molecule is a genomic sequence from a cell or in the cell. In other embodiments, the cell is a eukaryotic cell. In some embodiments, the eukaryotic cell is a mammalian cell. In some embodiments, the eukaryotic cell may be a rodent cell. In some embodiments, the eukaryotic cell may be a human cell. In further embodiments, the target sequence may be a viral sequence. In yet other embodiments, the target sequence may be a synthesized sequence. In some embodiments, the target sequence may be on a eukaryotic chromosome, such as a human chromosome.

In some embodiments, the target sequence may be located in a coding sequence of a gene, an intron sequence of a gene, a transcriptional control sequence of a gene, a translational control sequence of a gene, or a non-coding sequence between genes. In some embodiments, the gene may be a protein coding gene. In other embodiments, the gene may be a non-coding RNA gene. In some embodiments, the target sequence may comprise all or a portion of a disease-associated gene.

In some embodiments, the target sequence may be located in a non-genic functional site in the genome that controls aspects of chromatin organization, such as a scaffold site or locus control region. In some embodiments, the target sequence may be a genetic safe harbor site, i.e., a locus that facilitates safe genetic modification.

In some embodiments, the target sequence may be adjacent to a protospacer adjacent motif (PAM), a short sequence recognized by a CRISPR/Cas9 complex. In some embodiments, the PAM may be adjacent to or within 1, 2, 3, or 4, nucleotides of the 3' end of the target sequence. The length and the sequence of the PAM may depend on the Cas9 protein used. For example, the PAM may be selected from a consensus or a particular PAM sequence for a specific Cas9 nuclease or Cas9 ortholog, including those disclosed in FIG. 1 of Ran et al., (2015) Nature, 520:186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG (SpCas9 WT, SpCas9 nickase, dimeric dCas9-Fok1, SpCas9-HF1, SpCas9 K855A, eSpCas9 (1.0), eSpCas9 (1.1)), NGAN or NGNG (SpCas9 VQR variant), NGAG (SpCas9 EQR variant), NGCG (SpCas9 VRER variant), NAAG (SpCas9 QQR1 variant), NNGRRT or NNGRRN (SaCas9), NNNRRT (KKH SaCas9), NNNNRYAC (CjCas9), NNAGAAW (St1Cas9), NAAAAC (TdCas9), NGGNG (St3Cas9), NG (FnCas9), NAAAAN (TdCas9), NNAAAAW (StCas9), NNNNACA (CjCas9), GNNNCNNA (PmCas9), and NNNNGATT (NmCas9) (see e.g., Cong et al., (2013) Science 339:819-823; Kleinstiver et al., (2015) Nat Biotechnol 33:1293-1298; Kleinstiver et al., (2015) Nature 523:481-485; Kleinstiver et al., (2016) Nature 529:490-495; Tsai et al., (2014) Nat Biotechnol 32:569-576; Slaymaker et al., (2016) Science 351:84-88; Anders et al., (2016) Mol Cell 61:895-902; Kim et al., (2017) Nat Comm 8:14500; Fonfara et al., (2013) Nucleic Acids Res 42:2577-2590; Garneau et al., (2010) Nature 468:67-71; Magadan et al., (2012) PLoS ONE 7:e40913; Esvelt et al., (2013) Nat Methods 10(11):1116-1121 (wherein N is defined as any nucleotide, W is defined as either A or T, R is defined as a purine (A) or (G), and Y is defined as a pyrimidine (C) or (T)). In some embodiments, the PAM sequence is NGG. In some embodiments, the PAM sequence is NGAN. In some embodiments, the PAM sequence is NGNG. In some embodiments, the PAM is NNGRRT. In some embodiments, the PAM sequence is NGGNG. In some embodiments, the PAM sequence may be NNAAAAW.

Systems for Genome Editing

In some aspects, the disclosure provide systems for correcting a mutation in a genomic DNA molecule. In some embodiments, the system comprises an site-directed nuclease, optionally a gRNA, and a donor polynucleotide, such as those described herein. In some embodiments of the present disclosure, the system comprises an engineered nuclease. In some embodiments, the system comprises a site-directed nuclease. In some embodiments, the site-directed nuclease comprises a CRISPR/Cas nuclease system. In some embodiments, the Cas nuclease is Cas9. In some embodiments, the guide RNA comprising the CRISPR/Cas system is an sgRNA.

Modified Donor Polynucleotides

In some embodiments, donor polynucleotides are provided with chemistries suitable for delivery and stability within cells. Furthermore, in some embodiments, chemistries are provided that are useful for controlling the pharmacokinetics, biodistribution, bioavailability and/or efficacy of the donor polynucleotides described herein. Accordingly, in some embodiments donor polynucleotides described herein may be modified, e.g., comprise a modified sugar moiety, a modified internucleoside linkage, a modified nucleoside, a modified nucleotide and/or combinations thereof. In addition, the modified donor polynucleotides may exhibit one or more of the following properties: are not immune stimulatory; are nuclease resistant; have improved cell uptake compared to unmodified donor polynucleotides; and/or are not toxic to cells or mammals.

Nucleotide and nucleoside modifications have been shown to make a polynucleotide (e.g., a donor polynucleotide) into which they are incorporated more resistant to nuclease digestion than the native polynucleotide and these modified polynucleotides have been shown to survive intact for a longer time than unmodified polynucleotides. Specific examples of modified oligonucleotides include those comprising modified backbones (i.e. modified internucleoside linkage), for example, phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see e.g., De Mesmaeker et al., Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the polynucleotide is replaced with a polyamide backbone, the nucleotides being bound directly or indirectly to the aza nitrogen atoms of the polyamide backbone, see Nielsen et al., Science 1991, 254, 1497). Phosphorus-containing modified linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,031,272.1 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010).

Cyclohexenyl nucleic acid oligonucleotide mimetics are described in Wang et al., J. Am. Chem. Soc, 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5, 166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In some embodiments, the donor polynucleotides of the disclosure are stabilized against nucleolytic degradation such as by the incorporation of a modification (e.g., a nucleotide modification). In some embodiments, donor polynucleotides of the disclosure include a phosphorothioate at least the first, second, and/or third internucleotide linkage at the 5' and/or 3' end of the nucleotide sequence. In some embodiments, donor polynucleotides of the disclosure include one or more 2'-modified nucleotides, e.g., 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, donor polynucleotides of the disclosure include a phosphorothioate and a 2'-modified nucleotide as described herein.

Any of the modified chemistries described herein can be combined with each other, and that one, two, three, four, five, or more different types of modifications can be included within the same molecule. In some embodiments, the donor polynucleotide comprises 1, 2, 3, 4, 5, 6, 7, 8, 9, 10 or modifications.

mRNA Components

In some embodiments, the systems provided by the disclosure comprise an engineered nuclease encoded by an mRNA. In some embodiments, the compositions provided by the disclosure comprise a nuclease system, wherein the nuclease comprising the nuclease system is encoded by an mRNA. In some embodiments, the mRNA may be a naturally or non-naturally occurring mRNA. In some embodiments, the mRNA may include one or more modified nucleobases, nucleosides, or nucleotides, as described below, in which case it may be referred to as a "modified mRNA". In some embodiments, the mRNA may include a 5' untranslated region (5'-UTR), a 3' untranslated region (3'-UTR), and/or a coding region (e.g., an open reading frame). An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified. In some embodiments, an mRNA as described herein may include a 5' cap structure, a chain terminating nucleotide, optionally a Kozak or Kozak-like sequence (also known as a Kozak consensus sequence), a stem-loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., $m^7G(5')ppp(5')G$, commonly written as $m^7GpppG$. A cap species may also be an anti-reverse cap analog. A non-limiting list of possible cap species includes $m^7GpppG$, $m^7Gpppm^7G$, $m^73'dGpppG$, $m_2^{7,O3'}GpppG$, $m_2^{7,O3'}GppppG$, $m_2^{7,O2'}GppppG$, $m^7Gpppm^7G$, $m^73'dGpppG$, $m_2^{7,O3'}GpppG$, $m_2^{7,O3'}GppppG$, and $m_2^{7,O2'}GppppG$.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

Modified RNA

In some embodiments, an RNA of the disclosure (e.g.: gRNA or mRNA) comprises one or more modified nucleobases, nucleosides, nucleotides or internucleoside linkages. In some embodiments, modified mRNAs and/or gRNAs may have useful properties, including enhanced stability, intracellular retention, enhanced translation, and/or the lack of a substantial induction of the innate immune response of a cell into which the mRNA and/or gRNA is introduced, as compared to a reference unmodified mRNA and/or gRNA. Therefore, use of modified mRNAs and/or gRNAs may enhance the efficiency of protein production, intracellular retention of nucleic acids, as well as possess reduced immunogenicity.

In some embodiments, an mRNA and/or gRNA includes one or more (e.g., 1, 2, 3 or 4) different modified nucleobases, nucleosides, nucleotides or internucleoside linkages. In some embodiments, an mRNA and/or gRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified gRNA may have reduced degradation in a cell into which the gRNA is introduced, relative to a corresponding unmodified gRNA. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($τm^5U$), 1-taurinomethyl-pseudouridine, 5-taurinomethyl-2-thio-uridine ($Σm^5s^2U$), 1-taurinomethyl-4-thio-pseudouridine, 5-methyl-uridine ($m^5U$, i.e., having the nucleobase deoxythymine), 1-methyl-pseudouridine ($m^1ψ$), 5-methyl-2-thio-uridine ($m^5s^2U$), 1-methyl-4-thio-pseudouridine ($m^1s^4ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3ψ$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-prop enylamino)] uridine In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5c$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5 Cm$), N4,N4,2'-O-trimethyl-cytidine ($m^42 Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include □-thio-adenosine, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2 m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl)adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine (m$^6$Am), N6,N6,2'-O-trimethyl-adenosine (m$^6_2$Am), 1,2'-O-dimethyl-adenosine (m$^1$Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-0H-ara-adenosine, and N6-(19-aminopentaoxanonadecyl)-adenosine.

In some embodiments, the modified nucleobase is a modified guanine. Exemplary nucleobases and nucleosides having a modified guanine include □-thio-guanosine, inosine (I), 1-methyl-inosine (m$^1$I), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ$_0$), 7-aminomethyl-7-deaza-guanosine (preQ$_1$), archaeosine (G$^+$), 7-deaza-8-aza-guanosine, 6-thio-guanosine, 6-thio-7-deaza-guanosine, 6-thio-7-deaza-8-aza-guanosine, 7-methyl-guanosine (m$^7$G), 6-thio-7-methyl-guanosine, 7-methyl-inosine, 6-methoxy-guanosine, 1-methyl-guanosine (m$^1$G), N2-methyl-guanosine (m$^2$G), N2,N2-dimethyl-guanosine (m$^2_2$ G), N2,7-dimethyl-guanosine (m$^{2,7}$G), N2, N2,7-dimethyl-guanosine 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m$^2$Gm), N2,N2-dimethyl-2'-O-methyl-guanosine (m$^2_2$Gm), 1-methyl-2'-O-methyl-guanosine (m$^1$Gm), N2,7-dimethyl-2'-O-methyl-guanosine (m$^{2,7}$Gm), 2'-O-methyl-inosine (Im), 1,2'-O-dimethyl-inosine (m$^1$Im), 2'-O-ribosylguanosine (phosphate) (Gr(p)), 1-thio-guanosine, O6-methyl-guanosine, 2'-F-ara-guanosine, and 2'-F-guanosine.

In some embodiments, an mRNA and/or gRNA of the disclosure includes a combination of one or more of the aforementioned modified nucleobases (e.g., a combination of 2, 3 or 4 of the aforementioned modified nucleobases.)

In some embodiments, the modified nucleobase is pseudouridine (ψ), N1-methylpseudouridine (m$^1$ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.) In one embodiment, the modified nucleobase is N1-methylpseudouridine (m$^1$ψ) and the mRNA of the disclosure is fully modified with N1-methylpseudouridine (m$^1$ψ). In some embodiments, N1-methylpseudouridine (m$^1$ψ) represents from 75-100% of the uracils in the mRNA. In some embodiments, N1-methylpseudouridine (m$^1$ψ) represents 100% of the uracils in the mRNA.

In some embodiments, the modified nucleobase is a modified cytosine. Exemplary nucleobases and nucleosides having a modified cytosine include N4-acetyl-cytidine (ac$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, 2-thio-cytidine (s$^2$C), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified adenine. Exemplary nucleobases and nucleosides having a modified adenine include 7-deaza-adenine, 1-methyl-adenosine (m$^1$A), 2-methyl-adenine (m$^2$A), N6-methyl-adenosine (m$^6$A). In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified guanine. Exemplary nucleobases and nucleosides having a modified guanine include inosine (I), 1-methyl-inosine (m$^1$I), wyosine (imG), methylwyosine (mimG), 7-deaza-guanosine, 7-cyano-7-deaza-guanosine (preQ$_0$), 7-aminomethyl-7-deaza-guanosine (preQ$_1$), 7-methyl-guanosine (m$^7$G), 1-methyl-guanosine (m$^1$G), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m$^1$ψ), 5-methoxy-uridine (mo$^5$U), 5-methyl-cytidine (m$^5$C), pseudouridine (ψ), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In certain embodiments, an mRNA and/or a gRNA of the disclosure is uniformly modified (i.e., fully modified, modified through-out the entire sequence) for a particular modification. For example, an mRNA can be uniformly modified with N1-methylpseudouridine (m$^1$ψ) or 5-methyl-cytidine (m$^5$C), meaning that all uridines or all cytosine nucleosides in the mRNA sequence are replaced with N1-methylpseudouridine (m$^1$ψ) or 5-methyl-cytidine (m$^5$C). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Ribonucleoproteins

In certain aspects, the site-directed polypeptide (e.g.: Cas nuclease) and genome-targeting nucleic acid (e.g.:gRNA or sgRNA) may each be administered separately to a cell or a subject. In certain aspects, the site-directed polypeptide may be pre-complexed with one or more guide RNAs, or one or more sgRNAs. Such pre-complexed material is known as a ribonucleoprotein particle (RNP). In some embodiments, the nuclease system comprises a ribonucleoprotein (RNP). In some embodiments, the nuclease system comprises a Cas9 RNP comprising a purified Cas9 protein in complex with a gRNA. Cas9 protein can be expressed and purified by any means known in the art. Ribonucleoproteins are assembled in vitro and can be delivered directly to cells using standard electroporation or transfection techniques known in the art.

Vectors

In some embodiments, the site-directed nuclease (e.g., Cas nuclease) and the donor polynucleotide may be provided by one or more vectors. In some embodiments, the vector may be a DNA vector. In some embodiments, the vector may be circular. In other embodiments, the vector may be linear. Non-limiting exemplary vectors include plasmids, phagemids, cosmids, artificial chromosomes, minichromosomes, transposons, viral vectors, and expression vectors.

In some embodiments, the vector may be a viral vector. In some embodiments, the viral vector may be genetically modified from its wild-type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, herpes simplex virus (HSV-1) vectors, bacteriophage T4, baculovirus vectors, and retrovirus vectors. In some embodiments, the viral vector may be an AAV vector. In other embodiments, the viral vector may a lentivirus vector. In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal (Ψ) are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding a Cas9 protein, while a second AAV vector may contain one or more guide sequences and one or more copies of donor polynucleotide.

In certain embodiments, a viral vector may be modified to target a particular tissue or cell type. For example, viral surface proteins may be altered to decrease or eliminate viral protein binding to its natural cell surface receptor(s). The surface proteins may also be engineered to interact with a receptor specific to a desired cell type. Viral vectors may have altered host tropism, including limited or redirected tropism. Certain engineered viral vectors are described, for example, in WO2011130749 [HSV], WO2015009952 [HSV], U.S. Pat. No. 5,817,491 [retrovirus], WO2014135998 [T4], and WO2011125054 [T4]. In some embodiments, the vector may be capable of driving expression of one or more coding sequences in a cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild-type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding the nuclease described herein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter. In some embodiments, the nucleotide sequence encoding the nuclease may be operably linked to at least one transcriptional or translational control sequence.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1α) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1α promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech). In some embodiments, the promoter may be a tissue-specific promoter. In some embodiments, the tissue-specific promoter is exclusively or predominantly expressed in liver tissue. Non-limiting exemplary tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphs1 promoter, OG-2 promoter, SP-B promoter, SYN1 promoter, and WASP promoter.

In some embodiments, the nuclease encoded by the vector may be a Cas protein, such as a Cas9 protein or Cpf1 protein. The vector system may further comprise a vector comprising a nucleotide sequence encoding the guide RNA described herein. In some embodiments, the vector system may comprise one copy of the guide RNA. In other embodiments, the vector system may comprise more than one copy of the guide RNA. In embodiments with more than one guide RNA, the guide RNAs may be non-identical such that they target different target sequences, or have other different properties, such as activity or stability within the Cas9 RNP complex. In some embodiments, the nucleotide sequence encoding the guide RNA may be operably linked to at least one transcriptional or translational control sequence. In some embodiments, the nucleotide sequence encoding the guide RNA may be operably linked to at least one promoter. In some embodiments, the promoter may be recognized by RNA polymerase III (Pol III). Non-limiting examples of Pol III promoters include U6, H1 and tRNA promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In some embodiments, the nucleotide sequence encoding the guide RNA may be operably linked to a mouse or human tRNA promoter. In embodiments with more than one guide RNA, the promoters used to drive expression may be the same or different. In some embodiments, the nucleotide encoding the crRNA of the guide RNA and the nucleotide encoding the tracr RNA of the guide RNA may be provided on the same vector. In some embodiments, the nucleotide encoding the crRNA and the nucleotide encoding the tracr RNA may be driven by the same promoter. In some embodiments, the crRNA and tracr RNA may be transcribed into a single transcript. For example, the crRNA and tracr RNA may be processed from the single transcript to form a double-molecule guide RNA. Alternatively, the crRNA and tracr RNA may be transcribed into a single-molecule guide RNA. In other embodiments, the crRNA and the tracr RNA may be driven by their corresponding promoters on the same vector. In yet other embodiments, the crRNA and the tracr RNA may be encoded by different vectors.

In some embodiments, the nucleotide sequence encoding the guide RNA may be located on the same vector comprising the nucleotide sequence encoding a Cas9 protein. In some embodiments, expression of the guide RNA and of the Cas9 protein may be driven by different promoters. In some embodiments, expression of the guide RNA may be driven by the same promoter that drives expression of the Cas9 protein. In some embodiments, the guide RNA and the Cas9 protein transcript may be contained within a single transcript. For example, the guide RNA may be within an untranslated region (UTR) of the Cas9 protein transcript. In some embodiments, the guide RNA may be within the 5' UTR of the Cas9 protein transcript. In other embodiments, the guide RNA may be within the 3' UTR of the Cas9 protein transcript. In some embodiments, the intracellular half-life of the Cas9 protein transcript may be reduced by containing the guide RNA within its 3' UTR and thereby shortening the length of its 3' UTR. In additional embodiments, the guide RNA may be within an intron of the Cas9 protein transcript. In some embodiments, suitable splice sites may be added at the intron within which the guide RNA is located such that the guide RNA is properly spliced out of the transcript. In some embodiments, expression of the Cas9 protein and the guide RNA in close proximity on the same vector may facilitate more efficient formation of the CRISPR complex.

In some embodiments, the vector system may further comprise a vector comprising the donor polynucleotide described herein. In some embodiments, the vector system may comprise one copy of the donor polynucleotide. In other embodiments, the vector system may comprise more than one copy of the donor polynucleotide. In some embodiments, the vector system may comprise 2, 3, 4, 5, 6, 7, 8, 9, 10, or more copies of the donor polynucleotide. The multiple copies of the donor polynucleotide may be located on the same or different vectors. The multiple copies of the donor polynucleotide may also be adjacent to one another, or separated by other nucleotide sequences or vector elements.

A vector system may comprise 1-3 vectors. In some embodiments, the vector system may comprise one single vector. In other embodiments, the vector system may comprise two vectors. In additional embodiments, the vector system may comprise three vectors. When different guide RNAs or donor polynucleotides are used for multiplexing, or when multiple copies of the guide RNA or the donor polynucleotide are used, the vector system may comprise more than three vectors.

In some embodiments, the nucleotide sequence encoding a Cas9 protein, a nucleotide sequence encoding the guide RNA, and a donor polynucleotide may be located on the same or separate vectors. In some embodiments, all of the sequences may be located on the same vector. In some embodiments, two or more sequences may be located on the same vector. The sequences may be oriented in the same or different directions and in any order on the vector. In some embodiments, the nucleotide sequence encoding the Cas9 protein and the nucleotide sequence encoding the guide RNA may be located on the same vector. In some embodiments, the nucleotide sequence encoding the Cas9 protein and the donor polynucleotide may be located on the same vector. In some embodiments, the nucleotide sequence encoding the guide RNA and the donor polynucleotide may be located on the same vector. In a some embodiments, the vector system may comprise a first vector comprising the nucleotide sequence encoding the Cas9 protein, and a second vector comprising the nucleotide sequence encoding the guide RNA and the donor polynucleotide.

Nanoparticle Compositions

In some aspects, the disclosure provides nanoparticle compositions (e.g., lipid nanoparticles, LNPs) comprising a donor polynucleotide, a system, or components of a system described herein. The donor polynucleotides, systems, or components of the systems of the disclosure may be formulated, individually or combined together, in nanoparticles or other delivery vehicles, (e.g., polymeric nanoparticles) to facilitate cellular uptake and/or to protect them from degradation when delivered to a subject (e.g., a patient with a mutation). Illustrative nanoparticles are described in Panyam & Labhasetwar (2003) Adv Drug Deliv Rev 55:329-347 and Peer et al., (2007) Nature Nanotech. 2:751-760.

Nanoparticles are ultrafine particles typically ranging between 1 and 100 to 500 nanometres (nm) in size with a surrounding interfacial layer and often exhibiting a size-related or size-dependent property. Nanoparticle compositions are myriad and encompass lipid nanoparticles (LNPs), liposomes (e.g., lipid vesicles), and lipoplexes. For example, a nanoparticle composition can be a liposome having a lipid bilayer with a diameter of 500 nm or less. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide. The size of the nanoparticles may also change biodistribution, immune response, and cellular uptake.

As used herein, "size" or "mean size" in the context of nanoparticle compositions refers to the mean diameter of a nanoparticle composition.

In one embodiment, the polynucleotide encoding a polypeptide of interest are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

In some embodiments, the pKa of the nanoparticle is about 5-8. In some embodiments, the pKa of the nanoparticle is about 5. In some embodiments, the pKa of the nanoparticle is about 6. In some embodiments, the pKa of the nanoparticle is about 7. In some embodiments, the pKa of the nanoparticle is about 8.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

In certain embodiments, a donor polynucleotide or system of the disclosure is encapsulated within a nanoparticle. In some embodiments, one or more donor polynucleotides comprising a single nucleotide sequence is encapsulated within a nanoparticle. In some embodiments, one or more donor polynucleotides comprising different nucleotide sequences is encapsulated within a nanoparticle.

In some embodiments, a system of the disclosure is encapsulated within a nanoparticle. In some embodiments, one or more components of a system of the disclosure are individually encapsulated within a nanoparticle. In some embodiments, each component of a system of the disclosure is individually encapsulated within a nanoparticle. In some embodiments, a gRNA is encapsulated within a nanoparticle. In some embodiments, an mRNA encoding a nuclease (e.g., Cas9) is encapsulated within a nanoparticle. In some embodiments, a gRNA and an mRNA encoding a nuclease (e.g., Cas9) are encapsulated within a nanoparticle. In some embodiments, a gRNA, an mRNA encoding a nuclease (e.g., Cas9), and a donor polynucleotide are encapsulated within a nanoparticle.

Lipid Nanoparticles

In particular embodiments, a nanoparticle includes a lipid. Lipid nanoparticles include, but are not limited to, liposomes and micelles. Any of a number of lipids may be present, including cationic and/or ionizable lipids, anionic lipids, neutral lipids, amphipathic lipids, conjugated lipids (e.g., PEGylated lipids), and/or structural lipids. Such lipids can be used alone or in combination.

In some aspects, a donor polynucleotide, system, or one or more components of a system, such as those described herein, comprise a lipid nanoparticle (LNP). Each of the LNPs described herein may be used as a formulation for any of the donor polynucleotides, systems, or any one or more components of the systems described herein.

Cationic/Ionizable Lipids

In some embodiments, a lipid nanoparticle may comprise an cationic and/or ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipids. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure. In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126.

In yet another embodiment, the ionizable lipid may be selected from, but not limited to, formula CLI-CLXXXXII of U.S. Pat. No. 7,404,969.

In some embodiments, the lipid nanoparticle may include one or more (e.g., 1, 2, 3, 4, 5, 6, 7, or 8) cationic and/or ionizable lipids. Such cationic and/or ionizable lipids include, but are not limited to, 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraazaoctatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)[1,3]-dioxolane (DLin-KC2-DMA), 2-({8-[(3β)-cholest-5-en-3-yloxy]octyl}oxy)-N,N-dimethyl-3-[(9Z,12Z)-octadeca-9,12-dien-1-yloxy]prop an-1-amine (Octyl-CLinDMA), (2R)-2-({8-[(3β)-cholest-5-en-3-yloxy] octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.C1"); 3-β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethyl-ammonium trifluoracetate ("DOSPA"), dioctadecylamidoglycyl carboxyspermine ("DOGS"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE").

Additionally, a number of commercial preparations of cationic and/or ionizable lipids can be used, such as, e.g., LIPOFECTIN® (including DOTMA and DOPE, available from GIBCO/BRL), and LIPOFECTAMINE® (including DOSPA and DOPE, available from GIBCO/BRL). KL10, KL22, and KL25 are described, for example, in U.S. Pat. No. 8,691,750.

Anionic Lipids

Anionic lipids suitable for use in lipid nanoparticles of the disclosure include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Neutral Lipids

Neutral lipids (including both uncharged and zwitterionic lipids) suitable for use in lipid nanoparticles of the disclosure include, but are not limited to, diacylphosphatidylcholine, diacylphosphatidylethanolamine, ceramide, sphingomyelin, dihydrosphingomyelin, cephalin, sterols (e.g., cholesterol) and cerebrosides. In some embodiments, the lipid nanoparticle comprises cholesterol. Lipids having a variety of acyl chain groups of varying chain length and degree of saturation are available or may be isolated or synthesized by well-known techniques. Additionally, lipids having mixtures of saturated and unsaturated fatty acid chains and cyclic regions can be used. In some embodiments, the neutral lipids used in the disclosure are DOPE, DSPC, DPPC, POPC, or any related phosphatidylcholine. In some embodiments, the neutral lipid may be composed of sphingomyelin, dihydrosphingomyeline, or phospholipids with other head groups, such as serine and inositol.

Amphipathic Lipids

In some embodiments, amphipathic lipids are included in nanoparticles of the disclosure. Exemplary amphipathic lipids suitable for use in nanoparticles of the disclosure include, but are not limited to, sphingolipids, phospholipids, fatty acids, and amino lipids.

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular amphipathic lipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural amphipathic lipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Other phosphorus-lacking compounds, such as sphingolipids, glycosphingolipid families, diacylglycerols, and β-acyloxyacids, may also be used. Additionally, such amphipathic lipids can be readily mixed with other lipids, such as triglycerides and sterols.

PEGylated Lipids

The lipid component of a lipid nanoparticle composition may include one or more molecules comprising polyethylene glycol, such as PEG or PEG-modified lipids. Such species may be alternately referred to as PEGylated lipids. A PEGylated lipid (also known as a PEG lipid or a PEG-modified lipid) is a lipid modified with polyethylene glycol. A PEGylated lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, and PEG-modified dialkylglycerols. For example, a PEGylated lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

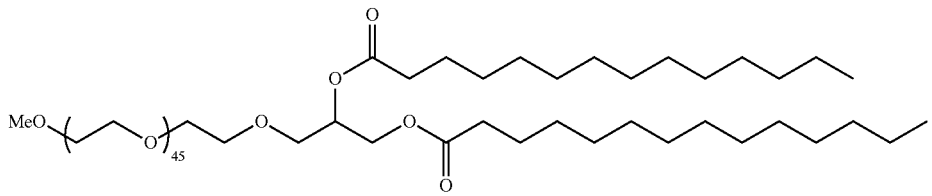

In one embodiment, PEG lipids useful in the present invention can be PEGylated lipids described in International Publication No. WO2012099755. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention. In some embodiments, the length of the PEG chain comprises about 250, about 500, about 1000, about 2000, about 3000, about 5000, about 10000 ethylene oxide units.

Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol.

Targeting Moieties

In certain embodiments, it is desirable to target a nanoparticle, e.g., a lipid nanoparticle, of the disclosure using a targeting moiety that is specific to a cell type and/or tissue type. In some embodiments, a nanoparticle may be targeted to a particular cell, tissue, and/or organ using a targeting moiety. In particular embodiments, a nanoparticle comprises a targeting moiety. Exemplary non-limiting targeting moieties include ligands, cell surface receptors, glycoproteins, vitamins (e.g., riboflavin) and antibodies (e.g., full-length antibodies, antibody fragments (e.g., Fv fragments, single chain Fv (scFv) fragments, Fab' fragments, or F(ab')2 fragments), single domain antibodies, camelid antibodies and fragments thereof, human antibodies and fragments thereof, monoclonal antibodies, and multispecific antibodies (e.g., bispecific antibodies)). In some embodiments, the targeting moiety may be a polypeptide. The targeting moiety may include the entire polypeptide (e.g., peptide or protein) or fragments thereof. A targeting moiety is typically positioned on the outer surface of the nanoparticle in such a manner that the targeting moiety is available for interaction with the target, for example, a cell surface receptor. A variety of different targeting moieties and methods are known and available in the art, including those described, e.g., in Sapra et al., Prog. Lipid Res. 42(5):439-62, 2003 and Abra et al., J. Liposome Res. 12:1-3, 2002.

In some embodiments, a lipid nanoparticle (e.g., a liposome) may include a surface coating of hydrophilic polymer chains, such as polyethylene glycol (PEG) chains (see, e.g., Allen et al., Biochimica et Biophysica Acta 1237: 99-108, 1995; DeFrees et al., Journal of the American Chemistry Society 118: 6101-6104, 1996; Blume et al., Biochimica et Biophysica Acta 1149: 180-184, 1993; Klibanov et al., Journal of Liposome Research 2: 321-334, 1992; U.S. Pat. No. 5,013,556; Zalipsky, Bioconjugate Chemistry 4: 296-299, 1993; Zalipsky, FEBS Letters 353: 71-74, 1994; Zalipsky, in Stealth Liposomes Chapter 9 (Lasic and Martin, Eds) CRC Press, Boca Raton Fla., 1995). In one approach, a targeting moiety for targeting the lipid nanoparticle is linked to the polar head group of lipids forming the nanoparticle. In another approach, the targeting moiety is attached to the distal ends of the PEG chains forming the hydrophilic polymer coating (see, e.g., Klibanov et al., Journal of Liposome Research 2: 321-334, 1992; Kirpotin et al., FEBS Letters 388: 115-118, 1996).

Standard methods for coupling the targeting moiety or moieties may be used. For example, phosphatidylethanolamine, which can be activated for attachment of targeting moieties, or derivatized lipophilic compounds, such as lipid-derivatized bleomycin, can be used. Antibody-targeted liposomes can be constructed using, for instance, liposomes that incorporate protein A (see, e.g., Renneisen et al., J. Bio. Chem., 265:16337-16342, 1990 and Leonetti et al., Proc. Natl. Acad. Sci. (USA), 87:2448-2451, 1990). Other examples of antibody conjugation are disclosed in U.S. Pat. No. 6,027,726. Examples of targeting moieties can also include other polypeptides that are specific to cellular components, including antigens associated with neoplasms or tumors. Polypeptides used as targeting moieties can be attached to the liposomes via covalent bonds (see, for example Heath, Covalent Attachment of Proteins to Liposomes, 149 Methods in Enzymology 111-119 (Academic Press, Inc. 1987)). Other targeting methods include the biotin-avidin system.

In some embodiments, a lipid nanoparticle of the disclosure includes a targeting moiety that targets the lipid nanoparticle to a cell including, but not limited to, hepatocytes, colon cells, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells (including primary tumor cells and metastatic tumor cells). In particular embodiments, the targeting moiety targets the lipid nanoparticle to a hepatocyte.

Lipidoids

The lipid nanoparticles described herein may be lipidoid-based. The synthesis of lipidoids has been extensively described and formulations containing these compounds are particularly suited for delivery of polynucleotides (see Mahon et al., Bioconjug Chem. 2010 21:1448-1454; Schroeder et al., J Intern Med. 2010 267:9-21; Akinc et al., Nat. Biotechnol. 2008 26:561-569; Love et al., Proc Natl Acad Sci USA. 2010 107:1864-1869; Siegwart et al., Proc Natl Acad Sci USA. 2011 108:12996-3001)

According to the present invention, complexes, micelles, liposomes or particles (e.g. nanoparticles) can be prepared containing these lipidoids and therefore, result in an effective delivery of a donor polynucleotide or system, as determined by, for example, the insertion of the donor polynucleotide into a gDNA, following the injection via localized and systemic routes of administration. Pharmaceutical compositions comprising lipidoid complexes can be administered by various means disclosed herein.

The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see e.g., Akinc et al., Mol Ther. 2009 17:872-879), use of lipidoid oligonucleotides to deliver the formulation to other cells types including, but not limited to, endothelial cells, myeloid cells, and muscle cells may not be similarly size-limited.

In one aspect, effective delivery to myeloid cells, such as monocytes, lipidoid formulations may have a similar component molar ratio. Different ratios of lipidoids and other components including, but not limited to, a neutral lipid (e.g., diacylphosphatidylcholine), cholesterol, a PEGylated lipid (e.g., PEG-DMPE), and a fatty acid (e.g., an omega-3 fatty acid) may be used to optimize the formulation of the donor polynucleotide or system for delivery to different cell types including, but not limited to, hepatocytes, myeloid cells, muscle cells, etc. Exemplary lipidoids include, but are not limited to, DLin-DMA, DLin-K-DMA, DLin-KC2-DMA, 98N12-5, C12-200 (including variants and derivatives), DLin-MC3-DMA and analogs thereof. The use of lipidoid formulations for the localized delivery of nucleic acids to cells (such as, but not limited to, adipose cells and muscle cells) via either subcutaneous or intramuscular delivery, may also not require all of the formulation components which may be required for systemic delivery, and as such may comprise the lipidoid and the donor polynucleotide or system.

In a further embodiment, combinations of different lipidoids may be used to improve the efficacy of a donor polynucleotide or system provided by the disclosure.

According to the present disclosure, a donor polynucleotide or system provided by the disclosure may be formulated by mixing the donor polynucleotide or system, or individual components of the system, with the lipidoid at a set ratio prior to addition to cells. In vivo formulations may require the addition of extra ingredients to facilitate circulation throughout the body. After formation of the particle, a donor polynucleotide, system, or individual components of a system provided by the disclosure is added and allowed to integrate with the complex. The encapsulation efficiency is determined using a standard dye exclusion assays.

In vivo delivery of donor polynucleotides and/or systems of the disclosure may be affected by many parameters, including, but not limited to, the formulation composition, nature of particle PEGylation, degree of loading, oligonucleotide to lipid ratio, and biophysical parameters such as particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), MD1, DLin-DMA, DLin-K-DMA, DLin-KC2-DMA and DLin-MC3-DMA can be tested for in vivo activity. The lipidoid referred to herein as "98N12-5" is disclosed by Akinc et al., Mol Ther. 2009 17:872-879). The lipidoid referred to herein as "C12-200" is disclosed by Love et al., Proc Natl Acad Sci USA. 2010 107:1864-1869 and Liu and Huang, Molecular Therapy. 2010 669-670.

The ability of a lipidoid-formulated donor polynucleotide or system to alter an nucleotide sequence in a gDNA (e.g., correct or induce a mutation) in vitro or in vivo can be determined by any technique known in the art or described herein (e.g., next-generation DNA sequencing).

Other Components

The nanoparticles disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

Pharmaceutical Compositions

The present disclosure includes pharmaceutical compositions comprising a donor polynucleotide, a gRNA, and a Cas9 protein, in combination with one or more pharmaceutically acceptable excipient, carrier or diluent. In particular embodiments, the donor polynucleotideis encapsulated in a nanoparticle, e.g., a lipid nanoparticle. In some embodiments, the gRNA is encapsulated in a nanoparticle. In some embodiments, a Cas nuclease (e.g. SpCas9) is encapsulated in a nanoparticle. In particular embodiments, an mRNA encoding a Cas nuclease or nanoparticle encapsulating a Cas nuclease is present in a pharmaceutical composition. In various embodiments, the one or more mRNA present in the pharmaceutical composition is encapsulated in a nanoparticle, e.g., a lipid nanoparticle. In particular embodiments, the molar ratio of the first mRNA to the second mRNA is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In particular embodiments, the molar ratio of the first mRNA to the second mRNA is greater than In some embodiments, the ratio between the lipid composition and the donor polynucleotide can be about 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide is about 20:1 or about 15:1.

In one embodiment, the lipid nanoparticles described herein can comprise polynucleotides (e.g., donor polynucleotide) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

Methods of Treatment

Provided herein are methods of treating a patient with a disease by correcting mutation in genomic DNA molecule. In some embodiments, the method may comprise introducing a donor polynucleotide, system, vector, or pharmaceutical composition described herein into a cell. In some embodiments, the method may comprise administering a donor polynucleotide, system, vector, or pharmaceutical composition to a subject in need thereof (e.g., a patient having a disease caused by a mutation).

Embodiments of the disclosure encompass methods for editing a target nucleic acid molecule (a genomic DNA) in a cell. In some embodiments, the method comprises introducing a donor polynucleotide described herein into a cell. In some embodiments, the method comprises contacting the cell with a pharmaceutical composition described herein. In some embodiments, the method comprises generating a stable cell line comprising a targeted edited nucleic acid molecule. In some embodiments, the cell is a eukaryotic cell. Non-limiting examples of eukaryotic cells include yeast cells, plant cells, insect cells, cells from an invertebrate animal, cells from a vertebrate animal, mammalian cells, rodent cells, mouse cells, rat cells, and human cells. In some embodiments, the eukaryotic cell may be a mammalian cell. In some embodiments, the eukaryotic cell may be a rodent cell. In some embodiments, the eukaryotic cell may be a human cell. Similarly, the target sequence may be from any such cells or in any such cells.

The donor polynucleotide, system, vector, or pharmaceutical composition described herein may be introduced into the cell via any methods known in the art, such as, e.g., viral or bacteriophage infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, shear-driven cell permeation, fusion to a cell-penetrating peptide followed by cell contact, microinjection, and nanoparticle-mediated delivery. In some embodiments, the vector system may be introduced into the cell via viral infection. In some embodiments, the vector system may be introduced into the cell via bacteriophage infection.

Embodiments of the invention also encompass treating a patient with donor polynucleotide, system, vector, or pharmaceutical composition described herein. In some embodiments, the method may comprise administering the donor polynucleotide, system, vector, or pharmaceutical composition described herein to the patient. The method may be used as a single therapy or in combination with other therapies available in the art. In some embodiments, the patient may have a mutation (such as, e.g., insertion, deletion, substitution, chromosome translocation) in a disease-associated gene. In some embodiments, administration of the donor polynucleotide, system, vector, or pharmaceutical composition may result in a mutation comprising an insertion, deletion, or substitution of one or more nucleotides of the disease-associated gene in the patient. Certain embodiments may include methods of repairing the patient's mutation in the disease-associated gene. In some embodiments, the mutation may result in one or more amino acid changes in a protein expressed from the disease-associated gene. In some embodiments, the mutation may result in one or more nucleotide changes in an RNA expressed from the disease-associated gene. In some embodiments, the mutation may alter the expression level of the disease-associated gene. In some embodiments, the mutation may result in increased or decreased expression of the gene. In some embodiments, the mutation may result in gene knockdown in the patient. In some embodiments, the administration of the donor polynucleotide, system, vector, or pharmaceutical composition may result in the correction of the patient's mutation in the disease-associated gene. In some embodiments, the administration of the donor polynucleotide, system, vector, or pharmaceutical composition may result in gene knockout in the patient. In some embodiments, the administration of the donor polynucleotide, system, vector, or pharmaceutical composition system may result in replacement of an exon sequence, an intron sequence, a transcriptional control sequence, a translational control sequence, or a non-coding sequence of the disease-associated gene. In some embodiments, the administration of the donor polynucleotide, system, vector, or pharmaceutical composition may result in integration of an exogenous sequence (e.g., the donor polynucleotide sequence) into the patient's genomic DNA. In some embodiments, the exogenous sequence may comprise a protein or RNA coding sequence operably linked to an exogenous promoter sequence such that, upon integration of the exogenous sequence into the patient's genomic DNA, the patient is capable of expressing the protein or RNA encoded by the integrated sequence. The exogenous sequence may provide a supplemental or replacement protein coding or non-coding sequence. For example, the administration of the donor polynucleotide, system, vector, or pharmaceutical composition may result in the replacement of the mutant portion of the disease-associated gene in the patient. In some embodiments, the mutant portion may include an exon of the disease-associated gene. In other embodiments, the integration of the exogenous sequence may result in the expression of the integrated sequence from an endogenous promoter sequence present on the patient's genomic DNA. For example, the administration of the donor polynucleotide, system, vector, or pharmaceutical composition may result in supply of a functional gene product of the disease-associated gene to rectify the patient's mutation. In yet other embodiments, the administration of the donor polynucleotide, system, vector, or pharmaceutical composition may result in integration of an exon sequence, an intron sequence, a transcriptional control sequence, a translational control sequence, or a non-coding sequence into the patient's genomic DNA.

Additional embodiments of the invention also encompass methods of treating the patient in a tissue-specific manner. In some embodiments, the method may comprise administering the donor polynucleotide, system, vector, or pharmaceutical composition comprising a tissue-specific promoter as described herein to the patient. Non-limiting examples of suitable tissues for treatment by the methods include the immune system, neuron, muscle, pancreas, blood, kidney, bone, lung, skin, liver, and breast tissues.

In some embodiments, the disclosure provides a method to correct a mutation in a genomic DNA molecule (gDNA) in a cell, the method comprising contacting the cell with a donor polynucleotide described herein, a system comprising a donor polynucleotide, a gRNA, and a site-directed nuclease, according to the disclosure, or a pharmaceutical composition described herein, wherein when the donor polynucleotide, system or composition contacts the cell, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising isolating a cell from the patient, contacting the cell with a donor polynucleotide described herein, a system comprising a donor polynucleotide, a gRNA, and a site-directed nuclease, according to the disclosure, or a pharmaceutical composition described herein, wherein, when the donor polynucleotide, system or composition contacts the cell, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising administering to the patient an effective amount of a donor polynucleotide described herein, a system comprising a donor polynucleotide, a gRNA, and a site-directed nuclease, according to the disclosure, or a pharmaceutical composition described herein, wherein, when the donor polynucleotide, system or composition is administered, a non-homologous end-joining (NHEJ) DNA repair pathway inserts the donor polynucleotide into a double-stranded DNA break introduced into the gDNA at a location proximal to the mutation, thereby correcting the mutation.

In some embodiments, the cell is a patient-specific induced pluripotent stem cell (iPSC). In some embodiments, the cell is a hepatocyte. In some embodiments, the method further comprises differentiating the iPSC comprising the corrected mutation into a differentiated cell; and implanting the differentiated cell into a patient. In some embodiments, treatment results in the translation of an mRNA transcribed from the genomic DNA molecule (gDNA) comprising the inserted donor polynucleotide, wherein the translation results in the formation of a translation product (protein) that alleviates the disease or that does not cause or contribute to the disease.

Kits

The present disclosure provides kits comprising a donor polynucleotide, a system comprising a donor polynucleotide, one or more gRNA molecules and a site-directed nuclease, or a pharmaceutical composition comprising the donor polynucleotide, the system, or a cell edited with the system as disclosed herein, and instructions for use. The kits may comprise, in a suitable container, the donor polynucleotide, the system, or the pharmaceutical composition, one or more controls, and various buffers, reagents, enzymes and other standard ingredients well known in the art. Certain embodiments include a kit with a donor polynucleotide disclosed herein with instructions for use in a CRISPR/Cas9 system to treat or delay progression of a disease or disorder in a subject. In some aspects the donor polynucleotide and the remaining components of a CRISPR/Cas9 system are provided in separate vials.

In some aspects, the disclosure provides a kit comprising a container which includes at least one vial, well, test tube, flask, bottle, syringe, or other container means, into which a donor polynucleotide, a system, or a pharmaceutical composition disclosed herein may be placed. Where an additional component is provided, the kit can contain additional containers into which this component may be placed. Containers and/or kits can include labeling with instructions for use and/or warnings.

In some aspects, the disclosure provides a kit comprising a donor polynucleotide, a system, or a pharmaceutical composition disclosed herein, and a package insert comprising instructions for administration in combination with a components of a CRISPR/Cas9 system, for use in for correcting a mutation in a genomic DNA molecule (gDNA) in a cell, wherein correction of a mutation is used to treat or delay progression of a disease or disorder in a subject resulting from a mutation.

In some embodiments, the disclosure provides a kit comprising a container comprising a donor polynucleotide, a system, or a pharmaceutical disclosed herein, for correcting a mutation in a genomic DNA molecule (gDNA) in a cell, and a package insert comprising instructions for use.

Definitions

Terms used in the claims and specification are defined as set forth below unless otherwise specified. In the case of direct conflict with a term used in a parent provisional patent application, the term used in the instant application shall control.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

About: As used herein, the term "about" (alternatively "approximately") will be understood by persons of ordinary skill and will vary to some extent depending on the context in which it is used. If there are uses of the term which are not clear to persons of ordinary skill given the context in which it is used, "about" will mean up to plus or minus 10% of the particular value.

Amino acid: As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

Amino acid substitution: As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

Base Composition: As used herein, the term "base composition" refers to the proportion of the total bases of a nucleic acid consisting of guanine+cytosine or thymine (or uracil)+adenine nucleobases.

Base Pair: As used herein, the term "base pair" refers to two nucleobases on opposite complementary polynucleotide strands, or regions of the same strand, that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds.

Base pairing interactions that do not follow these rules can occur in natural, non-natural, and synthetic nucleic acids and are referred to herein as "non-Watson-Crick base pairing" or alternatively "non-canonical base pairing". A "wobble base pair" is a pairing between two nucleobases in RNA molecules that does not follow Watson-Crick base pair rules. For example, inosine is a nucleoside that is structurally similar to guanosine, but is missing the 2-amino group. Inosine is able to form two hydrogen bonds with each of the four natural nucleobases (Oda et al., (1991) Nucleic Acids Res 19:5263-5267) and it is often used by researchers as a "universal" base, meaning that it can base pair with all the naturally-occurring or canonical bases. The four main wobble base pairs are the guanine-uracil (G-U) base pair, the hypoxanthine-uracil (I-U) base pair, the hypoxanthine-adenine (I-A) base pair, and the hypoxanthine-cytosine (I-C) base pair. In order to maintain consistency of nucleic acid nomenclature, "I" is used for hypoxanthine because hypoxanthine is the nucleobase of inosine; nomenclature otherwise follows the names of nucleobases and their corresponding nucleosides (e.g., "G" for both guanine and guanosine—as well as for deoxyguanosine). The thermodynamic stability of a wobble base pair is comparable to that of a Watson-Crick base pair. Wobble base pairs play a role in the formation of secondary structure in RNA molecules.

Codon: As used herein, the term "codon" refers to a sequence of three nucleotides that together form a unit of genetic code in a DNA or RNA molecule. A codon is operationally defined by the initial nucleotide from which translation starts and sets the frame for a run of successive nucleotide triplets, which is known as an "open reading frame" (ORF). For example, the string GGGAAACCC, if read from the first position, contains the codons GGG, AAA, and CCC; if read from the second position, it contains the codons GGA and AAC; and if read from the third position, GAA and ACC. Thus, every nucleic sequence read in its 5'→3' direction comprises three reading frames, each producing a possibly distinct amino acid sequence (in the given example, Gly-Lys-Pro, Gly-Asn, or Glu-Thr, respectively). DNA is double-stranded defining six possible reading frames, three in the forward orientation on one strand and three reverse on the opposite strand. Open reading frames encoding polypeptides are typically defined by a start codon, usually the first AUG codon in the sequence.

Corrects or induces a mutation: As used herein, the term "corrects or induces a mutation" refers to a function of a donor polynucleotide, such as those described herein, to incorporate a desired alteration into a nucleotide sequence comprising a genomic DNA (gDNA) molecule upon insertion of the donor polynucleotide into a double-strand break (DSB) induced in the gDNA molecule, thereby changing the nucleotide sequence of the gDNA.

The term "corrects a mutation" refers to an incorporation of a desired alteration by a donor polynucleotide that results in a change of one or more nucleotides in a gDNA that comprises a mutation (e.g., a deleterious or disease-causing mutation) such that the mutation is reverted or transmuted in a desired manner. The identification of a mutation to correct can be determined by comparison of the nucleotide sequence of a gDNA known, or suspected to, comprise the mutation to the nucleotide sequence of a wild-type gDNA.

The term "induces a mutation" refers to an incorporation of a desired alteration by a donor polynucleotide that results in a change of one or more nucleotides in a gDNA such that the gDNA is mutated in a desired manner. A mutation induced by a donor polynucleotide may be any type of mutation known in the art. In some embodiments, the induction of a mutation is for therapeutic purposes or results in a therapeutic effect.

Covalently linked: As used herein, the term "covalently linked" (alternatively "conjugated", "linked," "attached," "fused", or "tethered"), when used with respect to two or more moieties, means that the moieties are physically associated or connected with one another, by whatever means including chemical conjugation, recombinant techniques or enzymatic activity, either directly or via one or more additional moieties that serves as a linking agent, to form a structure that is sufficiently stable so that the moieties remain physically associated under the conditions in which the structure is used, e.g., physiological conditions.

Complementary: As used herein, the term "complementary" or "complementarity" refers to a relationship between the sequence of nucleotides comprising two polynucleotide strands, or regions of the same polynucleotide strand, and the formation of a duplex comprising the strands or regions, wherein the extent of consecutive base pairing between the two strands or regions is sufficient for the generation of a duplex structure. It is known that adenine (A) forms specific hydrogen bonds, or "base pairs", with thymine (T) or uracil (U). Similarly, it is known that a cytosine (C) base pairs with guanine (G). It is also known that non-canonical nucleobases (e.g., inosine) can hydrogen bond with natural bases. A sequence of nucleotides comprising a first strand of a polynucleotide, or a region, portion or fragment thereof, is said to be "sufficiently complementary" to a sequence of nucleotides comprising a second strand of the same or a different nucleic acid, or a region, portion, or fragment thereof, if, when the first and second strands are arranged in an antiparallel fashion, the extent of base pairing between the two strands maintains the duplex structure under the conditions in which the duplex structure is used (e.g., physiological conditions in a cell). It should be understood that complementary strands or regions of polynucleotides can include some base pairs that are non-complementary. Complementarity may be "partial," in which only some of the nucleobases comprising the polynucleotide are matched according to base pairing rules. Or, there may be "complete" or "total" complementarity between the nucleic acids. Although the degree of complementarity between polynucleotide strands or regions has significant effects on the efficiency and strength of hybridization between the strands or regions, it is not required for two complementary polynucleotides to base pair at every nucleotide position. In some embodiments, a first polynucleotide is 100% or "fully" complementary to a second polynucleotide and thus forms a base pair at every nucleotide position. In some embodiments, a first polynucleotide is not 100% complementary (e.g., is 90%, or 80% or 70% complementary) and contains mismatched nucleotides at one or more nucleotide positions. While perfect complementarity is often desired, some embodiments can include one or more but preferably 6, 5, 4, 3, 2, or 1 mismatches.

Contacting: As used herein, the term "contacting" means establishing a physical connection between two or more entities. For example, contacting a cell with an agent (e.g. an RNA, a lipid nanoparticle composition, or other pharmaceutical composition of the disclosure) means that the cell and the agent are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated RNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated RNA) and a cell may be contacted, for example, by adding the composition to the culture medium of the cell and may involve or result in transfection. Moreover, more than one cell may be contacted by an agent.

Denaturation: As used herein, the term "denaturation" refers to the process by which the hydrogen bonding between base paired nucleotides in a nucleic acid is disrupted, resulting in the loss of secondary and/or tertiary nucleic acid structure (e.g. the separation of previously annealed strands). Denaturation can occur by the application of an external substance, energy, or biochemical process to a nucleic acid.

Double-strand break: As used herein the term, "double-strand break" (DSB) refers to a DNA lesion generated when the two complementary strands of a DNA molecule are broken or cleaved, resulting in two free DNA ends or termini. DSBs may occur via exposure to environmental insults (e.g., irradiation, chemical agents, or UV light) or generated deliberately (e.g., via an engineered nuclease) and for a defined biological purpose (e.g. the insertion of a donor polynucleotide to correct a mutation).

Blunt-end: As used herein, the term "blunt-end" "blunt-ended" refers to the structure of an end of a duplexed or double-stranded nucleic acid (e.g., DNA), wherein both complementary strands comprising the duplex terminate, at least at one end, in a base pair. Hence, neither strand comprising the duplex extends further from the end than the other.

Duplex: As used herein, the term "duplex" refers to a structure formed by complementary strands of a double-stranded polynucleotide, or complementary regions of a single-stranded polynucleotide that folds back on itself. The duplex structure of a nucleic acid arises as a consequence of complementary nucleotide sequences being bound together, or hybridizing, by base pairing interactions.

$EC_{50}$: As used herein, the term "$EC_{50}$" refers to the concentration of a composition which induces a response, either in an in vitro or an in vivo assay, which is 50% of the maximal response, i.e., halfway between the maximal response and the baseline.

Effective dose: As used herein, the term "effective dose" or "effective dosage" is defined as an amount sufficient to achieve or at least partially achieve the desired effect.

Genome editing: As used herein, the term genome editing generally refers to the process of editing or changing the nucleotide sequence of a genome, preferably in a precise or predetermined manner. Examples of methods of genome editing described herein include methods of using site-directed nucleases to cut genomic DNA at a precise target location or sequence within a genome, thereby creating a DNA break (e.g., a DSB) within the target sequence, and repairing the DNA break such that the nucleotide sequence of the repaired genome has been changed at or near the site of the DNA break.

Double-strand DNA breaks (DSBs) can be and regularly are repaired by natural, endogenous cellular processes such as homology-directed repair (HDR) and non-homologous end-joining (NHEJ) (see e.g., Cox et al., (2015) Nature Medicine 21(2):121-131).

DNA repair by HDR utilizes a polynucleotide (often referred to as a "repair template" or "donor template") with a nucleotide sequence that is homologous to the sequences flanking the DSB. DNA repair by HDR mechanisms involves homologous recombination between the repair template and the cut genomic DNA molecule. Repair templates may be designed such that they insert or delete nucleotides in the genomic DNA molecule or change the nucleotide sequence of the genomic DNA molecule.

NHEJ mechanisms can repair a DSB by directly joining or ligating together the DNA ends that result from the DSB. Repair of a DSB by NHEJ can involve the random insertion or deletion of one or more nucleotides (i.e. indels). This aspect of DNA repair by NHEJ is often leveraged in genome editing methods to disrupt gene expression. NHEJ can also repair a DSB by insertion of an exogenous polynucleotide into the cut site in a homology-independent manner.

A third repair mechanism is microhomology-mediated end joining (MMEJ), also referred to as "alternative NHEJ", in which the genetic outcome is similar to NHEJ in that small deletions and insertions can occur at the cleavage site. MMEJ makes use of homologous sequences of a few basepairs flanking the DNA break site to drive a more favored DNA end joining repair outcome (see e.g., Cho and Greenberg, (2015) Nature 518, 174-176); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break. Each of the aforementioned DNA repair mechanisms can be used in genome editing methods to create desired genomic alterations. The first step in the genome editing process is to create typically one or two DNA breaks in a target sequence as close as possible to the site of intended mutation or alteration. This can achieved via the use of a site-directed nuclease, as described and illustrated herein.

Site-directed nuclease: As used herein, the term "site-directed nuclease" refers to one of several distinct classes of nucleases that can be programmed or engineered to recognize a specific target site (i.e., a target nucleotide sequence) in a DNA molecule (e.g., a genomic DNA molecule) and generate a DNA break (e.g., a DSB) within the DNA molecule at, near or within the specific site. Site-directed nucleases are useful in genome editing methods, such as those described herein. Site-directed nucleases include, but are not limited to, the zinc finger nucleases (ZFNs), transcription activator-like effector (TALE) nucleases, CRISPR/Cas nucleases (e.g., Cas9), homing endonucleases (also termed meganucleases), and other nucleases (see, e.g., Hafez and Hausner, Genome 55, 553-69 (2012); Carroll, Ann. Rev. Biochem. 83, 409-39 (2014); Gupta and Musunuru, J. Clin. Invest. 124, 4154-61 (2014); and Cox et al., supra. These differ mainly in the way they bind DNA and create the targeted, site-specific DNA break. Site-directed nucleases known in the art may produce a single-strand break (SSB) or a DSB. For the purposes of the present invention, the disclosure's reference to a "site-directed nuclease" refers to those nucleases that produce a DSB. After creation of a DSB, essentially the same natural cellular DNA repair mechanisms of NHEJ or HDR are co-opted to achieve the desired genetic modification. Therefore, it is contemplated that genome editing technologies or systems using site-directed nucleases can be used to achieve genetic and therapeutic outcomes described herein.

In need: As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

Insertion: As used herein, an "insertion" or an "addition" refers to a change in an amino acid or nucleotide sequence resulting in the addition of one or more amino acid residues or nucleotides, respectively, to a molecule as compared to a reference sequence, for example, the sequence found in a naturally-occurring molecule.

Intron: As used herein, the term "intron" refers to any nucleotide sequence within a gene that is removed by RNA splicing mechanisms during maturation of the final RNA product (e.g., an mRNA). An intron refers to both the DNA sequence within a gene and the corresponding sequence in a RNA transcript (e.g., a pre-mRNA). Sequences that are joined together in the final mature RNA after RNA splicing are "exons". As used herein, the term "intronic sequence" refers to a nucleotide sequence comprising an intron or a portion of an intron. Introns are found in the genes of most eukaryotic organisms and can be located in a wide range of genes, including those that generate proteins, ribosomal RNA (rRNA), and transfer RNA (tRNA). When proteins are generated from intron-containing genes, RNA splicing takes place as part of the RNA processing pathway that follows transcription and precedes translation.

Lipid: As used herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

Local administration: As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

Modified: As used herein "modified" or "modification" refers to a changed state or change in structure resulting from a modification of a polynucleotide, e.g., DNA. Polynucleotides may be modified in various ways including chemically, structurally, and/or functionally. For example, the DNA molecules of the present disclosure may be modified by the incorporation of a chemically-modified base that provides a biological activity. In one embodiment, the DNA is modified by the introduction of non-natural or chemically-modified bases, nucleosides and/or nucleotides, e.g., as it relates to the natural nucleobases adenine (A), guanine (G), cytosine (C), and thymine (T).

mRNA: As used herein, an "mRNA" refers to a messenger ribonucleic acid. An mRNA may be naturally or non-naturally occurring or synthetic. For example, an mRNA may include modified and/or non-naturally occurring components such as one or more nucleobases, nucleosides, nucleotides, or linkers. An mRNA may include a cap structure, a 5' transcript leader, a 5' untranslated region, an initiator codon, an open reading frame, a stop codon, a chain terminating nucleoside, a stem-loop, a hairpin, a polyA sequence, a polyadenylation signal, and/or one or more cis-regulatory elements. An mRNA may have a nucleotide sequence encoding a polypeptide. Translation of an mRNA, for example, in vivo translation of an mRNA inside a mammalian cell, may produce a polypeptide. Traditionally, the basic components of a natural mRNA molecule include at least a coding region, a 5'-untranslated region (5'-UTR), a 3'UTR, a 5' cap and a polyA sequence.

Naturally occurring: As used herein, the term "naturally occurring" as applied to an object refers to the fact that an object can be found in nature. For example, a polypeptide or polynucleotide sequence (e.g., a splice site), or components thereof such as amino acids or nucleotides, that is present in an organism (including viruses) that can be isolated from a source in nature and which has not been intentionally modified by man in the laboratory is naturally occurring.

Non-homologous end joining: As used herein, the term "non-homologous end joining" refers to a pathway that repairs double-strand breaks (DSBs) in DNA. NHEJ is referred to as "non-homologous" because the DNA termini are directly ligated without the need for a homologous template, in contrast to homology directed repair (HDR), which requires a homologous sequence to guide repair.

Non-replicative: As used herein, the term "non-replicative" refers to the characteristic of a DNA molecule as being unable to replicate within a cell or an organism. Certain DNA molecules (e.g., plasmids, viral genomes) contain sequence elements (e.g. origins of replications) that impart the DNA molecule with the ability to be copied, or replicated, by a cell or organism. The term "non-replicative" connotes those DNA molecules that do not contain such sequence elements.

Nucleic acid: As used herein, the term "nucleic acid" refers to deoxyribonucleotides or ribonucleotides and polymers or oligomers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Polymers of nucleotides are referred to as "polynucleotides". Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases. "Modified nucleosides" include, for example, as inosine and thymine, when the latter is found in or comprises RNA. A variety of modifications can be made to DNA and RNA; thus, "polynucleotide" embraces chemically, enzymatically, or metabolically modified forms.

Nucleic Acid Structure: As used herein, the term "nucleic acid structure" refers to the arrangement or organization of atoms, chemical constituents, elements, motifs, and/or sequence of nucleobases that comprise a nucleic acid (e.g. an RNA) and/or can refer to the two-dimensional or three-dimensional state of a nucleic acid. Accordingly, the term "RNA structure" refers to the arrangement or organization of atoms, chemical constituents, elements, motifs, and/or sequence of nucleobases comprising an RNA molecule (e.g. an mRNA) and/or can refer to the two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g. binding affinity, nuclease resistance, chemical stability) to a nucleic acid or a portion or segment thereof. Adenine, cytosine, guanine, thymine, and uracil are the primary or canonical nucleobases predominately found in natural nucleic acids. Other natural, non-natural, non-canonical and/or synthetic nucleobases, can be incorporated into nucleic acids, such as those disclosed herein.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof. As used herein, the term "nucleotide" refers to a nucleoside covalently linked to a phosphate group. As used herein, the term "ribonucleoside" refers to a nucleoside that comprise a ribose and a nucleobase (e.g., adenosine (A), cytidine (C), guanosine (G), 5-methyluridine ($m^5U$), uridine (U), or inosine (I)).

Operably linked: As used herein, a nucleic acid, or fragment or portion thereof, such as a polynucleotide or oligonucleotide is "operably linked" when it is placed into a functional relationship with another nucleic acid sequence, or fragment or portion thereof.

Polynucleotide/oligonucleotide: As used herein, the terms "polynucleotide" and "oligonucleotide" are used interchangeably and refer to a single-stranded or double-stranded polymer or oligomer of nucleotides or nucleoside monomers consisting of naturally-occurring bases, sugars and intersugar (backbone) linkages. The terms "polynucleotide" and "oligonucleotide" also includes polymers and oligomers comprising non-naturally occurring bases, sugars and intersugar (backbone) linkages, or portions thereof, which function similarly. Polynucleotides are not limited to any particular length of nucleotide sequence, as the term "polynucleotides" encompasses polymeric forms of nucleotides of any length. Short polynucleotides are typically referred to in the art as "oligonucleotides". In the context of the present disclosure, such modified or substituted polynucleotides and oligonucleotides are often preferred over native forms because the modification increases one or more desirable or beneficial biological properties or activities including, but not limited to, enhanced cellular uptake and/or increased stability in the presence of nucleases. In some embodiments, the agonists of the disclosure comprise polynucleotides and oligonucleotides that contain at least one region of modified nucleotides that confers one or more beneficial properties or increases biological activity (e.g., increased nuclease resistance, increased uptake into cells, increased duplex stability, increased binding affinity to a target polypeptide).

Palindromic sequence: As used herein, the term "palindromic sequence" (alternatively "palindrome") refers to a sequence of nucleotides that is self-complementary; wherein the sequence of nucleotides in the 5' to 3' direction is the same as the sequence of nucleotides comprising the complementary strand, when read in the 5' to 3'. For example, the sequence 5'-ACCTAGGT-3' is a palindromic sequence because its complementary sequence, 3'-TGGATCCA-5', when read in the 5' to 3' direction, is the same as the original sequence. In contrast, the sequence 5'-AGTGGCTG-3' is not a palindromic sequence because its complementary sequence, 3'-TCACCGAC-5', when read in the 5' to 3' direction, is not the same as the original sequence.

Parenteral administration: As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

Percent identity: As used herein, the term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

Pharmaceutically acceptable: As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

Pharmaceutically acceptable carrier: As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

Phosphate: The term "phosphate" as used herein means a salt or ester of phosphoric acid. Polyphosphates are salts or esters of polymeric oxyanions formed from tetrahedral $PO_4$ (phosphate) structural units linked together by sharing oxygen atoms. As used herein, the term "diphosphate" refers to a polyphosphate comprising two phosphate structural units. As used herein, the term "triphosphate" refers to a polyphosphate comprising three phosphate structural units Phosphate bioisostere: As used herein, the term "phosphate bioisostere" (alternatively "phosphate mimic") refers to chemical substituents or groups with similar physical or chemical properties to phosphate and which produce broadly similar biological properties to phosphate, including biphosphate and triphosphate moieties. In drug design, the purpose of exchanging one bioisostere for another is to enhance the desired biological or physical properties of a compound without making significant changes in chemical structure. The use of bioisosteres is widespread in drug development and is used, for example, to reduce toxicity, change bioavailability, or modify the activity or metabolism of the parental or lead compound (see e.g., Rye and Baell (2005) Curr Med Chem 12(26):3127-3141; Elliot et al., (2012) Med Chem Com 3(7):735-751).

Polypeptide: As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Preventing: As used herein, the term "preventing" or "prevent" when used in relation to a condition, refers to administration of a composition which reduces the frequency of, or delays the onset of, symptoms of a medical condition in a subject relative to a subject which does not receive the composition.

Purified: As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

Sense strand: As used herein the term "sense strand" or "coding strand" refers to a segment within double-stranded DNA (e.g., genomic DNA) with a 5' to 3' directionality and has the same nucleotide sequence as an mRNA transcribed from the segment. The transcription product is pre-mRNA transcript, which contains a sequence of nucleotides that is identical to that of the sense strand, with the exception that uracil will be incorporated into the mRNA at those positions where thymine is located in the DNA. The sense strand is complementary to the antisense strand of DNA, or template strand, which runs from 3' to 5'.

RNA splicing: As used herein, the term "splicing" (alternatively "RNA splicing") refers to the processing or editing of a nascent precursor messenger RNA (pre-mRNA) transcript into a mature messenger RNA (mRNA) in a cell. Nascent RNA transcripts such as pre-mRNA are comprised of both introns and exons. During the splicing reaction, introns are removed from the nascent RNA transcript and exons are ligated together. For nuclear-encoded genes, splicing takes place within the nucleus either during or immediately after transcription of an RNA (e.g., a pre-mRNA). Splicing is carried out in a series of reactions which are catalyzed by the spliceosome, a complex of snRNPs, that recognize cis-acting splicing signals contained within nascent RNA transcripts. The canonical splicing signals that are recognized by the spliceosome include the 5' splice site, the branch point, the polypyrimidine tract and the 3' splice site. The human branch point consensus sequence is YTNAY (YUNAY in RNA), wherein the underlined adenine (A) is the branch point, wherein "Y" indicates the presence of a pyrimidine nucleobase (cytosine (C) or thymine (T)), and wherein N indicate the presence of a nucleotide comprising any nucleobase (Gao et al., (2008) Nucleic Acids Res 36(7):2257-2267). The biochemical mechanism by which splicing occurs is well described in the art. The term "splicing signal", "RNA splicing signal" or "splicing motif" refers to a nucleotide sequence within a primary transcript (e.g. pre-mRNA) that is recognized by the splicing machinery of the cell. Introns are removed from primary transcripts (e.g. pre-mRNA) by the recognition and cleavage at splicing signals called "splice sites". These sites are located at the 5' and 3' ends of introns, and are referred to herein as a "5' splice site" and "3' splice site". Most commonly, the intronic RNA sequence that is removed begins with the dinucleotide GU at its 5' end, and ends with AG at its 3' end. These consensus sequences are known to be critical, because changing or mutation of one of the conserved nucleotides within 5' or 3' splice sites results in inhibition of splicing. A consensus sequence for a 3' splice site in DNA is YAG, where Y is a C or T. A consensus sequence for a 5' splice site in DNA is GTRAG, wherein R is an A or G.

A splicing signal known as a "branch point", located anywhere from 10 to 100 nucleotides upstream from the 3' end of an intron. The branch point always contains an adenine, but it is otherwise loosely conserved. A branch point consensus sequence is YTNAY, where Y indicates a pyrimidine, N denotes any nucleotide, and T denotes a nucleotide comprising thymine, and A denotes a nucleotide comprising adenine.

A splicing signal known as a "polypyrimidine tract" comprises a region within pre-mRNA that promotes the assembly of the splicing machinery or spliceosome, the protein complex specialized for carrying out RNA splicing during the process of post-transcriptional modification. The polypyrimidine tract is enrich with pyrimidine nucleotides, especially uracil, and is usually 15-20 base pairs long, located about 1-40 base pairs before the 3' end of the intron to be spliced.

Other exemplary splicing signals that communicate to the spliceosome include, but are not limited to, exonic splicing enhancers (ESE), exonic splicing silencers (ESS), intronic splicing enhancers (ISE) and intronic splicing silencers (ISS). It is known that splicing is partly promoted or affected by ESEs, ESSs, ISEs and ISSs, which are embedded within the nucleotide sequence of exons (ESEs and ESSs) and introns (ISEs and ISSs) (see e.g., Mersch et al., (2008) BMC Bioinformatics 9:369; Wang et al., (2004) Cell 119:831-845; Wang et al., (2012) Nat Struct Mol Biol 19(10):1044-1052; Havens et al., (2013) RNA 4:247-266).

Subject: As used herein, the term "subject" includes any human or non-human animal. For example, the methods and compositions of the present invention can be used to treat a subject with a disorder (e.g.: a genetic disorder). The term "non-human animal" includes all vertebrates, e.g., mammals and non-mammals, such as non-human primates, sheep, dog, cow, chickens, amphibians, reptiles, etc.

Therapeutic agent: As used herein, the term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the terms "therapeutically effective amount" or "therapeutically effective dose," or similar terms used herein are intended to mean an amount of an agent that will elicit the desired biological or medical response, such as, for example, at least partially arresting the condition or disease and its complications in a patient already suffering from the disease (e.g., an improvement in one or more symptoms of a cancer). Amounts effective for this use will depend on the severity of the disorder being treated and the general state of the patient's own immune system.

Treat: The terms "treat," "treating," and "treatment," as used herein, refer to therapeutic measures described herein. The methods of "treatment" employ administration of a composition of the disclosure to a subject, in need of such treatment, in order to, cure, delay, reduce the severity of, or ameliorate one or more symptoms of the disorder or recurring disorder, or in order to prolong the survival of a subject beyond that expected in the absence of such treatment.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions.

EQUIVALENTS AND SCOPE

Those skilled in the art will recognize, or be able to ascertain using no more than routine experimentation, many equivalents to the specific embodiments, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein.

It is also noted that the term "comprising" is intended to be open and permits but does not require the inclusion of additional elements or steps. When the term "comprising" is used herein, the term "consisting of" is thus also encompassed and disclosed Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Design of Donor Polynucleotides to Modulate Exon Definition and Correct a Mutation in a gDNA Molecule RNA splicing is a process shared among all eukaryotes that allows for processing of transcribed RNA into mRNA by the removal of introns and the joining of exons. In higher eukaryotes, such as vertebrates, where exons are small and intron are large the splicing machinery uses the exon as the unit of recognition. This process of recognizing and pairing splice sites across exons, termed exon definition, explains the narrow size distribution seen amongst vertebrate internal exons (average size of 134 nt). The distance between the 3' and 5' splice sites is critical for the accurate recognition and inclusion of exons. Previous studies have shown that spliceosome formation and exon definition are influenced by intron and exon size. Expanding the distance between 3' and 5' splice sites of a constitutive internal exon to >300 nt using cDNA sequences has been shown to lead to poor exon recognition due to an inefficiency in the ability of the spliceosome to define the exon (Sterner et al., (1996) Proc Natl Acad Sci USA 93(26):15081-15085)

Donor polynucleotides were designed to determine the effectiveness of the donor polynucleotide to modulate exon definition and to alter a nucleotide sequence (e.g., correct, or induce, a mutation in an exon or intron) in a gDNA molecule by changing one or more nucleotides. The donor polynucleotides were designed based on at least the following criteria: selection of a nucleotide sequence to alter (e.g., to correct or induce a mutation); and selection of one or more splicing signals to modulate splice site recognition or exon definition. The splicing signals include at least one or more of a branch point, a polypyrimidine tract, a 3' splice site, a 5' splice site, an exon or intron splicing enhancer or silencer, or a combination thereof.

Upon insertion into the gDNA, a first portion or segment of the donor polynucleotide comprises a nucleotide sequence comprising one or more nucleotides that alters a gDNA nucleotide sequence in a desired manner (e.g., to correct or induce a mutation) and a second portion or segment of the donor polynucleotide comprises one or more splicing signals required for accurate inclusion of the nucleotide(s) comprising the desired altered sequence into the final mRNA transcript. For example, a gDNA nucleotide sequence is altered by a donor polynucleotide to correct or induce a specific mutation(s) in an expressed gene and concomitantly provide one or more splicing signals required to ensure that the corrected or induced mutation(s) is transcribed into an mRNA. The donor polynucleotide is introduced into a cell and the efficiency by which NHEJ DNA repair machinery of the cell inserts the donor polynucleotide into a DSB introduced into the gDNA by a site-directed nuclease (e.g., a Cas nuclease) and the efficiency by which the altered nucleotide sequence is transcribed into an mRNA is determined.

For example, as shown in schematic in FIG. 1 that depicts the sense strand of a donor polynucleotide, a donor polynucleotide is designed to correct a deleterious or disease-causing mutation in an exon (indicated by X) by insertion into a double-strand break (DSB) introduced near the disease-causing mutation using a site-directed nuclease (e.g., Cas9). The DSB is repaired by the NHEJ-mediated insertion of a donor polynucleotide (shown in black) comprising one or more nucleotides that corrects the mutation (indicated by *) and comprising one or more splicing signals (e.g., a 3' splice site, a polypyrimidine tract, and/or a branch point). The insertion of the donor polynucleotide into the DSB generates a gene with two potential 3' splice sites for the exon.

Without being bound by theory, the insertion of the donor polynucleotide effectively inhibits or destroys the ability of the upstream (endogenous) 3' splice site to participate in exon definition, in part, by increasing the number of nucleotides (indicated by //) between the upstream (endogenous) 3' splice site and the next available 5' splice site. After insertion of the donor polynucleotide, the splicing machinery does not recognize the endogenous 3' and 5' splice sites as a pair that defines an exon. Instead, the splicing machinery recognizes the new 3' splice site comprising the donor polynucleotide (shown in black) and next available 5' splice site as the pair of splice sites that define the exon, as these splice sites are positioned such that they are in agreement with the exon definition theory of RNA splicing. Further, the presence of a new 3' splice site (and optionally additional splicing signals) proximal to and upstream of the one or more nucleotides that corrects the mutation (indicated by *) results in the definition of an exon that encodes the corrected mutation and its inclusion into an mRNA transcript.

Example 2: Donor Polynucleotides Inserted into a DSB by NHEJ Alters a gDNA Nucleotide Sequence and Introduces a Codon Change in an Exon Previous work has shown that the correction of a mutation in genomic DNA (gDNA) by the use of a donor polynucleotide to repair a DSB by HDR occurs at a higher rate in dividing cells than in non-dividing cells (data not shown). While HDR repair is often inefficient in non-dividing cells (e.g., cells in the G0 or G1 phase of the cell cycle), the NHEJ repair pathway remains an active DSB repair pathway in both dividing and non-diving cells. Thus, exploiting the NHEJ repair pathway for insertion of a donor polynucleotide into a DSB is ideal for introducing a site-specific correction of a mutation in both dividing and non-dividing cells. Unlike using a donor polynucleotide to repair a DSB by HDR, wherein the donor polynucleotide comprises homology arms that orient the donor polynucleotide in a single direction for repair of a DSB, repair of a DSB using a donor polynucleotide by NHEJ repair mechanisms can result in the insertion of the donor polynucleotide into a DSB in one of two orientations; forward or reverse. To evaluate the ability of a cell to use a donor polynucleotide to repair a CRISPR/Cas9-mediated DSB in gDNA via NHEJ DNA repair mechanisms and alter a nucleotide sequence of a gDNA in a desired manner, the NHEJ-mediated insertion of a donor polynucleotide (as opposed to integration of a donor polynucleotide by homologous recombination) in the orientation that results in the desired alteration (e.g., a corrective edit) into the gDNA of dividing hepatocyte-derived cells was determined.

A NHEJ-mediated insertion of a donor polynucleotide into a DSB in an orientation that is productive for incorporation of the desired nucleotide sequence alteration is referred to herein as a "corrective edit" or "corrective insertion". A "corrective insertion" includes a "perfect insertion" wherein the insertion is achieved without introducing a mutation to the gDNA sequence surrounding the corrected DSB or to termini of the inserted donor polynucleotide (e.g., the donor polynucleotide is inserted seamlessly into the gDNA DSB). A "corrective insertion" also includes a NHEJ-mediated insertion wherein one or more small mutations occurs within the sequence of the gDNA surrounding the corrected DSB, at the termini of the inserted donor polynucleotide or at an internal sequence within the inserted donor polynucleotide, but still yields a gDNA sequence that encodes the desired nucleotide sequence alteration (e.g., gene correction and/or splicing signals encoded by the donor polynucleotide).

Donor polynucleotides were designed based on the criteria set forth in Example 1 to introduce a nucleotide change in a coding exon at a location known to cause a disease. Altering a nucleotide sequence by the introduction of a codon change is useful for the correction of a disease-causing mutation in a coding exon. For example, the R83C mutation in exon 2 of the glucose-6-phosphatase catalytic subunit (G6PC) gene is known to cause Glycogen Storage Disease 1a (GSD1a) in humans. The therapeutic approach to correct a R83C mutation that results in GSD1a is to introduce a codon change in exon 2 that results in a C83R reversion in the G6PC polypeptide, and to provide one or more splicing signals to direct the inclusion of the revertant codon into an mRNA encoding the G6PC polypeptide. As a proof of principle for validating this therapeutic strategy to correct the R83C mutation, a donor polynucleotide was designed to alter the nucleotide sequence of exon 2 in the G6PC gene wherein a R83C mutation was introduced into exon 2 of the wild-type G6PC gene. This was done by designing and testing a donor polynucleotide in which the arginine (R) codon (CGT) in the wild-type G6PC gene corresponding to R83 in the human G6PC polypeptide was mutated to the disease-causing cysteine (C) codon (TGC).

Briefly, a single gRNA (sgRNA) comprising a spacer specific for exon 2 of the glucose-6-phosphatase catalytic subunit (G6PC) gene (sgRNA CH32, SEQ ID NO: 6; sgRNA CH32 spacer, SEQ ID NO: 81; G6PC target gene sequence+PAM, SEQ ID NO: 82) was selected. Modified sgRNAs with phosphorothiate bonds and 2'-O-methyl nucleotide residues can be used to generate the desired target gene DSB. Donor polynucleotides that were double-stranded oligonucleotides (dsODNs) of 25 to 125 nucleotides in length were made comprising 2 sequence elements: (1) an exonic sequence that incorporates a single codon change in the open reading frame of exon 2 corresponding to position 83 of the G6PC polypeptide; and (2) one or more splicing signals selected from either a 3' splice site alone, or in combination with a polypyrimidine tract, or further in combination with a branch point (as indicated in Table 1).

The target gene sequence of the CH32 sgRNA is shown in Table 4, the CH32 sgRNA spacer sequence is shown in Table 3, and the CH32 sgRNA sequence is shown in Table 2. Cas9/sgRNA forms a DSB three nucleotides upstream of the start of the PAM sequence. The exonic sequence encoded by the dsODN donor polynucleotide overlaps with the target gene sequence at three nucleotides downstream from the start of the PAM sequence, such the dsODN donor polynucleotide inserts into the cut site with the desired splicing signals and restoration of the exonic sequence with the encoded TGC mutation.

The sgRNA and each donor polynucleotide were transfected into HuH-7 cells (hepatocyte-derived cellular carcinoma cell line) that constitutively express SpCas9. The sgRNAs and donor polynucleotides were transfected concurrently into HuH-7 cells using a transfection reagent comprising cationic liposomes (Lipofectamine®MessengerMax™; ThermoFisher Scientific, Waltham, Mass.). Each well of cells in a 96 well plate was transfected with a 50 µl solution containing 34 ng sgRNA, 200 ng of dsDNA donor polynucleotides, and the amount of transfection reagent recommend by the manufacture.

Donor polynucleotides of increasing length (from 25-125) and comprising one or more splicing signal sequences were tested, as indicated in Table 1. After 48 h post-transfection, genomic DNA (gDNA) was isolated from the transfected HuH-7 cells using a commercially available DNA extraction kit (PrepGem; Zygem, Charlottesville, Va.) according to the manufacturer's instructions. To determine if the donor polynucleotides were inserted by NHEJ into the DSB generated by the CH32 sgRNA:spCas9 complex (CH32 target site, SEQ ID NO: 82), PCR amplicons were generated from the isolated gDNA and analyzed by next-generation sequencing (NGS). NGS sequencing was performed using paired-end runs of up to 300 nt on an Illumina NextSeq machine (Illumina, Inc., San Diego, Calif.). Samples were identified by standard dual barcoding. A limited cycle first round of PCR amplified an amplicon corresponding to an ~800 bp region surrounding the CH32 target site. The second round used the previously generated amplicons and generated the core amplicons to be sequenced, ~200 bp flanking the CH32 target site. Adapters needed for NGS were added in the last (third) round of PCR.

After paired-end sequencing of the core amplicons, the resulting FASTQ files were analyzed to determine the rates of insertion. In brief, the ends of the reads were joined using the PANDAseq program (Masella et al., (2012) BMC Bioinformatic s 13:31) and poor quality reads identified and removed using the FASTQ Quality Filter program provided in FASTX-Toolkit (hannonlab.cshl.edu/fastx_toolkit/index-.html). Identical reads were tabulated, pooled, then searched for the predicted sequence that results from insertion of an entire donor polynucleotide into the CH32 cleavage site. Sequencing reads that displayed both the predicted 5' and 3' junctions indicative of the donor polynucleotide, as well as the single codon change in exon 2 were considered positive for corrective insertion, these were compared to the total sequence reads and the results are shown in Table 1 as % Corrective Insertion.

TABLE 1

Unidirectional dsODN donor polynucleotides for introducing a codon change in the G6PC gene

| Donor Polynucleotide (size) | % Corrective Insertion | Nucleotide Sequence (5'-3', Sense Strand) | SEQ ID NO |
|---|---|---|---|
| CH32_25-0 (25 nt) | 0.012% | tagGATTCTCTTTGGACAGTGCCCT | 16 |
| CH32_50-0 (50 nt) | 8.088% | cccagaaacttgttctgccatagGATTCTCTTTGGACAGTGCCCT | 18 |
| CH32_75-0 (75 nt) | 0.019% | tgggcaaaagcattcattcagtaacccagaaacttgttctgccatagGATTCTCTTTGGACAGTGCCCT | 10 |
| CH32_100-0 (100 nt) | 0.015% | acactcttcttgaaggtgtaggctttgggcaaaagcattcattcagtaacccagaaacttgttctgttttccatagGATTCTCTTTGGACAGTGCCCT | 12 |
| CH32_125-0 (125 nt) | 0.000% | caacatgtgaaatccttctcaggctacactcttcttgaaggtgtaggctttgggcaaaagcattcattcagtaacccagaaacttgttctgttttccatagGATTCTCTTTGGACAGTGCCCT | 14 |

TABLE 1-continued

Unidirectional dsODN donor polynucleotides for introducing a codon change in the G6PC gene

| Donor Polynucleotide (size) | % Corrective Insertion Nucleotide Sequence (5'-3', Sense Strand) | SEQ ID NO |
|---|---|---|

Donor Polynucleotide Key

| Annotation | Donor Polynucleotide Design Element |
|---|---|
| lowercase | intronic sequence |
| *lowercase italics* | 3' splice site |
| lowercase solid underline | polyprimidine tract |
| lowercase dotted underline | branch point sequence |
| UPPERCASE | exonic sequence |
| UPPERCASE SOLID UNDERLINE | cysteine codon |
| UPPERCASE BOLD | desired altered nucleotide(s) |

TABLE 2 sgRNA sequences for directing a site-specific DSB in the G6PC gene

| Name | sgRNA Nucleotide Sequence (5'-3') | SEQ ID NO |
|---|---|---|
| CH32 sgRNA | UCUUUGGACAGCGUCCAUACGUUUUAGAGCUAGAA AUAGCAAGUUAAAAUAAGGCUAGUCCGUUAUCAAC UUGAAAAAGUGGCACCGAGUCGGUGCUUUU | 6 |
| CH34 sgRNA | UGGACAGCGUCCAUACUGGUGUUUUAGAGCUAGAA AUAGCAAGUUAAAAUAAGGCUAGUCCGUUAUCAAC UUGAAAAAGUGGCACCGAGUCGGUGCUUUU | 7 |
| CH36 sgRNA | GUAUCCAAAACCCACCAGUAGUUUUAGAGCUAGAAA UAGCAAGUUAAAAUAAGGCUAGUCCGUUAUCAACU UGAAAAAGUGGCACCGAGUCGGUGCUUUU | 8 |
| CH42 sgRNA | GUCAGUCUCACAGGUUACAGGUUUUAGAGCUAGAA AUAGCAAGUUAAAAUAAGGCUAGUCCGUUAUCAAC UUGAAAAAGUGGCACCGAGUCGGUGCUUUU | 70 |

TABLE 3 gRNA spacer sequence

| Name | sgRNA spacer sequence | SEQ ID NO |
|---|---|---|
| CH32 sgRNA spacer | UCUUUGGACAGCGUCCAUAC | 81 |
| CH34 sgRNA spacer | UGGACAGCGUCCAUACUGGU | 83 |
| CH36 sgRNA spacer | GUAUCCAAAACCCACCAGUA | 85 |
| CH42 sgRNA spacer | GUCAGUCUCACAGGUUACAG | 88 |

TABLE 4 sgRNA target gene sequence in the G6PC gene

| Name | Target gene(PAM) sequence | SEQ ID NO |
|---|---|---|
| CH32 target gene | TCTTTGGACAGCGTCCATAC(TGG) | 82 |
| CH34 target gene | TGGACAGCGTCCATACTGGT(GGG) | 84 |
| CH36 target gene | GTATCCAAAACCCACCAGTA(TGG) | 86 |
| CH42 target gene | GTCAGTCTCACAGGTTACAG(GGG) | 87 |

The results demonstrate that a donor polynucleotide can be precisely inserted at a site of a Cas9-mediated DSB by NHEJ DNA repair mechanisms in dividing cells, allowing for the alteration of a nucleotide sequence in a desired manner at a particular location in gDNA. In addition, the data suggest that a lower limit and upper limit of donor polynucleotide length for the insertion under these conditions is about 25 nt in length and about 75 nt in length, respectively, and that an optimal length of a donor polynucleotide for insertion of the corrective edits, from those tested, is about 50 nt in length.

To further evaluate the effect of donor polynucleotide length and position of the gRNA target site on the ability of a cell to insert a donor polynucleotide into a CRISPR/Cas9-mediated DSB in gDNA via NHEJ DNA repair mechanisms in a manner that results in a desired nucleotide sequence alteration in a gDNA, three different sgRNAs specific for G6PC exon 2 were selected as shown in Table 2 (CH32 sgRNA (SEQ ID NO: 6), CH34 sgRNA (SEQ ID NO: 7), and CH36 sgRNA (SEQ ID NO: 8); each gRNA targets a different site within G6PC exon 2 with target gene sequences shown in Table 4).

The sgRNAs were combined with a donor polynucleotide of various length (as set forth Table 5) and the ability to insert the donor polynucleotide into different positions within the genomic DNA of dividing hepatocyte-derived cells was determined. Briefly, HuH-7 cells constitutively expressing SpCas9 were transfected, as above, with three different sgRNAs specific for G6PC exon 2 (CH32 sgRNA, CH34 sgRNA, and CH36 sgRNA in Table 5). The sgRNAs were co-transfected with a corresponding donor polynucleotide each comprising at least a 3' splice site and an exonic sequence designed to make the single amino acid change of R to C in exon 2 of the G6PC gene. Following transfection as described above, the insertion of the donor polynucleotides into a DSB generated by each corresponding sgRNA in complex with SpCas9 was evaluated. The nucleotide sequences of the sgRNAs and donor polynucleotides are shown in Table 2 and Table 5 respectively. After 48 h post-transfection, the cells were processed to obtain gDNA and the percentage of total sequence reads incorporating a corrective edit encoded by the donor polynucleotides was determined by NGS analysis as described above.

gDNA is not limited to a single sgRNA and occurs independent of target site. In addition, the results show that donor polynucleotides that are 70 nucleotides in length or longer do not insert in to DSBs with appreciable frequency, further suggesting that an upper length limit of donor

TABLE 5

Sequences of dsODN donor polynucleotides for introducing a codon change in the G6PC gene

| Donor Polynucleotide (Size) | Donor Polynucleotide Sequence (5'-3', Sense Strand) | SEQ ID NO |
|---|---|---|
| En CH32 50-0 (50 nt) | ttcataaacttgttctgttttttatagGATTCTCTTTGGACAGTGCCCT | 20 |
| En CH32 55-0 (55 nt) | ttcatcccagaaacttgttctgccatagGATTCTCTTTGGACAGTGCCCT | 22 |
| En CH32 60-0 (60 nt) | attcattaaccccagaaacttgttctgttttccatagGATTCTCTTTGGACAGTGCCCT | 24 |
| CH32 65-0 (65 nt) | cattcattcagtaaccccagaaacttgttctgttttccatagGATTCTCTTTGGACAGTGCCCT | 26 |
| CH32 70-0 (70 nt) | aaaagcattcattcagtaaccccagaaacttgttctgttttccatagGATTCTCTTTGGACAGTGCCCT | 28 |
| En CH34 54-0 (54 nt) | ttcataaacttgttctgttttttatagGATTCTCTTTGGACAGTGCCCTTACT | 30 |
| En CH34 59-0 (59 nt) | ttcatcccagaaacttgttctgttttccatagGATTCTCTTTGGACAGTGCCCTTACT | 32 |
| En CH34 64-0 (64 nt) | attcattaaccccagaaacttgttctgttttccatagGATTCTCTTTGGACAGTGCCCTTACT | 34 |
| CH34 69-0 (69 nt) | cattcattcagtaaccccagaaacttgttctgttttccatagGATTCTCTTTGGACAGTGCCCTTACT | 36 |
| CH34 74-0 (74 nt) | aaaagcattcattcagtaaccccagaaacttgttctgttttccatagGATTCTCTTTGGACAGTGCCCTTACT | 38 |
| En CH36 53-0 (53 nt) | ttcataaacttgttctgttttttatagGATTCTCTTTGGACAGTGCCCTTAC | 40 |
| En CH36 58-0 (58 nt) | ttcatcccagaaacttgttctgttttccatagGATTCTCTTTGGACAGTGCCCTTAC | 42 |
| En CH36 63-0 (63 nt) | attcattaaccccagaaacttgttctgttttccatagGATTCTCTTTGGACAGTGCCCTTAC | 44 |
| CH36 68-0 (68 nt) | cattcattcagtaaccccagaaacttgttctgttttccatagGATTCTCTTTGGACAGTGCCCTTAC | 46 |
| CH36 73-0 (73 nt) | aaaagcattcattcagtaaccccagaaacttgttctgttttccatagGATTCTCTTTGGACAGTGCCCTTAC | 48 |

Donor Polynucleotide Key
| Annotation | Donor Polynucleotide Design Element |
|---|---|
| lowercase | intronic sequence |
| lowercase italics | 3' splice site |
| lowercase solid underline | polyprimidine tract |
| lowercase bold | nucleotide substitutions to strengthen pyrimidine tract |
| lowercase dotted underline | branch point sequence |
| UPPERCASE | exonic sequence |
| UPPERCASE SOLID UNDERLINE | cysteine codon |
| UPPERCASE BOLD | desired altered nucleotide(s) |

Figure 2C:
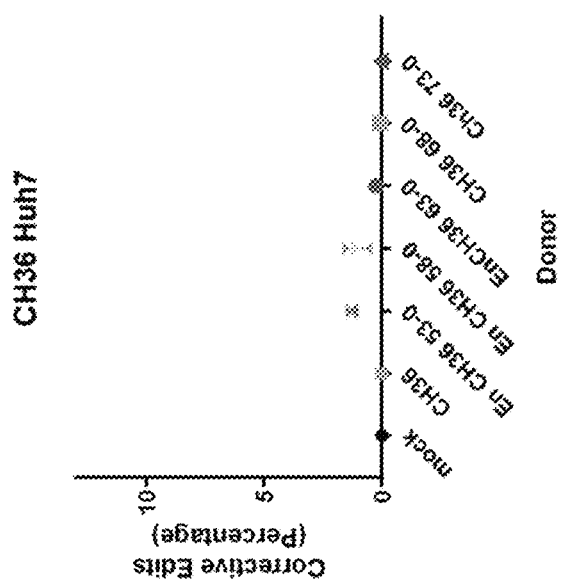
FIGS. 2A-2C provide dot plots depicting the percentage of total sequencing reads that correspond to specific nucleotide changes (e.g., a corrective edit) encoded by the donor polynucleotide, indicating NHEJ-mediated insertion of the donor polynucleotide into the target gene (e.g., G6PC exon 2), as determined by next-generation sequencing (NGS).
Figure 2B:
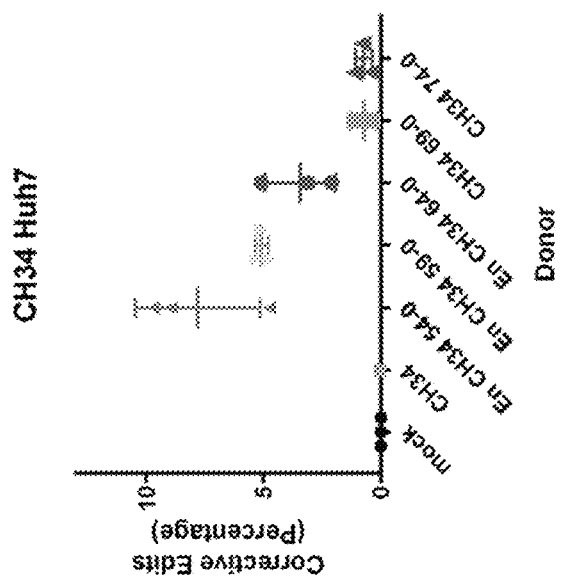
Figure 2A:
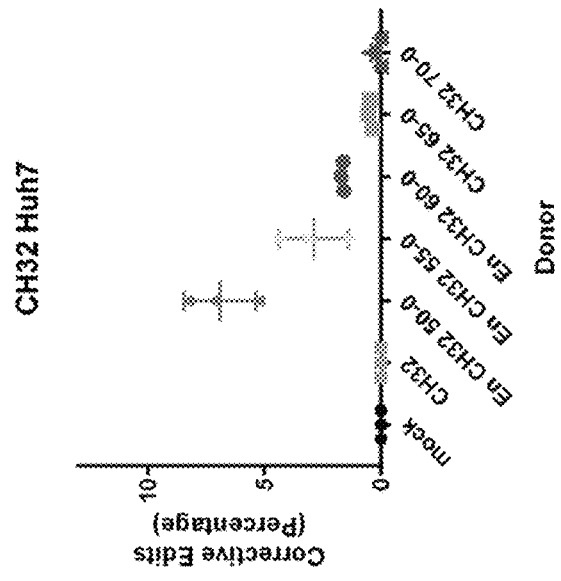

FIGS. 2A-2C show the percentage corrective insertion that was determined as described above, wherein percentage corrective edits are shown following NHEJ-mediated insertion of donor polynucleotide dsODNs into a DSB induced in the G6PC gene by Cas9 and sgRNA depicted by SEQ ID NO: 6 (FIG. 2A), SEQ ID NO: 7 (FIG. 2B), or SEQ ID NO: 8 (FIG. 2C). The data shown in FIGS. 2A-2C demonstrate that the insertion of the tested donor polynucleotides into polynucleotides for insertion into a DSB under these conditions is about 70 nucleotides in length, consistent with the results shown in Table 1. However, in subsequent studies, as detailed below, dsODN donor polynucleotides with longer lengths allowed for insertion into a DSB with efficiency comparable to a 50 nt dsODN. As described further in the Examples, the efficiency of insertion for longer length dsODN donor polynucleotides may depend upon the sgRNA, the gene locus being targeted, and the preparation of the dsODN reagents.

Example 3: Insertion of Donor Polynucleotides into the G6PC Gene of Non-Dividing Primary Human Hepatocytes Modulates G6PC Pre-mRNA Splicing To evaluate the effect of insertion of a donor polynucleotide into the G6PC locus on splicing of G6PC pre-mRNA in non-dividing primary human hepatocytes (PHHs) that express G6PC, the CH34_54-0 donor polynucleotide (CH34_54-0; SEQ ID NO: 30), which provided the highest level of insertion in dividing HuH-7 cells was selected and tested. The CH34_54-0 donor polynucleotide comprises an intronic sequence encoding a 3' splice site juxtaposed to an exonic sequence corresponding to the 5' end of the G6PC exon 2 comprising a codon that makes an amino acid change (R83C) in the exon 2 coding region upon insertion Briefly, PHHs in co-culture with mouse fibroblasts in a 24 well plate, were transfected with various concentrations of CH34_54-0 in transfection solution which included mRNA encoding SpCas9 (600 ng) and a sgRNA targeting G6PC exon 2 (CH34; SEQ ID NO: 7; 200 ng). A range of concentrations of the dsODN donor polynucleotide (from 0.56 ng and 10 ng) were tested. Lipofectamine RNAiMAX Transfection Reagent was used as recommend by the manufacture (ThermoFisher, USA) to promote tranfection of the cells. After 48 h post transfection, AllPrep DNA/RNA Mini Kit was used to simultaneously isolate total RNA and gDNA per the manufacturer's instructions (Qiagen, USA). To measure incorporation of a gene change in the mRNA, PCR primers specific to G6PC exon 1 and exon 3 were used to create cDNA amplicons for NGS analysis to determine the percentage of cDNA amplicons comprising an G6PC exon 2 encoding the amino acid change (R83C) in the coding region (% corrective edits). The cells were also processed to obtain gDNA and analyzed by NGS analysis to determine the % of corrective insertion of the donor polynucleotides. The sequence reads that were positive for corrective edits (i.e.: have the appropriate splice signals and desired nucleotide change(s)) were compared to the total sequence reads to determine the percent of corrective edits.

Figure 3:
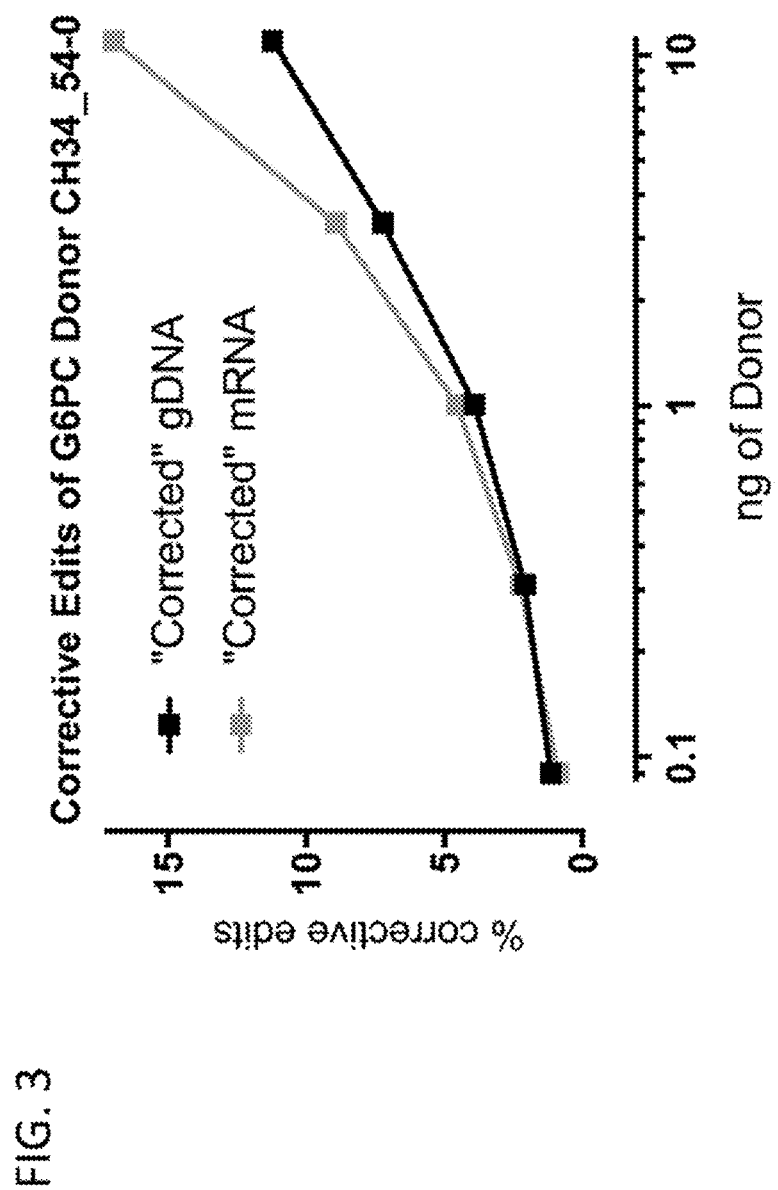
FIG. 3 provides a line graph showing the percentage of corrective edits that result from NHEJ-mediated insertion of the donor polynucleotide into the G6PC exon 2 gDNA locus (DNA) at the CH34 sgRNA target site. The insertion of the donor polynucleotide containing the additional splicing signals and a nucleotide change in the ORF results in a corrective edit in the G6PC DNA (black line), and also results in transcription of the G6PC gene that yields an mRNA containing the desired predicted edit (gray line). The level of corrective editing is also shown to be a function of the amount of donor polynucleotide used (ng of Donor).

FIG. 3 shows the percentage of corrective edits (determined as described above) that result from NHEJ-mediated insertion of the donor polynucleotide into the G6PC exon 2 gDNA locus (DNA) at the CH34 sgRNA target site (SEQ ID NO: 84). The insertion of the donor polynucleotide containing the additional splicing signals and a nucleotide change in the ORF results in a corrective edit in the G6PC DNA (black line), and also results in the G6PC gene expressing an mRNA containing the predicted gene edit (gray line). The level of corrective editing is also shown to be a function of the amount of donor polynucleotide present (ng of Donor). At the DNA level, the data demonstrate a dose dependent increase in insertion of the donor polynucleotide and that, at the highest concentration tested, approximately 10% of G6PC alleles had the donor polynucleotide correctly inserted into the Cas9-mediated DSB in non-dividing primary human hepatocytes. This represents an over 15-fold increase in the percentage of corrective editing events in cells as compared to correction of the gene using a homology donor polynucleotide and HDR-based repair approach. Previously, the HDR approach achieved only ~0.5% corrective edit in non-dividing cells (data not shown). In addition, cells transfected with the highest concentration of donor also showed a similar level of corrective edits in the mature G6PC RNA (>15%; FIG. 3). These data demonstrate that the insertion of the CH34_54-0 donor polynucleotide into a specific Cas9-mediated DSB in the G6PC gene results in the inclusion of the altered polynucleotide sequence (i.e., desired codon change) into a mature G6PC mRNA in a dose-dependent manner.

Example 4: Mice Treated with Donor Polynucleotides Modulates G6PC Pre-mRNA Splicing In Vivo To evaluate the effect of NHEJ-mediated insertion and corrective editing of a donor polynucleotide into the G6PC locus in vivo, mice were treated with mRNA encoding SpCas9, a sgRNA targeting murine G6PC exon 2 (Murine CH34; SEQ ID NO: 7) and the CH34_54-0 donor polynucleotide (SEQ ID NO: 30) described in Example 2.

Briefly, lipidoid-based nanoparticles (LNPs) were individually formulated to contain the murine homologue of the CH34 sgRNA (Murine CH34; SEQ ID NO: 89), mRNA encoding SpCas9 or the donor polynucleotide CH34_54-0 (SEQ ID NO: 30). The LNPs were formulated separately to contain the sgRNA, mRNA, and donor polynucleotide, each at a 20:1 nucleic acid:lipid ratio and then the LNPs were mixed prior to administration by injection. Mice (C57BL/6, 6-8 weeks old, 5 animals per group) were injected in the tail-veil with one of three treatments: PBS, an LNP mixture containing both murine CH34 gRNA LNPs at 0.5 mg/kg and SpCas9 mRNA LNPs at 0.5 mg/kg, or an LNP mixture containing murine CH34 gRNA LNPs at 0.5 mg/kg, SpCas9 mRNA LNPs at 0.5 mg/kg, and CH34_54-0 donor polynucleotide LNPs at 0.5 mg/kg. After 96 h post-injection, the livers of mice were harvested, gDNA extracted, NGS analysis performed and corrective edits were determined as described in Example 3.

Figure 4A:
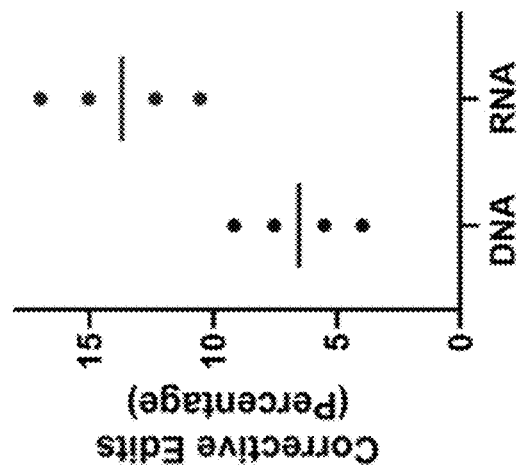
FIG. 4A provides a dot plot showing the percentage of total sequencing reads that correspond to a corrective edit that results from NHEJ-mediated insertion of the donor polynucleotide into the G6PC exon 2 gDNA locus of liver cells of mice treated with lipid nanoparticles (LNPs) comprising the donor polynucleotide, mRNA encoding Cas9, and G6PC-targeting gRNA.
Figure 4B:
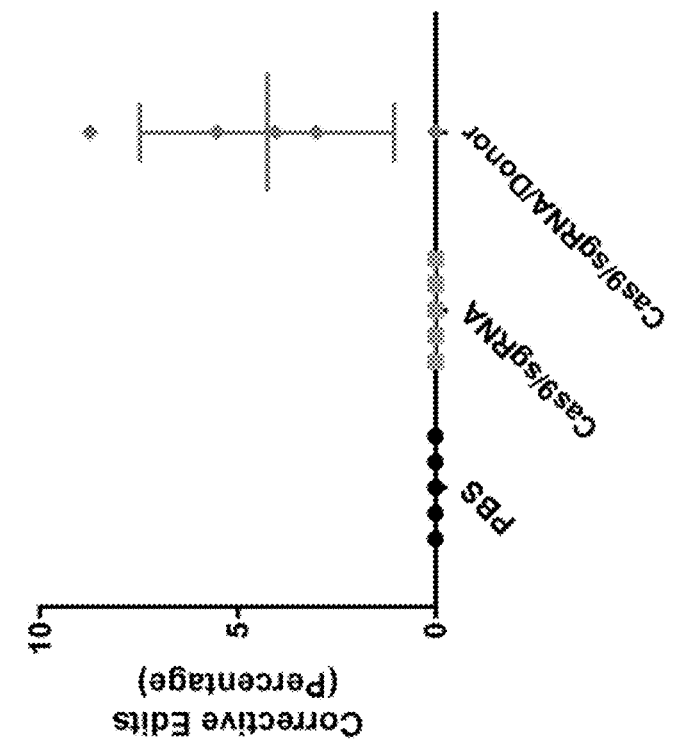
FIG. 4B provides a dot plot showing the percentage of corrective edits in gDNA and transcribed mRNA resulting from a perfect NHEJ-mediated insertion of a donor polynucleotide following in vivo administration of LNP comprising Cas9 mRNA, donor polynucleotide, and G6PC-targeting gRNA.

FIG. 4A shows the percentage of corrective edits (determined as described above) that resulted from NHEJ-mediated insertion of the donor polynucleotide, as indicated. Additionally, in a separate experiment, the percentage of corrective edits resulting from perfect insertion of the donor polynucleotide were determined in both the gDNA and in the mRNA transcript as described in Example 2. Increased levels of corrective editing were seen at the level of the gDNA and the mRNA transcript as shown in FIG. 4B. Notably, the incorporation of corrective edits is increased at the level of the mRNA transcript. It is known that a proportion of hepatocytes have multiple nuclei per cell that appear to have different expression levels and patterns (Kreutz, et al. (2017) *Front Physiol.* 8:862). Without being bound by theory, it is thought that correction of gDNA may be enhanced in the more actively-transcribed alleles of G6PC. If only actively transcribed gDNA is gene-edited, the percentage of gDNA encoding the target gene and incorporating a corrective edit would be lower than the percentage of corresponding mRNA encoding a corrective edit. The data shown in FIGS. 4A-4B demonstrate that LNPs can deliver all three components and that NHEJ-mediated insertion of donor polynucleotides occurs in mouse liver cells in vivo, resulting the desired gene edit (i.e., corrective edit).

Figure 5:
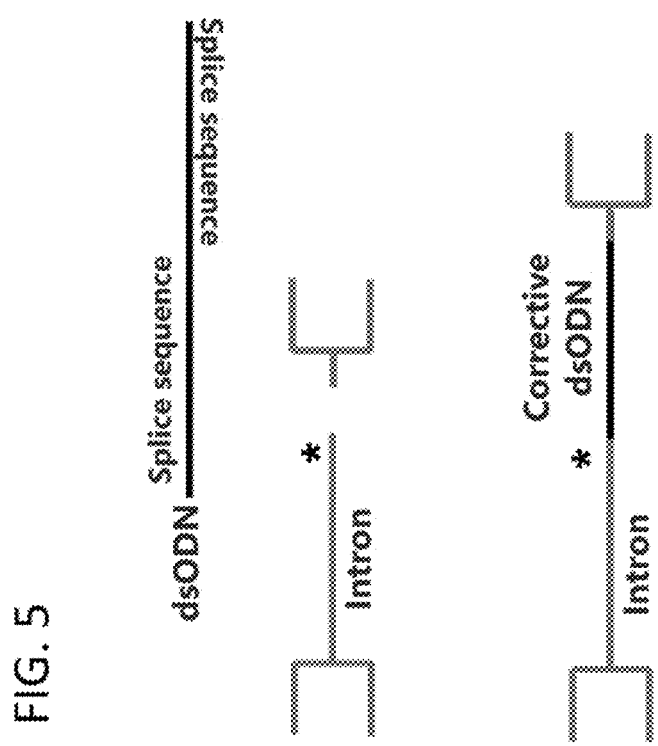
FIG. 5 provides a schematic describing the design of a bidirectional donor polynucleotide. The donor is designed to incorporate splicing sequences when inserted into a DNA DSB in either the forward or reverse direction.

Example 5: Bi-Directional Donor Polynucleotides Improves NHEJ-Mediated Insertion and Correction of G6PC or GAA in Hepatocyte-Derived Cells The donor polynucleotides described in Examples 1-4 were designed to result in a corrective insertion, when the donor polynucleotide was inserted in a single (forward)

orientation. However, given that a donor polynucleotide (e.g., donor dsODN) inserted into a DSB by NHEJ-repair pathway can be inserted in either the forward or reverse direction, it is ideal that the desired gene edit and splicing signals be incorporated regardless of which direction the donor polynucleotide is inserted. Thus, bidirectional donor polynucleotides were designed that would encode a corrective edit and desired splicing signals when inserted in either the forward or reverse orientation as shown in FIG. 5.

To determine the effectiveness of a bidirectional polynucleotide in hepatocyte-derived cells, a group of donor polynucleotides were designed for bi-directional insertion in either the G6PC gene or the GAA gene, which when mutated, is associated with Pompe disease. The mutation in the GAA gene occurs in an intron and affects splicing, therefore the donor polynucleotide was designed with a pyrimidine tract, and a branch point. The branch point was specifically designed to function if the donor is inserted in either the forward or reverse orientation. Because the G6PC donor polynucleotide requires exonic sequence to correct the mutation, the length of the CH42_25-0 donor did not allow for the use of the bidirectional donor, so this donor only inserts in a unidirectional manner.

A sgRNA which targets the region containing the most common mutation associated with adult onset Pompe disease (IVS 1 (−13T>G)), GAA-5 sgRNA (SEQ ID NO: 61), was selected and is depicted in Table 6. The IVS 1 (−13T>G) mutation disrupts the pyrimidine tract of exon 2 of the GAA gene. The disruption leads to exon 2 skipping and the activation of cryptic splice sites that negatively impact GAA gene expression and enzymatic activity of the gene product. The GAA-5 sgRNA depicted in Table 6 targets the region of the wild type GAA gene where this occurs (SEQ ID NO: 61).

TABLE 6 gRNA for directing a site-specific DSB in the GAA gene

| sgRNAs | Nucleotide Sequence (5'-3') | SEQ ID NO |
|---|---|---|
| WT GAA Target gene (PAM) | AGCCCGCTTTCTTCTCCCGC(AGG) | 90 |
| WT GAA5 sgRNA spacer | AGCCCGCUUUCUUCUCCCGC | 91 |
| WT GAA5 sgRNA | AGCCCGCUUUCUUCUCCCGCGUUUUAGAGCUAGAAAUAGCAAGUUAAAAUAAGGCUAGUCCGUUAUCAACUUGAAAAAGUGGCACCGAGUCGGUGCUUUU | 61 |

TABLE 6-continued gRNA for directing a site-specific DSB in the GAA gene

| sgRNAs | Nucleotide Sequence (5'-3') | SEQ ID NO |
|---|---|---|
| Mutant (Mt) GAA target gene (PAM) | AGCCCGCTTGCTTCTCCCGC(AGG) | 92 |
| Mt GAA sgRNA spacer | AGCCCGCUUGCUUCUCCCGC | 93 |
| Mt GAA sgRNA | AGCCCGCUUGCUUCUCCCGCGUUUUAGAGCUAGAAAUAGCAAGUUAAAAUAAGGCUAGUCCGUUAUCAACUUGAAAAAGUGGCACCGAGUCGGUGCUUUU | 94 |

The bidirectional donor dsODNs designed for insertion into the GAA gene are shown in Table 7. In the 5' to 3' direction, the donor dsODN sequences comprised a reverse and complement of the polypyrimidine tract CTTCTTCTCTTCTTCC (SEQ ID NO: 55), optionally a reverse and complement of the branch point sequence TACTGAC (SEQ ID NO: 52), a branch point sequence TATTAAC, and a polypyrimidine tract TTTTTTTCTTTTT (SEQ ID NO: 54). The 3' splice site coded by YAG/G (wherein Y is thymine or cytosine, and/indicates the border between exon and intron), is located in the gDNA. Insertion of a bidirectional donor comprising a branch point sequence and polypyrimidine tract allows correct splicing at the 3' splice site in the gDNA. As an example, the sense and antisense sequence of the 50 nt dsODN depicted by SEQ ID NO: 63 is shown in FIG. 6A. Regardless of whether the 50 nt dsODN is inserted in either the forward or reverse direction, the resulting gene encodes the desired corrective edits (e.g., incorporation of a branch point sequence and corrected polypyrimidine tract) as shown in FIG. 6B.

Notably, in the design of the dsODN donors, the splicing signals encoded in the forward direction do not encode the same sequence as the equivalent splicing signal encoded in the reverse direction. For example, the polypyrimidine tract TTTTTTTCTTTTT (SEQ ID NO: 54) encoded in the forward direction is different than the polypyrimidine trac in the reverse direction CTTCTTCTCTTCTTCC (SEQ ID NO: 55), though both conform to a polypyrimidine tract consensus sequences. Without being bound by theory, the purpose of this design element is to avoid self-annealing of a dsODN that could hinder insertion or of an mRNA transcribed from a gene with an inserted dsODN. Such self-annealing of the mRNA could result in poor mRNA expression level. Thus, for a given splicing signal in the forward direction, the equivalent splicing signal in the reverse direction has a different sequence, but both conform to a consensus sequence for the given splicing signal needed to achieve splicing of the transcribed mRNA.

TABLE 7

Bi-Directional dsODN donor polynucleotides for insertion of splicing signals into the GAA gene

| Donor Polynucleotide (size) | Nucleotide Sequence (5'-3') | SEQ ID NO |
|---|---|---|
| GAA 25-0_F (25 nt) | gagaagaagTATTAACtttttttct | 62 |
| GAA_50-0_F (50 nt) | tggaagaagagaagaagctgggTATTAACgcattttttttctttttaattc | 63 |

TABLE 7-continued

Bi-Directional dsODN donor polynucleotides for insertion of splicing signals into the GAA gene

| Donor Polynucleotide (size) | Nucleotide Sequence (5'-3') | SEQ ID NO |
|---|---|---|
| GAA_75-0_F (75 nt) | tggaagaagagaagaagctgggaatgtGTCAGTAaggcatgTATTAAC gcaaatgaattttttttcttttttaattc | 64 |
| GAA_100-0_F (100 nt) | tggaagaagagaagaagctgggaatgtGTCAGTAaggcatgagccaccgcg ccagccatgcaaatcTATTAACgcaaatgaattttttttcttttttaattc | 65 |

| Donor Polynucleotide Key Annotation | Donor Polynucleotide Design Element |
|---|---|
| lowercase | intronic sequence |
| lowercase dotted underline | delimiter sequence |
| lowercase bold | 3' splice site and polypyrimidine tract |
| lowercase double underline | reverse and complement polypyrimidine tract and 3' splice site |
| UPPERCASE SOLID UNDERLINE | sequence that conforms to the branch point consensus in either direction |
| UPPERCASE DOUBLE UNDERLINE | Reverse and complement of the branch point sequence TACTGAC |

*CH42 25-0 was designed as a unidirectional donor polynucleotide.

The combinations of sgRNA and bidirectional donor polynucleotides (except ch42 25-0 which is a unidirectional control) for NHEJ-mediated insertion into the G6PC gene are set forth in Table 2 and Table 8 respectively. The bidirectional donor dsODNs were designed to incorporate an upstream 5' splice site and wild type exonic coding sequence of the G6PC gene upon insertion into a cut site induced near the 3' end of exon 2 of the G6PC gene. In the 5' to 3' direction, the bidirectional donor dsODNs were designed to incorporate an exonic coding sequence, a 5' splice site, a reverse and complement of the 5' splice site GTGAGT (SEQ ID NO: XX), and a reverse and complement of the exonic coding sequence. Regardless of whether the donor dsODN is inserted in the forward or reverse direction, the resulting gene encodes the desired corrective edits (e.g., exonic coding sequence upstream of a 5' splice site).

TABLE 8

Bi-directional dsODN donor polynucleotides for introducing a codon change in the G6PC gene

| Donor Polynucleotide (size) | Nucleotide Sequence (5'-3') | SEQ ID NO |
|---|---|---|
| CH42 0-25* (25 nt) | AACCTGTGAGACTGGACCAG*gtaag* | 71 |
| CH42 0-50 (50 nt) | AACCTGTGAGACTGGACCAG*gtaag*actcacACTTGCGA AACCGGCCCAG | 73 |
| CH42 0-75 (75 nt) | AACCTGTGAGACTGGACCAG*gtaag*cgacgcgcatttctcacacg gcaggactcacACTTGCGAAACCGGCCCAG | 75 |
| CH42 0-100 (100 nt) | AACCTGTGAGACTGGACCAG*gtaag*cgacgcgcatttctcacacg gcagggagggccacacgcgtttgtttctcaactcacACTTGCGAAACCG GCCCAG | 77 |
| CH42 0-125 (125 nt) | AACCTGTGAGACTGGACCAG*gtaag*cgacgcgcatttctcacacg gcagggagggccacacgcgtttgtttctcacacgatgggcagggcgacacatgttac tcacACTTGCGAAACCGGCCCAG | 79 |

| Donor Polynucleotide Key Annotation | Donor Polynucleotide Design Element |
|---|---|
| lowercase | intronic sequence |
| *lowercase italics* | 5' splice site |
| lowercase solid underline | reverse and complement 5' splice site |
| lowercase dotted underline | delimiter sequence |
| UPPERCASE | exonic sequence |
| UPPERCASE BOLD | reverse and complement exonic sequence |

The percent insertion in either orientation (forward or reverse) in the GAA or G6PC gene was determined. Briefly, HuH-7 cells were independently transfected with 20 ng of donor polynucleotide, an sgRNA, and mRNA encoding SpCas9 as described in Example 2. Huh-7 cells express SpCas9, but were further transfected with mRNA encoding SpCas9 to improve editing efficiency. NGS analysis and determination of percent corrective insertion was determined as described above.

FIGS. 7A-7D depicts the percentage of corrective edits for the bidirectional donor polynucleotides targeting G6PC or GAA in Huh-7 cells. The results show that the bidirectionality of the donor polynucleotides dramatically increases the percentage of corrective insertions.

Figure 7A:
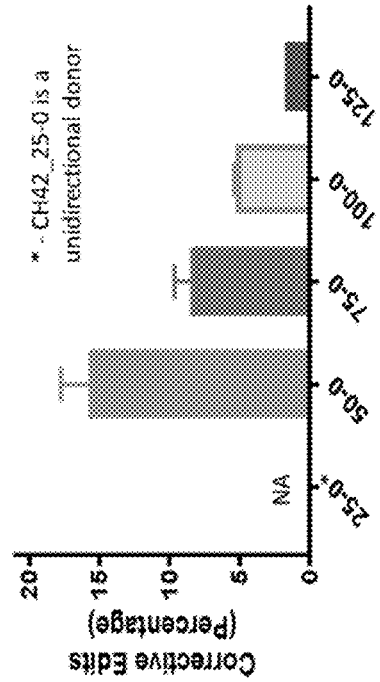
FIG. 7A and FIG. 7C provide bar graphs showing the percentage of corrective edits in cells treated with unidirectional donor polynucleotides that encode a corrective edit when inserted in the forward direction into a DSB induced in the G6PC (FIG. 7A) or GAA gene (FIG. 7C).
Figure 7B:
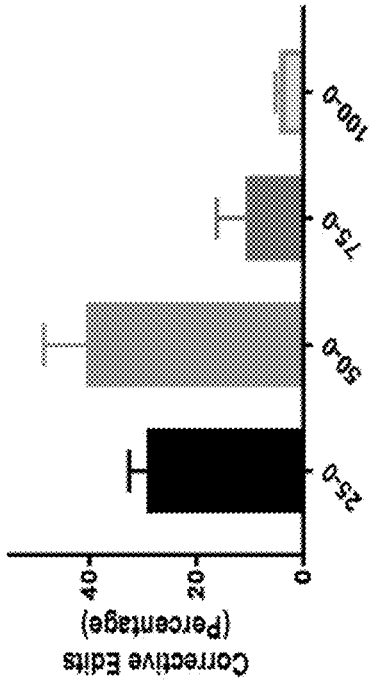
FIG. 7B and FIG. 7D provide bar graphs showing the percentage of corrective edits in cell treated with bidirectional donor polynucleotides that encode a corrective edit when inserted in either the forward direction or the reverse direction into a DSB induced in the G6PC (FIG. 7B) or GAA gene (FIG. 7D).
Figure 7C:
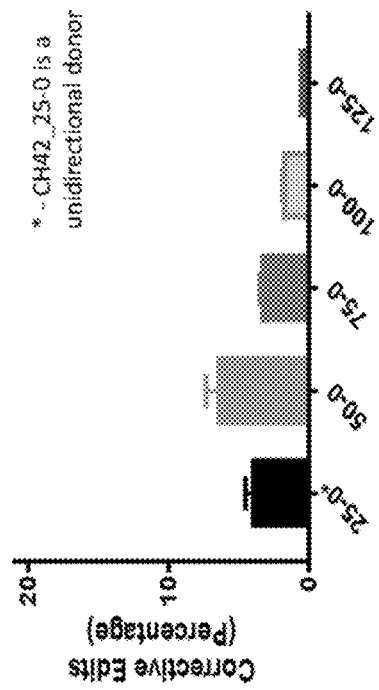
Figure 7D:
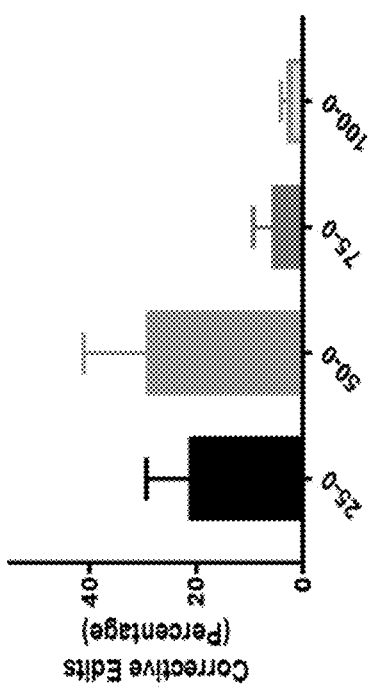

FIG. 7A and FIG. 7C show the percentage of corrective edits when the donor polynucleotide inserts in the forward direction (similar to a unidirectional donor polynucleotide) in the G6PC gene (FIG. 7A) and GAA gene (FIG. 7C). Furthermore, FIG. 7B and FIG. 7D demonstrate that the percentage of corrective insertions significantly increases with bidirectional insertion (insertion in either the forward or reverse direction). The bidirectional polynucleotides showed significant insertion at lengths between 25 and 75 nucleotides, with 50 nucleotides showing the highest insertion rate. The bidirectional 50-0 donor polynucleotide exhibited the highest percent corrective insertion overall. Consistent with the corrective insertions observed in Examples 1-3, significant levels of corrective editing was observed in cells transfected with bidirectional donor polynucleotides between 25-75 nt and up to 100 nt in length that target either the G6PC gene with an sgRNA distinct from the target guides shown above (e.g., CH42 sgRNA; FIG. 7A-7B), or the human GAA gene (FIG. 7C-7D).

Figure 8:
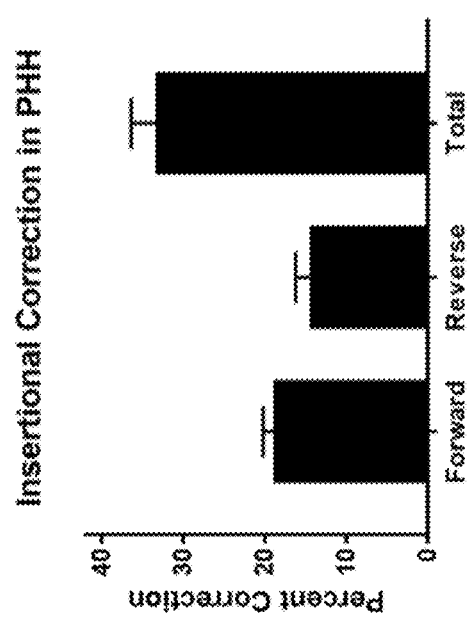
FIG. 8 provides a bar graph showing the percentage of corrective edits resulting from insertion of a 50 nt bidirectional donor into a DSB induced in the GAA gene in primary human hepatocytes. Depicted are percentage of total sequence reads resulting from perfect forward insertion of the donor, perfect reverse insertion, and combined total perfect insertion.

The levels of insertion of a 50 nt bidirectional donor into the GAA gene was further evaluated to determine the percentage of corrective edits resulting from insertion in the forward direction versus the reverse direction. PHH cells were transfected with sgRNA specific to a target sequence in the wild type GAA gene locus (SEQ ID NO: 61), mRNA encoding spCas9, and a 50 nt bidirectional donor (e.g., dsODN) shown by SEQ ID NO: 63. At 48 hours following transfection, the sequence of the GAA gene was determined by NGS as described in Example 2. The percentage of total sequence reads resulting from a perfect insertion in either the forward or the reverse direction was determined. As shown in FIG. 8, insertion in either the forward or the reverse direction was found to be comparable, with slightly higher levels of corrective edits induced by insertion in the forward direction.

Figure 9:
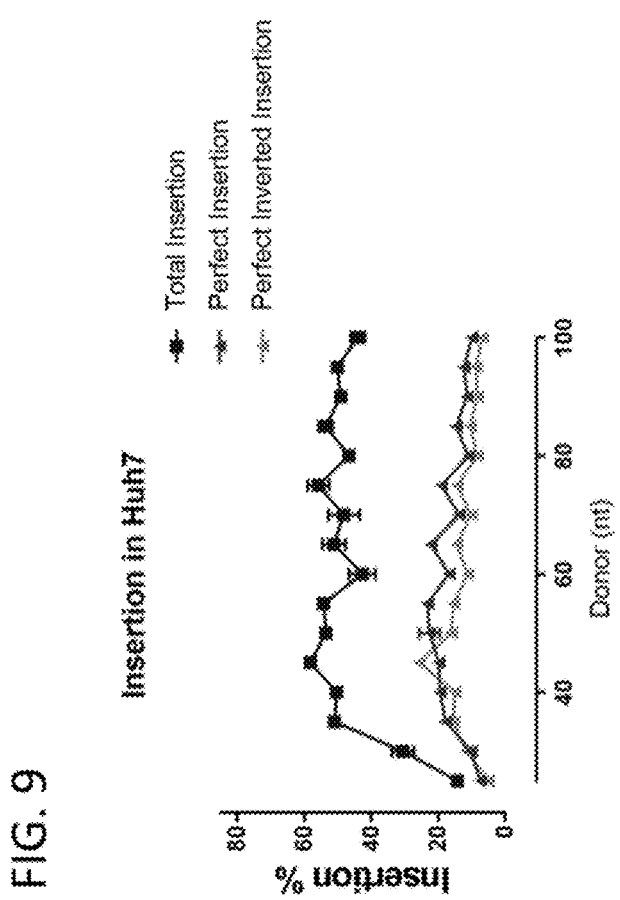
FIG. 9 provides a line graph showing the percentage of corrective edits resulting from insertion of bidirectional donors of varied lengths into a DSB induced in the GAA gene in Huh-7 cells. Shown is the percentage of corrective edits resulting from total insertion, as well as insertion in the forward (e.g., perfect insertion) or reverse direction (e.g., perfect inverted insertion).

Having observed that the efficiency of insertion was dependent upon the length of the donor polynucleotide, further studies were performed to evaluate this dependence for insertion into a site-specific DSB induced in the GAA gene by the sgRNA shown by SEQ ID NO: 61 in Table 6. Donor dsODNs were prepared that differed in length by 5 nt, ranging from a length of 25 nt to a length of 100 nt. These include sequences described in Table 7 and additional sequences with varied length. The sequences of the donor dsODNs that were designed and evaluated are shown in Table 9. Perfect NHEJ-mediated insertion into the GAA gene locus was evaluated in HuH-7 cells as described above. Interestingly, in contrast to the effect observed for insertion of a bidirectional donor in the GAA gene as shown in FIG. 7D, longer donor dsODNs (e.g., >50 nt) were observed to have similar efficacy of insertion to shorter dsODNs (e.g., 50 nt). Indeed, as shown in FIG. 9, a 100 nt donor dsODN induced similar levels of total insertion (e.g., perfect insertion in either the forward or reverse direction) as a 50 nt donor dsODN. A key differences was the vendor used to generate the dsODN reagents (dsODNs used to generate insertion shown in FIG. 7D were obtained from TriLink Biotechnologies, San Diego, Calif.; dsODNs used to generate insertion shown in FIG. 9 from BioSpring, Frankfurt, Germany). Thus, high efficiency insertion is achieved for long length donor dsODNs (e.g., length greater than 50 nt). However, without being bound by theory, the efficiency of insertion of long length donors dsODNs (e.g., length greater than 50 nt) may depend upon the quality of the donor polynucleotide reagent, the particular gene locus being edited, and/or the particular cut site selected based upon the gRNA.

TABLE 9

Bi-Directional Donor Polynucleotides for NHEJ-mediated insertion

| Donor Polynucleotide (size) | Nucleotide Sequence (5'-3') | SEQ ID NO |
|---|---|---|
| GAA_25 (25nt) | gagaagaagTATTAACtttttttct | 62 |
| GAA_30 (30nt) | aagagaagaagTATTAACttttttttctttt | 95 |
| GAA_35 (35nt) | aagaagagaagaagTATTAACttttttttcttttta | 96 |
| GAA_40 (40nt) | ggaagaagagaagaagTATTAACttttttttcttttaatt | 97 |
| GAA_45 (45nt) | tggaagaagagaagaagctTATTAACttttttttcttttaattc | 98 |
| GAA_50 (50nt) | tggaagaagagaagaagctgggTATTAACgcattttttttcttttaattc | 63 |
| GAA_55 (55nt) | tggaagaagagaagaagctgggTATTAACgcaaattttttttcttttaattc | 99 |
| GAA_60 (60nt) | tggaagaagagaagaagctgggaatgtTATTAACgcaaatgatttttttcttttaattc | 100 |
| GAA_65 (65nt) | tggaagaagagaagaagctgggaatgGTCAGTATATTAACgcaaatgtttttttcttttaattc | 101 |

TABLE 9-continued

Bi-Directional Donor Polynucleotides for NHEJ-mediated insertion

| Donor Polynucleotide (size) | Nucleotide Sequence (5'-3') | SEQ ID NO |
|---|---|---|
| GAA_70 (70nt) | tggaagaagagaagaagctgggaatgtGTCAGTAagTATTAACgcaaa tgaattttttctttttaattc | 102 |
| GAA_75 (75nt) | tggaagaagagaagaagctgggaatgtGTCAGTAaggcatgTATTAAC gcaaatgaattttttctttttaattc | 64 |
| GAA_80 (80nt) | tggaagaagagaagaagctgggaatgtGTCAGTAaggcatgagccaTATT AACgcaaatgaattttttctttttaattc | 103 |
| GAA_85 (85nt) | tggaagaagagaagaagctgggaatgtGTCAGTAaggcatgagccaccgcg TATTAACgcaaatgaattttttctttttaattc | 104 |
| GAA_90 (90nt) | tggaagaagagaagaagctgggaatgtGTCAGTAaggcatgagccaccgcg ccagcTATTAACgcaaatgaattttttctttttaattc | 105 |
| GAA_95 (95nt) | tgggaagaagagaagaagctgggaatgtGTCAGTAaggcatgagccaccgc gccagccatgcTATTAACgcaaatgaattttttctttttaattc | 106 |
| GAA_100 (100nt) | tggaagaagagaagaagctgggaatgtGTCAGTAaggcatgagccaccgcg ccagccatgcaaatcTATTAACgcaaatgaattttttctttttaattc | 65 |

Donor Polynucleotide Key
Annotation                       Donor Polynucleotide Design Element
lowercase                        intronic sequence
lowercase dotted underline       delimiter sequence
lowercase bold               3' splice site and polypyrimidine tract
lowercase double underline       reverse and complement polypyrimidine tract and 3' splice site
UPPERCASE SOLID UNDERLINE        sequence that conforms to the branch point consensus in either direction
UPPERCASE SOLID UNDERLINE        Reverse and complement of the branch point sequence TACTGAC

Figure 10C:
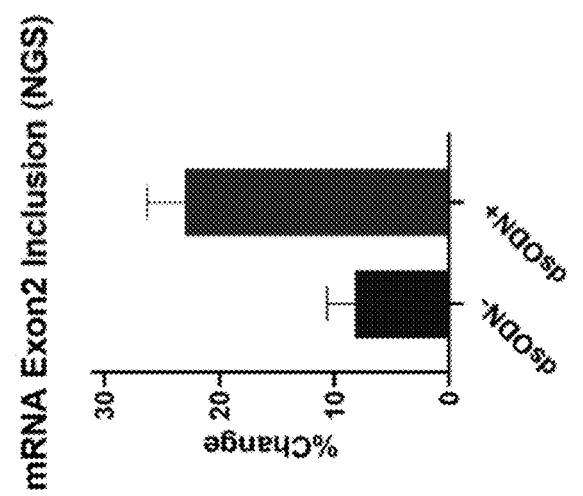
FIGS. 10A-10C provide bar graphs showing the percentage of corrective edits resulting from insertion of a bidirectional donor in a DSB induce in the GAA gene in fibroblast cells derived from patients with Pompe disease. Shown in FIG. 10A is the percentage of sequence reads of gDNA with the corrective edit encoded by the donor polynucleotide as determined by NGS. Shown in FIG. 10B is a quantification of mRNA transcripts encoding exon 2 normalized to the quantity of mRNA transcripts lacking exon 2 as determined by quantitative PCR (qPCR). Shown in FIG. 10C is the percent increase in the number of sequence reads encoding exon 2 in cells transfected with Cas9/gRNA and either with or without donor polynucleotide compared to mock transfected cells as determined by NGS.
Figure 10B:
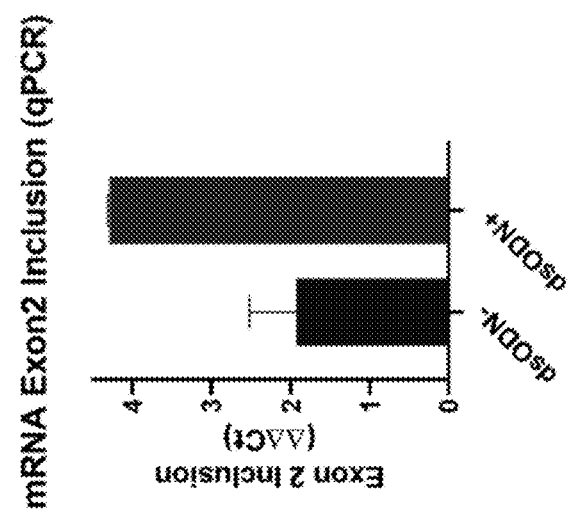
Figure 10A:
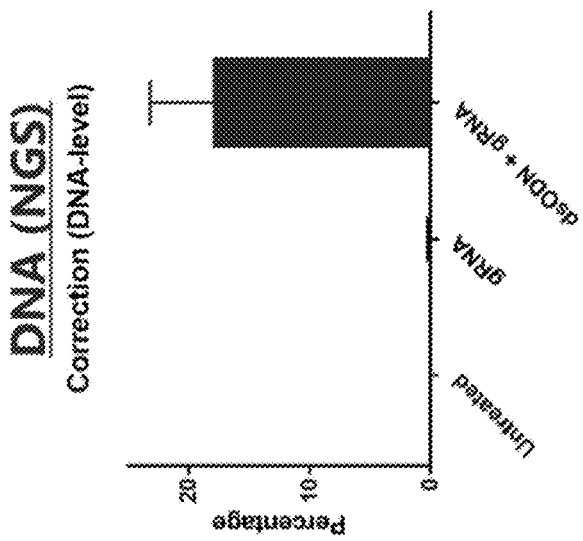

Example 6: Bi-Directional Donor Polynucleotides Improve NHEJ-Mediated Insertion in the GAA Gene in Fibroblast Cells Derived from Patients with Pompe Disease The efficiency of NHEJ-mediated insertion of a bidirectional donor polynucleotide (e.g., dsODN) into a DSB induced in the GAA locus by Cas9/gRNA was further evaluated in fibroblast cells derived from patients with Pompe disease. The cells were plated in cell culture medium and transiently transfected with gRNA targeting the mutant GAA allele (SEQ ID NO: 94), mRNA encoding spCas9, and a 50 nt bidirectional donor dsODN (SEQ ID NO: 63). At 48 hours post-transfection, gDNA was isolated from the cells and subjected to sequence analysis by NGS as described in Example 2. The percentage of total sequence reads comprising a perfect insertion of the dsODN in either the forward or the reverse direction was determined. The percentage of corrective edits resulting from perfect total insertion of the dsODN into the GAA locus is shown in FIG. 10A. Transfection with both Cas9/gRNA and dsODN resulted in high levels (exceeding 15% corrective editing) compared to control of Cas9/gRNA alone.

Additionally, the total RNA was isolated from transfected cells and evaluated for corrective editing using qPCR and NGS. For quantification of corrective editing by qPCR, two sets of qPCR probes were used. One set recognized mRNA transcripts of the GAA gene that include exon 2, while the second set recognized mRNA transcripts of the GAA gene that lack exon 2. The levels of mRNA that included exon 2 relative to the level of mRNA that lacked exon 2 was determined by qPCR. The ΔΔCt for exon inclusion is shown in FIG. 10B. Cells transfected with dsODN had elevated inclusion of exon 2 in mRNA transcribed from the mutant GAA gene, indicating increased correction of the GAA gene at the transcriptional level. This was further corroborated by sequencing the mRNA transcribed from the GAA gene using NGS. As shown in FIG. 10C, the percent increase in transcripts incorporating exon 2 compared to transcripts of mock transfected cells (e.g., untreated cells) was higher for cells transfected with donor dsODN. Together, these results validate the use of a bidirectional donor DNA for correction of a splicing mutation in the GAA gene in human cells.

SEQUENCE LISTING

| SEQ ID NO | Description | Sequence |
|---|---|---|
| 1 | Human glucose-6-phosphatase catalytic subunit (G6PC) mRNA nucleic acid sequence (NCBI Reference Sequence NM_000151.3) | ATAGCAGAGCAATCACCACCAAGCCTGGAATAACTGCAA GGGCTCTGCTGACATCTTCCTGAGGTGCCAAGGAAATGAG GATGGAGGAAGGAATGAATGTTCTCCATGACTTTGGGATC CAGTCAACACATTACCTCCAGGTGAATTACCAAGACTCCC AGGACTGGTTCATCTTGGTGTCCGTGATCGCAGACCTCAG GAATGCCTTCTACGTCCTCTTCCCCATCTGGTTCCATCTTC AGGAAGCTGTGGGCATTAAACTCCTTTGGGTAGCTGTGAT TGGAGACTGGCTCAACCTCGTCTTTAAGTGGATTCTCTTTG GACAGCGTCCATACTGGTGGGTTTTGGATACTGACTACTA CAGCAACACTTCCGTGCCCCTGATAAAGCAGTTCCCTGTA ACCTGTGAGACTGGACCAGGGAGCCCCTCTGGCCATGCCA TGGGCACAGCAGGTGTATACTACGTGATGGTCACATCTAC TCTTTCCATCTTTCAGGGAAAGATAAAGCCGACCTACAGA TTTCGGTGCTTGAATGTCATTTTGTGGTTGGGATTCTGGGC TGTGCAGCTGAATGTCTGTCTGTCACGAATCTACCTTGCTG CTCATTTTCCTCATCAAGTTGTTGCTGGAGTCCTGTCAGGC ATTGCTGTTGCAGAAACTTTCAGCCACATCCACAGCATCT ATAATGCCAGCCTCAAGAAATATTTTCTCATTACCTTCTTC CTGTTCAGCTTCGCCATCGGATTTTATCTGCTGCTCAAGGG ACTGGGTGTAGACCTCCTGTGGACTCTGGAGAAAGCCCAG AGGTGGTGCGAGCAGCCAGAATGGGTCCACATTGACACC ACACCCTTTGCCAGCCTCCTCAAGAACCTGGGCACGCTCT TTGGCCTGGGGCTGGCTCTCAACTCCAGCATGTACAGGGA GAGCTGCAAGGGGAAACTCAGCAAGTGGCTCCCATTCCGC CTCAGCTCTATTGTAGCCTCCCTCGTCCTCCTGCACGTCTT TGACTCCTTGAAACCCCCATCCCAAGTCGAGCTGGTCTTCT ACGTCTTGTCCTTCTGCAAGAGTGCGGTAGTGCCCCTGGC ATCCGTCAGTGTCATCCCCTACTGCCTCGCCCAGGTCCTGG GCCAGCCGCACAAGAAGTCGTTGTAAGAGATGTGGAGTCT TCGGTGTTTAAAGTCAACAACCATGCCAGGGATTGAGGAG GACTACTATTTGAAGCAATGGGCACTGGTATTTGGAGCAA GTGACATGCCATCCATTCTGCCGTCGTGGAATTAAATCAC GGATGGCAGATTGGAGGGTCGCCTGGCTTATTCCCATGTG TGACTCCAGCCTGCCCTCAGCACAGACTCTTTCAGATGGA GGTGCCATATCACGTACACCATATGCAAGTTTCCCGCCAG GAGGTCCTCCTCTCTCTACTTGAATACTCTCACAAGTAGGG AGCTCACTCCCACTGGAACAGCCCATTTTATCTTTGAATGG TCTTCTGCCAGCCCATTTTGAGGCCAGAGGTGCTGTCAGCT CAGGTGGTCCTCTTTTACAATCCTAATCATATTGGGTAATG TTTTTGAAAAGCTAATGAAGCTATTGAGAAAGACCTGTTG CTAGAAGTTGGGTTGTTCTGGATTTTCCCCTGAAGACTTAC TTATTCTTCCGTCACATATACAAAAGCAAGACTTCCAGGT AGGGCCAGCTCACAAGCCCAGGCTGGAGATCCTAACTGA GAATTTTCTACCTGTGTTCATTCTTACCGAGAAAAGGAGA AAGGAGCTCTGAATCTGATAGGAAAAGAAGGCTGCCTAA GGAGGAGTTTTTAGTATGTGGCGTATCATGCAAGTGCTAT GCCAAGCCATGTCTAAATGGCTTTAATTATATAGTAATGC ACTCTCAGTAATGGGGACCAGCTTAAGTATAATTAATAG ATGGTTAGTGGGGTAATTCTGCTTCTAGTATTTTTTTTACT GTGCATACATGTTCATCGTATTTCCTTGGATTTCTGAATGG CTGCAGTGACCCAGATATTGCACTAGGTCAAAACATTCAG GTATAGCTGACATCTCCTCTATCACATTACATCATCCTCCT TATAAGCCCAGCTCTGCTTTTTCCAGATTCTTCCACTGGCT CCACATCCACCCCACTGGATCTTCAGAAGGCTAGAGGGCG ACTCTGGTGGTGCTTTTGTATGTTTCAATTAGGCTCTGAAA TCTTGGGCAAAATGACAAGGGGAGGGCCAGGATTCCTCTC TCAGGTCACTCCAGTGTTACTTTTAATTCCTAGAGGGTAAA TATGACTTCCTTTCTCTATCCCAAGCCAACCAAGAGCACATT CTTAAAGGAAAAGTCAACATCTTCTCTCTTTTTTTTTTTTT TGAGACAGGGTCTCACTATGTTGCCCAGGCTGCTCTTGAA TTCCTGGGCTCAAGCAGTCCTCCCACCCTACCACAGCGTC CCGCGTAGCTGGGACTACAGGTGCAAGCCACTATGTCCAG CTAGCCAACTCCTCCTTGCCTGCTTTTCTTTTTTTTCTTTT TTTGAGACGGCGCACCTATCACCCAGGCTGGAGTGGAGTG GCACGATCTTGGCTCACTGCAACCTCTTCCTCCTGGTTCAA GCGATTCTCATGTCTCAGCCTCCTCAGTAGCTAGGACTACC GGCGTGCACCACCATGCCAGGCTAATTTTTATATTTTTAGA ATTTTAGAAGAGATGGGATTTCATCATGTTGGCCAGGCTG GTCTCGAACTCCTGACCTCAAGTGATCCACCTGCCTTGGCC TCCCAAGGTGCTAGGATTACAGGCATGAGCCACCGCACCG GGCCCTCCTTGCCTGTTTTTCAATCTCATCTGATATGCAGA GTATTTCTGCCCCACCCACCTACCCCCAAAAAAAGCTGA AGCCTATTTATTTGAAAGTCCTTGTTTTTGCTACTAATTAT ATAGTATACCATACATTATCATTCAAAACAACCATCCTGC TCATAACATCTTTGAAAAGAAAAATATATATGTGCAGTAT |

SEQUENCE LISTING

| SEQ ID NO | Description | Sequence |
|---|---|---|
| | | TTTATTAAAGCAACATTTTATTTAAGAATAAAGTCTTGTTA<br>ATTACTATATTTTAGATGCAATGTGATCTGAAGTTTCTAAT<br>TCTGGCCCAACTAAATTTCTAGCTCTGTTTCCCTAAACAAA<br>TAATTTGGTTTCTCTGTGCCTGCATTTTCCCTTTGGAGAAG<br>AAAAGTGCTCTCTCTTGAGTTGACCGAGAGTCCCATTAGG<br>GATAGGGAGACTTAAATGCATCCACAGGGGCACAGGCAG<br>AGTTGAGCACATAAACGGAGGCCCAAAATCAGCATAGAA<br>CCAGAAAGATTCAGAGTTGGCCAAGAATGAACATTGGCTA<br>CCAGACCACAAGTCAGCATGAGTTGCTCTATGGCATCAAA<br>TTGCAACTTGAGAGTAGATGGGCAGGGTCACTATCAAATT<br>AAGCAATCAGGGCACACAAGTTGCAGTAACACAACAAGA<br>CTAGGCCAGCTCTGGAATCCAGTAACTCAGTGTCAGCAAG<br>GTTTTGGGTTATAGTTCAAGAAAGTCTAAACAGAGCCAGT<br>CACAGCACCAAGGAATGCTCAAGGGAGCTATTGCAGGTTT<br>CTCTGCTAAGAGATTTATTTCATCCTGGGTGCAGGGTTCGA<br>CCTCCAAAGGCCTCAAATCATCACCGTATCAATGGATTTC<br>CTGAGGGTAAGCTCCGCTATTTCACACCTGAACTCCGGAG<br>TCTGTATATTCAGGGAAGATTGCATTCTCCTACTGGATTTG<br>GGCTCTCAGAGGGCGTTGTGGGAACCAGGCCCCTCACAGA<br>ATCAAATGGTCCCAACCAGGGAGAAAGAAAATAGTCTTTT<br>TTTTTTTTTAATAGAGATGGGGGTCTCACTATGCTGCCCA<br>GGCTGGTCTTGAACTCCTGGGTTCAAGTGATCCTCCTGCCT<br>CAGCCTCCCAAAGTGCTGGGATTACAGTGTGAGCCACTGC<br>GCTTGGCCAGAAATGGTTTTGATCTGTCTGAACTGAACCC<br>TACTGCTTAGGCATAGCCCCATCCTTGATAATCTATTTGCT<br>CCCAAGGACCAAGTCCAAGATCCTTACAAGAAAGGTCTGC<br>CAGAAAGTAAATACTGCCCCCACTCCCTGAAGTTTATGAG<br>GTTGATAAGAAAACATAACAGATAAAGTTTATTGAGTGCT<br>AACTTTAAAAAAAAA |
| 2 | Human glucose-6-phosphatase catalytic subunit (G6PC) amino acid sequence (NCBI Reference Sequence NP_000142.2) | MEEGMNVLHDFGIQSTHYLQVNYQDSQDWFILVSVIADLRN<br>AFYVLFPIWFHLQEAVGIKLLWVAVIGDWLNLVFKWILFGQ<br>RPYWWVLDTDYYSNTSVPLIKQFPVTCETGPGSPSGHAMGT<br>AGVYYVMVTSTLSIFQGKIKPTYRFRCLNVILWLGFWAVQL<br>NVCLSRIYLAAHFPHQVVAGVLSGIAVAETFSHIHSIYNASLK<br>KYFLITFFLFSFAIGFYLLLKGLGVDLLWTLEKAQRWCEQPE<br>WVHIDTTPFASLLKNLGTLFGLGLALNSSMYRESCKGKLSK<br>WLPFRLSSIVASLVLLHVFDSLKPPSQVELVFYVLSFCKSAVV<br>PLASVSVIPYCLAQVLGQPHKKSL |
| 3 | CH32-CTX1 sgRNA | USCSUSUUGGACAGCGUCCAUACGUUUUAGAGCUAGAAA<br>UAGCAAGUUAAAAUAAGGCUAGUCCGUUAUCAACUUGA<br>AAAAGUGGCACCGAGUCGGUGCUSUSUSU |
| 4 | CH34-CTX1 sgRNA | USGSGSACAGCGUCCAUACUGGUGUUUUAGAGCUAGAAA<br>UAGCAAGUUAAAAUAAGGCUAGUCCGUUAUCAACUUGA<br>AAAAGUGGCACCGAGUCGGUGCUSUSUSU |
| 5 | CH36-CTX1 sgRNA | GSUSASUCCAAAACCCACCAGUAGUUUUAGAGCUAGAAA<br>UAGCAAGUUAAAAUAAGGCUAGUCCGUUAUCAACUUGA<br>AAAAGUGGCACCGAGUCGGUGCUSUSUSU |
| 6 | CH32 sgRNA | UCUUUGGACAGCGUCCAUACGUUUUAGAGCUAGAAAUA<br>GCAAGUUAAAAUAAGGCUAGUCCGUUAUCAACUUGAAA<br>AAGUGGCACCGAGUCGGUGCUUUU |
| 7 | CH34 sgRNA | UGGACAGCGUCCAUACUGGUGUUUUAGAGCUAGAAAUA<br>GCAAGUUAAAAUAAGGCUAGUCCGUUAUCAACUUGAAA<br>AAGUGGCACCGAGUCGGUGCUUUU |
| 8 | CH36 sgRNA | GUAUCCAAAACCCACCAGUAGUUUUAGAGCUAGAAAUA<br>GCAAGUUAAAAUAAGGCUAGUCCGUUAUCAACUUGAAA<br>AAGUGGCACCGAGUCGGUGCUUUU |
| 9 | CH32_75-0 Antisense | AGGGCACTGTCCAAAGAGAATCCTATGGAAAAACAGAAC<br>AAGTTTCTGGGGTTACTGAATGAATGCTTTTGCCCA |
| 10 | CH32_75-0 Sense | TGGGCAAAAGCATTCATTCAGTAACCCCAGAAACTTGTTC<br>TGTTTTTCCATAGGATTCTCTTTGGACAGTGCCCT |
| 11 | CH32_100-0 AntiSense | AGGGCACTGTCCAAAGAGAATCCTATGGAAAAACAGAAC<br>AAGTTTCTGGGGTTACTGAATGAATGCTTTTGCCCAAAGC<br>CTACACCTTCAAGAAGAGTGT |

SEQUENCE LISTING

| SEQ ID NO | Description | Sequence |
|---|---|---|
| 12 | CH32_100-0 Sense | ACACTCTTCTTGAAGGTGTAGGCTTTGGGCAAAAGCATTC ATTCAGTAACCCCAGAAACTTGTTCTGTTTTTCCATAGGAT TCTCTTTGGACAGTGCCCT |
| 13 | CH32_125-0 AntiSense | AGGGCACTGTCCAAAGAGAATCCTATGGAAAAACAGAAC AAGTTTCTGGGGTTACTGAATGAATGCTTTTGCCCAAAGC CTACACCTTCAAGAAGAGTGTAGCCTGAGAAGGATTTCAC ATGTTG |
| 14 | CH32_125-0 Sense | CAACATGTGAAATCCTTCTCAGGCTACACTCTTCTTGAAG GTGTAGGCTTTGGGCAAAAGCATTCATTCAGTAACCCCAG AAACTTGTTCTGTTTTTCCATAGGATTCTCTTTGGACAGTG CCCT |
| 15 | CH32_25-0 AntiSense | AGGGCACTGTCCAAAGAGAATCCTA |
| 16 | CH32_25-0 Sense | TAGGATTCTCTTTGGACAGTGCCCT |
| 17 | CH32_50-0 AntiSense | AGGGCACTGTCCAAAGAGAATCCTATGGAAAAACAGAAC AAGTTTCTGGG |
| 18 | CH32_50-0 Sense | CCCAGAAACTTGTTCTGTTTTTCCATAGGATTCTCTTTGGA CAGTGCCCT |
| 19 | Enhanced CH32_50-0 AntiSense | AGGGCACTGTCCAAAGAGAATCCTATAAAAAAACAGAAC AAGTTTATGAA |
| 20 | Enhanced CH32_50-0 Sense | TTCATAAACTTGTTCTGTTTTTTTATAGGATTCTCTTTGGAC AGTGCCCT |
| 21 | Enhanced CH32_55-0 AntiSense | AGGGCACTGTCCAAAGAGAATCCTATGGAAAAACAGAAC AAGTTTCTGGGATGAA |
| 22 | Enhanced CH32_55-0 Sense | TTCATCCCAGAAACTTGTTCTGTTTTTCCATAGGATTCTCT TTGGACAGTGCCCT |
| 23 | Enhanced CH32_60-0 AntiSense | AGGGCACTGTCCAAAGAGAATCCTATGGAAAAACAGAAC AAGTTTCTGGGGTTAATGAAT |
| 24 | Enhanced CH32_60-0 Sense | ATTCATTAACCCCAGAAACTTGTTCTGTTTTTCCATAGGAT TCTCTTTGGACAGTGCCCT |
| 25 | CH32_65-0 AntiSense | AGGGCACTGTCCAAAGAGAATCCTATGGAAAAACAGAAC AAGTTTCTGGGGTTACTGAATGAATG |
| 26 | CH32_65-0 Sense | CATTCATTCAGTAACCCCAGAAACTTGTTCTGTTTTTCCAT AGGATTCTCTTTGGACAGTGCCCT |
| 27 | CH32_70-0 AntiSense | AGGGCACTGTCCAAAGAGAATCCTATGGAAAAACAGAAC AAGTTTCTGGGGTTACTGAATGAATGCTTTT |
| 28 | CH32_70-0 Sense | AAAAGCATTCATTCAGTAACCCCAGAAACTTGTTCTGTTTT TCCATAGGATTCTCTTTGGACAGTGCCCT |
| 29 | Enhanced CH34_54-0 (C) AntiSense | AGTAAGGGCACTGTCCAAAGAGAATCCTATAAAAAACA GAACAAGTTTATGAA |
| 30 | Enhanced CH34_54-0 (C) Sense | TTCATAAACTTGTTCTGTTTTTTTATAGGATTCTCTTTGGAC AGTGCCCTTACT |
| 31 | Enhanced CH34_59-0 AntiSense | AGTAAGGGCACTGTCCAAAGAGAATCCTATGGAAAAACA GAACAAGTTTCTGGGATGAA |
| 32 | Enhanced CH34_59-0 Sense | TTCATCCCAGAAACTTGTTCTGTTTTTCCATAGGATTCTCT TTGGACAGTGCCCTTACT |
| 33 | Enhanced CH34_64-0 AntiSense | AGTAAGGGCACTGTCCAAAGAGAATCCTATGGAAAAACA GAACAAGTTTCTGGGGTTAATGAAT |
| 34 | Enhanced CH34_64-0 Sense | ATTCATTAACCCCAGAAACTTGTTCTGTTTTTCCATAGGAT TCTCTTTGGACAGTGCCCTTACT |

SEQUENCE LISTING

| SEQ ID NO | Description | Sequence |
|---|---|---|
| 35 | CH34_69-0 AntiSense | AGTAAGGGCACTGTCCAAAGAGAATCCTATGGAAAAACA GAACAAGTTTCTGGGGTTACTGAATGAATG |
| 36 | CH34_69-0 Sense | CATTCATTCAGTAACCCCAGAAACTTGTTCTGTTTTTCCAT AGGATTCTCTTTGGACAGTGCCCTTACT |
| 37 | CH34_74-0 AntiSense | AGTAAGGGCACTGTCCAAAGAGAATCCTATGGAAAAACA GAACAAGTTTCTGGGGTTACTGAATGAATGCTTTT |
| 38 | CH34_74-0 Sense | AAAAGCATTCATTCAGTAACCCCAGAAACTTGTTCTGTTTT TCCATAGGATTCTCTTTGGACAGTGCCCTTACT |
| 39 | Enhanced CH36_53-0 AntiSense | GTAAGGGCACTGTCCAAAGAGAATCCTATAAAAAAACAG AACAAGTTTATGAA |
| 40 | Enhanced CH36_53-0 Sense | TTCATAAACTTGTTCTGTTTTTTTATAGGATTCTCTTTGGAC AGTGCCCTTAC |
| 41 | Enhanced CH36_58-0 AntiSense | GTAAGGGCACTGTCCAAAGAGAATCCTATGGAAAAACAG AACAAGTTTCTGGGATGAA |
| 42 | Enhanced CH36_58-0 Sense | TTCATCCCAGAAACTTGTTCTGTTTTTCCATAGGATTCTCT TTGGACAGTGCCCTTAC |
| 43 | Enhanced CH36_63-0 AntiSense | GTAAGGGCACTGTCCAAAGAGAATCCTATGGAAAAACAG AACAAGTTTCTGGGGTTAATGAAT |
| 44 | Enhanced CH36_63-0 Sense | ATTCATTAACCCCAGAAACTTGTTCTGTTTTTCCATAGGAT TCTCTTTGGACAGTGCCCTTAC |
| 45 | CH36_68-0 AntiSense | GTAAGGGCACTGTCCAAAGAGAATCCTATGGAAAAACAG AACAAGTTTCTGGGGTTACTGAATGAATG |
| 46 | CH36_68-0 Sense | CATTCATTCAGTAACCCCAGAAACTTGTTCTGTTTTTCCAT AGGATTCTCTTTGGACAGTGCCCTTAC |
| 47 | CH36_73-0 AntiSense | GTAAGGGCACTGTCCAAAGAGAATCCTATGGAAAAACAG AACAAGTTTCTGGGGTTACTGAATGAATGCTTTT |
| 48 | CH36_73-0 Sense | AAAAGCATTCATTCAGTAACCCCAGAAACTTGTTCTGTTTT TCCATAGGATTCTCTTTGGACAGTGCCCTTAC |
| 49 | branch point consensus sequence | YTNAY, wherein Y = C or T; wherein N = A, G, C or T |
| 50 | branch point sequence | TATTAAC |
| 51 | branch point sequence | GTTAATA |
| 52 | branch point sequence | TACTGAC |
| 53 | polypyrimidine tract | TTTTTTTCT |
| 54 | polypyrimidine tract | TTTTTTTCTTTTT |
| 55 | polypyrimidine tract | CTTCTTCTCTTCTTCC |
| 56 | SV40 nuclear localization signal (NLS) | PKKKRKV |
| 57 | SV40 nuclear localization signal (NLS) | PKKKRRV |
| 58 | nucleoplasmin nuclear localization signal (NLS) | KRPAATKKAGQAKKKK |

-continued

| SEQUENCE LISTING | | |
|---|---|---|
| SEQ ID NO | Description | Sequence |
| 59 | S. pyogenes target sequence and PAM | $N_{19-21}$NRG, wherein N = A, G, C or T; and R = A or G |
| 60 | 6xHis | HHHHHH |
| 61 | GAA5 sgRNA | AGCCCGCUUUCUUCUCCCGCGUUUUAGAGCUAGAAAUAG CAAGUUAAAAUAAGGCUAGUCCGUUAUCAACUUGAAAA AGUGGCACCGAGUCGGUGCUUUU |
| 62 | GAA_25-0_F | GAGAAGAAGTATTAACTTTTTTCT |
| 63 | GAA_50-0_F | TGGAAGAAGAGAAGAAGCTGGGTATTAACGCATTTTTTC TTTTTAATTC |
| 64 | GAA_75-0_F | TGGAAGAAGAGAAGAAGCTGGGAATGTGTCAGTAAGGCA TGTATTAACGCAAATGAATTTTTTCTTTTTAATTC |
| 65 | GAA_100-0_F | TGGAAGAAGAGAAGAAGCTGGGAATGTGTCAGTAAGGCA TGAGCCACCGCGCCAGCCATGCAAATCTATTAACGCAAAT GAATTTTTTCTTTTTAATTC |
| 66 | GAA_25-0_R | AGAAAAAAGTTAATACTTCTTCTC |
| 67 | GAA_50-0_R | GAATTAAAAGAAAAAAATGCGTTAATACCCAGCTTCTTC TCTTCTTCCA |
| 68 | GAA_75-0_R | GAATTAAAAGAAAAAAATTCATTTGCGTTAATACATGCC TTACTGACACATTCCCAGCTTCTTCTCTTCTTCCA |
| 69 | GAA_100-0_R | GAATTAAAAGAAAAAAATTCATTTGCGTTAATAGATTTG CATGGCTGGCGCGGTGGCTCATGCCTTACTGACACATTCC CAGCTTCTTCTCTTCTTCCA |
| 70 | CH42 sgRNA | GUCAGUCUCACAGGUUACAGGUUUUAGAGCUAGAAAUA GCAAGUUAAAAUAAGGCUAGUCCGUUAUCAACUUGAAA AAGUGGCACCGAGUCGGUGCUUUU |
| 71 | CH42_25-0_F | AACCTGTGAGACTGGACCAGGTAAG |
| 72 | CH42_25-0_R | CTTACCTGGTCCAGTCTCACAGGTT |
| 73 | CH42_50-0_F | AACCTGTGAGACTGGACCAGGTAAGACTCACACTTGCGAA ACCGGCCCAG |
| 74 | CH42_50-0_R | CTGGGCCGGTTTCGCAAGTGTGAGTCTTACCTGGTCCAGT CTCACAGGTT |
| 75 | CH42_75-0_F | AACCTGTGAGACTGGACCAGGTAAGCGACGCGCATTTCTC ACACGGCAGGACTCACACTTGCGAAACCGGCCCAG |
| 76 | CH42_75-0_R | CTGGGCCGGTTTCGCAAGTGTGAGTCCTGCCGTGTGAGAA ATGCGCGTCGCTTACCTGGTCCAGTCTCACAGGTT |
| 77 | CH42_100-0_F | AACCTGTGAGACTGGACCAGGTAAGCGACGCGCATTTCTC ACACGGCAGGGAGGGCCACACGCGTTTGTTTCTCAACTCA CACTTGCGAAACCGGCCCAG |
| 78 | CH42_100-0_R | CTGGGCCGGTTTCGCAAGTGTGAGTTGAGAAACAAACGCG TGTGGCCCTCCCTGCCGTGTGAGAAATGCGCGTCGCTTAC CTGGTCCAGTCTCACAGGTT |
| 79 | CH42_125-0_F | AACCTGTGAGACTGGACCAGGTAAGCGACGCGCATTTCTC ACACGGCAGGGAGGGCCACACGCGTTTGTTTCTCACACGA TGGGCAGGGCGACACATGTTACTCACACTTGCGAAACCGG CCCAG |
| 80 | CH42_125-0_R | CTGGGCCGGTTTCGCAAGTGTGAGTAACATGTGTCGCCCT GCCCATCGTGTGAGAAACAAACGCGTGTGGCCCTCCCTGC CGTGTGAGAAATGCGCGTCGCTTACCTGGTCCAGTCTCAC AGGTT |

SEQUENCE LISTING

| SEQ ID NO | Description | Sequence |
|---|---|---|
| 81 | CH32 sgRNA spacer | UCUUUGGACAGCGUCCAUAC |
| 82 | CH32 target gene(PAM) | TCTTTGGACAGCGTCCATAC(TGG) |
| 83 | CH34 sgRNA spacer | UGGACAGCGUCCAUACUGGU |
| 84 | CH34 target gene(PAM) | TGGACAGCGTCCATACTGGT(GGG) |
| 85 | CH36 sgRNA spacer | GUAUCCAAAACCCACCAGUA |
| 86 | CH36 target gene (PAM) | GTATCCAAAACCCACCAGTA(TGG) |
| 87 | CH42 target gene (PAM) | GTCAGTCTCACAGGTTACAG(GGG) |
| 88 | CH42 sgRNA spacer | GUCAGUCUCACAGGUUACAG |
| 89 | Murine CH34-CTX1 sgRNA | USGSGSACAACGCCCGUAUUGGUGUUUUAGAGCUAGAAAUAGCAAGUUAAAAUAAGGCUAGUCCGUUAUCAACUUGAAAAAGUGGCACCGAGUCGGUGCUSUSUSU |
| 90 | WT GAA Target gene(PAM) | AGCCCGCTTTCTTCTCCCGC(AGG) |
| 91 | WT GAA5 sgRNA spacer | AGCCCGCUUUCUUCUCCCGC |
| 92 | Mutant (Mt) GAA target gene(PAM) | AGCCCGCTTGCTTCTCCCGC(AGG) |
| 93 | Mt GAA sgRNA spacer | AGCCCGCUUGCUUCUCCCGC |
| 94 | Mt GAA sgRNA | AGCCCGCUUGCUUCUCCCGCGUUUUAGAGCUAGAAAUAGCAAGUUAAAAUAAGGCUAGUCCGUUAUCAACUUGAAAAAGUGGCACCGAGUCGGUGCUUUU |
| 95 | GAA_30 F | AAGAGAAGAAGTATTAACTTTTTTTCTTTT |
| 96 | GAA_35 F | AAGAAGAGAAGAAGTATTAACTTTTTTTCTTTTTA |
| 97 | GAA_40 F | GGAAGAAGAGAAGAAGTATTAACTTTTTTTCTTTTTAATT |
| 98 | GAA_45 F | TGGAAGAAGAGAAGAAGCTTATTAACTTTTTTTCTTTTAATTC |
| 99 | GAA_55 F | TGGAAGAAGAGAAGAAGCTGGGTATTAACGCAAATTTTTTTTCTTTTTAATTC |
| 100 | GAA_60 F | TGGAAGAAGAGAAGAAGCTGGGAATGTTATTAACGCAAATGATTTTTTCTTTTTAATTC |
| 101 | GAA_65 F | TGGAAGAAGAGAAGAAGCTGGGAATGGTCAGTATATTAACGCAAATGTTTTTTCTTTTTAATTC |
| 102 | GAA_70 F | TGGAAGAAGAGAAGAAGCTGGGAATGTGTCAGTAAGTATTAACGCAAATGAATTTTTTCTTTTTAATTC |
| 103 | GAA_80 F | TGGAAGAAGAGAAGAAGCTGGGAATGTGTCAGTAAGGCATGAGCCATATTAACGCAAATGAATTTTTTCTTTTTAATTC |
| 104 | GAA_85 F | TGGAAGAAGAGAAGAAGCTGGGAATGTGTCAGTAAGGCATGAGCCACCGCGTATTAACGCAAATGAATTTTTTCTTTTTAATTC |

SEQUENCE LISTING

| SEQ ID NO | Description | Sequence |
|---|---|---|
| 105 | GAA_90 F | TGGAAGAAGAGAAGAAGCTGGGAATGTGTCAGTAAG GCATGAGCCACCGCGCCAGCTATTAACGCAAATGAA TTTTTTTCTTTTTAATTC |
| 106 | GAA_95 F | TGGGAAGAAGAGAAGAAGCTGGGAATGTGTCAGTAA GGCATGAGCCACCGCGCCAGCCATGCTATTAACGCA AATGAATTTTTTTCTTTTTAATTC |
| 107 | CH32 Mutant-CTX1 sgRNA spacer | UCUUUGGACAGCGUCCAUAC |
| 108 | CH34 Mutant-CTX1 sgRNA spacer | UGGACAGCGUCCAUACUGGU |

What is claimed:

1. A donor polynucleotide comprising a non-replicative double-stranded DNA molecule (dsDNA) comprising a nucleotide sequence which corrects a mutation that causes Glycogen Storage Disease 1a in a genomic DNA (gDNA) molecule molecule in a cell, wherein the mutation is a protein-coding mutation proximal to a 3' splice site in the human G6PC gene, the donor polynucleotide comprising,
   (i) a first strand comprising from 5' to 3': (a) a nucleotide sequence comprising splicing signals to control processing of a precursor mRNA (pre-mRNA) transcribed from the gDNA, wherein the splicing signals are a branch point, a polypyrimidine tract, and a natural or enhanced 3' splice site; and (b) a nucleotide sequence comprising an exonic sequence which corrects the mutation; and
   (ii) a second strand comprising a nucleotide sequence complementary to the first strand, wherein the donor polynucleotide is at least 25 and up to 500 nucleotides in length, and wherein when the donor polynucleotide is introduced into the cell in combination with a site-directed nuclease, a non-homologous end-joining (NHEJ) DNA repair pathway inserts the donor polynucleotide into a double-stranded DNA break (DSB) introduced into the gDNA by the site-directed nuclease at a location proximal to the mutation, thereby correcting the mutation;
   wherein the branch point sequence comprises the nucleotide sequence TTCAT, wherein the polypyrimidine tract comprises the nucleotide sequence CTTGTTCTGTTTTTTT (SEQ ID NO: 109), wherein the 3' splice site comprises the nucleotide sequence TAG.

2. The donor polynucleotide of claim 1, wherein the donor polynucleotide is up to 400, 300, 200, 100, 80, 70, or 60 nucleotides in length.

3. The donor polynucleotide of claim 1, wherein the donor polynucleotide is 30-70 or 40-60 nucleotides in length.

4. The donor polynucleotide of claim 1, wherein the mutation is an amino acid substitution of arginine (R) at position 83 in the G6PC gene, and wherein the exonic sequence comprises a codon encoding arginine (R) corresponding to the codon at position 83 in the G6PC gene.

5. The donor polynucleotide of claim 1, wherein insertion of the donor polynucleotide into the DSB results in the formation of an exon in the gDNA comprising the exonic sequence.

6. The donor polynucleotide of claim 1, wherein the splicing signals direct the inclusion of an exon comprising the exonic sequence which corrects the mutation into an mRNA.

7. The donor polynucleotide of claim 1, wherein the exonic sequence comprises the nucleotide sequence GATTCTCTTTGGACAGCGCCCTTACT (SEQ ID NO: 110).

8. The donor polynucleotide of claim 1, wherein the donor polynucleotide comprises two blunt ends.

9. A pharmaceutical composition comprising the donor polynucleotide according to claim 1 and a pharmaceutically acceptable carrier.

* * * * *

SEQUENCE LISTING

<160> NUMBER OF SEQ ID NOS: 110

<210> SEQ ID NO 1
<211> LENGTH: 4169
<212> TYPE: DNA
<213> ORGANISM: Homo sapiens
<220> FEATURE:
<221> NAME/KEY: misc_feature
<223> OTHER INFORMATION: Human glucose-6-phosphatase catalytic subunit (G6PC) mRNA nucleic acid sequence

<400> SEQUENCE: 1

```
atagcagagc aatcaccacc aagcctggaa taactgcaag ggctctgctg acatcttcct      60
gaggtgccaa ggaaatgagg atggaggaag gaatgaatgt tctccatgac tttgggatcc     120
agtcaacaca ttacctccag gtgaattacc aagactccca ggactggttc atcttggtgt     180
ccgtgatcgc agacctcagg aatgccttct acgtcctctt ccccatctgg ttccatcttc     240
aggaagctgt gggcattaaa ctcctttggg tagctgtgat tggagactgg ctcaacctcg     300
tctttaagtg gattctcttt ggacagcgtc catactggtg ggttttggat actgactact     360
acagcaacac ttccgtgccc ctgataaagc agttccctgt aacctgtgag actggaccag     420
ggagcccctc tggccatgcc atgggcacag caggtgtata ctacgtgatg gtcacatcta     480
ctctttccat ctttcaggga aagataaagc cgacctacag atttcggtgc ttgaatgtca     540
ttttgtggtt gggattctgg gctgtgcagc tgaatgtctg tctgtcacga atctaccttg     600
ctgctcattt tcctcatcaa gttgttgctg gagtcctgtc aggcattgct gttgcagaaa     660
cttttcagcca catccacagc atctataatg ccagcctcaa gaaatatttt ctcattacct     720
tcttcctgtt cagcttcgcc atcggatttt atctgctgct caagggactg gtgtagacc      780
tcctgtggac tctggagaaa gcccagaggt ggtgcgagca gccagaatgg tccacattg      840
acaccacacc ctttgccagc ctcctcaaga acctgggcac gctctttggc ctggggctgg     900
ctctcaactc cagcatgtac agggagagct gcaaggggaa actcagcaag tggctcccat     960
tccgcctcag ctctattgta gcctccctcg tcctcctgca cgtctttgac tccttgaaac    1020
ccccatccca agtcgagctg gtcttctacg tcttgtcctt ctgcaagagt gcggtagtgc    1080
ccctggcatc cgtcagtgtc atcccctact gcctcgccca ggtcctgggc cagccgcaca    1140
```

```
agaagtcgtt gtaagagatg tggagtcttc ggtgtttaaa gtcaacaacc atgccaggga    1200
ttgaggagga ctactatttg aagcaatggg cactggtatt tggagcaagt gacatgccat    1260
ccattctgcc gtcgtggaat taaatcacgg atggcagatt ggagggtcgc ctggcttatt    1320
cccatgtgtg actccagcct gccctcagca cagactcttt cagatggagg tgccatatca    1380
cgtacaccat atgcaagttt cccgccagga ggtcctcctc tctctacttg aatactctca    1440
caagtaggga gctcactccc actggaacag cccattttat ctttgaatgg tcttctgcca    1500
gcccattttg aggccagagg tgctgtcagc tcaggtggtc ctcttttaca atcctaatca    1560
tattgggtaa tgtttttgaa aagctaatga agctattgag aaagacctgt tgctagaagt    1620
tgggttgttc tggattttcc cctgaagact tacttattct tccgtcacat atacaaaagc    1680
aagacttcca ggtagggcca gctcacaagc ccaggctgga gatcctaact gagaattttc    1740
tacctgtgtt cattcttacc gagaaaagga gaaggagct ctgaatctga taggaaaaga    1800
aggctgccta aggaggagtt tttagtatgt ggcgtatcat gcaagtgcta tgccaagcca    1860
tgtctaaatg gctttaatta tatagtaatg cactctcagt aatgggggac cagcttaagt    1920
ataattaata gatggttagt ggggtaattc tgcttctagt atttttttta ctgtgcatac    1980
atgttcatcg tatttccttg gatttctgaa tggctgcagt gacccagata ttgcactagg    2040
tcaaaacatt caggtatagc tgacatctcc tctatcacat tacatcatcc tcctataag    2100 cccagctctg cttttccag attcttccac tggctccaca tccaccccac tggatcttca    2160
gaaggctaga gggcgactct ggtggtgctt ttgtatgttt caattaggct ctgaaatctt    2220
gggcaaaatg acaaggggag ggccaggatt cctctctcag gtcactccag tgttactttt    2280
aattcctaga gggtaaatat gactcctttc tctatcccaa gccaaccaag agcacattct    2340
taaaggaaaa gtcaacatct tctctctttt tttttttttt tgagacaggg tctcactatg    2400
ttgcccaggc tgctcttgaa ttcctgggct caagcagtcc tcccacccta ccacagcgtc    2460
ccgcgtagct gggactacag gtgcaagcca ctatgtccag ctagccaact cctccttgcc    2520
tgcttttctt ttttttttctt ttttttgagac ggcgcaccta tcacccaggc tggagtggag    2580
tggcacgatc ttggctcact gcaacctctt cctcctggtt caagcgattc tcatgtctca    2640
gcctcctcag tagctaggac taccggcgtg caccaccatg ccaggctaat ttttatattt    2700
ttagaatttt agaagagatg ggatttcatc atgttggcca ggctggtctc gaactcctga    2760
cctcaagtga tccacctgcc ttggcctccc aaggtgctag gattacaggc atgagccacc    2820
gcaccgggcc ctccttgcct gttttttcaat ctcatctgat atgcagagta tttctgcccc    2880
acccacctac cccccaaaaa aagctgaagc ctatttattt gaaagtcctt gttttgtgcta    2940 ctaattatat agtataccat acattatcat tcaaaacaac catcctgctc ataacatctt    3000
tgaaaagaaa aatatatatg tgcagtattt tattaaagca acatttttatt taagaataaa    3060 gtcttgttaa ttactatatt ttagatgcaa tgtgatctga agtttctaat tctgccccaa    3120
ctaaatttct agctctgttt ccctaaacaa ataatttggt ttctctgtgc ctgcattttc    3180
cctttggaga agaaaagtgc tctctcttga gttgaccgag agtcccatta gggatagga    3240 gacttaaatg catccacagg ggcacaggca gagttgagca cataaacgga ggcccaaaat    3300
cagcatagaa ccagaaagat tcagagttgg ccaagaatga acattggcta ccagaccaca    3360
agtcagcatg agttgctcta tggcatcaaa ttgcaacttg agagtagatg ggcagggtca    3420
ctatcaaatt aagcaatcag ggcacacaag ttgcagtaac acaacaagac taggccagct    3480
```

-continued

```
ctggaatcca gtaactcagt gtcagcaagg ttttgggtta tagttcaaga aagtctaaac    3540
agagccagtc acagcaccaa ggaatgctca agggagctat tgcaggtttc tctgctaaga    3600
gatttatttc atcctgggtg cagggttcga cctccaaagg cctcaaatca tcaccgtatc    3660
aatggatttc ctgagggtaa gctccgctat ttcacacctg aactccggag tctgtatatt    3720
cagggaagat tgcattctcc tactggattt gggctctcag agggcgttgt gggaaccagg    3780
cccctcacag aatcaaatgg tcccaaccag ggagaaagaa aatagtcttt ttttttttt    3840 taatagagat gggggtctca ctatgctgcc caggctggtc ttgaactcct gggttcaagt    3900
gatcctcctg cctcagcctc ccaaagtgct gggattacag tgtgagccac tgcgcttggc    3960
cagaaatggt tttgatctgt ctgaactgaa ccctactgct taggcatagc cccatccttg    4020
ataatctatt tgctcccaag gaccaagtcc aagatcctta caagaaaggt ctgccagaaa    4080
gtaaatactg cccccactcc ctgaagttta tgaggttgat aagaaaacat aacagataaa    4140
gtttattgag tgctaacttt aaaaaaaaa                                      4169
```

<210> SEQ ID NO 2
<211> LENGTH: 357
<212> TYPE: PRT
<213> ORGANISM: Homo sapiens
<220> FEATURE:
<221> NAME/KEY: misc_feature
<223> OTHER INFORMATION: Human glucose-6-phosphatase catalytic subunit
      (G6PC) amino acid sequence

<400> SEQUENCE: 2

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
```

```
            225                 230                 235                 240
Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355

<210> SEQ ID NO 3
<211> LENGTH: 106
<212> TYPE: RNA
<213> ORGANISM: Artificial Sequence
<220> FEATURE:
<223> OTHER INFORMATION: Synthetic: CH32-CTX1 sgRNA

<400> SEQUENCE: 3
uscsusuugg acagcgucca ucguuuuag agcuagaaau agcaaguuaa aauaaggcua      60
guccguuauc aacuugaaaa aguggcaccg agucggugcu sususu                  106

<210> SEQ ID NO 4
<211> LENGTH: 106
<212> TYPE: RNA
<213> ORGANISM: Artificial Sequence
<220> FEATURE:
<223> OTHER INFORMATION: Synthetic: CH34-CTX1 sgRNA

<400> SEQUENCE: 4
usgsgsacag cguccauacu gguguuuuag agcuagaaau agcaaguuaa aauaaggcua      60
guccguuauc aacuugaaaa aguggcaccg agucggugcu sususu                  106

<210> SEQ ID NO 5
<211> LENGTH: 106
<212> TYPE: RNA
<213> ORGANISM: Artificial Sequence
<220> FEATURE:
<223> OTHER INFORMATION: Synthetic: CH36-CTX1 sgRNA

<400> SEQUENCE: 5
gsusasucca aaacccacca guaguuuuag agcuagaaau agcaaguuaa aauaaggcua      60
guccguuauc aacuugaaaa aguggcaccg agucggugcu sususu                  106

<210> SEQ ID NO 6
<211> LENGTH: 100
<212> TYPE: RNA
<213> ORGANISM: Artificial Sequence
<220> FEATURE:
<223> OTHER INFORMATION: Synthetic: CH32 sgRNA

<400> SEQUENCE: 6
ucuuuggaca gcguccauac guuuuagagc uagaaauagc aaguuaaaau aaggcuaguc      60
```

```
cguuaucaac uugaaaaagu ggcaccgagu cggugcuuuu                          100
```

<210> SEQ ID NO 7
<211> LENGTH: 100
<212> TYPE: RNA
<213> ORGANISM: Artificial Sequence
<220> FEATURE:
<223> OTHER INFORMATION: Synthetic: CH34 sgRNA

<400> SEQUENCE: 7

```
uggacagcgu ccauacuggu guuuuagagc uagaaauagc aaguuaaaau aaggcuaguc    60
cguuaucaac uugaaaaagu ggcaccgagu cggugcuuuu                          100
```

<210> SEQ ID NO 8
<211> LENGTH: 100
<212> TYPE: RNA
<213> ORGANISM: Artificial Sequence
<220> FEATURE:
<223> OTHER INFORMATION: Synthetic: CH36 sgRNA

<400> SEQUENCE: 8

```
guauccaaaa cccaccagua guuuuagagc uagaaauagc aaguuaaaau aaggcuaguc    60
cguuaucaac uugaaaaagu ggcaccgagu cggugcuuuu                          100
```

<210> SEQ ID NO 9
<211> LENGTH: 75
<212> TYPE: DNA
<213> ORGANISM: Artificial Sequence
<220> FEATURE:
<223> OTHER INFORMATION: Synthetic: CH32_75-0 Antisense

<400> SEQUENCE: 9

```
agggcactgt ccaaagagaa tcctatggaa aaacagaaca agtttctggg gttactgaat    60
gaatgctttt gccca                                                     75
```

<210> SEQ ID NO 10
<211> LENGTH: 75
<212> TYPE: DNA
<213> ORGANISM: Artificial Sequence
<220> FEATURE:
<223> OTHER INFORMATION: Synthetic: CH32_75-0 Sense

<400> SEQUENCE: 10

```
tgggcaaaag cattcattca gtaaccccag aaacttgttc tgttttttcca taggattctc   60 tttggacagt gccct                                                     75
```

<210> SEQ ID NO 11
<211> LENGTH: 100
<212> TYPE: DNA
<213> ORGANISM: Artificial Sequence
<220> FEATURE:
<223> OTHER INFORMATION: Synthetic: CH32_100-0 AntiSense

<400> SEQUENCE: 11

```
agggcactgt ccaaagagaa tcctatggaa aaacagaaca agtttctggg gttactgaat    60
gaatgctttt gcccaaagcc tacaccttca agaagagtgt                          100
```

<210> SEQ ID NO 12
<211> LENGTH: 100
<212> TYPE: DNA
<213> ORGANISM: Artificial Sequence
<220> FEATURE:

<223> OTHER INFORMATION: Synthetic: CH32_100-0 Sense

<400> SEQUENCE: 12

```
acactcttct tgaaggtgta ggctttgggc aaaagcattc attcagtaac cccagaaact    60
tgttctgttt ttccatagga ttctctttgg acagtgccct                         100
```

<210> SEQ ID NO 13
<211> LENGTH: 125
<212> TYPE: DNA
<213> ORGANISM: Artificial Sequence
<220> FEATURE:
<223> OTHER INFORMATION: Synthetic: CH32_125-0 AntiSense

<400> SEQUENCE: 13

```
agggcactgt ccaaagagaa tcctatggaa aaacagaaca agtttctggg gttactgaat    60
gaatgctttt gcccaaagcc tacaccttca agaagagtgt agcctgagaa ggatttcaca   120
tgttg                                                               125
```

<210> SEQ ID NO 14
<211> LENGTH: 125
<212> TYPE: DNA
<213> ORGANISM: Artificial Sequence
<220> FEATURE:
<223> OTHER INFORMATION: Synthetic: CH32_125-0 Sense

<400> SEQUENCE: 14

```
caacatgtga atccttctc aggctacact cttcttgaag gtgtaggctt tgggcaaaag     60
cattcattca gtaaccccag aaacttgttc tgttttttcca taggattctc tttggacagt  120
gccct                                                               125
```

<210> SEQ ID NO 15
<211> LENGTH: 25
<212> TYPE: DNA
<213> ORGANISM: Artificial Sequence
<220> FEATURE:
<223> OTHER INFORMATION: Synthetic: CH32_25-0 AntiSense

<400> SEQUENCE: 15

```
agggcactgt ccaaagagaa tccta                                          25
```

<210> SEQ ID NO 16
<211> LENGTH: 25
<212> TYPE: DNA
<213> ORGANISM: Artificial Sequence
<220> FEATURE:
<223> OTHER INFORMATION: Synthetic: CH32_25-0 Sense

<400> SEQUENCE: 16

```
taggattctc tttggacagt gccct                                          25
```

<210> SEQ ID NO 17
<211> LENGTH: 50
<212> TYPE: DNA
<213> ORGANISM: Artificial Sequence
<220> FEATURE:
<223> OTHER INFORMATION: Synthetic: CH32_50-0 AntiSense

<400> SEQUENCE: 17

```
agggcactgt ccaaagagaa tcctatggaa aaacagaaca agtttctggg              50
```

<210> SEQ ID NO 18
<211> LENGTH: 50

```
<212> TYPE: DNA
<213> ORGANISM: Artificial Sequence
<220> FEATURE:
<223> OTHER INFORMATION: Synthetic: CH32_50-0 Sense

<400> SEQUENCE: 18
cccagaaact tgttctgttt ttccatagga ttctctttgg acagtgccct            50

<210> SEQ ID NO 19
<211> LENGTH: 50
<212> TYPE: DNA
<213> ORGANISM: Artificial Sequence
<220> FEATURE:
<223> OTHER INFORMATION: Synthetic: Enhanced CH32_50-0 AntiSense

<400> SEQUENCE: 19
agggcactgt ccaaagagaa tcctataaaa aaacagaaca gtttatgaa             50

<210> SEQ ID NO 20
<211> LENGTH: 50
<212> TYPE: DNA
<213> ORGANISM: Artificial Sequence
<220> FEATURE:
<223> OTHER INFORMATION: Synthetic: Enhanced CH32_50-0 Sense

<400> SEQUENCE: 20
ttcataaact tgttctgttt ttttatagga ttctctttgg acagtgccct            50

<210> SEQ ID NO 21
<211> LENGTH: 55
<212> TYPE: DNA
<213> ORGANISM: Artificial Sequence
<220> FEATURE:
<223> OTHER INFORMATION: Synthetic: Enhanced CH32_55-0 AntiSense

<400> SEQUENCE: 21
agggcactgt ccaaagagaa tcctatggaa aaacagaaca gtttctggg atgaa       55

<210> SEQ ID NO 22
<211> LENGTH: 55
<212> TYPE: DNA
<213> ORGANISM: Artificial Sequence
<220> FEATURE:
<223> OTHER INFORMATION: Synthetic: Enhanced CH32_55-0 Sense

<400> SEQUENCE: 22
ttcatcccag aaacttgttc tgtttttcca taggattctc tttggacagt gccct      55

<210> SEQ ID NO 23
<211> LENGTH: 60
<212> TYPE: DNA
<213> ORGANISM: Artificial Sequence
<220> FEATURE:
<223> OTHER INFORMATION: Synthetic: Enhanced CH32_60-0 AntiSense

<400> SEQUENCE: 23
agggcactgt ccaaagagaa tcctatggaa aaacagaaca gtttctggg gttaatgaat  60

<210> SEQ ID NO 24
<211> LENGTH: 60
<212> TYPE: DNA
<213> ORGANISM: Artificial Sequence
<220> FEATURE:
<223> OTHER INFORMATION: Synthetic: Enhanced CH32_60-0 Sense

<400> SEQUENCE: 24
```
attcattaac cccagaaact tgttctgttt ttccatagga ttctctttgg acagtgccct    60

<210> SEQ ID NO 25
<211> LENGTH: 65
<212> TYPE: DNA
<213> ORGANISM: Artificial Sequence
<220> FEATURE:
<223> OTHER INFORMATION: Synthetic: CH32_65-0 AntiSense

<400> SEQUENCE: 25
agggcactgt ccaaagagaa tcctatggaa aaacagaaca agtttctggg gttactgaat    60
gaatg    65

<210> SEQ ID NO 26
<211> LENGTH: 65
<212> TYPE: DNA
<213> ORGANISM: Artificial Sequence
<220> FEATURE:
<223> OTHER INFORMATION: Synthetic: CH32_65-0 Sense

<400> SEQUENCE: 26
cattcattca gtaacccag aaacttgttc tgttttcca taggattctc tttggacagt    60
gccct    65

<210> SEQ ID NO 27
<211> LENGTH: 70
<212> TYPE: DNA
<213> ORGANISM: Artificial Sequence
<220> FEATURE:
<223> OTHER INFORMATION: Synthetic: CH32_70-0 AntiSense

<400> SEQUENCE: 27
agggcactgt ccaaagagaa tcctatggaa aaacagaaca agtttctggg gttactgaat    60
gaatgctttt    70

<210> SEQ ID NO 28
<211> LENGTH: 70
<212> TYPE: DNA
<213> ORGANISM: Artificial Sequence
<220> FEATURE:
<223> OTHER INFORMATION: Synthetic: CH32_70-0 Sense

<400> SEQUENCE: 28
aaaagcattc attcagtaac cccagaaact tgttctgttt ttccatagga ttctctttgg    60
acagtgccct    70

<210> SEQ ID NO 29
<211> LENGTH: 54
<212> TYPE: DNA
<213> ORGANISM: Artificial Sequence
<220> FEATURE:
<223> OTHER INFORMATION: Synthetic: Enhanced CH34_54-0 (C) AntiSense

<400> SEQUENCE: 29
agtaagggca ctgtccaaag agaatcctat aaaaaaacag aacaagttta tgaa    54

<210> SEQ ID NO 30
<211> LENGTH: 54
<212> TYPE: DNA
<213> ORGANISM: Artificial Sequence
<220> FEATURE:
<223> OTHER INFORMATION: Synthetic: Enhanced CH34_54-0 (C) Sense

<400> SEQUENCE: 30
ttcataaact tgttctgttt ttttatagga ttctctttgg acagtgccct tact                54

<210> SEQ ID NO 31
<211> LENGTH: 59
<212> TYPE: DNA
<213> ORGANISM: Artificial Sequence
<220> FEATURE:
<223> OTHER INFORMATION: Synthetic: Enhanced CH34_59-0 AntiSense

<400> SEQUENCE: 31
agtaagggca ctgtccaaag agaatcctat ggaaaaacag aacaagtttc tgggatgaa    59

<210> SEQ ID NO 32
<211> LENGTH: 59
<212> TYPE: DNA
<213> ORGANISM: Artificial Sequence
<220> FEATURE:
<223> OTHER INFORMATION: Synthetic: Enhanced CH34_59-0 Sense

<400> SEQUENCE: 32
ttcatcccag aaacttgttc tgtttttcca taggattctc tttggacagt gcccttact    59

<210> SEQ ID NO 33
<211> LENGTH: 64
<212> TYPE: DNA
<213> ORGANISM: Artificial Sequence
<220> FEATURE:
<223> OTHER INFORMATION: Synthetic: Enhanced CH34_64-0 AntiSense

<400> SEQUENCE: 33
agtaagggca ctgtccaaag agaatcctat ggaaaaacag aacaagtttc tggggttaat    60
gaat                                                                64

<210> SEQ ID NO 34
<211> LENGTH: 64
<212> TYPE: DNA
<213> ORGANISM: Artificial Sequence
<220> FEATURE:
<223> OTHER INFORMATION: Synthetic: Enhanced CH34_64-0 Sense

<400> SEQUENCE: 34
attcattaac cccagaaact tgttctgttt tccatagga ttctctttgg acagtgccct     60
tact                                                                64

<210> SEQ ID NO 35
<211> LENGTH: 69
<212> TYPE: DNA
<213> ORGANISM: Artificial Sequence
<220> FEATURE:
<223> OTHER INFORMATION: Synthetic: CH34_69-0 AntiSense

<400> SEQUENCE: 35
agtaagggca ctgtccaaag agaatcctat ggaaaaacag aacaagtttc tggggttact    60
gaatgaatg                                                           69

<210> SEQ ID NO 36
<211> LENGTH: 69
<212> TYPE: DNA
<213> ORGANISM: Artificial Sequence
<220> FEATURE:
<223> OTHER INFORMATION: Synthetic: CH34_69-0 Sense

<400> SEQUENCE: 36
cattcattca gtaaccccag aaacttgttc tgttttttcca taggattctc tttggacagt    60
gcccttact                                                             69

<210> SEQ ID NO 37
<211> LENGTH: 74
<212> TYPE: DNA
<213> ORGANISM: Artificial Sequence
<220> FEATURE:
<223> OTHER INFORMATION: Synthetic: CH34_74-0 AntiSense

<400> SEQUENCE: 37
agtaagggca ctgtccaaag agaatcctat ggaaaaacag aacaagtttc tggggttact    60
gaatgaatgc tttt                                                       74

<210> SEQ ID NO 38
<211> LENGTH: 74
<212> TYPE: DNA
<213> ORGANISM: Artificial Sequence
<220> FEATURE:
<223> OTHER INFORMATION: Synthetic: CH34_74-0 Sense

<400> SEQUENCE: 38
aaaagcattc attcagtaac cccagaaact tgttctgttt tccatagga ttctctttgg     60 acagtgccct tact                                                       74

<210> SEQ ID NO 39
<211> LENGTH: 53
<212> TYPE: DNA
<213> ORGANISM: Artificial Sequence
<220> FEATURE:
<223> OTHER INFORMATION: Synthetic: Enhanced CH36_53-0 AntiSense

<400> SEQUENCE: 39
gtaagggcac tgtccaaaga gaatcctata aaaaaacaga acaagtttat gaa            53

<210> SEQ ID NO 40
<211> LENGTH: 53
<212> TYPE: DNA
<213> ORGANISM: Artificial Sequence
<220> FEATURE:
<223> OTHER INFORMATION: Synthetic: Enhanced CH36_53-0 Sense

<400> SEQUENCE: 40
ttcataaact tgttctgttt ttttatagga ttctctttgg acagtgccct tac            53

<210> SEQ ID NO 41
<211> LENGTH: 58
<212> TYPE: DNA
<213> ORGANISM: Artificial Sequence
<220> FEATURE:
<223> OTHER INFORMATION: Synthetic: Enhanced CH36_58-0 AntiSense

<400> SEQUENCE: 41
gtaagggcac tgtccaaaga gaatcctatg gaaaaacaga acaagtttct gggatgaa      58

<210> SEQ ID NO 42
<211> LENGTH: 58
<212> TYPE: DNA
<213> ORGANISM: Artificial Sequence
<220> FEATURE:
<223> OTHER INFORMATION: Synthetic: Enhanced CH36_58-0 Sense

<400> SEQUENCE: 42
ttcatcccag aaacttgttc tgttttttcca taggattctc tttggacagt gcccttac     58

<210> SEQ ID NO 43
<211> LENGTH: 63
<212> TYPE: DNA
<213> ORGANISM: Artificial Sequence
<220> FEATURE:
<223> OTHER INFORMATION: Synthetic: Enhanced CH36_63-0 AntiSense

<400> SEQUENCE: 43
gtaagggcac tgtccaaaga gaatcctatg gaaaaacaga acaagtttct ggggttaatg    60
aat                                                                  63

<210> SEQ ID NO 44
<211> LENGTH: 63
<212> TYPE: DNA
<213> ORGANISM: Artificial Sequence
<220> FEATURE:
<223> OTHER INFORMATION: Synthetic: Enhanced CH36_63-0 Sense

<400> SEQUENCE: 44
attcattaac cccagaaact tgttctgttt ttccatagga ttctctttgg acagtgccct    60
tac                                                                  63

<210> SEQ ID NO 45
<211> LENGTH: 68
<212> TYPE: DNA
<213> ORGANISM: Artificial Sequence
<220> FEATURE:
<223> OTHER INFORMATION: Synthetic: CH36_68-0 AntiSense

<400> SEQUENCE: 45
gtaagggcac tgtccaaaga gaatcctatg gaaaaacaga acaagtttct ggggttactg    60
aatgaatg                                                             68

<210> SEQ ID NO 46
<211> LENGTH: 68
<212> TYPE: DNA
<213> ORGANISM: Artificial Sequence
<220> FEATURE:
<223> OTHER INFORMATION: Synthetic: CH36_68-0 Sense

<400> SEQUENCE: 46
cattcattca gtaacccag aaacttgttc tgttttttcca taggattctc tttggacagt    60
gcccttac                                                             68

<210> SEQ ID NO 47
<211> LENGTH: 73
<212> TYPE: DNA
<213> ORGANISM: Artificial Sequence
<220> FEATURE:
<223> OTHER INFORMATION: Synthetic: CH36_73-0 AntiSense

<400> SEQUENCE: 47
gtaagggcac tgtccaaaga gaatcctatg gaaaaacaga acaagtttct ggggttactg    60
aatgaatgct ttt                                                       73

<210> SEQ ID NO 48
<211> LENGTH: 73
<212> TYPE: DNA
<213> ORGANISM: Artificial Sequence
<220> FEATURE:
<223> OTHER INFORMATION: Synthetic: CH36_73-0 Sense

```
<400> SEQUENCE: 48
aaaagcattc attcagtaac cccagaaact tgttctgttt ttccatagga ttctctttgg     60
acagtgccct tac                                                      73

<210> SEQ ID NO 49
<211> LENGTH: 5
<212> TYPE: DNA
<213> ORGANISM: Artificial Sequence
<220> FEATURE:
<223> OTHER INFORMATION: Synthetic: branch point consensus sequence
<220> FEATURE:
<221> NAME/KEY: misc_feature
<222> LOCATION: (3)..(3)
<223> OTHER INFORMATION: n is a, c, g, or t

<400> SEQUENCE: 49 ytnay                                                                5

<210> SEQ ID NO 50
<211> LENGTH: 7
<212> TYPE: DNA
<213> ORGANISM: Artificial Sequence
<220> FEATURE:
<223> OTHER INFORMATION: Synthetic: branch point sequence

<400> SEQUENCE: 50 tattaac                                                              7

<210> SEQ ID NO 51
<211> LENGTH: 7
<212> TYPE: DNA
<213> ORGANISM: Artificial Sequence
<220> FEATURE:
<223> OTHER INFORMATION: Synthetic: branch point sequence

<400> SEQUENCE: 51 gttaata                                                              7

<210> SEQ ID NO 52
<211> LENGTH: 7
<212> TYPE: DNA
<213> ORGANISM: Artificial Sequence
<220> FEATURE:
<223> OTHER INFORMATION: Synthetic: branch point sequence

<400> SEQUENCE: 52 tactgac                                                              7

<210> SEQ ID NO 53
<211> LENGTH: 9
<212> TYPE: DNA
<213> ORGANISM: Artificial Sequence
<220> FEATURE:
<223> OTHER INFORMATION: Synthetic: polypyrimidine tract

<400> SEQUENCE: 53 tttttttct                                                            9

<210> SEQ ID NO 54
<211> LENGTH: 13
<212> TYPE: DNA
<213> ORGANISM: Artificial Sequence
<220> FEATURE:
<223> OTHER INFORMATION: Synthetic: polypyrimidine tract

<400> SEQUENCE: 54
```

```
tttttttcttt ttt                                                13
```

<210> SEQ ID NO 55
<211> LENGTH: 16
<212> TYPE: DNA
<213> ORGANISM: Artificial Sequence
<220> FEATURE:
<223> OTHER INFORMATION: Synthetic: polypyrimidine tract

<400> SEQUENCE: 55

```
cttcttctct tcttcc                                              16
```

<210> SEQ ID NO 56
<211> LENGTH: 7
<212> TYPE: PRT
<213> ORGANISM: Artificial Sequence
<220> FEATURE:
<223> OTHER INFORMATION: Synthetic: SV40 nuclear localization signal
      (NLS)

<400> SEQUENCE: 56

Pro Lys Lys Lys Arg Lys Val
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic: SV40 nuclear localization signal
      (NLS)

<400> SEQUENCE: 57

Pro Lys Lys Lys Arg Arg Val
1               5

<210> SEQ ID NO 58
<211> LENGTH: 16
<212> TYPE: PRT
<213> ORGANISM: Artificial Sequence
<220> FEATURE:
<223> OTHER INFORMATION: Synthetic: nucleoplasmin nuclear localization
      signal (NLS)

<400> SEQUENCE: 58

Lys Arg Pro Ala Ala Thr Lys Lys Ala Gly Gln Ala Lys Lys Lys Lys
1               5                   10                  15

<210> SEQ ID NO 59
<211> LENGTH: 24
<212> TYPE: DNA
<213> ORGANISM: S. pyogenes
<220> FEATURE:
<221> NAME/KEY: misc_feature
<223> OTHER INFORMATION: S. pyogenes target sequence and PAM
<220> FEATURE:
<221> NAME/KEY: misc_feature
<222> LOCATION: (1)..(22)
<223> OTHER INFORMATION: n is a, c, g, or t
<220> FEATURE:
<221> NAME/KEY: misc_feature
<222> LOCATION: (20)..(21)
<223> OTHER INFORMATION: n may or may not be present

<400> SEQUENCE: 59

```
nnnnnnnnn nnnnnnnnn nnrg                                       24
```

```
<210> SEQ ID NO 60
<211> LENGTH: 6
<212> TYPE: PRT
<213> ORGANISM: Artificial Sequence
<220> FEATURE:
<223> OTHER INFORMATION: Synthetic: 6xHis

<400> SEQUENCE: 60

His His His His His His
1               5

<210> SEQ ID NO 61
<211> LENGTH: 100
<212> TYPE: RNA
<213> ORGANISM: Artificial Sequence
<220> FEATURE:
<223> OTHER INFORMATION: Synthetic: GAA5 sgRNA

<400> SEQUENCE: 61
agcccgcuuu cuucucccgc guuuuagagc uagaaauagc aaguuaaaau aaggcuaguc    60
cguuaucaac uugaaaaagu ggcaccgagu cggugcuuuu                         100

<210> SEQ ID NO 62
<211> LENGTH: 25
<212> TYPE: DNA
<213> ORGANISM: Artificial Sequence
<220> FEATURE:
<223> OTHER INFORMATION: Synthetic: GAA_25-0_F

<400> SEQUENCE: 62
gagaagaagt attaactttt tttct                                          25

<210> SEQ ID NO 63
<211> LENGTH: 50
<212> TYPE: DNA
<213> ORGANISM: Artificial Sequence
<220> FEATURE:
<223> OTHER INFORMATION: Synthetic: GAA_50-0_F

<400> SEQUENCE: 63
tggaagaaga gaagaagctg ggtattaacg cattttttc tttttaattc                50

<210> SEQ ID NO 64
<211> LENGTH: 75
<212> TYPE: DNA
<213> ORGANISM: Artificial Sequence
<220> FEATURE:
<223> OTHER INFORMATION: Synthetic: GAA_75-0_F

<400> SEQUENCE: 64
tggaagaaga gaagaagctg ggaatgtgtc agtaaggcat gtattaacgc aaatgaattt    60
ttttcttttt aattc                                                     75

<210> SEQ ID NO 65
<211> LENGTH: 100
<212> TYPE: DNA
<213> ORGANISM: Artificial Sequence
<220> FEATURE:
<223> OTHER INFORMATION: Synthetic: GAA_100-0_F

<400> SEQUENCE: 65
tggaagaaga gaagaagctg ggaatgtgtc agtaaggcat gagccaccgc gccagccatg    60
caaatctatt aacgcaaatg aattttttc tttttaattc                          100
```

```
<210> SEQ ID NO 66
<211> LENGTH: 25
<212> TYPE: DNA
<213> ORGANISM: Artificial Sequence
<220> FEATURE:
<223> OTHER INFORMATION: Synthetic: GAA_25-0_R

<400> SEQUENCE: 66
agaaaaaaag ttaatacttc ttctc                                              25

<210> SEQ ID NO 67
<211> LENGTH: 50
<212> TYPE: DNA
<213> ORGANISM: Artificial Sequence
<220> FEATURE:
<223> OTHER INFORMATION: Synthetic: GAA_50-0_R

<400> SEQUENCE: 67
gaattaaaaa gaaaaaaatg cgttaatacc cagcttcttc tcttcttcca                   50

<210> SEQ ID NO 68
<211> LENGTH: 75
<212> TYPE: DNA
<213> ORGANISM: Artificial Sequence
<220> FEATURE:
<223> OTHER INFORMATION: Synthetic: GAA_75-0_R

<400> SEQUENCE: 68
gaattaaaaa gaaaaaaatt catttgcgtt aatacatgcc ttactgacac attcccagct        60
tcttctcttc ttcca                                                         75

<210> SEQ ID NO 69
<211> LENGTH: 100
<212> TYPE: DNA
<213> ORGANISM: Artificial Sequence
<220> FEATURE:
<223> OTHER INFORMATION: Synthetic: GAA_100-0_R

<400> SEQUENCE: 69
gaattaaaaa gaaaaaaatt catttgcgtt aatagatttg catggctggc gcggtggctc        60
atgccttact gacacattcc cagcttcttc tcttcttcca                             100

<210> SEQ ID NO 70
<211> LENGTH: 100
<212> TYPE: RNA
<213> ORGANISM: Artificial Sequence
<220> FEATURE:
<223> OTHER INFORMATION: Synthetic: CH42 sgRNA

<400> SEQUENCE: 70
gucagucuca cagguuacag guuuuagagc uagaaauagc aaguuaaaau aaggcuaguc        60
cguuaucaac uugaaaaagu ggcaccgagu cggugcuuuu                             100

<210> SEQ ID NO 71
<211> LENGTH: 25
<212> TYPE: DNA
<213> ORGANISM: Artificial Sequence
<220> FEATURE:
<223> OTHER INFORMATION: Synthetic: CH42_25-0_F

<400> SEQUENCE: 71
aacctgtgag actggaccag gtaag                                              25

<210> SEQ ID NO 72
```

```
<211> LENGTH: 25
<212> TYPE: DNA
<213> ORGANISM: Artificial Sequence
<220> FEATURE:
<223> OTHER INFORMATION: Synthetic: CH42_25-0_R

<400> SEQUENCE: 72
cttacctggt ccagtctcac aggtt                                           25

<210> SEQ ID NO 73
<211> LENGTH: 50
<212> TYPE: DNA
<213> ORGANISM: Artificial Sequence
<220> FEATURE:
<223> OTHER INFORMATION: Synthetic: CH42_50-0_F

<400> SEQUENCE: 73
aacctgtgag actggaccag gtaagactca cacttgcgaa accggcccag                50

<210> SEQ ID NO 74
<211> LENGTH: 50
<212> TYPE: DNA
<213> ORGANISM: Artificial Sequence
<220> FEATURE:
<223> OTHER INFORMATION: Synthetic: CH42_50-0_R

<400> SEQUENCE: 74
ctgggccggt tcgcaagtg tgagtcttac ctggtccagt ctcacaggtt                 50

<210> SEQ ID NO 75
<211> LENGTH: 75
<212> TYPE: DNA
<213> ORGANISM: Artificial Sequence
<220> FEATURE:
<223> OTHER INFORMATION: Synthetic: CH42_75-0_F

<400> SEQUENCE: 75
aacctgtgag actggaccag gtaagcgacg cgcatttctc acacggcagg actcacactt     60
gcgaaaccgg cccag                                                      75

<210> SEQ ID NO 76
<211> LENGTH: 75
<212> TYPE: DNA
<213> ORGANISM: Artificial Sequence
<220> FEATURE:
<223> OTHER INFORMATION: Synthetic: CH42_75-0_R

<400> SEQUENCE: 76
ctgggccggt tcgcaagtg tgagtcctgc cgtgtgagaa atgcgcgtcg cttacctggt      60
ccagtctcac aggtt                                                      75

<210> SEQ ID NO 77
<211> LENGTH: 100
<212> TYPE: DNA
<213> ORGANISM: Artificial Sequence
<220> FEATURE:
<223> OTHER INFORMATION: Synthetic: CH42_100-0_F

<400> SEQUENCE: 77
aacctgtgag actggaccag gtaagcgacg cgcatttctc acacggcagg agggccaca     60 cgcgtttgtt tctcaactca cacttgcgaa accggcccag                          100

<210> SEQ ID NO 78
<211> LENGTH: 100
```

```
<212> TYPE: DNA
<213> ORGANISM: Artificial Sequence
<220> FEATURE:
<223> OTHER INFORMATION: Synthetic: CH42_100-0_R

<400> SEQUENCE: 78
ctgggccggt tcgcaagtg tgagttgaga acaaacgcg tgtggccctc cctgccgtgt      60
gagaaatgcg cgtcgcttac ctggtccagt ctcacaggtt                         100

<210> SEQ ID NO 79
<211> LENGTH: 125
<212> TYPE: DNA
<213> ORGANISM: Artificial Sequence
<220> FEATURE:
<223> OTHER INFORMATION: Synthetic: CH42_125-0_F

<400> SEQUENCE: 79
aacctgtgag actggaccag gtaagcgacg cgcatttctc acacggcagg gagggccaca    60
cgcgtttgtt tctcacacga tgggcagggc gacacatgtt actcacactt gcgaaccgg   120 cccag                                                              125

<210> SEQ ID NO 80
<211> LENGTH: 125
<212> TYPE: DNA
<213> ORGANISM: Artificial Sequence
<220> FEATURE:
<223> OTHER INFORMATION: Synthetic: CH42_125-0_R

<400> SEQUENCE: 80
ctgggccggt tcgcaagtg tgagtaacat gtgtcgccct gcccatcgtg tgagaaacaa     60
acgcgtgtgg ccctccctgc cgtgtgagaa atgcgcgtcg cttacctggt ccagtctcac   120
aggtt                                                              125

<210> SEQ ID NO 81
<211> LENGTH: 20
<212> TYPE: RNA
<213> ORGANISM: Artificial Sequence
<220> FEATURE:
<223> OTHER INFORMATION: Synthetic: CH32 sgRNA spacer

<400> SEQUENCE: 81
ucuuuggaca gcguccauac                                               20

<210> SEQ ID NO 82
<211> LENGTH: 23
<212> TYPE: DNA
<213> ORGANISM: Artificial Sequence
<220> FEATURE:
<223> OTHER INFORMATION: Synthetic: CH32 target gene(PAM)

<400> SEQUENCE: 82
tctttggaca gcgtccatac tgg                                           23

<210> SEQ ID NO 83
<211> LENGTH: 20
<212> TYPE: RNA
<213> ORGANISM: Artificial Sequence
<220> FEATURE:
<223> OTHER INFORMATION: Synthetic: CH34 sgRNA spacer

<400> SEQUENCE: 83
uggacagcgu ccauacuggu                                               20
```

```
<210> SEQ ID NO 84
<211> LENGTH: 23
<212> TYPE: DNA
<213> ORGANISM: Artificial Sequence
<220> FEATURE:
<223> OTHER INFORMATION: Synthetic: CH34 target gene(PAM)

<400> SEQUENCE: 84
tggacagcgt ccatactggt ggg                                              23

<210> SEQ ID NO 85
<211> LENGTH: 20
<212> TYPE: RNA
<213> ORGANISM: Artificial Sequence
<220> FEATURE:
<223> OTHER INFORMATION: Synthetic: CH36 sgRNA spacer

<400> SEQUENCE: 85
guauccaaaa cccaccagua                                                  20

<210> SEQ ID NO 86
<211> LENGTH: 23
<212> TYPE: DNA
<213> ORGANISM: Artificial Sequence
<220> FEATURE:
<223> OTHER INFORMATION: Synthetic: CH36 target gene (PAM)

<400> SEQUENCE: 86
gtatccaaaa cccaccagta tgg                                              23

<210> SEQ ID NO 87
<211> LENGTH: 23
<212> TYPE: DNA
<213> ORGANISM: Artificial Sequence
<220> FEATURE:
<223> OTHER INFORMATION: Synthetic: CH42 target gene (PAM)

<400> SEQUENCE: 87
gtcagtctca caggttacag ggg                                              23

<210> SEQ ID NO 88
<211> LENGTH: 20
<212> TYPE: RNA
<213> ORGANISM: Artificial Sequence
<220> FEATURE:
<223> OTHER INFORMATION: Synthetic: CH42 sgRNA spacer

<400> SEQUENCE: 88
gucagucuca cagguuacag                                                  20

<210> SEQ ID NO 89
<211> LENGTH: 106
<212> TYPE: RNA
<213> ORGANISM: Artificial Sequence
<220> FEATURE:
<223> OTHER INFORMATION: Synthetic: Murine CH34-CTX1 sgRNA

<400> SEQUENCE: 89
usgsgsacaa cgcccguauu gguguuuuag agcuagaaau agcaaguuaa aauaaggcua       60
guccguuauc aacuugaaaa aguggcaccg agucggugcu sususu                     106

<210> SEQ ID NO 90
<211> LENGTH: 23
<212> TYPE: DNA
<213> ORGANISM: Artificial Sequence
```

```
<220> FEATURE:
<223> OTHER INFORMATION: Synthetic: WT GAA Target gene(PAM)

<400> SEQUENCE: 90
agcccgcttt cttctcccgc agg                                          23

<210> SEQ ID NO 91
<211> LENGTH: 20
<212> TYPE: RNA
<213> ORGANISM: Artificial Sequence
<220> FEATURE:
<223> OTHER INFORMATION: Synthetic: WT GAA5 sgRNA spacer

<400> SEQUENCE: 91
agcccgcuuu cuucucccgc                                              20

<210> SEQ ID NO 92
<211> LENGTH: 23
<212> TYPE: DNA
<213> ORGANISM: Artificial Sequence
<220> FEATURE:
<223> OTHER INFORMATION: Synthetic: Mutant (Mt) GAA target gene(PAM)

<400> SEQUENCE: 92
agcccgcttg cttctcccgc agg                                          23

<210> SEQ ID NO 93
<211> LENGTH: 20
<212> TYPE: RNA
<213> ORGANISM: Artificial Sequence
<220> FEATURE:
<223> OTHER INFORMATION: Synthetic: Mt GAA sgRNA spacer

<400> SEQUENCE: 93
agcccgcuug cuucucccgc                                              20

<210> SEQ ID NO 94
<211> LENGTH: 100
<212> TYPE: RNA
<213> ORGANISM: Artificial Sequence
<220> FEATURE:
<223> OTHER INFORMATION: Synthetic: Mt GAA sgRNA

<400> SEQUENCE: 94
agcccgcuug cuucucccgc guuuuagagc uagaaauagc aaguuaaaau aaggcuaguc   60
cguuaucaac uugaaaaagu ggcaccgagu cggugcuuuu                       100

<210> SEQ ID NO 95
<211> LENGTH: 30
<212> TYPE: DNA
<213> ORGANISM: Artificial Sequence
<220> FEATURE:
<223> OTHER INFORMATION: Synthetic: GAA_30 F

<400> SEQUENCE: 95
aagagaagaa gtattaactt tttttctttt                                   30

<210> SEQ ID NO 96
<211> LENGTH: 35
<212> TYPE: DNA
<213> ORGANISM: Artificial Sequence
<220> FEATURE:
<223> OTHER INFORMATION: Synthetic: GAA_35 F

<400> SEQUENCE: 96
```
aagaagagaa gaagtattaa cttttttct tttta                         35

<210> SEQ ID NO 97
<211> LENGTH: 40
<212> TYPE: DNA
<213> ORGANISM: Artificial Sequence
<220> FEATURE:
<223> OTHER INFORMATION: Synthetic: GAA_40 F

<400> SEQUENCE: 97
ggaagaagag aagaagtatt aactttttt cttttaatt                      40

<210> SEQ ID NO 98
<211> LENGTH: 43
<212> TYPE: DNA
<213> ORGANISM: Artificial Sequence
<220> FEATURE:
<223> OTHER INFORMATION: Synthetic: GAA_45 F

<400> SEQUENCE: 98
tggaagaaga gaagaagctt attaactttt tttcttttaa ttc                43

<210> SEQ ID NO 99
<211> LENGTH: 53
<212> TYPE: DNA
<213> ORGANISM: Artificial Sequence
<220> FEATURE:
<223> OTHER INFORMATION: Synthetic: GAA_55 F

<400> SEQUENCE: 99
tggaagaaga gaagaagctg ggtattaacg caaattttt tctttttaa ttc       53

<210> SEQ ID NO 100
<211> LENGTH: 60
<212> TYPE: DNA
<213> ORGANISM: Artificial Sequence
<220> FEATURE:
<223> OTHER INFORMATION: Synthetic: GAA_60 F

<400> SEQUENCE: 100
tggaagaaga gaagaagctg ggaatgttat taacgcaaat gatttttttc ttttaattc   60

<210> SEQ ID NO 101
<211> LENGTH: 65
<212> TYPE: DNA
<213> ORGANISM: Artificial Sequence
<220> FEATURE:
<223> OTHER INFORMATION: Synthetic: GAA_65 F

<400> SEQUENCE: 101
tggaagaaga gaagaagctg ggaatggtca gtatattaac gcaaatgttt ttttcttttt   60
aattc                                                              65

<210> SEQ ID NO 102
<211> LENGTH: 70
<212> TYPE: DNA
<213> ORGANISM: Artificial Sequence
<220> FEATURE:
<223> OTHER INFORMATION: Synthetic: GAA_70 F

<400> SEQUENCE: 102
tggaagaaga gaagaagctg ggaatgtgtc agtaagtatt aacgcaaatg aatttttttc   60
tttttaattc                                                         70

```
<210> SEQ ID NO 103
<211> LENGTH: 80
<212> TYPE: DNA
<213> ORGANISM: Artificial Sequence
<220> FEATURE:
<223> OTHER INFORMATION: Synthetic: GAA_80 F

<400> SEQUENCE: 103
tggaagaaga gaagaagctg ggaatgtgtc agtaaggcat gagccatatt aacgcaaatg    60 aattttttc ttttaattc                                                 80

<210> SEQ ID NO 104
<211> LENGTH: 85
<212> TYPE: DNA
<213> ORGANISM: Artificial Sequence
<220> FEATURE:
<223> OTHER INFORMATION: Synthetic: GAA_85 F

<400> SEQUENCE: 104
tggaagaaga gaagaagctg ggaatgtgtc agtaaggcat gagccaccgc gtattaacgc    60
aaatgaattt tttctttttt aattc                                         85

<210> SEQ ID NO 105
<211> LENGTH: 90
<212> TYPE: DNA
<213> ORGANISM: Artificial Sequence
<220> FEATURE:
<223> OTHER INFORMATION: Synthetic: GAA_90 F

<400> SEQUENCE: 105
tggaagaaga gaagaagctg ggaatgtgtc agtaaggcat gagccaccgc gccagctatt    60
aacgcaaatg aattttttc ttttaattc                                      90

<210> SEQ ID NO 106
<211> LENGTH: 96
<212> TYPE: DNA
<213> ORGANISM: Artificial Sequence
<220> FEATURE:
<223> OTHER INFORMATION: Synthetic: GAA_95 F

<400> SEQUENCE: 106
tgggaagaag agaagaagct gggaatgtgt cagtaaggca tgagccaccg cgccagccat    60
gctattaacg caaatgaatt ttttctttt taattc                              96

<210> SEQ ID NO 107
<211> LENGTH: 20
<212> TYPE: RNA
<213> ORGANISM: Artificial Sequence
<220> FEATURE:
<223> OTHER INFORMATION: Synthetic: CH32 Mutant-CTX1 sgRNA spacer

<400> SEQUENCE: 107
ucuuuggaca gcguccauac                                               20

<210> SEQ ID NO 108
<211> LENGTH: 20
<212> TYPE: RNA
<213> ORGANISM: Artificial Sequence
<220> FEATURE:
<223> OTHER INFORMATION: Synthetic: CH34 Mutant-CTX1 sgRNA spacer

<400> SEQUENCE: 108
uggacagcgu ccauacuggu                                               20
```

```
<210> SEQ ID NO 109
<211> LENGTH: 16
<212> TYPE: DNA
<213> ORGANISM: Artificial Sequence
<220> FEATURE:
<223> OTHER INFORMATION: Synthetic: polypyrimidine tract

<400> SEQUENCE: 109
cttgttctgt tttttt                                                    16

<210> SEQ ID NO 110
<211> LENGTH: 26
<212> TYPE: DNA
<213> ORGANISM: Artificial Sequence
<220> FEATURE:
<223> OTHER INFORMATION: Synthetic: exonic sequence

<400> SEQUENCE: 110
gattctcttt ggacagcgcc cttact                                         26
```